United States Patent
Mahadevan et al.

(10) Patent No.: US 8,420,678 B2
(45) Date of Patent: Apr. 16, 2013

(54) SMALL MOLECULE INHIBITORS OF THE PLECKSTRIN HOMOLOGY DOMAIN AND METHODS FOR USING SAME

(75) Inventors: Daruka Mahadevan, Tucson, AZ (US); Emmanuelle J. Meuillet, Oro Valley, AZ (US); Eugene A. Mash, Jr., Tucson, AZ (US); Vijay M. Gohkale, Tucson, AZ (US); Garth Powis, Houston, TX (US); Shuxing Zhang, Pearland, TX (US)

(73) Assignees: Board of Regents, The University of Texas System, Austin, TX (US); Arizona Board of Regents on Behalf of the University of Arizona, Tucson, AZ (US)

( * ) Notice: Subject to any disclaimer, the term of this patent is extended or adjusted under 35 U.S.C. 154(b) by 72 days.

(21) Appl. No.: 12/937,898

(22) PCT Filed: Apr. 14, 2009

(86) PCT No.: PCT/US2009/040575
§ 371 (c)(1),
(2), (4) Date: Feb. 7, 2011

(87) PCT Pub. No.: WO2009/129267
PCT Pub. Date: Oct. 22, 2009

(65) Prior Publication Data
US 2011/0144066 A1   Jun. 16, 2011

Related U.S. Application Data

(60) Provisional application No. 61/124,053, filed on Apr. 14, 2008, provisional application No. 61/199,497, filed on Nov. 17, 2008.

(51) Int. Cl.
*A61K 31/433* (2006.01)
*C07D 285/135* (2006.01)
(52) U.S. Cl.
USPC .................................. 514/363; 548/138
(58) Field of Classification Search .......... 514/363; 548/138
See application file for complete search history.

(56) References Cited

U.S. PATENT DOCUMENTS

| | | | | |
|---|---|---|---|---|
| 3,821,222 | A | 6/1974 | Moore | 544/316 |
| 4,017,489 | A | 4/1977 | Lawrence | 544/135 |
| 4,694,015 | A | 9/1987 | Sebille et al. | 514/375 |
| 2004/0092524 | A1 | 5/2004 | Perez et al. | 514/249 |
| 2007/0213378 | A1 | 9/2007 | Thomas et al. | 514/362 |
| 2007/0293516 | A1 | 12/2007 | Knight et al. | 514/262.1 |

FOREIGN PATENT DOCUMENTS

| | | |
|---|---|---|
| CA | 775563 | 1/1968 |
| DE | 25 56 011 | 6/1977 |
| DE | 34 43 225 | 6/1985 |
| WO | WO 90/15600 | 12/1990 |
| WO | WO 03/076436 | 9/2003 |
| WO | WO 2005/000862 | 1/2005 |
| WO | WO 2005/005421 | 1/2005 |
| WO | WO 2005/097758 | 10/2005 |
| WO | WO 2006/046914 | 5/2006 |
| WO | WO 2007/039173 | 4/2007 |
| WO | WO 2011/032169 | 3/2011 |

OTHER PUBLICATIONS

Chemical Abstract Database: compound (CAS RN 919458-54-1), entering date Feb. 6, 2007.*
Chemical Abstract Database: compound (CAS RN 477483-04-8), entering date Dec. 12, 2002.*
Chemical Abstract Database: compound (CAS RN 477482-99-8), entering date Dec. 12, 2002.*
Extended European Search Report issued in European Patent Application No. 11181871, dated Feb. 8, 2012.
Miyahara et al., "Antitumor activity of 2-Acylamino-1,3,4-thiadiazoles and related compounds," *Chem Pharm Bul.*, 30(12):4402-4406, 1982.
Sassiver an d Shepard , "2-Sulfanilamido-5-methoxy-,1,3,4-thiadiazole and related compounds," *J Med Chem.*, 9(4):541-545, 1966.
Stein et al., "Discovery and structure of activity relationships of sulfonamide $ET_A$—selective antagonists," *J Med Chem.*, 38: 1344-1354, 1995.
Anwar, et al., "Reactions of some 5-aryl-2-thiono-1, 3, 4-thiadiazoles," *Romanian Journal of Chemistry*, 26:1127-34, 1981.
International Search Report and Written Opinion, issued in PCT/US2009/040575, dated Dec. 15, 2009.
Mahadevan, et al., "Discovery of a novel class of AKT pleckstrin homology domain inhibitors," *Mol. Cancer Ther.*, 7:2621-32, 2008.
Mahieu, et al., "Synthesis of new thiosulfonates and disulfides from sulfonyl chlorides and thiols," *Synthetic Communications*, 16:1709-22, 1986.
Powell, et al., "Bile acid hydrophobicity is correlated with induction of apoptosis and/or growth arrest in HCT116 cells," *Biochem. J.*, 356:481-6, 2001.
Runge, et al., "Über einige unsymmetrishce heterocyclische Disulfide, II," *J. Fuer Praktische Chemie*, 21:39-49, 1963.
Thomas, et al., "High-resolution structure of the pleckstrin homology domain of protein kinase b/akt bound to phosphatidylinositol (3,4,5)-trisphosphate," *Curr. Biol.*, 12:1256-62, 2002.

(Continued)

*Primary Examiner* — Yong Chu
(74) *Attorney, Agent, or Firm* — Parker Highlander PLLC

(57) ABSTRACT

Pleckstrin homology domain binding compounds, pharmaceutical compositions including such compounds, and methods for their use are described herein.

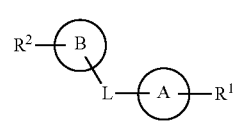

(I)

3 Claims, 23 Drawing Sheets

OTHER PUBLICATIONS

Calleja, et al., "Intramolecular and intermolecular interactions of protein kinase B define its activation in vivo," *PLoS Biol.*, 5:e95, 2007.

Castillo, et al., "Preferential inhibition of Akt and killing of Akt-dependent cancer cells by rationally designed phosphatidylinositol ether lipid analogues," *Cancer Res.*, 64:2782-92, 2004.

Feldman, et al., "Novel small molecule inhibitors of 3'-phosphoinositide-dependent Kinsase 1 (PDK-1)," *Eur. J. Cancer Suppl.*, 2(249):77, 2004.

Gills, et al., "Spectrum of activity and molecular correlates of response to phosphatidylinositol ether lipid analogues, novel lipid-based inhibitors of Akt," *Mol. Cancer Ther.*,5:713-22, 2006.

Giranda, et al., "Novel ATP-competitive AKT inhibitors slow the progression of tumor in vivo," *Eur. J. Cancer Suppl.*, 2(246):76-77, 2004.

International Search Report and Written Opinion, issued in Application No. PCT/US2010/048813, dated May 26, 2011.

Kim, et al., "Targeting the phosphatidylinositol-3 kinase/Akt pathway for the treatment of cancer," *Curr. Opin. Investig. Drugs*, 6:1250-8, 2005.

Kumar and Madison, "AKT crystal structure and AKT-specific inhibitors," *Oncogene*, 24:7493-501, 2005.

Meuillet, et al., "In vivo molecular pharmacology and antitumor activity of the targeted Akt inhibitor PX-316," *Oncol. Res.*, 14:513-27, 2004 (abstract only).

Meuillet, et al., "Specific inhibition of the Akt1 pleckstrin homology domain by D-3-deoxy-phosphatidyl-myo-inositol analogues," *Mol. Cancer Ther.*, 2:389-99, 2003.

Milburn, et al., "Binding of phosphatidylinositol 3,4,5-trisphosphate to the pleckstrin homology domain of protein kinase B induces a conformational change," *Biochem. J.*, 375:531-8, 2003.

\* cited by examiner

C

HaCaT

HaCaT-II,4

SMALL MOLECULE INHIBITORS OF THE PLECKSTRIN HOMOLOGY DOMAIN AND METHODS FOR USING SAME

CROSS REFERENCE

This application is a national phase application under 35 U.S.C. §371 of International Application No. PCT/US2009/040575 filed Apr. 14, 2009, which claims priority to U.S. Provisional Patent Application No. 61/124,053 filed Apr. 14, 2008 and Provisional Patent Application No. 61/199,497 filed Nov. 17, 2008. The entire text of each of the above-referenced disclosures is specifically incorporated herein by reference without disclaimer.

This application claims priority from U.S. Provisional Application No. 61/124,053 filed Apr. 14, 2008 entitled "Novel Inhibitors of AKT" and U.S. Provisional Application No. 61/199,497 filed Nov. 17, 2008 entitled "Active Inhibitors for AKT," each of which is incorporated herein by reference in its entirety.

This invention was made with government support under grant No. 5 R01 CA061015-11, awarded by NIH/NCI. The government has certain rights in the present invention.

BACKGROUND

Pleckstrin homology (PH) domains contain 100-120 amino acids and are found in over 250 human proteins. About 40 PH domains are known to bind phosphorylated phosphatidylinositide (PtdIns) lipids held in cell membranes. PtdIns phosphorylation and the subsequent binding of PH domain-containing proteins are vital components of signal transduction pathways that regulate cell growth and survival. For example, phosphorylation of $PtdIns(4,5)P_2$ to produce $PtdIns(3,4,5)P_3$ by PtdIns 3-K signals the recruitment and binding of AKT to the inner leaflet of the plasma membrane via recognition of the PH domain. The phosphatidylinositol-3-kinase (PtdIns-3-kinase)/Akt pathway is a survival signaling pathway that is activated in many types of human cancer. Cancer cells are resistant to the mechanisms that cause programmed cell death (apoptosis) in normal cells because they contain these activated survival signaling pathways. The PH domains of proteins, and specifically in this case in Akt, provide novel molecular targets for new types of drugs to prevent and treat cancer.

The PtdIns 3-kinase (PtdIns 3-K)/AKT pathway is of critically importance for cell proliferation and survival. Phosphorylation of PtdIns(4,5)P2 to produce PtdIns(3,4,5)P3 by PtdIns 3-K signals the recruitment and docking of AKT to the inner leaflet of the plasma membrane via its pleckstrin homology (PH) domain. AKT is then phosphorylated at Thr308 by the plasma membrane bound PtdIns dependent kinase-1 (PDK1) and on Ser473 by either intergrin linked kinase (ILK), by the kinase activity of AKT itself or and on Ser473 by either intergrin linked kinase (ILK), by the kinase activity of AKT itself or by mammalian target of rapamycin (mTOR)-rictor (TORC2). Once fully phosphorylated, AKT translocates back to the cytosol and nucleus, where it phosphorylates a variety of downstream targets including pro-apoptotic promoters such as forkhead transcription factors FKHR and AFX, as well as the Bcl-2 family member Bad, which is directly inhibited by phosphorylation via AKT. AKT promotes cell survival by activating CREB, and promotes proliferation by activating p70S6kinase and GSK-3β which contributes to cyclin D accumulation of cell cycle entry. AKT also acts as a mediator for VEGF production and angiogenesis by phosphorylation of mTOR, and defects in the PtdIns 3-K/AKT pathway are found in a variety of cancers, with most abnormalities occurring with mutation events in PTEN. Given the importance of AKT in proliferation and survival signaling, it has the potential to be an important target for cancer drug discovery.

Three genes encode AKT within the mammalian species to produce AKT-1/α, AKT-2/β, and AKT-3/γ isoforms of AKT of which AKT-1 and AKT-2 are expressed throughout the organism while AKT-3 is predominantly expressed in the brain, heart, and kidney. The three isoforms share a high degree of sequence homology within their PH domains but diverge within other regions. However, despite these differences they appear to have similar effects on cellular growth and apoptosis, and these similarities in biological and physiological properties between isoforms coupled with the similarities between their PH domains offers a fortuitous advantage in designing drugs that inhibit all AKT activity.

SUMMARY OF THE INVENTION

An aspect of the present invention relates to a compound of formula II:

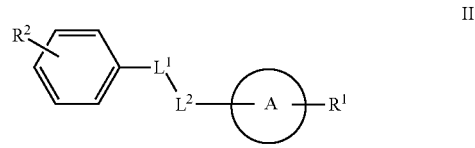

or pharmaceutically acceptable salt thereof, wherein: $L^1$ and $L^2$ are each, independently, —S—, —S(O)$_2$—, —C(O)—, —P(O)(OH)—, —NH—, —N(CH$_3$)—, —N(R$^3$)—, —CH$_2$—, or —C(R$^3$)$_2$—; each $R^3$ is, independently, —H, —CH$_3$, CH$_2$CH$_3$, CH$_2$CH$_2$CH$_3$, NH$_2$, or —C$_6$H$_5$; ring A is a substituted or unsubstituted, 5- or 6-membered ring having 1-3 ring-forming heteroatoms, and wherein ring A is optionally substituted with a methyl, methoxy, sulfonyl, or sulfonic acid ester group in addition to $R^1$; $R^1$ is —H, —CH$_3$, —CH$_2$CH$_3$, —CH$_2$(CH$_2$)$_m$CH$_3$, —C(CH$_3$)$_3$, —CH$_2$CH$_2$R$^4$, —OH, —OCH$_3$, —CH$_2$OH, —C(O)OH, —CH$_2$C(O)OH, —CH$_2$CH$_2$C(O)OH, —C(O)R$^4$, —C(O)OR$^4$, —CH$_2$C(O)OR$^4$, —CH$_2$CH$_2$C(O)OR$^4$, —NH$_2$, CH$_2$NH$_2$, —NHC(O)CH$_3$, —S(O)$_2$R$^4$, —CH$_2$S(O)$_2$R$^4$, C$_6$H$_5$, —C$_6$H$_4$R$^4$, —CH$_2$C$_6$H$_5$, —S(O$_2$C$_6$H$_5$, —CH$_2$S(O)$_2$C$_6$H$_5$, heteroaryl, heteroarylalkyl, morpholino, or halogen; $R^4$ is —H, —OH, —NH$_2$, —CH$_3$, —CH$_2$CH$_3$, —CH$_2$CH$_2$CH$_3$, —OCH$_3$, —C(O)OH, —C$_6$H$_5$, —C$_6$H$_4$R$^5$, —CH$_2$C$_6$H$_5$, —CH$_2$C$_6$H$_4$R$^5$, halogen, heteroaryl, heteroarylalkyl, or piperazinyl; $R^5$ is —H, —OH, —NH$_2$, —CH$_3$, —CH$_2$CH$_3$, —CH$_2$CH$_2$CH$_3$, —C(O)OH, or halogen; $R^2$ is —H, —CH$_3$, —C(CH$_3$)$_3$, C$_1$-C$_{20}$ alkyl, —OH, —NH$_2$, —OR$^6$, —NHC(O)R$^6$, —NR$^{6a}$R$^{6b}$, —NHS(O)$_2$R$^6$, —S(O)$_2$OH, —CH(O), —C(O)OH, —C(O)OR$^6$, —CH$_2$OH, —CH$_2$C(O)OH, —S(O$_2$)NH$_2$, —CH$_2$(CH$_2$)$_p$R$^6$—, CH$_2$(CH$_2$)$_p$OR$^6$, —CH$_2$—O—(CH$_2$)$_p$OR$^6$, —CH$_2$(CH$_2$)$_p$SO$_2$R$^6$, —CH$_2$(CH$_2$)$_p$NHR$^6$, —C$_6$H$_5$, or —C$_6$H$_4$R$^6$, and wherein the $C_1$-$C_{20}$ alkyl of $R^2$ is optionally substituted with one or more substituents independently selected from halogen, OH, —NH$_2$, —NHC(O)R$^6$, and —NR$^{6a}$R$^{6b}$; or $R^2$ is

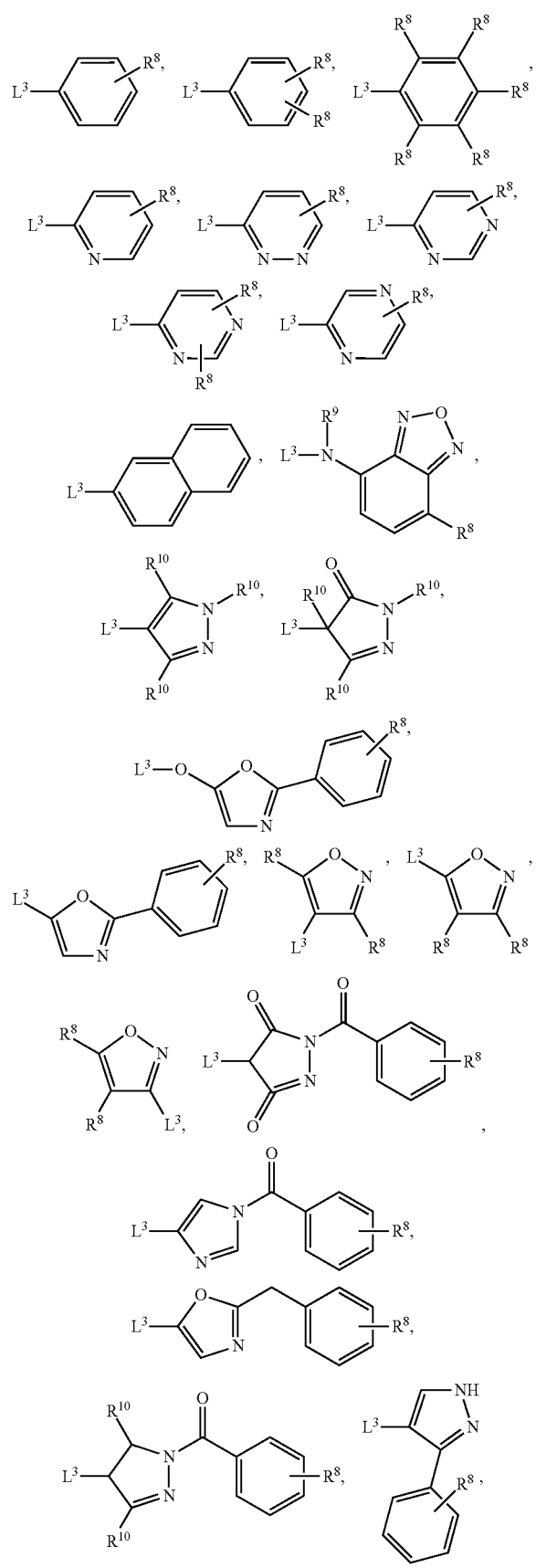

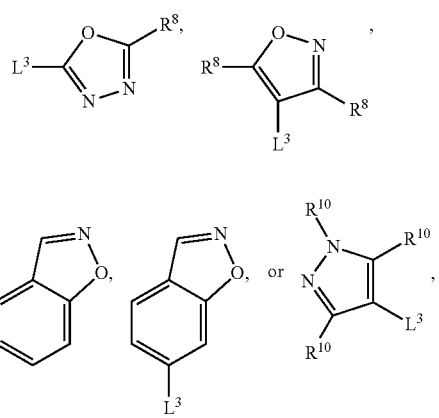

wherein $R^2$ is attached to the phenyl ring of Formula II through $L^3$; $R^6$ is —H, —NH$_2$, —OH, —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, halogen, aryl, heteroaryl, or C$_1$-C$_{20}$ alkyl, wherein each of the aryl, heteroaryl, or C$_1$-C$_{20}$ alkyl is optionally substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; $R^{6a}$ is H or methyl; $R^{6b}$ is methyl, 7-nitrobenzo[c][1,2,5]oxadiazol-4-yl, or —C(O)C$_6$H$_5$; $L^3$ is a bond, —CH$_2$—, —CH$_2$(CH$_2$)$_q$—, —CH(OH)—, —C(O)—, —O—, —NH—, —S—, —CH$_2$CH$_2$—, —CH=CH—, —N=N—, —OCH$_2$—, —OP(O)(OH)—, —NHS(O)$_2$—, —SCH$_2$—, —S(O)$_2$CH$_2$—, —S(O)$_2$O—, or —C(O)NH—; $R^7$ and $R^8$ are each independently —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen; $R^{10}$ is —H, —CH$_3$, —OH, —OCH$_3$, —C$_6$H$_5$, —C$_6$H$_4$R$^9$,

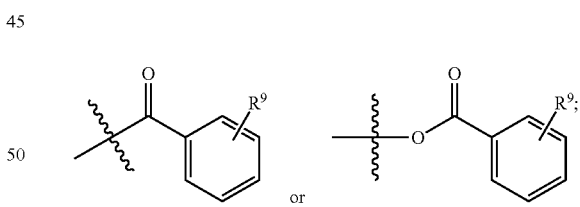

$R^9$ is —H, —CH$_3$, —C(CH$_3$), —OH, —NH$_2$, NO$_2$, —OCH$_3$, —C(O)OH, —C(O)NH$_2$, or halogen; and m, p and q are each independently an integer selected from 1 to 20; with the provisos that: $R^1$ is not —S(O)$_2$NH$_2$ when $R^2$ is NH$_2$; $L^3$ is not —NHC(O)— or —NH— when the moiety of

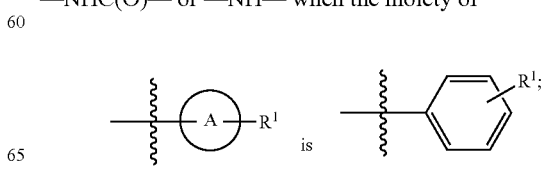

L³ is not —NHS(O)₂— when the moiety of

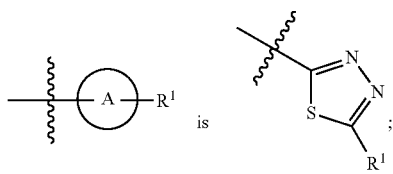 is 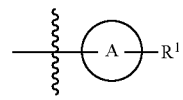;

R¹ is not —C(O)OR⁴ or —OR⁴ when the moiety of

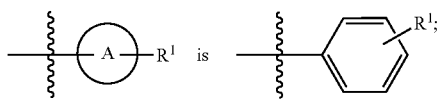

L³ is not —NHC(O)— when the moiety of

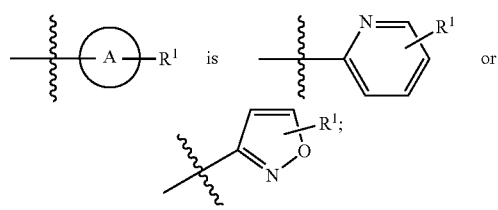

L³ is not —S(O)₂NH— when the moiety of

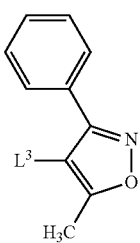

or R² is not

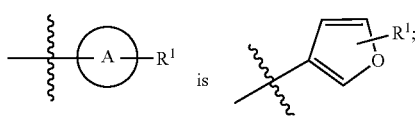

when the moiety of

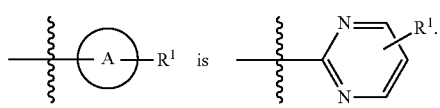

In certain embodiments, L¹ is —S—, —S(O)₂—, —C(O)—, or —P(O)(OH)—. L² may be —NH—, —NR³, —CH₂—, or —C(R³)₂—. L¹ may be —NH—, —NR³, —CH₂—, or —C(R³)₂—. L² may be —S—, —S(O)₂—, —C(O)—, or —P(O)(OH)—. In certain embodiments, L¹ is —S(O)₂— and L² is —NH—. A may be a 5-membered heteroaryl ring.

In certain embodiments, the moiety of:

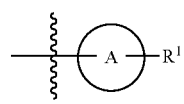

is selected from:

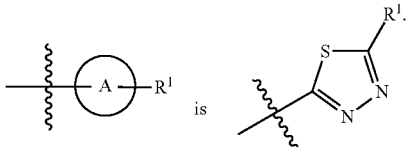

Ring A may be optionally substituted with a methyl, methoxy, sulfonyl, or sulfonic acid ester group in addition to R¹. In certain embodiments, the moiety of Ring A may be a phenyl ring or a 6-membered heteroaryl ring.

The moiety of may be selected from:

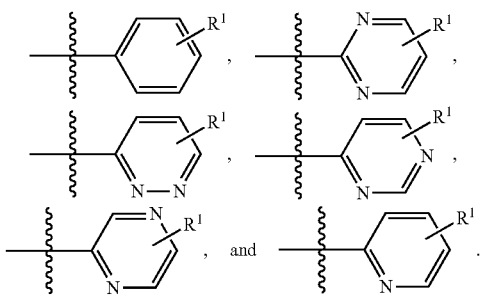

Ring A may be optionally substituted with a methyl, methoxy, sulfonyl, or sulfonic acid ester group in addition to $R^1$. In certain embodiments, the moiety of

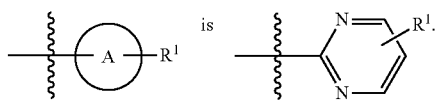

$R^2$ may be positioned and arranged in the para or meta position. In certain embodiments, the compound is not compound 316, compound 331, compound 332, compound 333, compound 360, or compound 335.

Another aspect of the present invention relates to a compound of formula III:

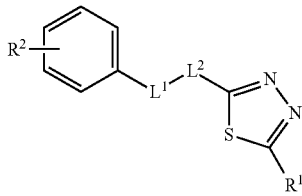

or pharmaceutically acceptable salt thereof, wherein: $L^1$ and $L^2$ are each, independently, —S—, —S(O)$_2$—, —C(O)—, —P(O)(OH)—, —NH—, —N(CH$_3$)—, —N(R$^3$)—, —CH$_2$—, or —C(R$^3$)$_2$—; each $R^3$ is, independently, —CH$_3$, CH$_2$CH$_3$, CH$_2$CH$_2$CH$_3$, NH$_2$, or —C$_6$H$_5$; $R^1$ is —H, —CH$_3$, —CH$_2$CH$_3$, —C(CH$_3$)$_3$, —C(O)OH, —CH$_2$C(O)OH, —CH$_2$C(O)OCH$_3$, —H$_2$C(O)OCH$_2$CH$_3$, —OH, CH$_2$OH, —NH$_2$, —CH$_2$NH$_2$, —OCH$_3$, S(O)$_2$NH$_2$, S(O)$_2$C$_6$H$_5$, or S(O)$_2$CH$_2$C$_6$H$_5$; $R^2$ is —NH$_2$, —NHC(O)R$^6$, —NR$^{6a}$R$^{6b}$, —NHS(O)$_2$R$^6$, —OH, —OR$^6$, C(O)OH, or C$_1$-C$_{20}$ alkyl, wherein the C$_1$-C$_{20}$ alkyl is optionally substituted with one or more substituents independently selected from halogen, C$_{1-6}$ alkyl, OH, —NH$_2$, —NHC(O)R$^6$, and —NR$^{6a}$R$^{6b}$; R$^6$ is —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl is optionally substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —H$_2$C$_6$H$_4$R$^7$, and halogen; R$^{6a}$ is H or methyl; R$^{6b}$ is methyl, 7-nitrobenzo[c][1,2,5]oxadiazol-4-yl, or —C(O)C$_6$H$_5$; and R$^7$ is —H, —CH$_3$, heteroaryl, —C(CH$_3$)$_3$, —OH, —NH$_2$, NHC(O)CH$_3$, S(O)$_2$OH, As(O)$_2$OH, NO$_2$, —OCH$_3$, —OCH$_2$CH$_3$, —C(O)OH, —C(O)NH$_2$, or halogen.

In certain embodiments, $L^1$ may be —S—, —S(O)$_{2-5}$—C(O)—, or —P(O)(OH)—. In other embodiments, $L^2$ may be —NH—, —NR$^3$, —CH$_2$—, or —C(R$^3$)$_2$—. $L^1$ may be —NH—, —NR$^3$, —CH$_2$—, or —C(R$^3$)$_2$—. $L^2$ may be —S—, —S(O)$_2$—, —C(O)—, or —P(O)(OH)—. In certain embodiments, $L^1$ is —S(O)$_2$— and $L^2$ is —NH—. $R^2$ may be positioned and arranged in the para or meta position.

In certain embodiments, the compound is a compound of Formula III-a:

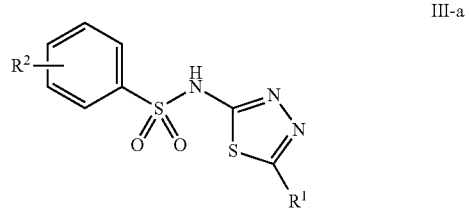

wherein: $R^1$ is —H or —CH$_3$; $R^2$ is —NH$_2$, —NHC(O)R$^6{}_5$— NHS(O)$_2$R$^6$, or C$_1$-C$_{20}$ alkyl, wherein the C$_1$-C$_{20}$ alkyl is optionally substituted with one or more substituents independently selected from halogen, C$_{1-6}$ alkyl, OH, —NH$_2$, —NHC(O)R$^6$, and —NR$^{6a}$R$^{6b}$; R$^6$ is —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, and wherein each of the aryl, heteroaryl, or C$_1$-C$_{20}$ alkyl is optionally substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; R$^{6a}$ is H or methyl; R$^{6b}$ is methyl, 7-nitrobenzo[c][1,2,5]oxadiazol-4-yl, or —C(O)C$_6$H$_5$; and R$^7$ is —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In certain embodiments, $R^1$ is H; and $R^2$ is C$_1$-C$_{20}$ alkyl optionally substituted with one or more substituents independently selected from halogen, OH, —NH$_2$, —NHC(O)R$^6$, and —NR$^{6a}$R$^{6b}$; R$^6$ is —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl is optionally substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; R$^{6a}$ is H or methyl; R$^{6b}$ is methyl, 7-nitrobenzo[c][1,2,5]oxadiazol-4-yl, or —C(O)C$_6$H$_5$; and R$^7$ is —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In certain embodiments, R$^2$ is —NH$_2$ or —NHS(O)$_2$R$^6$; R$^6$ is —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl is optionally substituted with one or more substituents independently selected from —NH$_2$, —OH, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; and R$^7$ is —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In certain embodiments, R$^2$ is —NHS(O)$_2$R$^6$; R$^6$ is aryl or heteroaryl, each optionally substituted with one or more substituents independently selected from —NH$_2$, —OH, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; and R$^7$ is —H, —CH$_3$, heteroaryl, —C(CH$_3$)$_3$, —OH, —NH$_2$, NHC(O)CH$_3$, S(O)$_2$OH, As(O)$_2$OH, NO$_2$, —OCH$_3$, —OCH$_2$CH$_3$, —C(O)OH, —C(O)NH$_2$, or halogen. R$^2$ may be positioned and arranged in the para position. In certain embodiments, R$^1$ is H; and R$^2$ is —NH$_2$. In certain embodiments, R$^1$ is H; and R$^2$ is C$_{1-20}$ alkyl.

Yet another aspect of the present invention relates to a compound of formula IV:

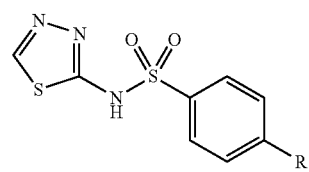

IV or pharmaceutically acceptable salt thereof wherein: R is an amine, methyl, alkyl, alkene, alkyne, aminoalkyl, alkyl carbamate, alkyl acetamide, alkyl sulfonyl, alkyl sulfonic acid ester, or alkyl sulfonamide. R may be a linear or branched C$_2$-C$_{20}$ alkyl, linear or branched C$_2$-C$_{20}$ alkene, linear or branched C$_2$-C$_{20}$ alkyne, linear or branched C$_2$-C$_{20}$ aminoalkyl, linear or branched C$_2$-C$_{20}$ alkyl carbamate branched C$_2$-C$_{20}$ alkyl acetamide, linear or branched C$_2$-C$_{20}$ sulfonyl, linear or branched C$_2$-C$_{20}$ sulfonic acid ester, or linear or branched C$_2$-C$_{20}$ sulfonamide. R may be a linear C$_2$-C$_{20}$ alkyl. R may be an alkyl acetamide of formula —NHC(O)CH$_1$CH$_3$ wherein n is 0 to 20. R may be selected from —CH$_{11}$CH$_3$ and —NHC(O)CH$_{11}$CH$_3$.

Another aspect of the present invention relates to a compound of formula:

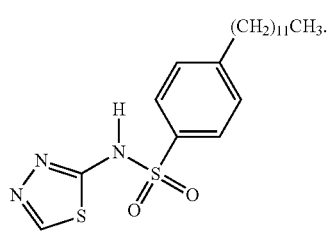

Yet another aspect of the present invention relates to a compound of formula:

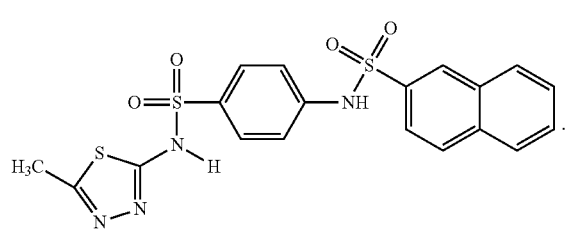 [SMILES: Cc1nnc(NS(=O)(=O)c2ccc(NS(=O)(=O)c3ccc4ccccc4c3)cc2)s1]

Another aspect of the present invention relates to a compound of formula:

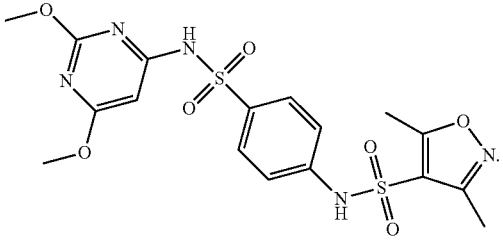 [SMILES: COc1cc(NS(=O)(=O)c2ccc(NS(=O)(=O)c3c(C)noc3C)cc2)nc(OC)n1]

Yet another aspect of the present invention relates to a compound of formula:

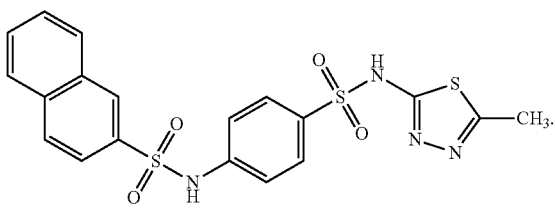 [SMILES: Cc1nnc(NS(=O)(=O)c2ccc(NS(=O)(=O)c3ccc4ccccc4c3)cc2)s1]

Another aspect of the present invention relates to pharmaceutical composition comprising, a compound of formula II:

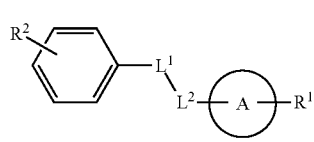

II or pharmaceutically acceptable salt thereof, wherein: L$^1$ and L$^2$ are each, independently, —S—, —S(O)$_2$—, —C(O)—, —P(O)(OH)—, —NH—, —N(CH$_3$)—, —N(R$^3$)—, —CH$_2$—, or —C(R$^3$)$_2$—; each R$^3$ is, independently, —H, —CH$_3$, CH$_2$CH$_3$, CH$_2$CH$_2$CH$_3$, NH$_2$, or —C$_6$H$_5$; ring A is a substituted or unsubstituted, 5- or 6-membered ring having 1-3 ring-forming heteroatoms, and wherein ring A is optionally substituted with a methyl, methoxy, sulfonyl, or sulfonic acid ester group in addition to R$^1$; R$^1$ is —H, —CH$_3$, —CH$_2$CH$_3$, —CH$_2$(CH$_2$)$_m$CH$_3$, —C(CH$_3$)$_3$, —CH$_2$CH$_2$R$^4$, —OH, —OCH$_3$, —CH$_2$OH, —C(O)OH, —CH$_2$C(O)OH, —CH$_2$CH$_2$C(O)OH, —C(O)R$^4$, —C(O)OR$^4$, —CH$_2$C(O)OR$^4$, —CH$_2$CH$_2$C(O)OR$^4$, —NH$_2$, CH$_2$NH$_2$, —NHC(O)CH$_3$, —S(O)$_2$R$^4$, —CH$_2$S(O)$_2$R$^4$, C$_6$H$_5$, —C$_6$H$_4$R$^4$, —CH$_2$C$_6$H$_5$, —S(O$_2$)C$_6$H$_5$, —CH$_2$S(O)$_2$C$_6$H$_5$, heteroaryl, heteroarylalkyl, morpholino, or halogen; R$^4$ is —H, —OH, —NH$_2$, —CH$_3$, —CH$_2$CH$_3$, —CH$_2$CH$_2$CH$_3$, —OCH$_3$, —C(O)OH, —C$_6$H$_5$, —C$_6$H$_4$R$^5$, —CH$_2$C$_6$H$_5$, —CH$_2$C$_6$H$_4$R$^5$, halogen, heteroaryl, heteroarylalkyl, or piperazinyl; R$^5$ is —H, —OH, —NH$_2$, —CH$_3$, —CH$_2$CH$_3$, —CH$_2$CH$_2$CH$_3$, —C(O)OH, or halogen; R$^2$ is —H, —CH$_3$, —C(CH$_3$)$_3$, C$_1$-C$_{20}$ alkyl, —OH, —NH$_2$, —OR$^6$, —NHC(O)R$^6$, —NR$^{6a}$R$^{6b}$, —NHS(O)$_2$R$^6$, —S(O)$_2$OH, —CH(O), —C(O)OH, —C(O)OR$^6$, —CH$_2$OH, —CH$_2$C(O)OH, —S(O$_2$)NH$_2$, —CH$_2$(CH$_2$)$_p$R$^6$—, CH$_2$(CH$_2$)$_p$OR$^6$, —CH$_2$—O—(CH$_2$)$_p$OR$^6$, —CH$_2$(CH$_2$)$_p$SO$_2$R$^6$, —CH$_2$(CH$_2$)$_p$NHR$^6$, —C$_6$H$_5$, or —C$_6$H$_4$R$^6$, and wherein the C$_1$-C$_{20}$ alkyl of R$^2$ is optionally substituted with one or more substituents independently selected from halogen, OH, —NH$_2$, —NHC(O)R$^6$, and —NR$^{6a}$R$^{6b}$; or R$^2$ is

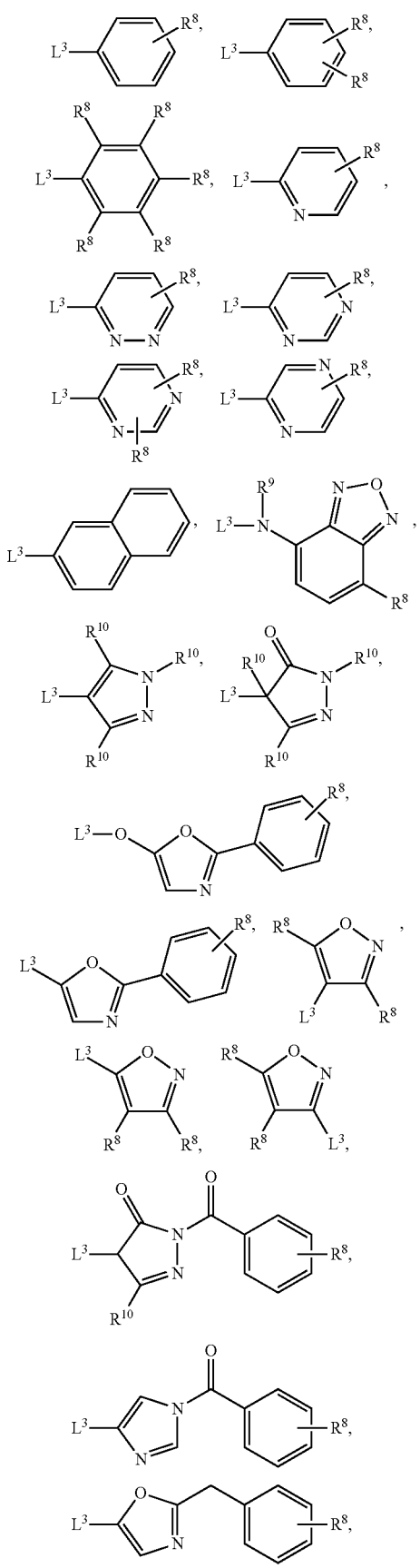

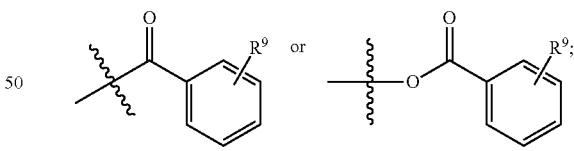

wherein R² is attached to the phenyl ring of Formula II through L³; R⁶ is —H, —NH₂, —OH, —CH₃, —CH₂CH₃, —CH₂CH₂CH₃, —C₆H₅, —C₆H₄R⁷, —CH₂C₆H₅, —CH₂C₆H₄R⁷, halogen, aryl, heteroaryl, or $C_1$-$C_{20}$ alkyl, wherein each of the aryl, heteroaryl, or $C_1$-$C_{20}$ alkyl is optionally substituted with one or more substituents independently selected from —NH₂, —OH, —NH₂, —CH₃, —CH₂CH₃, —CH₂CH₂CH₃, $C_{1-6}$ alkyl, —C₆H₅, —C₆H₄R⁷, —CH₂C₆H₅, —CH₂C₆H₄R⁷, and halogen; $R^{6a}$ is H or methyl; $R^{6b}$ is methyl, 7-nitrobenzo[c][1,2,5]oxadiazol-4-yl, or —C(O)C₆H₅; L³ is a bond, —CH₂—, —CH₂(CH₂)$_q$—, —CH(OH)—, —C(O)—, —O—, —NH—, —S—, —CH₂CH₂—, —CH═CH—, —N═N—, —OCH₂—, —OP(O)(OH)—, —NHS(O)₂—, —SCH₂—, —S(O)₂CH₂—, —S(O)₂O—, or —C(O)NH—; R⁷ and R⁸ are each independently —H, —CH₃, heteroaryl, —C(CH₃)₃, —OH, —NH₂, NHC(O)CH₃, S(O)₂OH, —P(O)₂OH, As(O)₂OH, NO₂, —OCH₃, —OCH₂CH₃, —C(O)OH, —C(O)NH₂, or halogen; R¹⁰ is —H, —CH₃, —OH, —OCH₃, —C₆H₅, —C₆H₄R⁹,

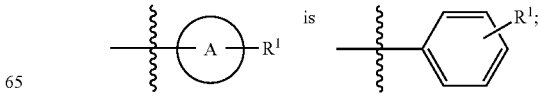

R⁹ is —H, —CH₃, —C(CH₃), —OH, —NH₂, NO₂, —OCH₃, —C(O)OH, —C(O)NH₂, or halogen; and m, p and q are each independently an integer selected from 1 to 20; with the provisos that:
R¹ is not —S(O)₂NH₂ when R² is NH₂; L³ is not —NHC(O)— or —NH— when the moiety of $L^3$ is not —NHS(O)$_2$— when the moiety of

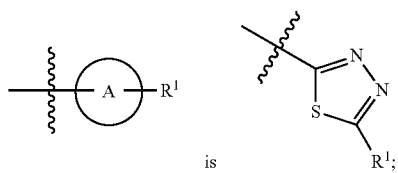

is $R^1$ is not —C(O)OR$^4$ or —OR$^4$ when the moiety of

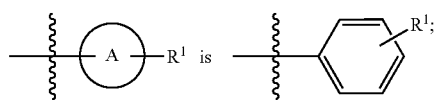

$L^3$ is not —NHC(O)— when the moiety of

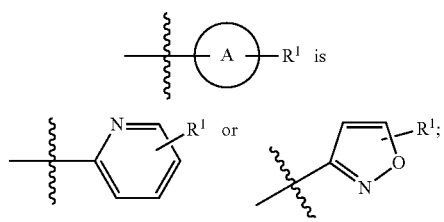

$L^3$ is not —S(O)$_2$NH— when the moiety of

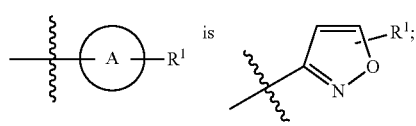

or $R^2$ is not

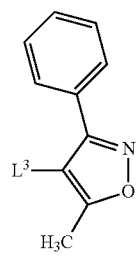

when the moiety of

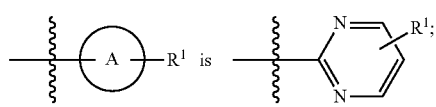

and a pharmaceutically acceptable carrier or excipient.

In certain embodiments, ring A is a 5-membered heteroaryl ring. Ring A may be

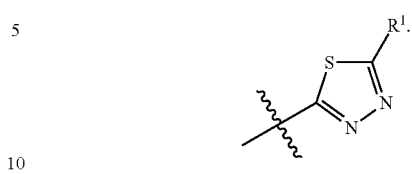

Ring A may be optionally substituted with a methyl, methoxy, sulfonyl, or sulfonic acid ester group in addition to $R^1$. Ring A may be a phenyl ring or a 6-membered heteroaryl ring. Ring A may be

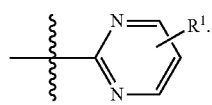

Ring A may be optionally substituted with a methyl, methoxy, sulfonyl, or sulfonic acid ester group in addition to $R^1$. $R^2$ may be positioned and arranged in the para position. In certain embodiments, the compound is not compound 316, compound 331, compound 332, compound 333, compound 360, or compound 335.

Yet another aspect of the present invention relates to a pharmaceutical composition comprising, a compound selected from:

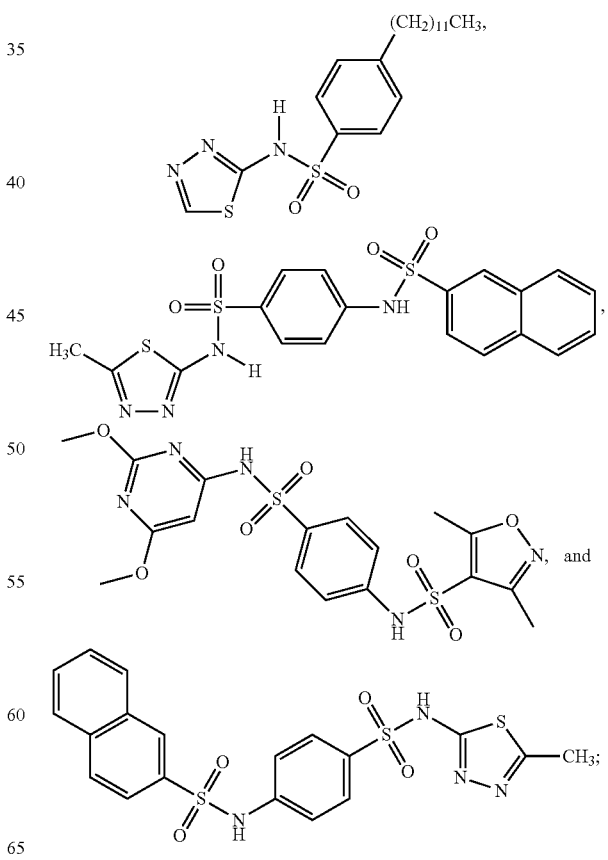

and a pharmaceutically acceptable carrier or excipient.

Another aspect of the present invention relates to a compound of formula V:

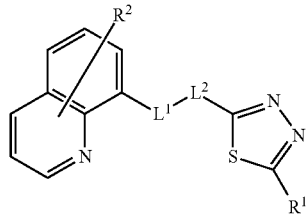

or pharmaceutically acceptable salt thereof, wherein: $L^1$ and $L^2$ are each, independently, —S—, —S(O)$_2$—, —C(O)—, —P(O)(OH)—, —NH—, —N(CH$_3$)—, —N(R$^3$)—, —CH$_2$—, or —C(R$^3$)$_2$—; each R$^3$ is, independently, —H, —CH$_3$, CH$_2$CH$_3$, CH$_2$CH$_2$CH$_3$, NH$_2$, or —C$_6$H$_5$; R$^1$ is —H, —CH$_3$, —CH$_2$CH$_3$, —C(CH$_3$)$_3$, —C(O)OH, —CH$_2$C(O)OH, —CH$_2$C(O)OCH$_3$, —CH$_2$C(O)OCH$_2$CH$_3$, —OH, CH$_2$OH, —NH$_2$, —CH$_2$NH$_2$, —OCH$_3$, S(O)$_2$NH$_2$, S(O)$_2$C$_6$H$_5$, or S(O)$_2$CH$_2$C$_6$H$_5$; R$^2$ is —NH$_2$, —NHC(O)R$^6$, —NR$^{6a}$R$^{6b}$, —NHS(O)$_2$R$^6$, —OH, —OR$^6$, C(O)OH, or C$_1$-C$_{20}$ alkyl, wherein the C$_1$-C$_{20}$ alkyl is optionally substituted with one or more substituents independently selected from halogen, C$_{1-6}$ alkyl, OH, —NH$_2$, —NHC(O)R$^6$, and —NR$^{6a}$R$^{6b}$; R$^6$ is —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl is optionally substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —H$_2$C$_6$H$_4$R$^7$, and halogen; R$^{6a}$ is H or methyl; R$^{6b}$ is methyl, 7-nitrobenzo[c][1,2,5]oxadiazol-4-yl, or —C(O)C$_6$H$_5$; and R$^7$ is —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In certain embodiments, $L^1$ may be —S—, —S(O)$_2$—, —C(O)—, or —P(O)(OH)—. $L^2$ may be —NH—, —NR$^3$, —CH$_2$—, or —C(R$^3$)$_2$—. $L^1$ may be —NH—, —NR$^3$, —CH$_2$—, or —C(R$^3$)$_2$—. $L^2$ may be —S—, —S(O)$_{2-5}$—C(O)—, or —P(O)(OH)—. In certain embodiments, $L^1$ is —S(O)$_2$—; $L^2$ is —NH—; and R$^1$ is S(O)$_2$NH$_2$.

Yet another aspect of the present invention relates to a compound of formula IX:

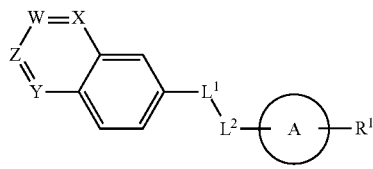

wherein: $L^1$ is —S—, —S(O)$_2$—, or —C(O)—; $L^2$ is —NH— or —CH$_2$—; ring A is a substituted or unsubstituted, 5- or 6-membered ring having 1-3 ring-forming heteroatoms or substituted or unsubstituted phenyl, wherein ring A is optionally substituted with a methyl or methoxy group in addition to R$^1$; R$^1$ is —H, —CH$_3$, —CH$_2$CH$_3$, —C(CH$_3$)$_3$, —C(O)OH, —CH$_2$C(O)OH, —CH$_2$C(O)OCH$_3$, —CH$_2$C(O)OCH$_2$CH$_3$, —OH, CH$_2$OH, —NH$_2$, —CH$_2$NH$_2$, —OCH$_3$, S(O)$_2$NH$_2$, S(O)$_2$C$_6$H$_5$, or S(O)$_2$CH$_2$C$_6$H$_5$; and W, X, Y, and Z are each independently N or CH, provided that at least one of W, X, Y, and Z is N.

Another aspect of the present invention relates to a compound of formula:

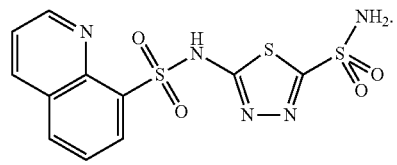 [SMILES: NS(=O)(=O)c1nnc(NS(=O)(=O)c2cccc3cccnc23)s1]

Yet another aspect of the present invention relates to a compound of formula VI:

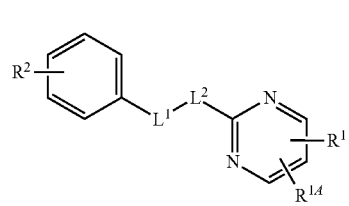

or pharmaceutically acceptable salt thereof, wherein: $L^1$ and $L^2$ are each, independently, —S—, —S(O)$_2$—, —C(O)—, —P(O)(OH)—, —NH—, —N(CH$_3$)—, —N(R$^3$)—, —CH$_2$—, or —C(R$^3$)$_2$—; each R$^3$ is, independently, —H, —CH$_3$, CH$_2$CH$_3$, CH$_2$CH$_2$CH$_3$, NH$_2$, or —C$_6$H$_5$; R$^1$ is —H, —CH$_3$, or —OCH$_3$; R$^A$ is —H, —CH$_3$, or —OCH$_3$; R$^2$ is —NH$_2$, —NHC(O)R$^6$, —NR$^{6a}$R$^{6b}$, —NHS(O)$_2$R$^6$, —OH, —OR$^6$, C(O)OH, or C$_1$-C$_{20}$ alkyl, wherein the C$_1$-C$_{20}$ alkyl is optionally substituted with one or more substituents independently selected from halogen, C$_{1-6}$ alkyl, OH, —NH$_2$, —NHC(O)R$^6$, and —NR$^{6a}$R$^{6b}$; R$^6$ is —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl is optionally substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; R$^{6a}$ is H or methyl; R$^{6b}$ is methyl, 7-nitrobenzo[c][1,2,5]oxadiazol-4-yl, or —C(O)C$_6$H$_5$; R$^7$ is —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen; or R$^2$ is

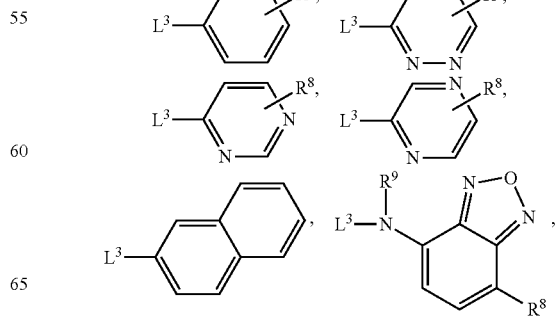

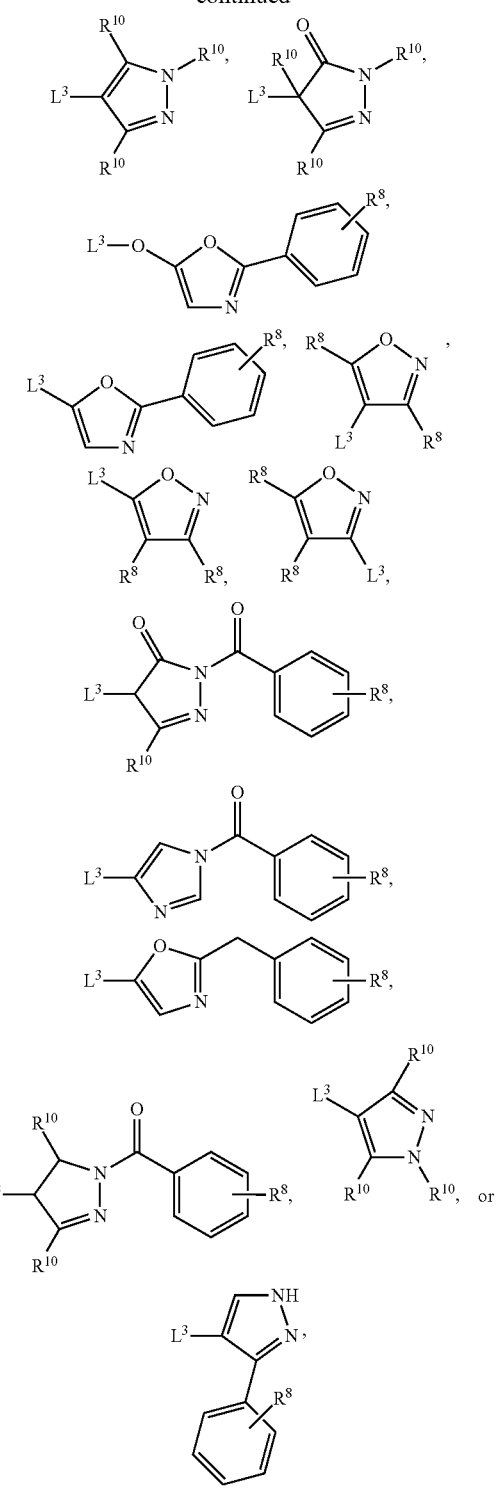

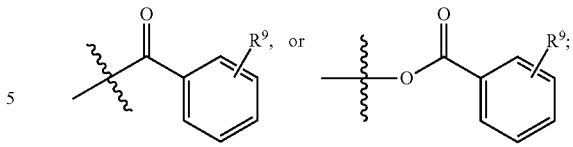

$R^9$ is —H, —CH$_3$, —C(CH$_3$), —OH, —NH$_2$, NO$_2$, —OCH$_3$, —C(O)OH, —C(O)NH$_2$, or halogen; and s is 1 to 20. L$^1$ may be —S—, —S(O)$_2$—, —C(O)—, or —P(O)(OH)—. L$^2$ may be —NH—, —NR$^3$, —CH$_2$—, or —C(R$^3$)$_2$—. L$^1$ may be —NH—, —NR$^3$, —CH$_2$—, or —C(R$^3$)$_2$—. L$^2$ may be —S—, —S(O)$_2$—, —C(O)—, or —P(O)(OH)—.

In certain embodiments, L$^1$ is —S(O)$_2$—; L$^2$ is —NH—; R$^2$ is —NHS(O)$_2$R$^6$; R$^6$ is aryl, heteroaryl, or C$_1$-C$_{20}$ alkyl, wherein each of the aryl, heteroaryl, or C$_1$-C$_{20}$ alkyl, each optionally substituted with one or more substituents independently selected from —NH$_2$, —OH, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; R$^7$ is —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen; or R$^2$ is

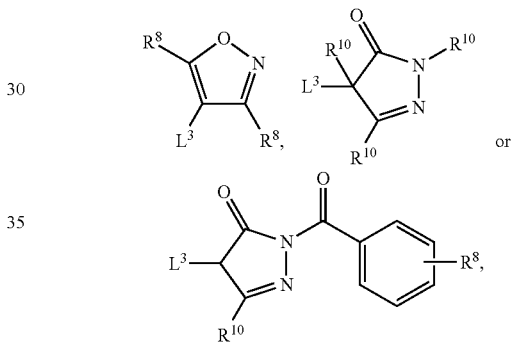

wherein R$^2$ is attached to the benzene ring of Formula V through L$^3$; and L$^3$ is —NHS(O)$_2$— or —N=N—. In certain embodiments, R$^2$ is

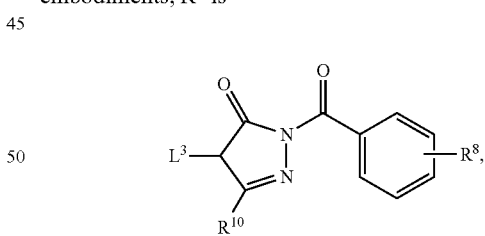

wherein R$^2$ is attached to the benzene ring of Formula V through L$^3$; and L$^3$ is —N=N—.

In certain embodiments, R$^2$ is —NHS(O)$_2$R$^6$; R$^6$ is aryl or heteroaryl, each optionally substituted with one or more substituents independently selected from —NH$_2$, —OH, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; and R$^7$ is —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

Another aspect of the present invention relates to a compound of formula:

wherein R$^2$ is attached to the benzene ring of Formula V through L$^3$; L$^3$ is a bond, —CH$_2$—, —CH$_2$(CH$_2$)$_s$—, —CH(OH)—, —C(O)—, —O—, —NH—, —S—, —CH$_2$CH$_2$—, —CH=CH—, —N=N—, —OCH$_2$—, —NHP(O)(OH)—, —NHS(O)$_2$—, —SCH$_2$—, —S(O)$_2$CH$_2$—, or —NHC(O)—; R$^8$ is —H, —CH$_3$, —C(CH$_3$), —OH, —NH$_2$, NO$_2$, —OCH$_3$, —C(O)OH, —C(O)NH$_2$, or halogen; R$^{10}$ is —H, —CH$_3$, —OH, —OCH$_3$, —C$_6$H$_5$,

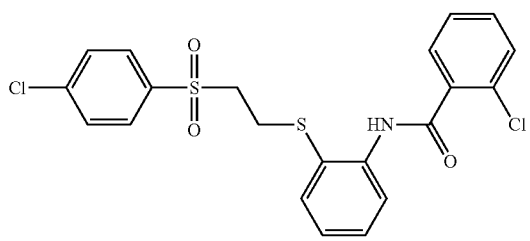 [SMILES: O=C(Nc1ccccc1SCCS(=O)(=O)c1ccc(Cl)cc1)c1ccccc1Cl]

Yet another aspect of the present invention relates to a compound of formula VII:

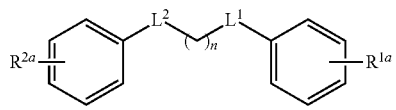

VII wherein: $L^1$ is —S(O)$_2$— or —C(O)—; $L^2$ is —CH$_2$—, —O—, or —S—; n is 1 or 2; $R^{1a}$ is halogen, —C(O)OH, OH, or

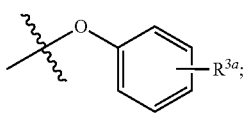

$R^{3a}$ is halogen, —H, —NH$_2$, C(CH$_3$)$_3$, or C(F)$_3$; $R^{2a}$ is —NH$_2$, —NO$_2$, —C(O)OH, —CH$_2$C(O)OH, or

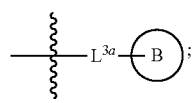

$L^{3a}$ is a bond, —NHC(O)—, —C(O)—, —NH—, or —O—; and ring B is a aryl or heteroaryl having one or two ring-forming N heteroatoms, each optionally substituted with one or more substituents independently selected from CH$_3$, —OH, —NH$_2$, —NO$_2$, —C(CH$_3$)$_3$, —C(O)OH, —S(O)$_2$OH, As(O)$_3$H, NHC(O)CH$_3$, —OH, —OCH$_3$, —OCH$_2$CH$_3$, and halogen. In certain embodiments, $L^1$ is —S(O)$_2$—; $L^2$ is —S—; and n is 2. In certain embodiments, $R^{1a}$ is halogen; $R^{2a}$ is —NH$_2$, or

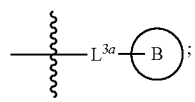

$L^{3a}$ is —NHC(O)— or —NH—; and ring B is a aryl or heteroaryl having one or two ring-forming N heteroatoms, each optionally substituted with one or more substituents independently selected from CH$_3$, —OH, —NH$_2$, —NO$_2$, —C(CH$_3$)$_3$, —C(O)OH, —S(O)$_2$OH, As(O)$_3$H, NHC(O)CH$_3$, —OH, —OCH$_3$, —OCH$_2$CH$_3$, and halogen.

Another aspect of the present invention relates to a compound of formula:

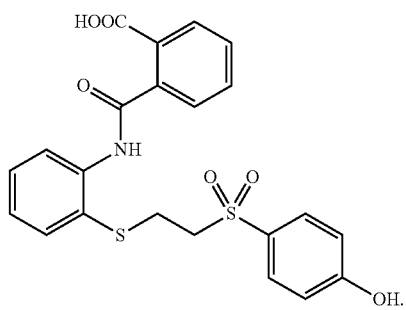 [SMILES: O=C(O)c1ccccc1C(=O)Nc1ccccc1SCCS(=O)(=O)c1ccc(O)cc1]

Yet another aspect of the present invention relates to a compound of formula VIII:

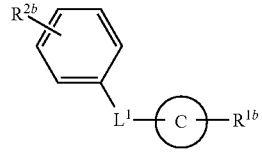

VIII wherein: $L^1$ is —S(O)$_2$— or —C(O)—; ring C is aryl, piperazine, or imidazole; $R^{1b}$ is an aryl group substituted with one or more C(O)OH, CH$_2$C(O)OH, or imidazole; $R^{2b}$ is

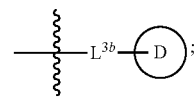

$L^{3b}$ is a bond, —O—, or —S(O)$_2$—; and ring D is a 5- to 9-membered, substituted or unsubstituted, cyclic of bicyclic ring having 0-3 ring-forming heteroatoms selected from N and O, wherein ring D is optionally substituted with one or more substituents independently selected from —CH$_3$, —OCH$_3$, —NH$_2$, —NO$_2$, and halogen. Ring C may be a piperazine ring.

Another aspect of the present invention relates to a compound of formula VIII:

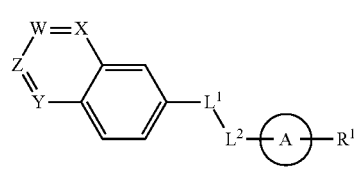

VIII wherein: $L^1$ is —S—, —S(O)$_2$—, or —C(O)—; $L^2$ is —NH— or —CH$_2$—; ring A is a substituted or unsubstituted, 5- or 6-membered ring having 1-3 ring-forming heteroatoms or substituted or unsubstituted phenyl, wherein ring A is optionally substituted with a methyl or methoxy group in addition to $R^1$; $R^1$ is —H, —CH$_3$, —CH$_2$CH$_3$, —C(CH$_3$)$_3$, —C(O)OH, —CH$_2$C(O)OH, —CH$_2$C(O)OCH$_3$, —CH$_2$C(O)OCH$_2$CH$_3$, —OH, CH$_2$OH, —NH$_2$, —CH$_2$NH$_2$, —OCH$_3$, S(O)$_2$NH$_2$, S(O)$_2$C$_6$H$_5$, or S(O)$_2$CH$_2$C$_6$H$_5$; and W, X, Y, and Z are each independently N or CH, provided that at least one of W, X, Y, and Z is N.

Yet another aspect of the present invention relates to a method for treating a proliferative disorder comprising: administering a pharmaceutically acceptable amount of a compound of formula I:

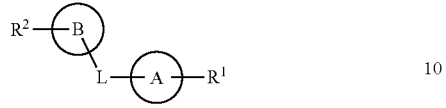

I or pharmaceutically acceptable salt thereof, wherein: L is —S—, —S(O)$_2$—, —C(O)—, —P(O)(OH)—, —NH—, —N(R$^3$)—, —CH$_2$—, —C(R$^3$)$_2$—, -L$^1$-L$^2$-, or -L$^1$-(CH$_2$)$_n$-L$^2$-; or L—(CH$_2$)—OC(O)—(CH$_2$)$_2$—CH(C(O)OH)—NHC(O)O—(CH$_2$)— or —(CH$_2$)—OC(O)—(CH$_2$)—CH(C(O)OH)—NHC(O)O—(CH$_2$)—; L$^1$ and L$^2$ are each, independently, —O—, —S—, —S(O)$_2$—, —C(O)—, —P(O)(OH)—, —NH—, —NR$^3$, —CH$_2$—, —C(R$^3$)$_2$—, or piperazinyl; n is 1 or 2; each R$^3$ is independently —H, —CH$_3$, —CH$_2$CH$_3$, —CH$_2$CH$_2$CH$_3$, —NH$_2$, —C$_6$H$_5$ heteroarylalkyl, or C(O)R$^{3a}$; R$^{3a}$ is C$_{1-6}$ alkyl or aryl, each substituted with 0, 1, or 2 substituents independently selected from halogen and CN; ring A is a substituted or unsubstituted, 5- or 6-membered ring having 1-3 ring-forming heteroatoms or substituted or unsubstituted phenyl, wherein ring A is optionally substituted with a methyl or methoxy group in addition to R$^1$; R$^1$ is —H, —CH$_3$, —CH$_2$CH$_3$, —CH$_2$(CH$_2$)—CH$_3$, —C(CH$_3$)$_3$, —CH$_2$CH$_2$R$^4$, —OH, —OCH$_3$, —CH$_2$OH, —C(O)OH, —CH$_2$C(O)OH, —CH$_2$CH$_2$C(O)OH, —C(O)R$^4$, —C(O)OR$^4$, —CH$_2$C(O)OR$^4$, —CH$_2$CH$_2$C(O)OR$^4$, —NH$_2$, —CH$_2$NH$_2$, —S(O)$_2$R$^4$, —CH$_2$S(O)$_2$R$^4$, C$_6$H$_5$, —C$_6$H$_4$R$^4$, —CH$_2$C$_6$H$_5$, —S(O$_2$)C$_6$H$_5$, —CH$_2$S(O)$_2$C$_6$H$_5$, heteroaryl, heteroarylalkyl, morpholino, or halogen; R$^4$ is —H, —OH, —NH$_2$, —CH$_3$, —CH$_2$CH$_3$, —CH$_2$CH$_2$CH$_3$, —OCH$_3$, —C(O)OH, —C$_6$H$_5$, —C$_6$H$_4$R$^5$, —CH$_2$C$_6$H$_5$, —CH$_2$C$_6$H$_4$R$^5$, halogen, heteroaryl, heteroarylalkyl, or piperazinyl; R$^5$ is —H, —OH, —NH$_2$, —CH$_3$, —CH$_2$CH$_3$, —CH$_2$CH$_2$CH$_3$, —C(O)OH, or halogen; ring B is a substituted or unsubstituted, 5-14 membered aromatic or polyaromatic ring having 1 to 2 ring-forming heteromatoms or a substituted or unsubstituted phenyl; R$^2$ is —H, —CH$_3$, —C(CH$_3$)$_3$, C$_1$-C$_{20}$ alkyl, —OH, —NH$_2$, —OR$^6$, —NHC(O)R$^6$, —NR$^{6a}$R$^{6b}$, —NHS(O)$_2$R$^6$, —S(O)$_2$OH, —CH(O), —C(O)OH, —C(O)OR$^6$, —CH$_2$OH, —CH$_2$C(O)OH, —S(O)$_2$NH$_2$, —CH$_2$(CH$_2$)$_p$R$^6$—, CH$_2$(CH$_2$)$_p$OR$^6$, —CH$_2$—O—(CH$_2$)$_p$OR$^6$, —CH$_2$(CH$_2$)$_p$SO$_2$R$^6$, —CH$_2$(CH$_2$)$_p$NHR$^6$, —C$_6$H$_5$, or —C$_6$H$_4$R$^6$; wherein the C$_1$-C$_{20}$ alkyl of R$^2$ is optionally substituted with one or more substituents independently selected from halogen, OH, —NH$_2$, —NHC(O)R$^6$, and —NR$^{6a}$R$^{6b}$; R$^2$ is

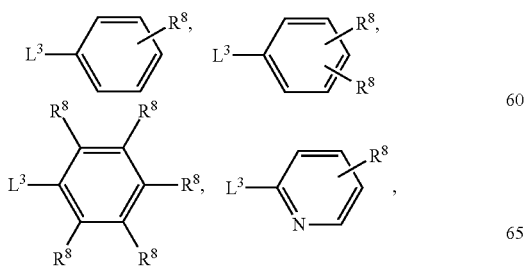

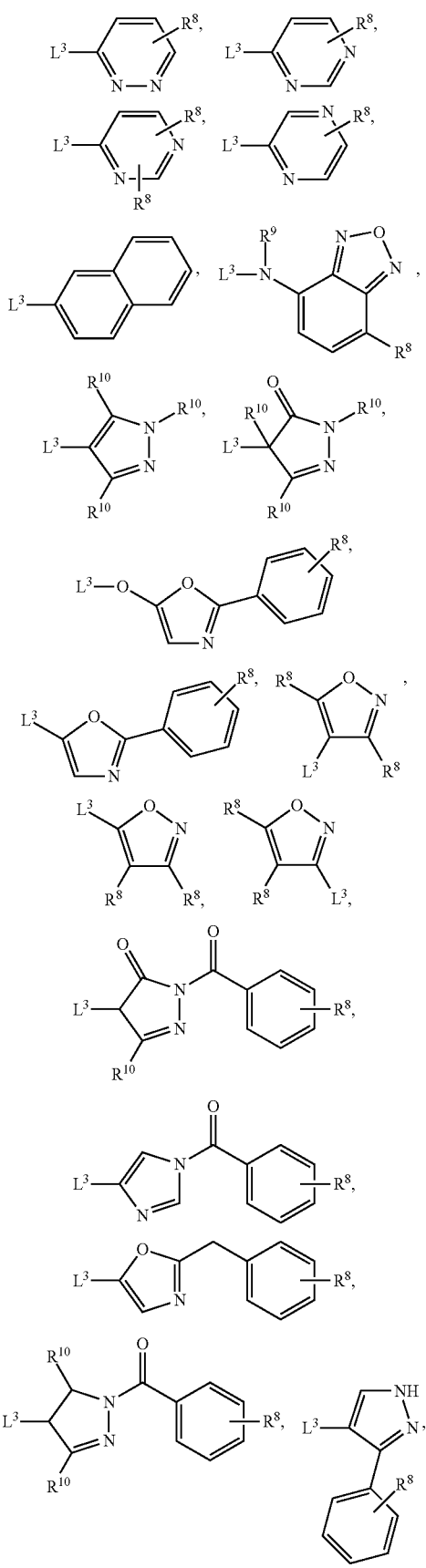

-continued

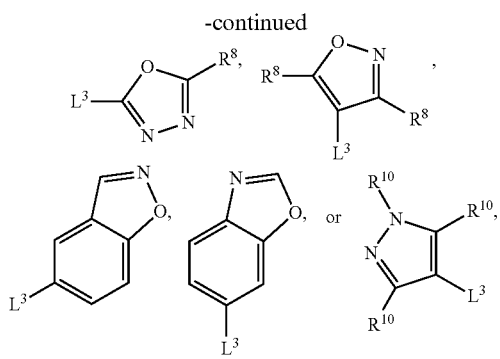

wherein $R^2$ is attached to ring B through $L^3$; $R^6$ is —H, —NH$_2$, —OH, —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, halogen, aryl, heteroaryl, or C$_1$-C$_{20}$ alkyl, wherein each of the aryl, heteroaryl, or C$_1$-C$_{20}$ alkyl is optionally substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; $R^{6a}$ is H or methyl; $R^{6b}$ is methyl, 7-nitrobenzo[c][1,2,5]oxadiazol-4-yl, or —C(O)C$_6$H$_5$; $L^3$ is a bond, —CH$_2$—, —CH$_2$(CH$_2$)$_q$—, —CH(OH)—, —C(O)—, —O—, —NH—, —S—, —CH$_2$CH$_2$—, —CH=CH—, —N=N—, —OCH$_2$—, —OP(O)(OH)—, —NHS(O)$_2$—, —SCH$_2$—, —S(O)$_2$CH$_2$—, —S(O)$_2$O—, or —C(O)NH—; $R^7$ and $R^8$ are each independently —H, —CH$_3$, heteroaryl, —C(CH$_3$)$_3$, —OH, —NH$_2$, NHC(O)CH$_3$, S(O)$_2$OH, As(O)$_2$OH, NO$_2$, —OCH$_3$, —OCH$_2$CH$_3$, —C(O)OH, —C(O)NH$_2$, or halogen; $R^{10}$ is —H, —CH$_3$, —OH, —OCH$_3$, —C$_6$H$_5$, —C$_6$H$_4$R$^9$,

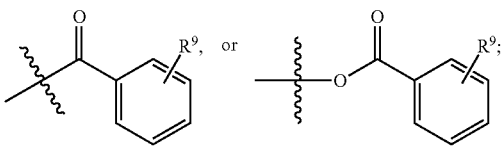

$R^9$ is —H, —CH$_3$, —C(CH$_3$), —OH, —NH$_2$, NO$_2$, —OCH$_3$, —C(O)OH, —C(O)NH$_2$, or halogen; and m, p and q are each independently an integer selected from 1 to 20; to a patient in need thereof.

The method may further comprise administering a second active agent. The second active agent or secondary agent may be selected from doxorubicin, paclitaxel, methotrexate, tamoxifen, cyclophosphamide, vincristine, etoposide, streptozotocin and 5-fluorouracil. The patient may exhibit symptoms of a proliferative disease selected from breast cancer, lung cancer, head and neck cancer, brain cancer, abdominal cancer, colon cancer, colorectal cancer, esophageal cancer, gastrointestinal cancer, glioma, liver cancer, tongue cancer, neuroblastoma, osteosarcoma, ovarian cancer, pancreatic cancer, renal cancer, prostate cancer, retinoblastoma, Wilm's tumor, multiple myeloma, lymphoma, blood cancer, skin cancer and melanoma.

DETAILED DESCRIPTION

Figure 1:
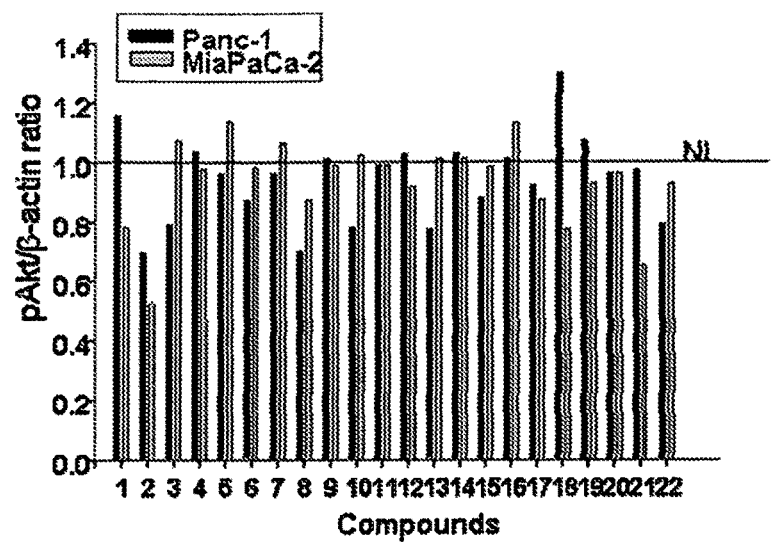
FIG. 1 is a graphical representation of an in vitro screen.

Before the compositions and methods of the invention are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must be noted that, as used herein, and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

The term "alkyl" as employed herein by itself or as part of another group refers to both straight and branched chain radicals of up to 25 carbons, unless the chain length is otherwise limited, such as methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl, nonyl, or decyl.

The term "alkenyl" is used herein to mean a straight or branched chain radical of 2-10 carbon atoms, unless the chain length is otherwise limited, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like. Preferably, the alkenyl chain is 2 to 20 carbon atoms in length, most preferably from 2 to 12 carbon atoms in length.

The term "alkynyl" is used herein to mean a straight or branched chain radical of 2-10 carbon atoms, unless the chain length is otherwise limited, wherein there is at least one triple bond between two of the carbon atoms in the chain, including, but not limited to, ethynyl, 1-propynyl, 2-propynyl, and the like. Preferably, the alkynyl chain is 2 to 20 carbon atoms in length, most preferably from 2 to 12 carbon atoms in length.

In all instances herein where there is an alkenyl or alkynyl moiety as a substituent group, the unsaturated linkage, i.e., the vinyl or ethenyl linkage, is preferably not directly attached to a nitrogen, oxygen or sulfur moiety.

The term "alkoxy" or "alkyloxy" refers to any of the above alkyl groups linked to an oxygen atom. Typical examples are methoxy, ethoxy, isopropyloxy, sec-butyloxy, and t-butyloxy.

The term "aryl" as employed herein by itself or as part of another group refers to monocyclic or bicyclic aromatic groups containing from 6 to 12 carbons in the ring portion, preferably 6-10 carbons in the ring portion. Typical examples include phenyl, biphenyl, naphthyl or tetrahydronaphthyl.

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "heterocycle" may refer to a "heteroaryl." "Heteroaryl" as employed herein refers to groups having 5 to 14 ring atoms; 6, 10 or 14 pi electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

The term "heterocycle" may also refer to a "heterocycloalkyl." "Heterocycloalkyls" as used herein may refer to any saturated or partially unsaturated heterocycle. By itself or as part of another group, "heterocycle" may refer to a saturated or partially unsaturated ring system having 5 to 14 ring atoms selected from carbon atoms and 1, 2, 3, or 4 oxygen, nitrogen, or sulfur heteroatoms. Typical saturated examples include pyrrolidinyl, imidazolidinyl, pyrazolidinyl, tetrahydrofuranyl, tetrahydropyranyl, piperidyl, piperazinyl, quinuclidinyl, morpholinyl, and dioxacyclohexyl. Typical partially unsaturated examples include pyrrolinyl, imidazolinyl, pyrazolinyl, dihydropyridinyl, tetrahydropyridinyl, and dihydropyranyl. Either of these systems can be fused to a benzene ring. When a substituent is oxo (i.e., =O), then 2 hydrogens on the atom are replaced. When aromatic moieties are substituted by an oxo group, the aromatic ring is replaced by the corresponding partially unsaturated ring. For example, a pyridyl group substituted by oxo results in a pyridone.

The terms "heteroarylalkyl" or "heteroaralkyl" as employed herein both refer to a heteroaryl group attached to an alkyl group. Typical examples include 2-(3-pyridyl)ethyl, 3-(2-furyl)-n-propyl, 3-(3-thienyl)-n-propyl, and 4-(1-isoquinolinyl)-n-butyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "cycloalkylalkyl" or "cycloalkyl(alkyl)" as employed herein, by itself or as part of another group, refers to a cycloalkyl group attached to an alkyl group.

Typical examples are 2-cyclopentylethyl, cyclohexylmethyl, cyclopentylmethyl, 3-cyclohexyl-n-propyl, and 5-cyclobutyl-n-pentyl.

The term "cycloalkenyl" as employed herein, by itself or as part of another group, refers to cycloalkenyl groups containing 3 to 9 carbon atoms and 1 to 3 carbon-carbon double bonds. Typical examples include cyclopropenyl, cyclobutenyl, cyclopentenyl, cyclohexenyl, cyclohexadienyl, cycloheptenyl, cycloheptadienyl, cyclooctenyl, cyclooctadienyl, cyclooctatrienyl, cyclononenyl, and cyclononadienyl.

The term "halogen" or "halo" as employed herein by itself or as part of another group refers to chlorine, bromine, fluorine or iodine.

The term "monoalkylamine" or "monoalkylamino" as employed herein by itself or as part of another group refers to the group $NH_2$ wherein one hydrogen has been replaced by an alkyl group, as defined above.

The term "dialkylamine" or "dialkylamino" as employed herein by itself or as part of another group refers to the group $NH_2$ wherein both hydrogens have been replaced by alkyl groups, as defined above.

The term "hydroxyalkyl" as employed herein refers to any of the above alkyl groups wherein one or more hydrogens thereof are substituted by one or more hydroxyl moieties.

The term "haloalkyl" as employed herein refers to any of the above alkyl groups wherein one or more hydrogens thereof are substituted by one or more halo moieties. Typical examples include fluoromethyl, difluoromethyl, trifluoromethyl, trichloroethyl, trifluoroethyl, fluoropropyl, and bromobutyl.

The term "carboxyalkyl" as employed herein refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound form a saturated or unsaturated 5-, 6-, or 7-membered ring.

The terms "hydroxy" and "hydroxyl" are used interchangeably to refer to the radical —OH. The terms "pyridyl" and "pyridinyl" are used interchangeably to refer to a monovalent radical of pyridine. The terms "carbamoyl" and "aminocarbonyl" are used interchangeably to refer to the radical $NH_2-C(O)-$. The terms "ureido" and "aminocarbonylamino" are used interchangeably to refer to the radical $NH_2-C(O)-NH-$.

"Optional" or "optionally" may be taken to mean that the subsequently described structure, event or circumstance may or may not occur, and that the description includes instances where the event occurs and instances where it does not.

The phrase "optionally substituted" when not explicitly defined refers to a group or groups being optionally substituted with one or more substituents independently selected from the group consisting of hydroxy, nitro, trifluoromethyl, halogen, $C_{1-6}$ alkyl, $C_{1-6}$ haloalkyl, $C_{1-6}$ alkoxy, $C_{1-6}$ alkylenedioxy, $C_{1-6}$ aminoalkyl, $C_{1-6}$ hydroxyalkyl, $C_{2-4}$ alkenyl, $C_{2-4}$ alkynyl, $C_{6-10}$ aryl, phenoxy, benzyloxy, 5-10 membered heteroaryl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, $C_{2-6}$ alkoxycarbonylalkyl, carboxy, $C_{2-6}$ hydroxyalkoxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl)amino, bis ($C_{2-10}$ carboxyalkyl)amino, $C_{2-6}$ carboxyalkoxy, $C_{2-6}$ carboxyalkyl, carboxyalkylamino, guanidinoalkyl, hydroxyguanidinoalkyl, cyano, trifluoromethoxy, perfluoroethoxy, amino carbonylamino, mono($C_{1-4}$)alkylaminocarbonylamino, di($C_{1-4}$)alkylaminocarbonylamino, N—($C_{1-4}$)alkyl-N-aminocarbonyl-amino, N—($C_{1-4}$)alkyl-N-mono($C_{1-4}$)alkyl aminocarbonyl-amino or N—($C_{1-4}$)alkyl-N-di($C_{1-4}$)alkylaminocarbonylamino.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by oral administration, injection, infusion, absorption or by any method in combination with other known techniques. Such combination techniques include heating, radiation and ultrasound.

The term "target", as used herein, refers to the material for which either deactivation, rupture, disruption or destruction or preservation, maintenance, restoration or improvement of function or state is desired. For example, diseased cells, pathogens, or infectious material may be considered undesirable material in a diseased subject and may be a target for therapy.

Generally speaking, the term "tissue" refers to any aggregation of similarly specialized cells, which are united in the performance of a particular function.

The term "improves" is used to convey that the present invention changes the appearance, form, characteristics and/or physical attributes of the tissue to which it is being provided, applied or administered. "Improves" may also refer to the overall physical state of an individual to whom an active agent has been administered. For example, the overall physical state of an individual may "improve" if one or more symptoms of a neurodegenerative disorder are alleviated by administration of an active agent.

As used herein, the term "therapeutic" means an agent utilized to treat, combat, ameliorate or prevent an unwanted condition or disease of a patient.

The terms "therapeutically effective amount" or "therapeutic dose" as used herein are interchangeable and may refer to the amount of an active agent or pharmaceutical compound or composition that elicits a biological or medicinal response in a tissue, system, animal, individual or human that is being sought by a researcher, veterinarian, medical doctor or other clinician. A biological or medicinal response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experienced or exhibited by the individual.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to slowing the progression of the disorder, disease or condition. In some embodiments, the term refers to alleviating the symptoms associated with the specific disorder, disease or condition. In some embodiments, the term refers to restoring function, which was impaired or lost due to a specific disorder, disease or condition.

The term "patient" generally refers to any living organism to which to compounds described herein are administered and may include, but is not limited to, any non-human mammal, primate or human. Such "patients" may or may not be exhibiting the signs, symptoms or pathology of the particular diseased state.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain an ATK inhibitor or a pharmaceutically acceptable salt of ATK inhibitor as the active ingredient.

For the purposes of this disclosure, a "salt" is any acid addition salt, preferably a pharmaceutically acceptable acid addition salt, including but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, which is hereby incorporated by reference in its entirety describes pharmaceutically acceptable salts in detail.

As used herein, the term "daily dose amount" refers to the amount of pramipexole per day that is administered or prescribed to a patient. This amount can be administered in multiple unit doses or in a single unit dose, in a single time during the day or at multiple times during the day.

A "dose amount" as used herein, is generally equal to the dosage of the active ingredient, which may be administered per day. For example, a non-effective dose amount of 10 mg/day to 10,000 mg/day of an ATK inhibitor.

The term "unit dose" as used herein may be taken to indicate a discrete amount of the therapeutic composition that contains a predetermined amount of the active compound. The amount of the active compound is generally equal to the dosage of the active ingredient, which may be administered on or more times per day. For example, the unit dose may be a fraction of the desired daily dose which may be given in fractional increments, such as, for example, one-half or one-third the dosage.

Various embodiments of the invention presented herein are directed to small molecules that bind to the Pleckstrin Homology domain (PH) of ATK protein kinases and inhibit their activity, pharmaceutical compositions including such small molecules, and methods for using such small molecules to treat proliferative diseases such as, for example, cancer. In particular, certain embodiments of the invention are directed to molecules that include two or more substituted or unsubstituted 5- or 6 membered rings having 0-3 ring forming heteroatoms connected by flexible linkers. For example, various embodiments of the invention may include compounds of general formula I:

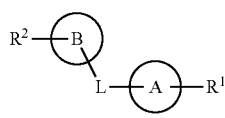

I or pharmaceutically acceptable salts or solvates thereof, wherein:

L may be —S—, —S(O)$_2$—, —C(O)—, —P(O)(OH)—, —NH—, —N(R$^3$)—, —CH$_2$—, —C(R$^3$)$_2$—, -L$^1$-L$^2$-, -L$^1$—(CH$_2$)$_n$-L$^2$-, —(CH$_2$)—OC(O)—(CH$_2$)$_2$—CH(C(O)OH)—NHC(O)O—(CH$_2$)—, or —(CH$_2$)—OC(O)—(CH$_2$)—CH(C(O)OH)—NHC(O)O—(CH$_2$)—;

L$^1$ and L$^2$ may each, independently, be —O—, —S—, —S(O)$_2$—, —C(O)—, —P(O)(OH)—, —NH—, —NR$^3$, —CH$_2$—, —C(R$^3$)$_2$—, or piperazinyl;

n may be 1 or 2;

each R$^3$ may, independently, be —H, —CH$_3$, —CH$_2$CH$_3$, —CH$_2$CH$_2$CH$_3$, —NH$_2$, —C$_6$H$_5$ heteroarylalkyl, or C(O)R$^{3a}$;

R$^{3a}$ may be C$_{1-6}$ alkyl or aryl, each substituted with 0, 1, or 2 substituents independently selected from halogen and CN;

ring A may be a substituted or unsubstituted, 5- or 6-membered ring having 1-3 ring-forming heteroatoms or substituted or unsubstituted phenyl, and in some embodiments, ring A may be substituted with one or more methyl, methoxy, sulfonyl, sulfonic acid ester group in addition to R$^1$;

R$^1$ may be —H, —CH$_3$, —CH$_2$CH$_3$, —CH$_2$(CH$_2$)$_m$CH$_3$, —C(CH$_3$)$_3$, —CH$_2$CH$_2$R$^4$, —OH, —OCH$_3$, —CH$_2$OH, —C(O)OH, —CH$_2$C(O)OH, —CH$_2$CH$_2$C(O)OH, —C(O)R$^4$, —C(O)OR$^4$, —CH$_2$C(O)OR$^4$, —CH$_2$CH$_2$C(O)OR$^4$, —NH$_2$, CH$_2$NH$_2$, —S(O)$_2$R$^4$, —CH$_2$S(O)$_2$R$^4$, C$_6$H$_5$, —C$_6$H$_4$R$^4$, —CH$_2$C$_6$H$_5$, —S(O$_2$)C$_6$H$_5$, —CH$_2$S(O)$_2$C$_6$H$_5$, heteroaryl, heteroarylalkyl, morpholino, or halogen;

R$^4$ may be —H, —OH, —NH$_2$, —CH$_3$, —CH$_2$CH$_3$, —CH$_2$CH$_2$CH$_3$, —OCH$_3$, —C(O)OH, —C$_6$H$_5$, —C$_6$H$_4$R$^5$, —CH$_2$C$_6$H$_5$, —CH$_2$C$_6$H$_4$R$^5$, halogen, heteroaryl, heteroarylalkyl, or piperazinyl;

R$^5$ may be —H, —OH, —NH$_2$, —CH$_3$, —CH$_2$CH$_3$, —CH$_2$CH$_2$CH$_3$, —C(O)OH, or halogen;

ring B may be a substituted or unsubstituted, 5-14 membered aromatic or polyaromatic ring having 1 to 2 ring-forming heteroatoms, and in particular embodiments, ring B may be a substituted or unsubstituted phenyl;

R$^2$ may be —H, —CH$_3$, —C(CH$_3$)$_3$, C$_1$-C$_{20}$ alkyl, —OH, —NH$_2$, —OR$^6$, —NHC(O)R$^6$, —NR$^{6a}$R$^{6b}$, —NHS(O)$_2$R$^6$, —S(O)$_2$OH, —CH(O), —C(O)OH, —C(O)OR$^6$, —CH$_2$OH, —CH$_2$C(O)OH, —S(O)$_2$NH$_2$, —CH$_2$(CH$_2$)$_p$R$^6$—, —CH$_2$(CH$_2$)$_p$OR$^6$, —CH$_2$—O—(CH$_2$)$_p$OR$^6$, —CH$_2$(CH$_2$)$_p$SO$_2$R$^6$, —CH$_2$(CH$_2$)$_p$NHR$^6$, —C$_6$H$_5$, or —C$_6$H$_4$R$^6$, wherein when R$^2$ is C$_1$-C$_{20}$ alkyl it may be optionally substituted with one or more substituents independently selected from halogen, OH, —NH$_2$, —NHC(O)R$^6$, and —NR$^{6a}$R$^{6b}$;

or R$^2$ may be

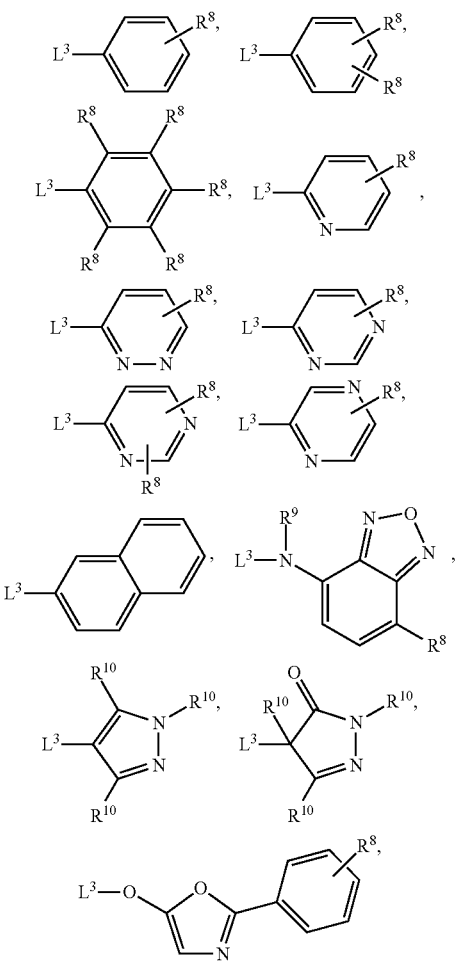

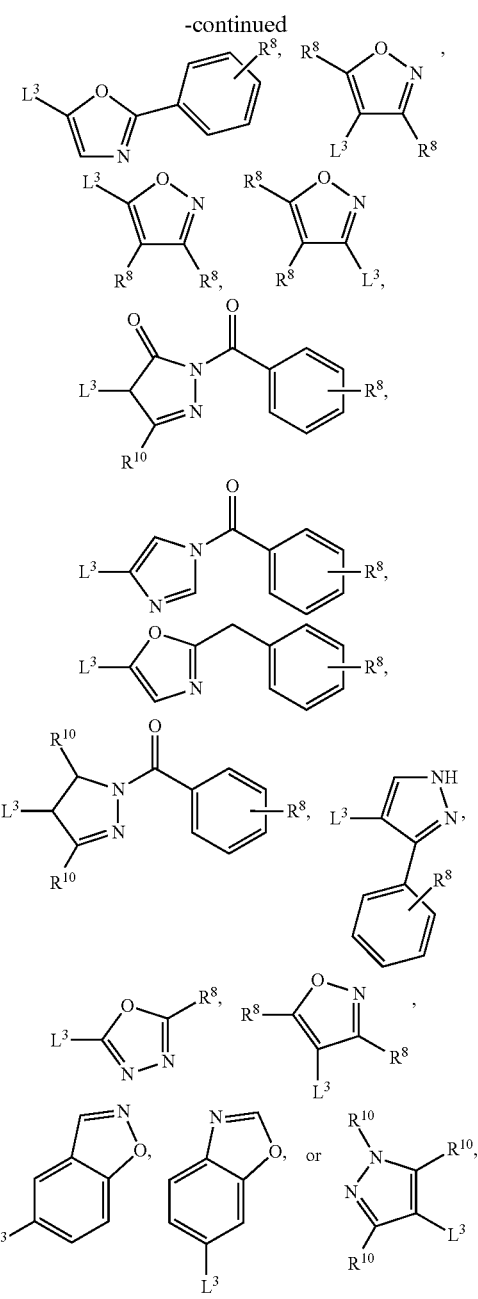

wherein R² is attached to ring B through L³;

R⁶ may be —H, —NH₂, —OH, —CH₃, —CH₂CH₃, —CH₂CH₂CH₃, —C₆H₅, —C₆H₄R⁷, —CH₂C₆H₅, —CH₂C₆H₄R⁷, halogen, aryl, heteroaryl, or C₁-C₂₀ alkyl, wherein each of the aryl, heteroaryl, or C₁-C₂₀ alkyl which may be optionally substituted with one or more substituents independently selected from —NH₂, —OH, —NH₂, —CH₃, —CH₂CH₃, —CH₂CH₂CH₃, C₁₋₆ alkyl, —C₆H₅, —C₆H₄R⁷, —CH₂C₆H₅, —CH₂C₆H₄R⁷, and halogen;

R⁶ᵃ may be H or methyl;

R⁶ᵇ may be methyl, 7-nitrobenzo[c][1,2,5]oxadiazol-4-yl, or —C(O)C₆H₅;

L³ may be a bond, —CH₂—, —CH₂(CH₂)q—, —CH(OH)—, —C(O)—, —O—, —NH—, —S—, —CH₂CH₂—, —CH=CH—, —N=N—, —OCH₂—, —OP(O)(OH)—, —NHS(O)₂—, —SCH₂—, —S(O)₂CH₂—, —S(O)₂O—, or —C(O)NH—;

each R⁷ and R⁸ may, independently, be —H, —CH₃, heteroaryl, —C(CH₃)₃, —OH, —NH₂, NHC(O)CH₃, S(O)₂OH, —P(O)₂OH, As(O)₂OH, NO₂, —OCH₃, —OCH₂CH₃, —C(O)OH, —C(O)NH₂, or halogen;

R¹⁰ may be —H, —CH₃, —OH, —OCH₃, —C₆H₅, —C₆H₄R⁹,

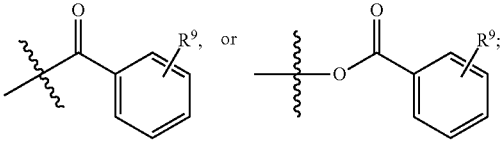

R⁹ may be —H, —CH₃, —C(CH₃), —OH, —NH₂, NO₂, —OCH₃, —C(O)OH, —C(O)NH₂, or halogen; and m, p and q may each independently be an integer selected from 1 to 20.

In particular embodiments, the compounds of the invention may be of general formula II:

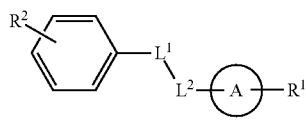

or pharmaceutically acceptable salt or solvate thereof, wherein:

L¹ and L² may each, independently, be —S—, —S(O)₂—, —C(O)—, —P(O)(OH)—, —NH—, —N(CH₃)—, —N(R³)—, —CH₂—, or —C(R³)₂—;

each R³ may, independently, be —H, —CH₃, CH₂CH₃, CH₂CH₂CH₃, NH₂, or —C₆H₅;

ring A may be a substituted or unsubstituted, 5- or 6-membered ring having 1-3 ring-forming heteroatoms and, in some embodiments, ring A may optionally be substituted with a methyl, methoxy, sulfonyl, or sulfonic acid ester group in addition to R¹;

R¹ may be —H, —CH₃, —CH₂CH₃, —CH₂(CH₂)ₘCH₃, —C(CH₃)₃, —CH₂CH₂R⁴, —OH, —OCH₃, —CH₂OH, —C(O)OH, —CH₂C(O)OH, —CH₂CH₂C(O)OH, —C(O)R⁴, —C(O)OR⁴, —CH₂C(O)OR⁴, —CH₂CH₂C(O)OR⁴, —NH₂, CH₂NH₂, —S(O)₂R⁴, —CH₂S(O)₂R⁴, C₆H₅, —C₆H₄R⁴, —CH₂C₆H₅, —S(O₂)C₆H₅, —CH₂S(O)₂C₆H₅, heteroaryl, heteroarylalkyl, morpholino, or halogen;

R⁴ may be —H, —OH, —NH₂, —CH₃, —CH₂CH₃, —CH₂CH₂CH₃, —OCH₃, —C(O)OH, —C₆H₅, —C₆H₄R⁵, —CH₂C₆H₅, —CH₂C₆H₄R⁵, halogen, heteroaryl, heteroarylalkyl, or piperazinyl;

R⁵ may be —H, —OH, —NH₂, —CH₃, —CH₂CH₃, —CH₂CH₂CH₃, —C(O)OH, or halogen;

R² may be —H, —CH₃, —C(CH₃)₃, C₁-C₂₀ alkyl, —OH, —NH₂, —OR⁶, —NHC(O)R⁶, —NR⁶ᵃR⁶ᵇ, —NHS(O)₂R⁶, —S(O)₂OH, —CH(O), —C(O)OH, —C(O)OR⁶, —CH₂OH, —CH₂C(O)OH, —S(O₂)NH₂, —CH₂(CH₂)ₚR⁶—, CH₂(CH₂)ₚOR⁶, —CH₂—O—(CH₂)ₚOR⁶, —CH₂(CH₂)ₚSO₂R⁶, —CH₂(CH₂)ₚNHR⁶, —C₆H₅, or —C₆H₄R⁶, wherein when $R^2$ is $C_1$-$C_{20}$ alkyl, it may be optionally substituted with one or more substituents independently selected from halogen, OH, —$NH_2$, —NHC(O)$R^6$, and —$NR^{6a}R^{6b}$;

or $R^2$ may be

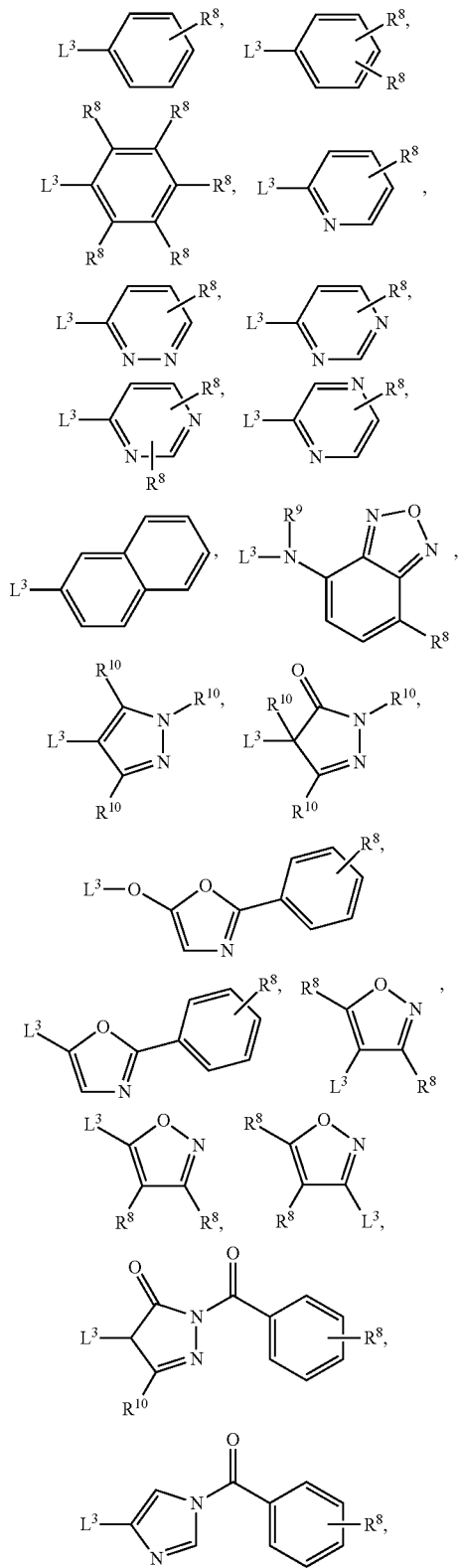

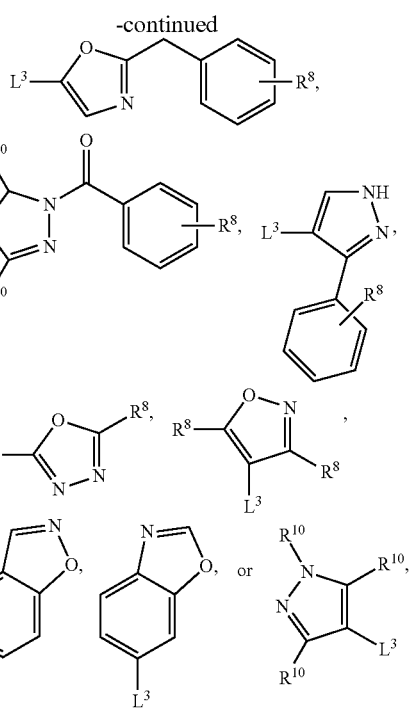

wherein $R^2$ is attached to the phenyl ring of Formula II through $L^3$;

$R^6$ may be —H, —$NH_2$, —OH, —$CH_3$, —$CH_2CH_3$, —$CH_2CH_2CH_3$, —$C_6H_5$, —$C_6H_4R^7$, —$CH_2C_6H_5$, —$CH_2C_6H_4R^7$, halogen, aryl, heteroaryl, or $C_1$-$C_{20}$ alkyl, wherein each of the aryl, heteroaryl, or $C_1$-$C_{20}$ alkyl may be optionally substituted with one or more substituents independently selected from —$NH_2$, —OH, —$NH_2$, —$CH_3$, —$CH_2CH_3$, —$CH_2CH_2CH_3$, $C_{1-6}$ alkyl, —$C_6H_5$, —$C_6H_4R^7$, —$CH_2C_6H_5$, —$CH_2C_6H_4R^7$, and halogen;

$R^{6a}$ may be H or methyl;

$R^{6b}$ may be methyl, 7-nitrobenzo[c][1,2,5]oxadiazol-4-yl, or —C(O)$C_6H_5$;

$L^3$ may be a bond, —$CH_2$—, —$CH_2(CH_2)_q$—, —CH(OH)—, —C(O)—, —O—, —NH—, —S—, —$CH_2CH_2$—, —CH=CH—, —N=N—, —$OCH_2$—, —OP(O)(OH)—, —NHS(O)$_2$—, —$SCH_2$—, —S(O)$_2CH_2$—, —S(O)$_2$O—, or —C(O)NH—;

each $R^7$ and $R^8$ may, independently, be —H, —$CH_3$, heteroaryl, —C($CH_3$)$_3$, —OH, —$NH_2$, NHC(O)$CH_3$, S(O)$_2$OH, —P(O)$_2$OH, As(O)$_2$OH, $NO_2$, —$OCH_3$, —$OCH_2CH_3$, —C(O)OH, —C(O)$NH_2$, or halogen;

$R^{10}$ may be —H, —$CH_3$, —OH, —$OCH_3$, —$C_6H_5$, —$C_6H_4R^9$,

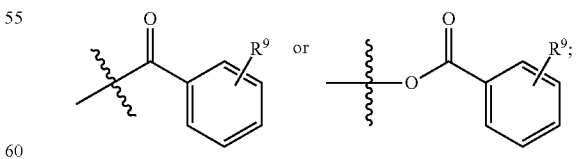

$R^9$ may be —H, —$CH_3$, —C($CH_3$), —OH, —$NH_2$, $NO_2$, —$OCH_3$, —C(O)OH, —C(O)$NH_2$, or halogen; and m, p and q are each independently an integer selected from 1 to 20.

In some embodiments in the compound of general formula II or pharmaceutically acceptable salt or solvate thereof, $L^1$ may be —S—, —S(O)$_2$—, —C(O)—, or —P(O)(OH)—, and in other embodiments, L$^2$ may be —NH—, —NR$^3$, —CH$_2$—, or —C(R$^3$)$_2$—. In still other embodiments, L$^1$ may be —NH—, —NR$^3$, —CH$_2$—, or —C(R$^3$)$_2$—, and in yet other embodiments, L$^2$ may be —S—, —S(O)$_2$—, —C(O)—, or —P(O)(OH)—. In certain embodiments, L$^1$ may be —S(O)$_2$— and L$^2$ is —NH—.

In various embodiments, ring A of the compounds of general formula II or pharmaceutically acceptable salt or solvate thereof, may be a 5-membered heteroaryl ring. For example, in certain embodiments, the moiety of

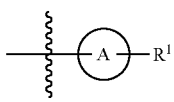

may be selected from:

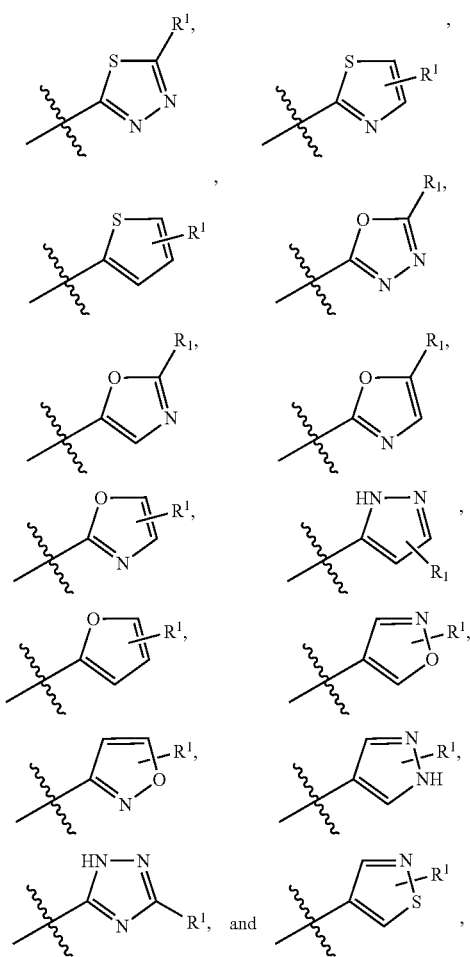

and in some embodiments ring A may be optionally substituted with one or more methyl, methoxy, sulfonyl, or sulfonic acid ester group in addition to R$^1$, and in particular embodiments, the moiety of

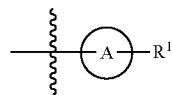

may be

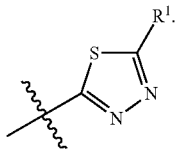

In still other embodiments, ring A may be a phenyl ring or a 6-membered heteroaryl ring. For example, in some embodiments, the moiety of

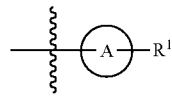

may be selected from:

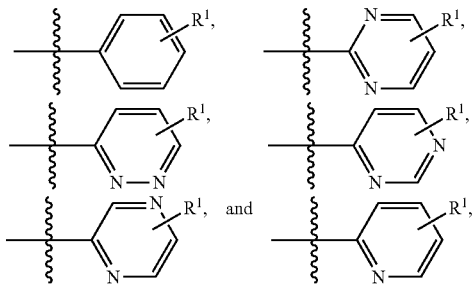

and in certain embodiments, ring A may be optionally substituted with one or more methyl, methoxy group, sulfonyl or sulfonic acid ester group in addition to R$^1$.

In particular embodiments, the moiety of

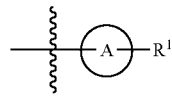

in compounds of general formula II may be

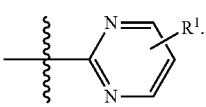

In some embodiments, in the compounds of general formula II or pharmaceutically acceptable salt or solvate thereof, R$^1$ may not be —S(O)$_2$NH$_2$ when R$^2$ is NH$_2$; L$^3$ may not be —NHC(O)— or —NH— when the moiety of

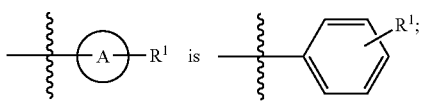

$L^3$ may not be —NHS(O)$_2$— when the moiety of

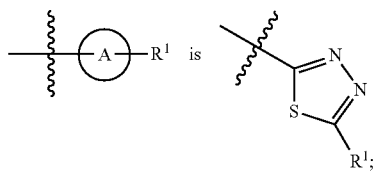

$R^1$ may not be —C(O)OR$^4$ or —OR$^4$ when the moiety of

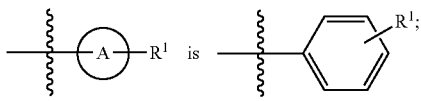

$L^3$ may not be —NHC(O)— when the moiety of

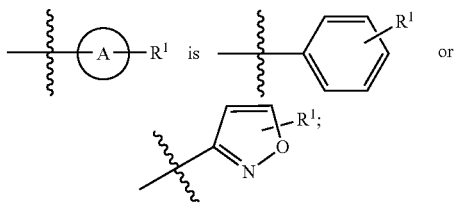

or $L^3$ may not be —S(O)$_2$NH— when the moiety of

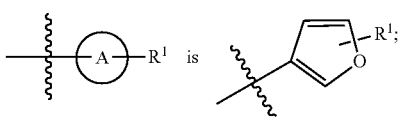

or $R^2$ may not be

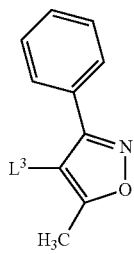

when the moiety of

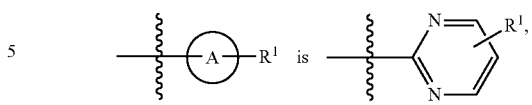

or any combination thereof.

Particular embodiments of the invention include compounds of general formula III:

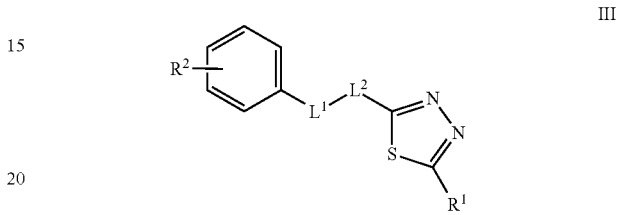

III or pharmaceutically acceptable salt or solvate thereof, wherein:

$L^1$ and $L^2$ may each, independently, be —S—, —S(O)$_2$—, —C(O)—, —P(O)(OH)—, —NH—, —N(CH$_3$)—, —N(R$^3$)—, —CH$_2$—, or —C(R$^3$)$_2$—;

each $R^3$ may, independently, be —H, —CH$_3$, CH$_2$CH$_3$, CH$_2$CH$_2$CH$_3$, NH$_2$, or —C$_6$H$_5$;

$R^1$ may be —H, —CH$_3$, —CH$_2$CH$_3$, —C(CH$_3$)$_3$, —C(O)OH, —CH$_2$C(O)OH, —CH$_2$C(O)OCH$_3$, —CH$_2$C(O)OCH$_2$CH$_3$, —OH, CH$_2$OH, —NH$_2$, —CH$_2$NH$_2$, —OCH$_3$, S(O)$_2$NH$_2$, S(O)$_2$C$_6$H$_5$, or S(O)$_2$CH$_2$C$_6$H$_5$;

$R^2$ may be —NH$_2$, —NHC(O)R$^6$, —NR$^{6a}$R$^{6b}$, —NHS(O)$_2$R$^6$, —OH, —OR$^6$, C(O)OH, or C$_1$-C$_{20}$ alkyl, wherein each C$_1$-C$_{20}$ alkyl may be optionally substituted with one or more substituents independently selected from halogen, C$_{1-6}$ alkyl, OH, —NH$_2$, —NHC(O)R$^6$, and —NR$^{6a}$R$^{6b}$;

each $R^6$ may, independently, be —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl may be optionally substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen;

$R^{6a}$ may be H or methyl;

$R^{6b}$ may be methyl, 7-nitrobenzo[c][1,2,5]oxadiazol-4-yl, or —C(O)C$_6$H$_5$; and $R^7$ may be —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In some embodiments in the compound of general formula III or pharmaceutically acceptable salt or solvate thereof, $L^1$ may be —S—, —S(O)$_2$—, —C(O)—, or —P(O)(OH)—, and in other embodiments, $L^2$ may be —NH—, —NR$^3$, —CH$_2$—, or —C(R$^3$)$_2$—. In still other embodiments, $L^1$ may be —NH—, —NR$^3$, —CH$_2$—, or —C(R$^3$)$_2$—, and in yet other embodiments, $L^2$ may be —S—, —S(O)$_2$—, —C(O)—, or —P(O)(OH)—. In certain embodiments, L1 may be —S—, —S(O)$_2$—, or —C(O)—, and L2 may be —NH—, or —CH$_2$—, and in some embodiments, $L^1$ may be —S(O)$_2$— and $L^2$ is —NH—.

In particular embodiments, the compounds of general formula III or pharmaceutically acceptable salt or solvate thereof, wherein the compound is a compound of Formula III-a:

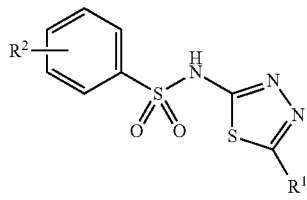

III-a wherein:

$R^1$ may be —H or —CH$_3$;

$R^2$ may be —NH$_2$, —NHC(O)R$^6$, —NHS(O)$_2$R$^6$, or C$_1$-C$_{20}$ alkyl, wherein the C$_1$-C$_{20}$ alkyl may optionally be substituted with one or more substituents independently selected from halogen, C$_{1-6}$ alkyl, OH, —NH$_2$, —NHC(O)R$^6$, and —NR$^{6a}$R$^{6b}$;

$R^6$ is —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl may optionally be substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen;

$R^{6a}$ may be H or methyl;

$R^{6b}$ may be methyl, 7-nitrobenzo[c][1,2,5]oxadiazol-4-yl, or —C(O)C$_6$H$_5$; and $R^7$ may be —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In some embodiments of the compound of general formula III-a or pharmaceutically acceptable salt or solvate thereof:

$R^1$ may be H;

$R^2$ may be C$_1$-C$_{20}$ alkyl optionally substituted with one or more substituents independently selected from halogen, OH, —NH$_2$, —NHC(O)R$^6$, and —NR$^{6a}$R$^{6b}$;

$R^6$ may be —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl may optionally be substituted with one or more substituents independently selected from —NH$_2$, —OH, —NH$_2$, —C$_{1-6}$ alkyl, —C$_6$H$_5$, —C$_6$H$_4$R$^7$, —CH$_2$C$_6$H$_5$, —CH$_2$C$_6$H$_4$R$^7$, and halogen;

$R^{6a}$ may be H or methyl;

$R^{6b}$ may be methyl, 7-nitrobenzo[c][1,2,5]oxadiazol-4-yl, or —C(O)C$_6$H$_5$; and $R^7$ may be —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In other embodiments of the compounds of general formula III-a or pharmaceutically acceptable salt or solvate thereof:

$R^2$ may be —NH$_2$ or —NHS(O)$_2$R$^6$;

$R^6$ may be —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl may optionally be substituted with one or more substituents independently selected from —NH$_2$, —OH, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; and $R^7$ may be —H, —CH$_3$, heteroaryl, —C(CH$_3$)$_3$, —OH, —NH$_2$, NHC(O)CH$_3$, S(O)$_2$OH, As(O)$_2$OH, NO$_2$, —OCH$_3$, —OCH$_2$CH$_3$, —C(O)OH, —C(O)NH$_2$, or halogen.

In still other embodiments of the compounds of general formula III-a or pharmaceutically acceptable salt or solvate thereof:

$R^2$ may be —NHS(O)$_2$R$^6$;

$R^6$ may be aryl or heteroaryl, each of which may be optionally substituted with one or more substituents independently selected from —NH$_2$, —OH, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen; and $R^7$ may be —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In certain embodiments, $R^1$ may be H and $R^2$ may be —NH$_2$ in the compounds of general formula III-a.

In any of the embodiments of formulae III and III-a above, $R^2$ may be substituted on any carbon atom of the phenyl ring. For example, in some embodiments, $R^2$ may be positioned and arranged in the para configuration, and in other embodiments, $R_2$ may be positioned and arranged in the meta or ortho configuration.

Particular embodiments are directed to compounds of general formula IV:

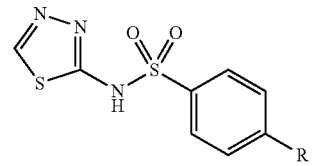

IV or pharmaceutically acceptable salt or solvate thereof wherein R may be an amine, methyl, alkyl, alkene, alkyne, aminoalkyl, alkyl carbamate, alkyl acetamide, alkyl sulfonyl, alkyl sulfonic acid ester, or alkyl sulfonamide such as, for example, a linear or branched C$_2$ to C$_{20}$ alkyl, linear or branched C$_2$ to C$_{20}$ alkene, linear or branched C$_2$ to C$_{20}$ alkyne, linear or branched C$_2$ to C$_{20}$ aminoalkyl, linear or branched C$_2$ to C$_{20}$ alkyl carbamate branched C$_2$ to C$_{20}$ alkyl acetamide, linear or branched C$_2$ to C$_{20}$ sulfonyl, linear or branched C$_2$ to C$_{20}$ sulfonic acid ester, or linear or branched C$_2$ to C$_{20}$ sulfonamide. In some embodiments, R may be a linear C$_2$-C$_{20}$ alkyl, and in other embodiments, R may be an alkyl acetamide of formula —NHC(O)CH$_1$CH$_3$ wherein n is 0 to 20. In particular embodiments, R may be —CH$_{11}$CH$_3$ or —NHC(O)CH$_{11}$CH$_3$, and in one exemplary embodiment, a compound of the invention may be:

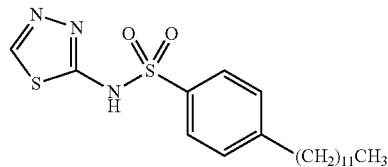

In still other embodiments, compounds encompassed by the invention may be of general formula IV:

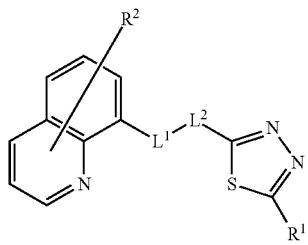

V or pharmaceutically acceptable salt or solvate thereof, wherein:

$L^1$ and $L^2$ may each, independently, be —S—, —S(O)$_2$—, —C(O)—, —P(O)(OH)—, —NH—, —N(CH$_3$)—, —N(R$^3$)—, —CH$_2$—, or —C(R$^3$)$_2$—;

each $R^3$ may, independently, be —H, —CH$_3$, CH$_2$CH$_3$, CH$_2$CH$_2$CH$_3$, NH$_2$, or —C$_6$H$_5$;

$R^1$ may be —H, —CH$_3$, —CH$_2$CH$_3$, —C(CH$_3$)$_3$, —C(O)OH, —CH$_2$C(O)OH, —CH$_2$C(O)OCH$_3$, —CH$_2$C(O)OCH$_2$CH$_3$, —OH, CH$_2$OH, —NH$_2$, —CH$_2$NH$_2$, —OCH$_3$, S(O)$_2$NH$_2$, S(O)$_2$C$_6$H$_5$, or S(O)$_2$CH$_2$C$_6$H$_5$;

$R^2$ may be —NH$_2$, —NHC(O)R$^6$, —NR$^{6a}$R$^{6b}$, —NHS(O)$_2$R$^6$, —OH, —OR$^6$, C(O)OH, or C$_1$-C$_{20}$ alkyl, and wherein each C$_1$-C$_{20}$ alkyl may optionally be substituted with one or more substituents independently selected from halogen, C$_{1-6}$ alkyl, OH, —NH$_2$, —NHC(O)R$^6$, and —NR$^{6a}$R$^{6b}$;

$R^6$ may be —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl may optionally be substituted with one or more substituents independently selected from —NH$_2$, —OH, —NH$_2$, —CH$_3$, —CH$_2$CH$_3$, —CH$_2$CH$_2$CH$_3$, C$_{1-6}$ alkyl, —C$_6$H$_5$, —C$_6$H$_4$R$^7$, —CH$_2$C$_6$H$_5$, —CH$_2$C$_6$H$_4$R$^7$, and halogen;

$R^{6a}$ may be H or methyl;

$R^{6b}$ may be methyl, 7-nitrobenzo[c][1,2,5]oxadiazol-4-yl, or —C(O)C$_6$H$_5$; and $R^7$ may be —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In some embodiments in the compound of general formula V or pharmaceutically acceptable salt or solvate thereof, $L^1$ may be —S—, —S(O)$_2$—, —C(O)—, or —P(O)(OH)—, and in other embodiments, $L^2$ may be —NH—, —NR$^3$, —CH$_2$—, or —C(R$^3$)$_2$—. In still other embodiments, $L^1$ may be —NH—, —NR$^3$, —CH$_2$—, or —C(R$^3$)$_2$—, and in yet other embodiments, $L^2$ may be —S—, —S(O)$_2$—, —C(O)—, or —P(O)(OH)—. In certain embodiments, $L^1$ may be —S—, —S(O)$_2$—, or —C(O)—, and $L^2$ may be —NH—, or —CH$_2$—, and in some embodiments, $L^1$ may be —S(O)$_2$— and $L^2$ is —NH—.

In other embodiments of compounds of general formula V or pharmaceutically acceptable salts or solvates thereof:

$L^1$ may be —S(O)$_2$—;

$L^2$ may be —NH—; and $R^1$ may be S(O)$_2$NH$_2$.

Yet other embodiments of the invention are directed to compounds of general formula V:

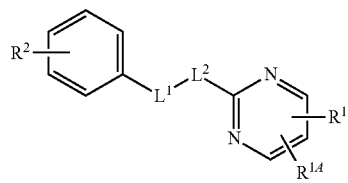

VI or pharmaceutically acceptable salt or solvate thereof, wherein:

$L^1$ and $L^2$ may each, independently, be —S—, —S(O)$_2$—, —C(O)—, —P(O)(OH)—, —NH—, —N(CH$_3$)—, —N(R$^3$)—, —CH$_2$—, or —C(R$^3$)$_2$—;

each $R^3$ may, independently, be —H, —CH$_3$, CH$_2$CH$_3$, CH$_2$CH$_2$CH$_3$, NH$_2$, or —C$_6$H$_5$;

$R^1$ may be —H, —CH$_3$, or —OCH$_3$;

$R^{1A}$ may be —H, —CH$_3$, or —OCH$_3$;

$R^2$ may be —NH$_2$, —NHC(O)R$^6$, —NR$^{6a}$R$^{6b}$, —NHS(O)$_2$R$^6$, —OH, —OR$^6$, C(O)OH, or C$_1$-C$_{20}$ alkyl, and each C$_1$-C$_{20}$ alkyl may be optionally substituted with one or more substituents independently selected from halogen, C$_{1-6}$ alkyl, OH, —NH$_2$, —NHC(O)R$^6$, and —NR$^{6a}$R$^{6b}$;

$R^6$ may be —CH$_3$, —CH$_2$CH$_3$, —CH$_2$CH$_2$CH$_3$, —C$_6$H$_5$, —C$_6$H$_4$R$^7$, —CH$_2$C$_6$H$_5$, —CH$_2$C$_6$H$_4$R$^7$, aryl, heteroaryl, or C$_1$-C$_{20}$ alkyl, wherein each of the aryl, heteroaryl, or C$_1$-C$_{20}$ alkyl may be optionally substituted with one or more substituents independently selected from —NH$_2$, —OH, —NH$_2$, —C$_{1-6}$ alkyl, —C$_6$H$_5$, —C$_6$H$_4$R$^7$, —CH$_2$C$_6$H$_5$, —CH$_2$C$_6$H$_4$R$^7$, and halogen;

$R^{6a}$ may be H or methyl;

$R^{6b}$ may be methyl, 7-nitrobenzo[c][1,2,5]oxadiazol-4-yl, or —C(O)C$_6$H$_5$;

$R^7$ may be —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen;

or $R^2$ may be

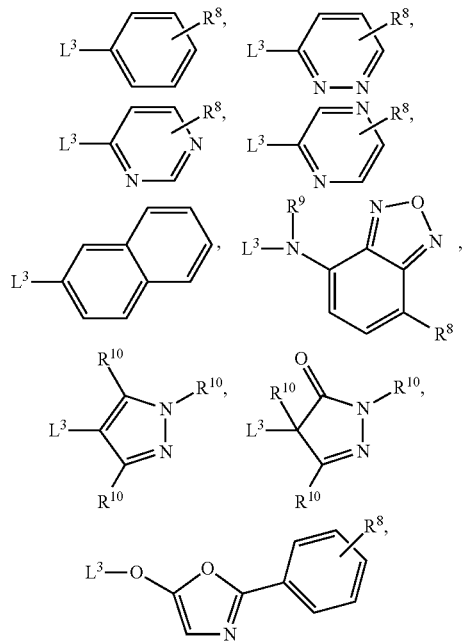

-continued

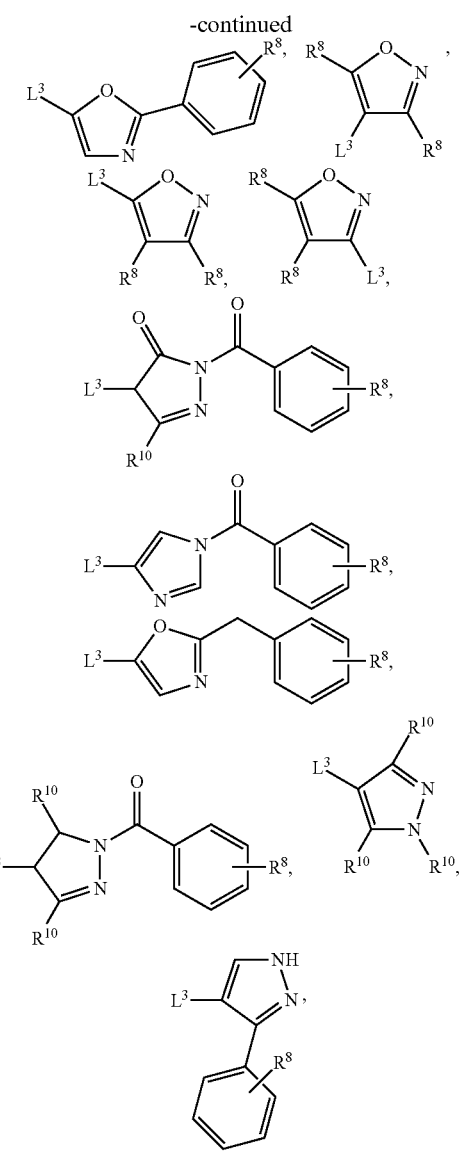

wherein R² is attached to the phenyl ring of Formula V through L³;

L³ may be a bond, —CH₂—, —CH₂(CH₂)ₛ—, —CH(OH)—, —C(O)—, —O—, —NH—, —S—, —CH₂CH₂—, —CH=CH—, —N=N—, —OCH₂—, —NHP(O)(OH)—, —NHS(O)₂—, —SCH₂—, —S(O)₂CH₂—, or —NHC(O)—;

R⁸ may be —H, —CH₃, —C(CH₃), —OH, —NH₂, NO₂, —OCH₃, —C(O)OH, —C(O)NH₂, or halogen;

R¹⁰ may be —H, —CH₃, —OH, —OCH₃, —C₆H₅,

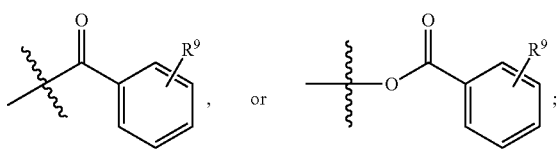

R⁹ may be —H, —CH₃, —C(CH₃), —OH, —NH₂, NO₂, —OCH₃, —C(O)OH, —C(O)NH₂, or halogen; and
s may be 1 to 20.

In some embodiments in the compound of general formula VI or pharmaceutically acceptable salt or solvate thereof, L¹ may be —S—, —S(O)₂—, —C(O)—, or —P(O)(OH)—, and in other embodiments, L² may be —NH—, —NR³, —CH₂—, or —C(R³)₂—. In still other embodiments, L¹ may be —NH—, —NR³, —CH₂—, or —C(R³)₂—, and in yet other embodiments, L² may be —S—, —S(O)₂—, —C(O)—, or —P(O)(OH)—. In certain embodiments, L¹ may be —S—, —S(O)₂—, or —C(O)—, and L² may be —NH—, or —CH₂—, and in some embodiments, L¹ may be —S(O)₂— and L² is —NH—.

In other embodiments of compounds of formula VI or pharmaceutically acceptable salts or solvates thereof:
L¹ may be —S(O)₂—;
L² may be —NH—;
R² may be —NHS(O)₂R⁶;
R⁶ may be aryl, heteroaryl, or C₁-C₂₀ alkyl, wherein each of the aryl, heteroaryl, or C₁-C₂₀ alkyl, may be optionally substituted with one or more substituents independently selected from —NH₂, —OH, —CH₃, —CH₂CH₃, —CH₂CH₂CH₃, C₁₋₆ alkyl, —C₆H₅, —C₆H₄R⁷, —CH₂C₆H₅, —CH₂C₆H₄R⁷, and halogen;
R⁷ may be —H, —CH₃, heteroaryl, —C(CH₃)₃, —OH, —NH₂, NHC(O)CH₃, S(O)₂OH, —P(O)₂OH, As(O)₂OH, NO₂, —OCH₃, —OCH₂CH₃, —C(O)OH, —C(O)NH₂, or halogen.

In some embodiments of formula VI, R² may be

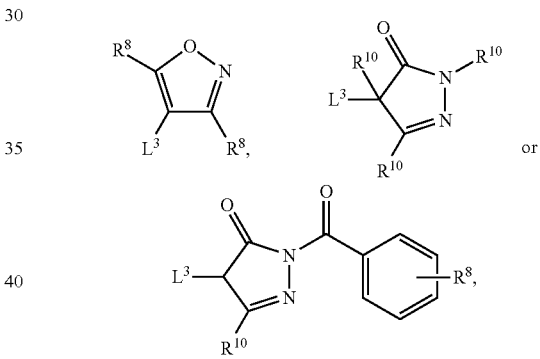

wherein R² is attached to the benzene ring of formula VI through L³, and L³ may be —NHS(O)₂— or —N=N—. In other embodiments, R² may be

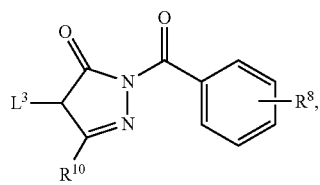

wherein R² is attached to the benzene ring of formula VI through L³ and L³ may be —N=N—. In yet other embodiments of formula VI or pharmaceutically acceptable salts or solvates thereof:
R² may be —NHS(O)₂R⁶;
R⁶ may be aryl or heteroaryl, each of which may optionally be substituted with one or more substituents independently selected from —NH₂, —OH, —CH₃, —CH₂CH₃, —CH₂CH₂CH₃, C₁₋₆ alkyl, —C₆H₅, —C₆H₄R⁷, —CH₂C₆H₅, —CH₂C₆H₄R⁷, and halogen; and R[7] may be —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

Still other embodiments of the invention are directed to compounds of general formula VII:

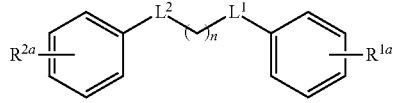

VII wherein:
L$^1$ and L$^2$ may be —S(O)$_2$—, —C(O)—, —CH$_2$—, —O—, or —S—;
n may be 1 or 2;
R$^{1a}$ may be halogen, —C(O)OH, or

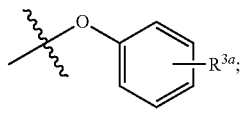

R$^{3a}$ may be halogen, —H, —NH$_2$, C(CH$_3$)$_3$, or C(F)$_3$;
R$^{2a}$ may be —NH$_2$, —NO$_2$, —C(O)OH, —CH$_2$C(O)OH, or

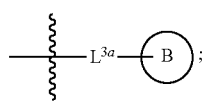

L$^{3a}$ may be a bond, —NHC(O)—, —C(O)—, —NH—, or —O—; and ring B may be an aryl or heteroaryl having one or two ring-forming N heteroatoms, each of which may optionally be substituted with one or more substituents independently selected from CH$_3$, —OH, —NH$_2$, —NO$_2$, —C(CH$_3$)$_3$, —C(O)OH, —S(O)$_2$OH, —P(O)$_2$OH, As(O)$_3$H, NHC(O)CH$_3$, —OH, —OCH$_3$, —OCH$_2$CH$_3$, and halogen.

In some embodiments of formula VII or pharmaceutically acceptable salts or solvates thereof, L$^1$ may be —S(O)$_2$—; L$^2$ may be —S—; and n may be 2, and in other embodiments:
R$^{1a}$ may be halogen;
R$^{2a}$ may be —NH$_2$, or

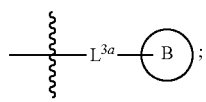

L$^{3a}$ may be —NHC(O)— or —NH—; and ring B may be an aryl or heteroaryl having one or two ring-forming N heteroatoms, each of which may optionally be substituted with one or more substituents independently selected from CH$_3$, —OH, —NH$_2$, —NO$_2$, —C(CH$_3$)$_3$, —C(O)OH, —S(O)$_2$OH, —P(O)$_2$OH, As(O)$_3$H, NHC(O)CH$_3$, —OH, —OCH$_3$, —OCH$_2$CH$_3$, and halogen.

Further embodiments of the invention are directed to compounds of general formula VIII:

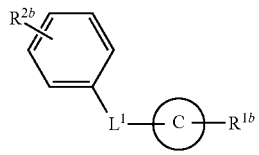

VIII or pharmaceutically acceptable salts or solvates thereof wherein:
L$^1$ may be —S(O)$_2$— or —C(O)—;
ring C may be aryl, piperazine, or imidazole;
R$^{1b}$ may be an aryl group substituted with one or more C(O)OH, CH$_2$C(O)OH, or imidazole;
R$^{2b}$ may be

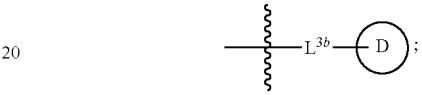

L$^{3b}$ may be a bond, —O—, or —S(O)$_2$—; and
ring D may be a substituted or unsubstituted, 5- to 9-membered cyclic of bicyclic ring having 0-3 ring-forming heteroatoms selected from N and O, wherein ring D may optionally be substituted with one or more substituents independently selected from —CH$_3$, —OCH$_3$, —NH$_2$, —NO$_2$, and halogen.

In particular embodiments of formula VII or pharmaceutically acceptable salts or solvates thereof, ring C may be a piperazine ring.

Still further embodiments of the invention include compound of formula VIII:

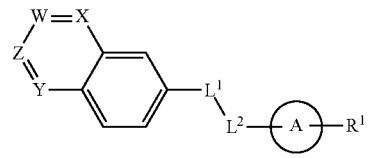

IX or pharmaceutically acceptable salts or solvates thereof wherein:
L$^1$ and L$^2$ may be —S—, —S(O)$_2$—, —C(O)—, —NH— or —CH$_2$—;
ring A may be a substituted or unsubstituted, 5- or 6-membered ring having 1-3 ring-forming heteroatoms or ring A may be a substituted or unsubstituted phenyl, wherein ring A may be optionally substituted with a methyl, methoxy group, sulfonyl, or sulfonic acid ester in addition to R$^1$;
R$^1$ may be —H, —CH$_3$, —CH$_2$CH$_3$, —C(CH$_3$)$_3$, —C(O)OH, —CH$_2$C(O)OH, —CH$_2$C(O)OCH$_3$, —CH$_2$C(O)OCH$_2$CH$_3$, —OH, CH$_2$OH, —NH$_2$, —CH$_2$NH$_2$, —OCH$_3$, S(O)$_2$NH$_2$, S(O)$_2$C$_6$H$_5$, or S(O)$_2$CH$_2$C$_6$H$_5$; and
W, X, Y, and Z may each independently be N or CH.

In some embodiments, L$^1$ may be —S—, —S(O)$_2$—, or —C(O)—, and L$^2$ may be —NH— or —CH$_2$—. In other embodiments, the bicylcic ring of formula VIII may be naphthalene, and in still other embodiment, at least one of W, X, Y, and Z of the bicyclic ring of formula VIII may be N.

Various embodiments of the invention are directed to specific compounds encompassed in general formulae I-VIII. For example, individual compounds of the invention include, but are not limited to:

100 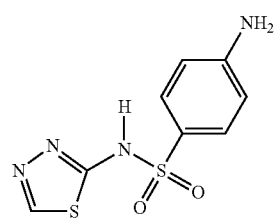
101 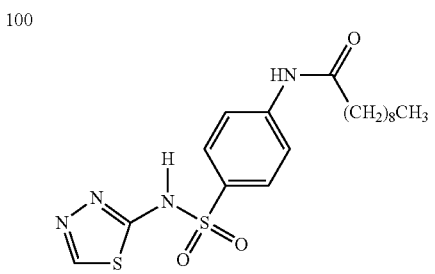
102 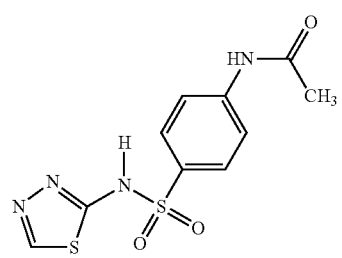
103 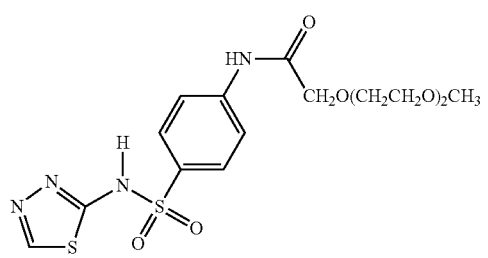
103b 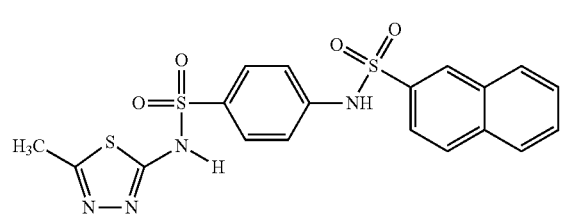
104p 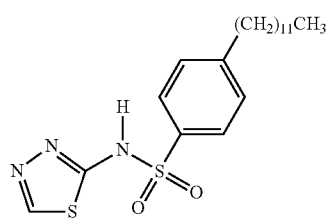
104o 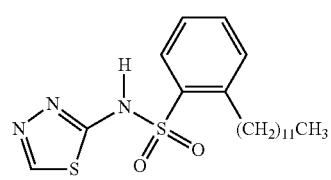
104m 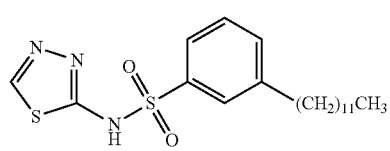
105 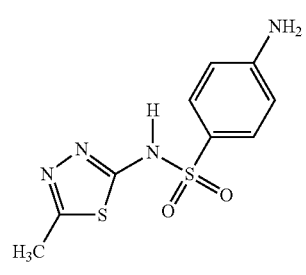
106 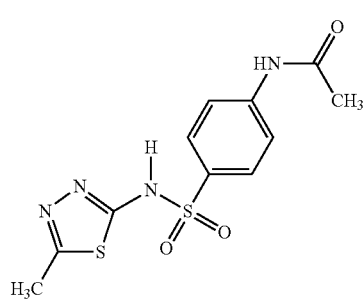
107 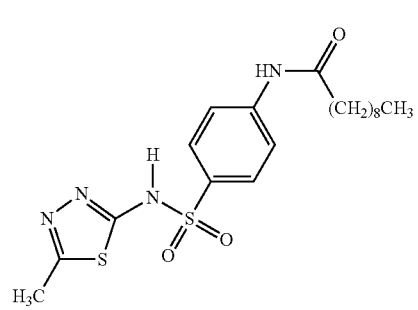
108 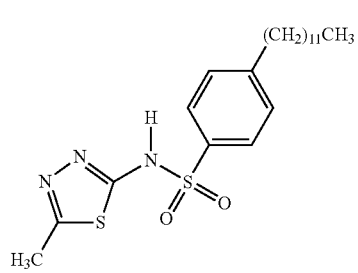

-continued
109 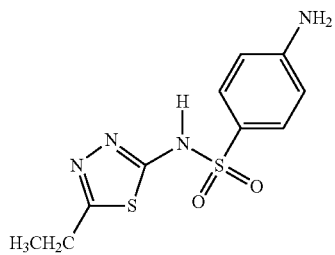
110 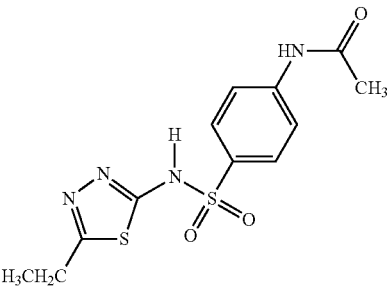
111 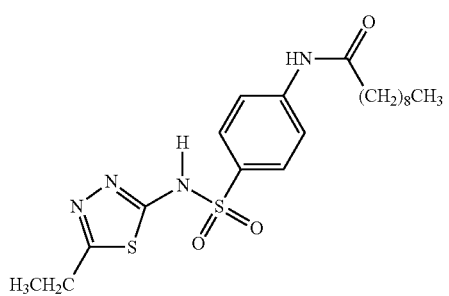
112 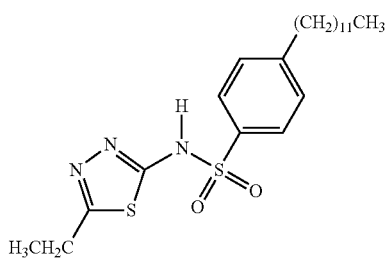
113 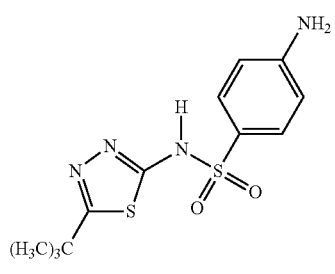
114 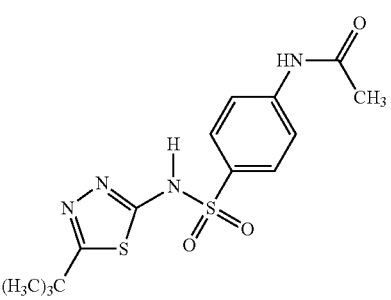
115 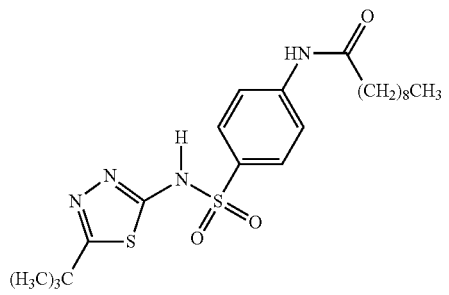
116 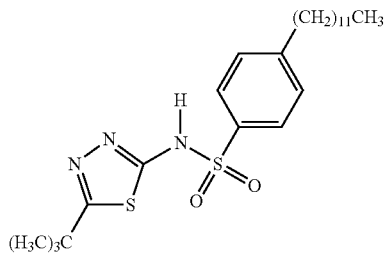
117 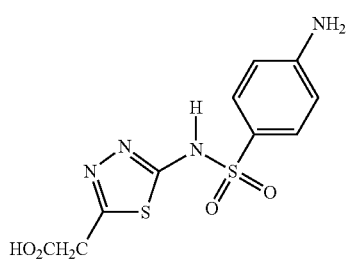
117E 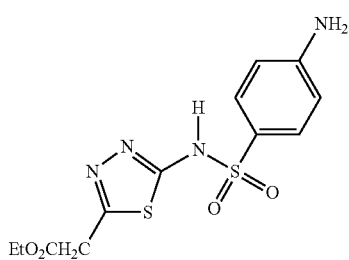

-continued
118
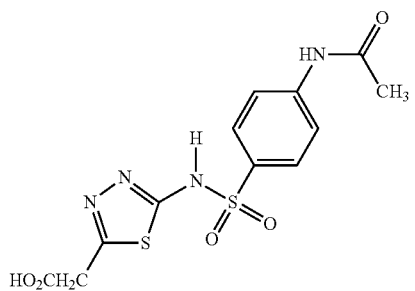
118E
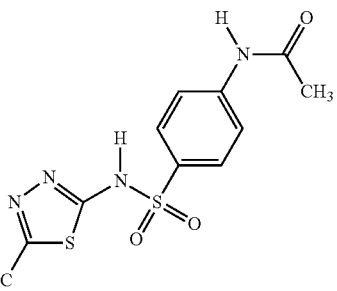
119
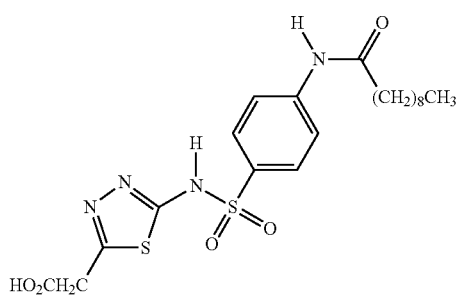
119E
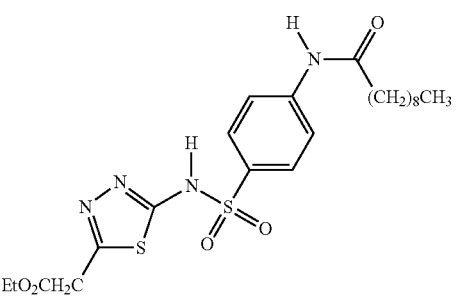
120
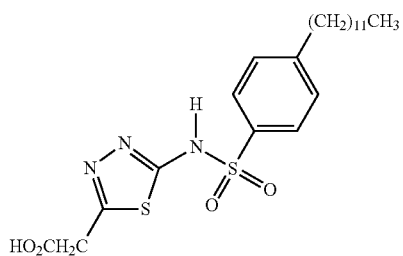
120E
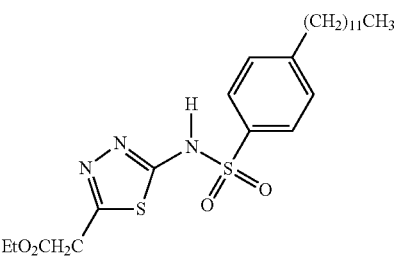
121
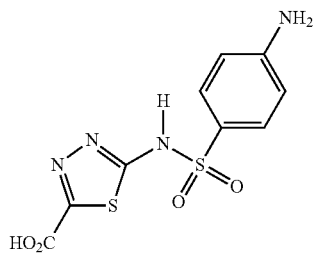
122
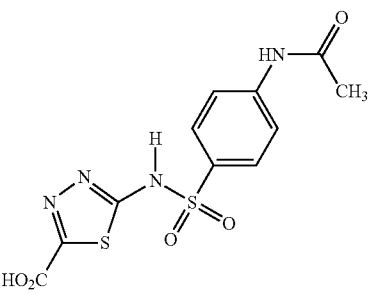
122E
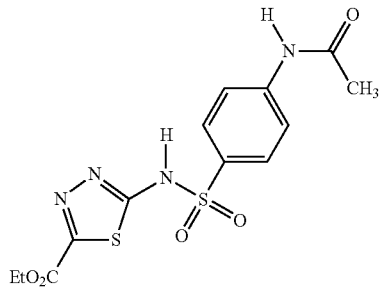
123
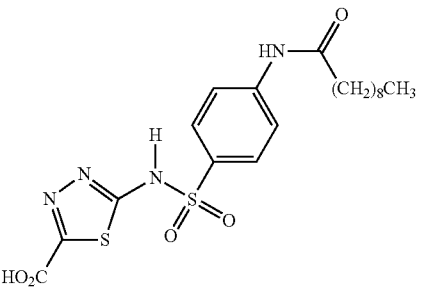

-continued
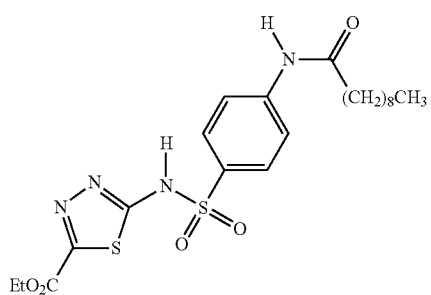
123E
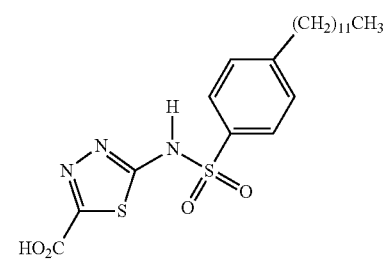
124
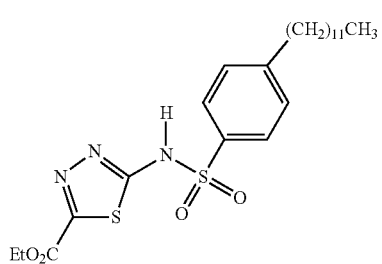
124E
125
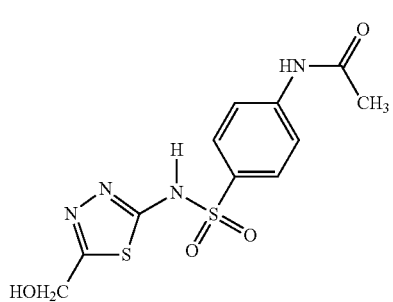
126
127
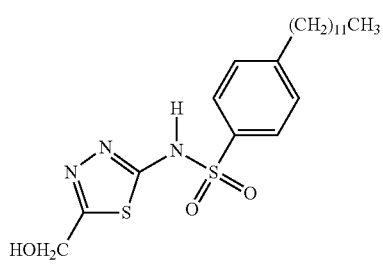
128
128
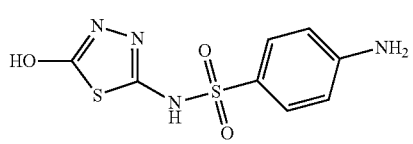
128c
128d
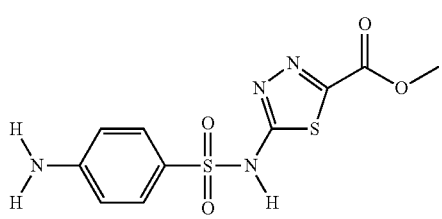
129
130

-continued
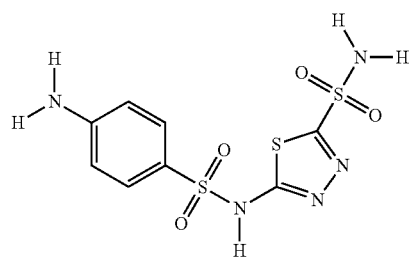  131
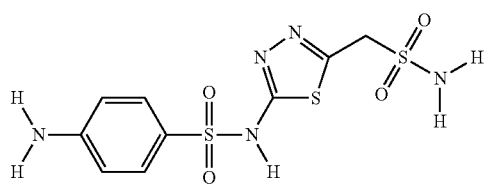  132
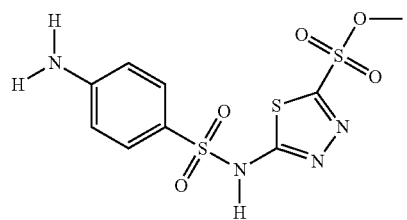  133
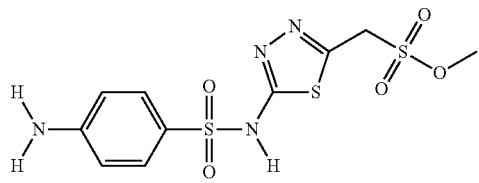  134
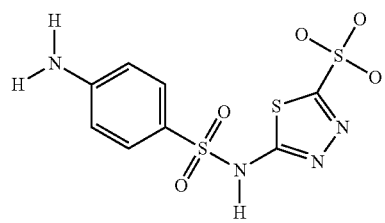  135
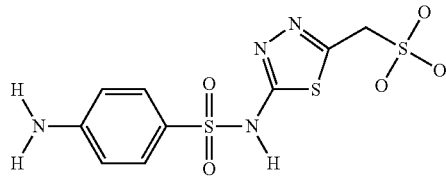  136
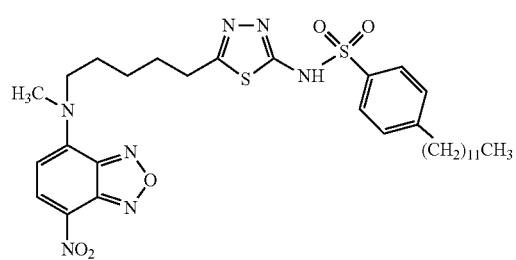  137
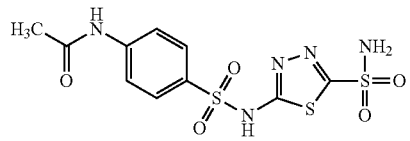  138
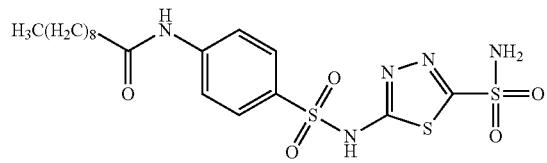  139
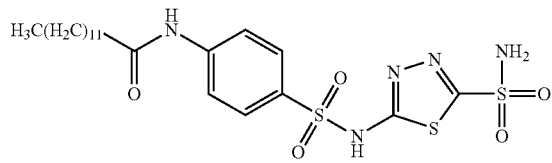  140
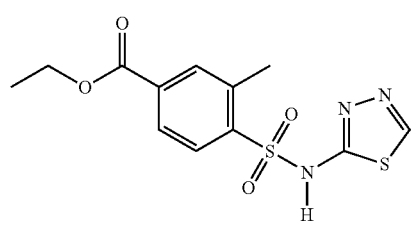  141
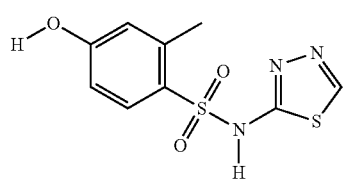  142
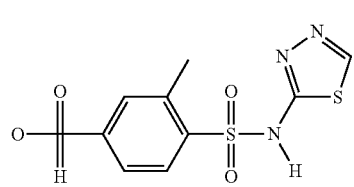  143
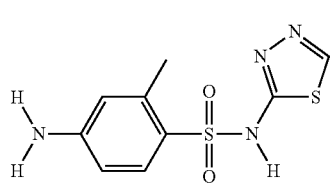  144

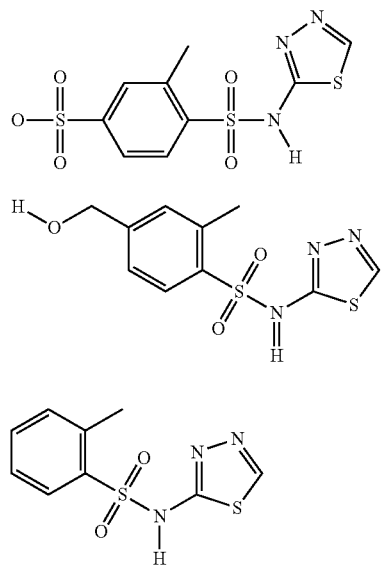
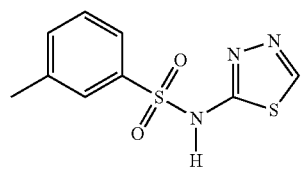
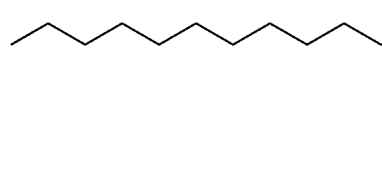
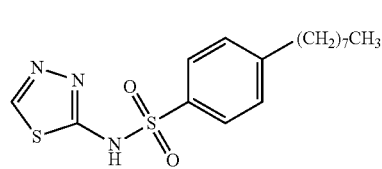
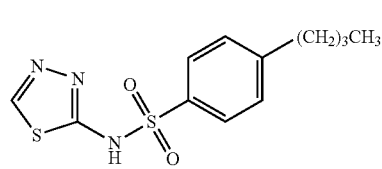
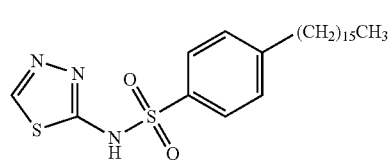
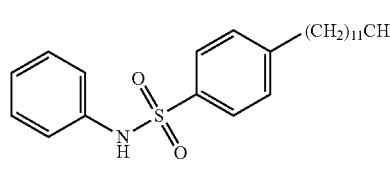

-continued
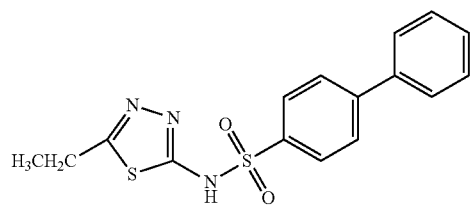
162
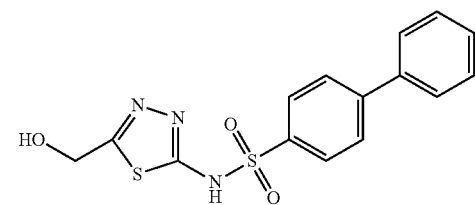
163
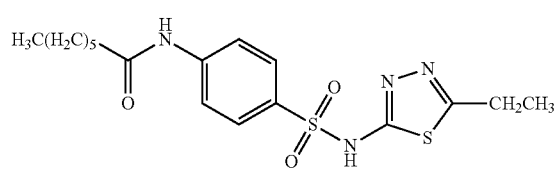
164
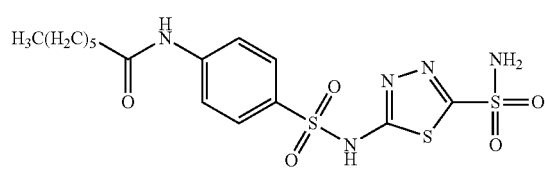
165
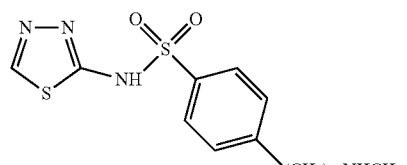
166
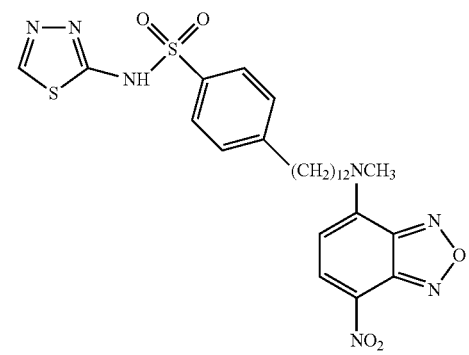
168
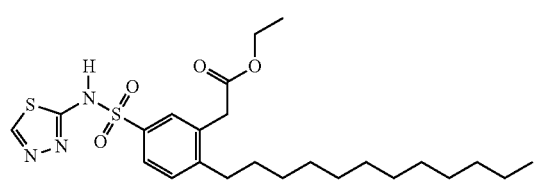
169
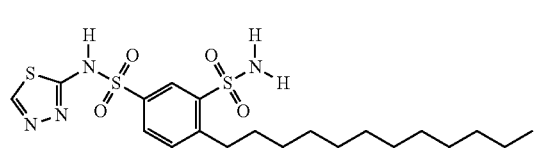
170
176
177
178
179
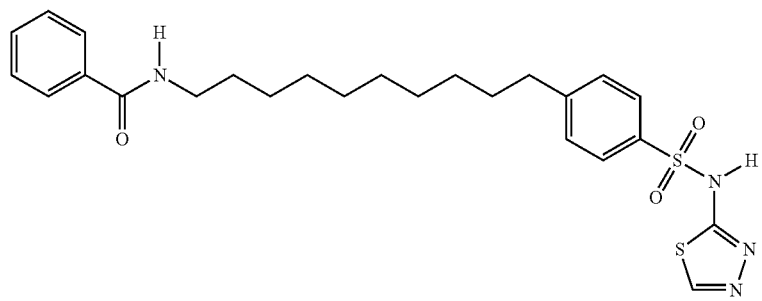
180

-continued
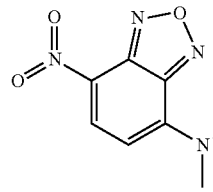
181
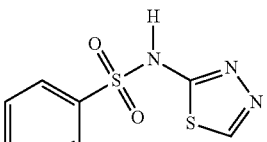
181
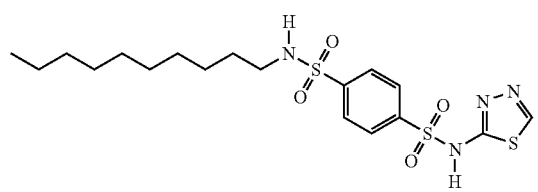
181
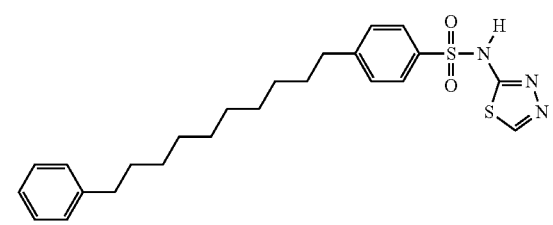
182
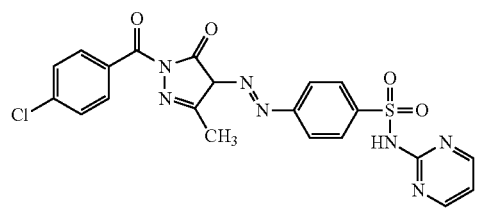
316
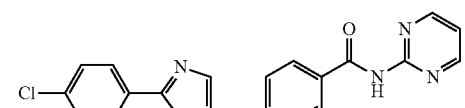
317
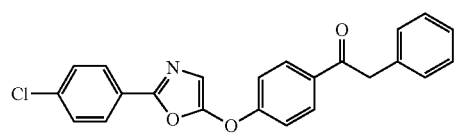
318
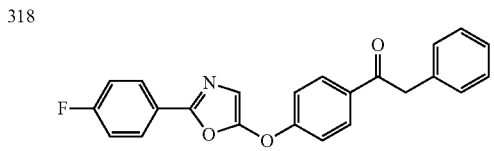
319
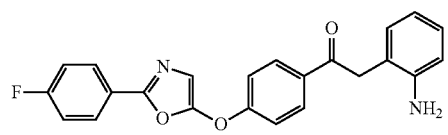
320
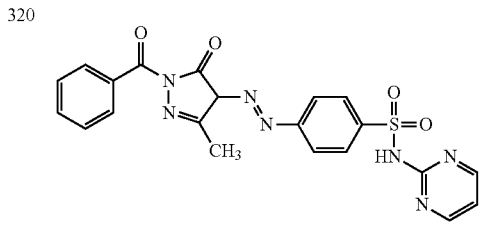
331
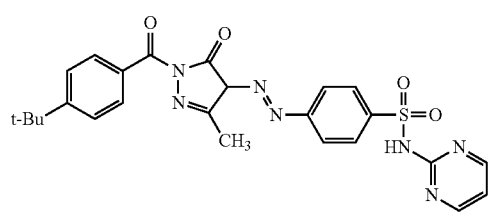
332
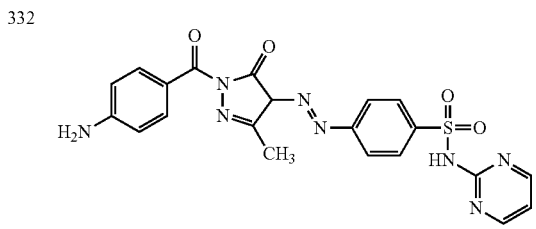
333
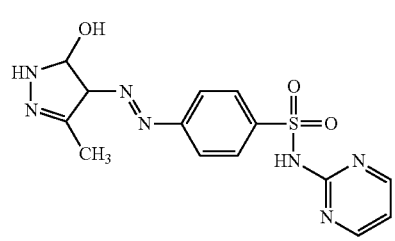
334
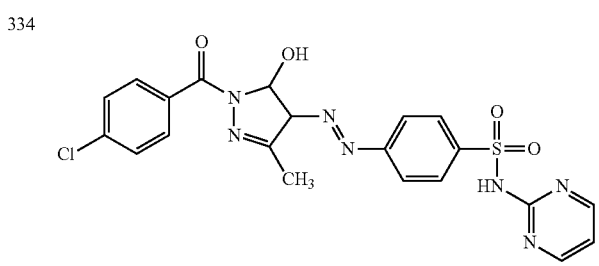
335

-continued
336 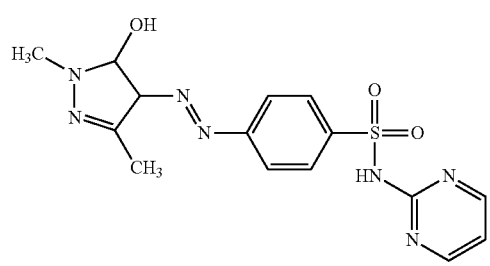 337 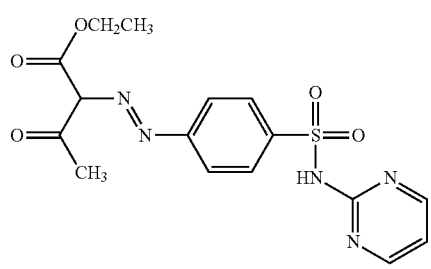
338 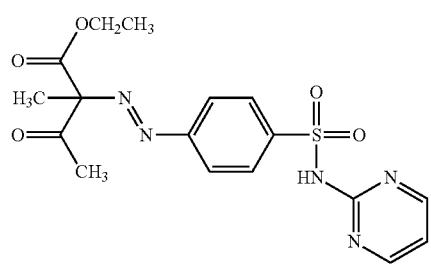
339 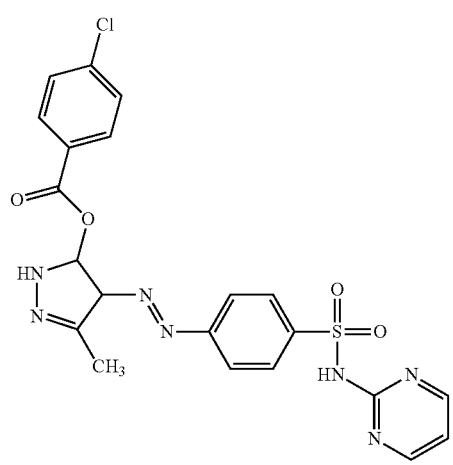
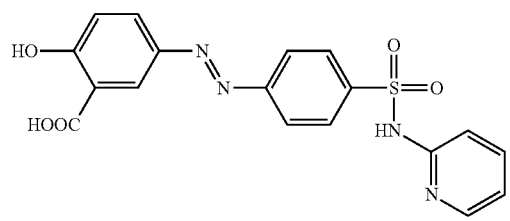
341 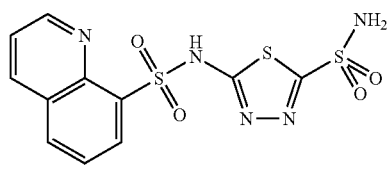 345
346 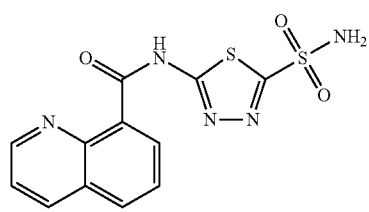 347 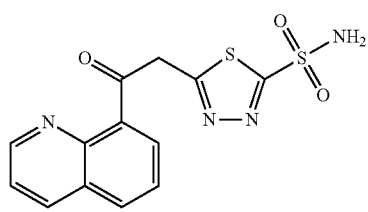
348 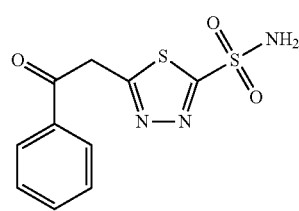 349 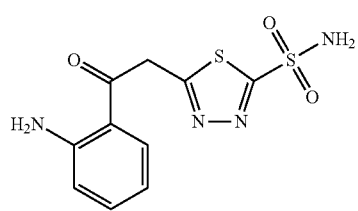
350 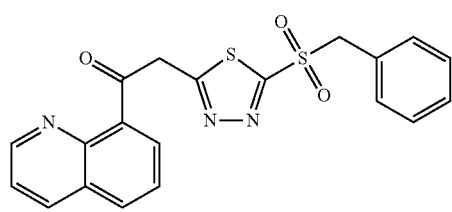 351 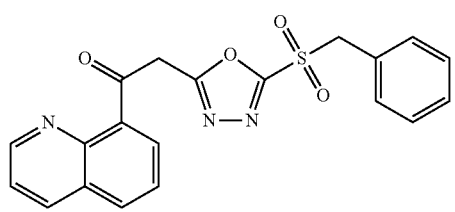

-continued
352 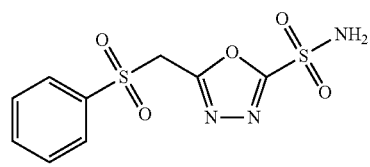 353 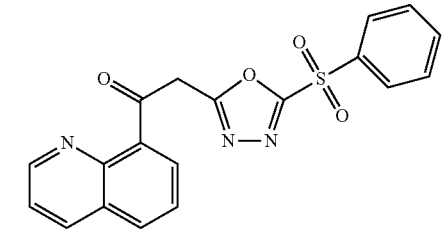
356 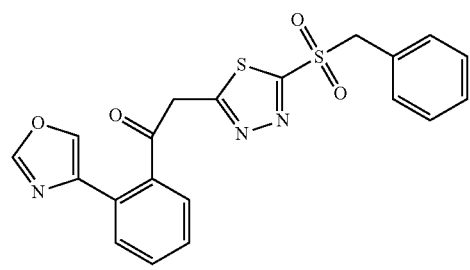 357
358 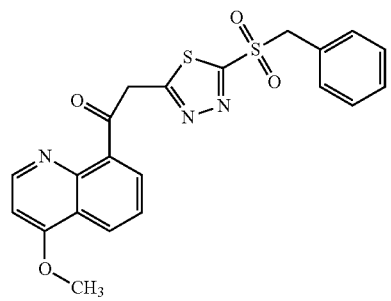 359
360 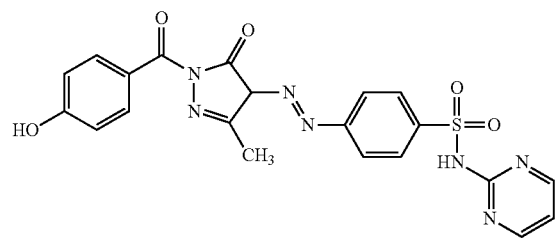 361
362 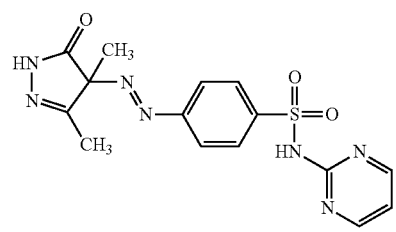 363
364 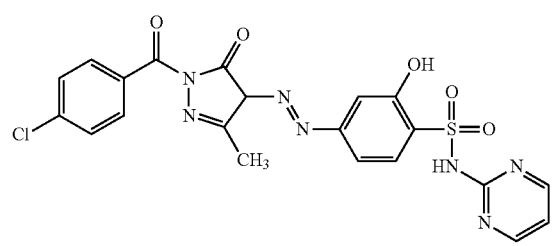 365 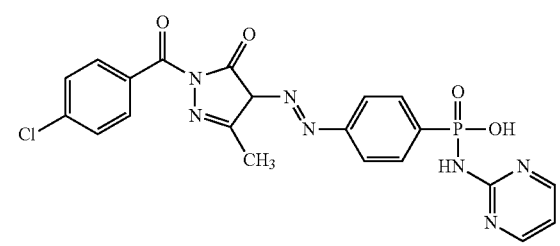

-continued
366 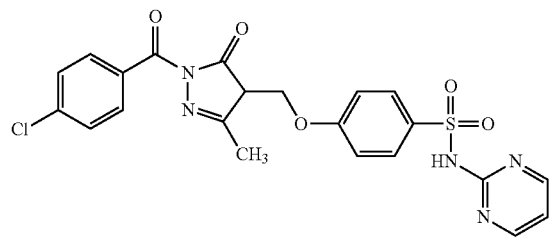
367 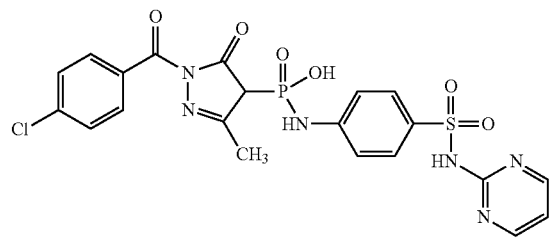
368 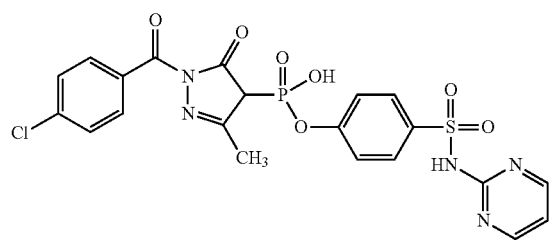
369 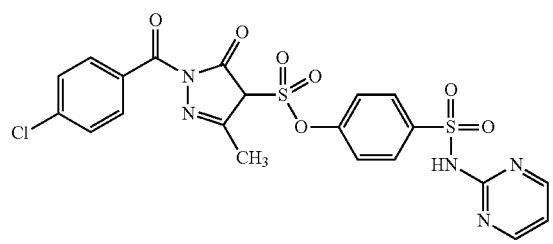
370 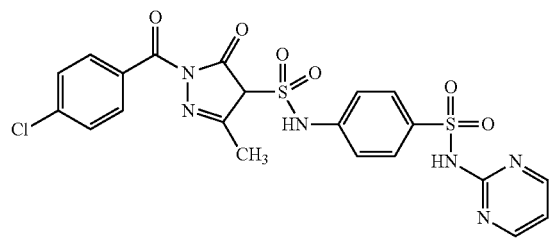
371 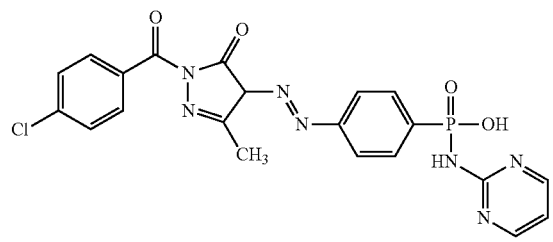
372 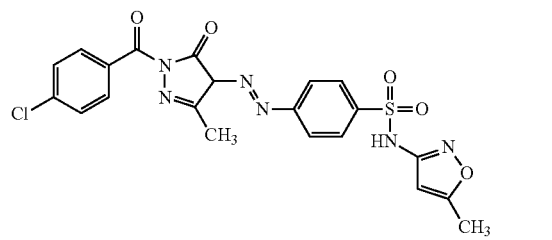
373 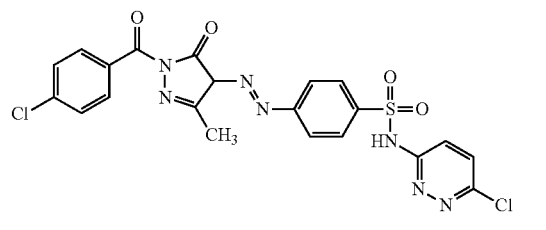
374 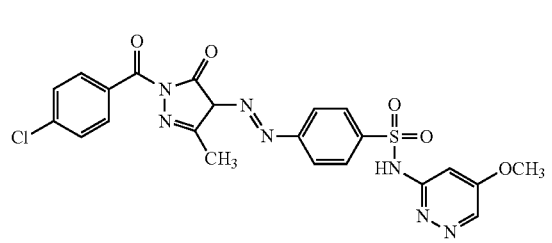
375 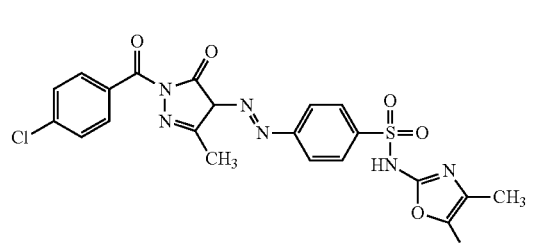
376 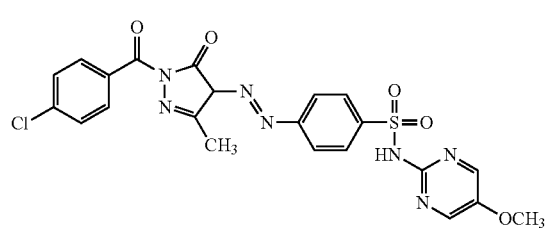
377 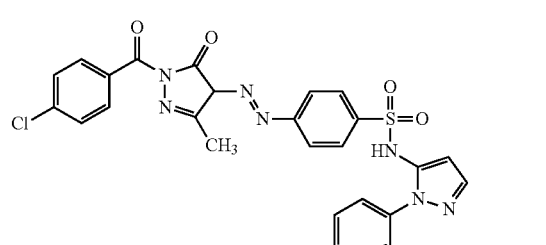

| 69 | 70 |
|---|---|
| 378 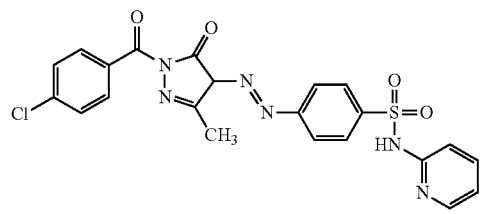 | 379 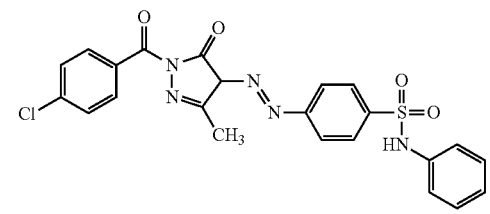 |
| 380 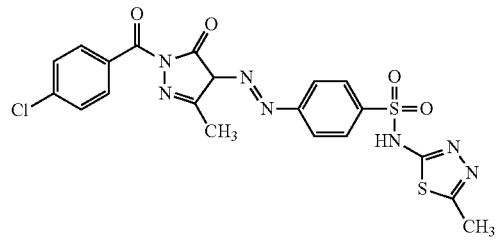 | 382 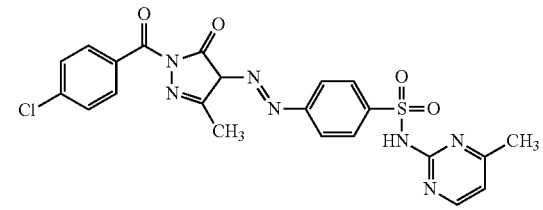 |
| 383 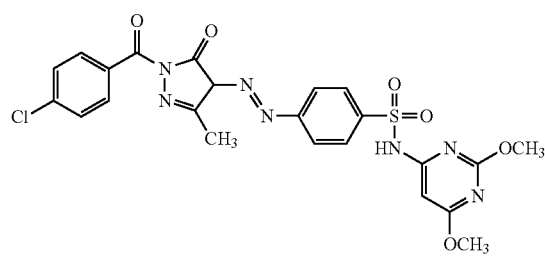 | 384 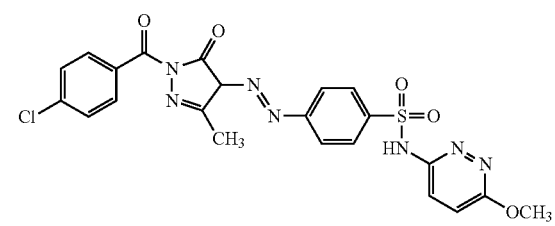 |
| 385 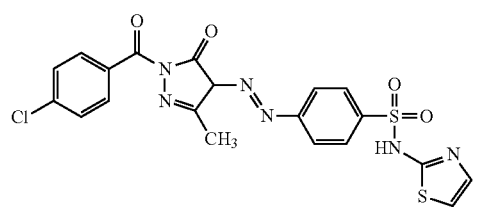 | 388 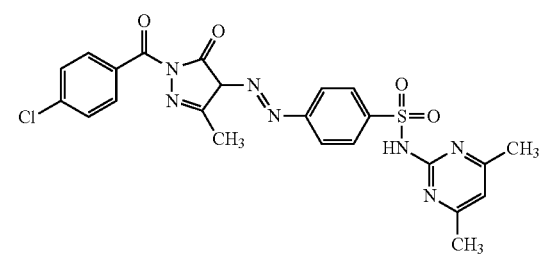 |
| 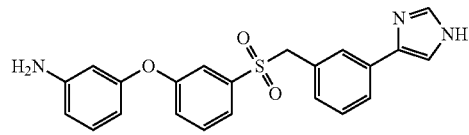 | 398 415 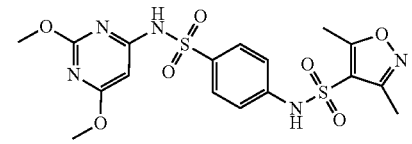 |
| 416 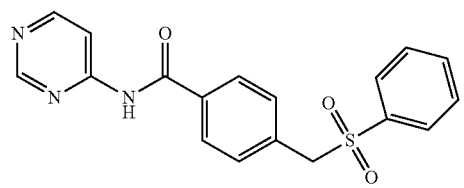 | 422 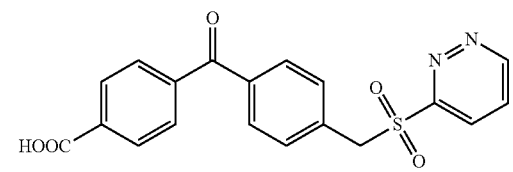 |
| 423 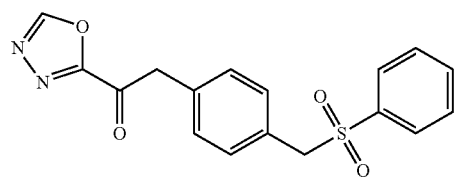 | 424 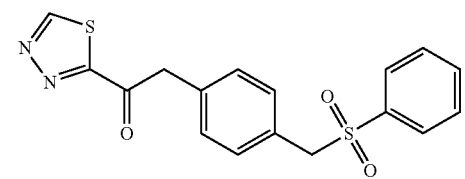 |

-continued
425
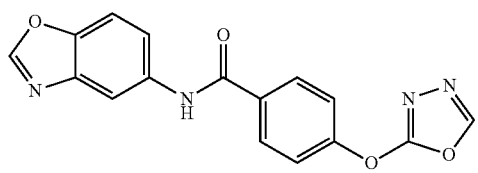
426
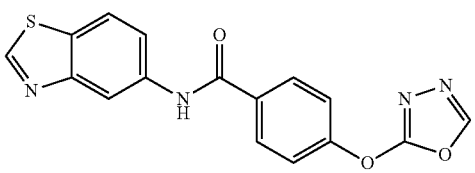
427
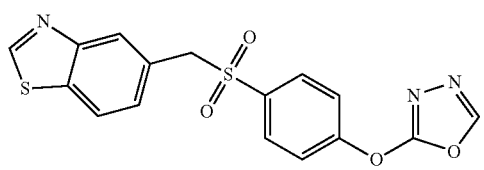
436
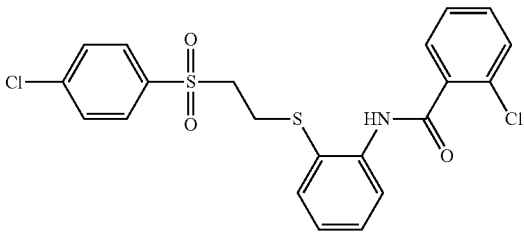
437
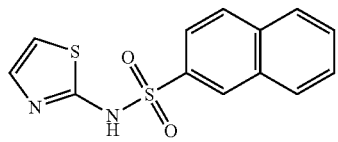
438
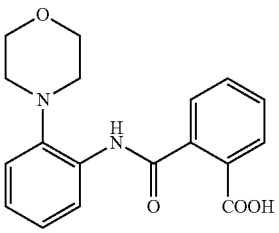
439
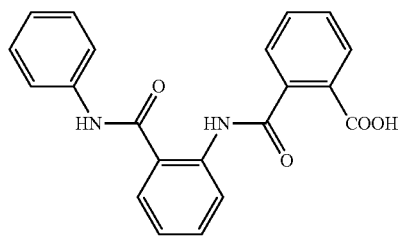
440
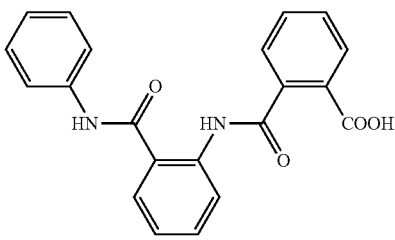
441
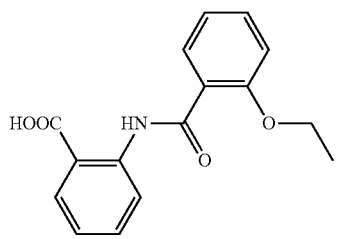
442
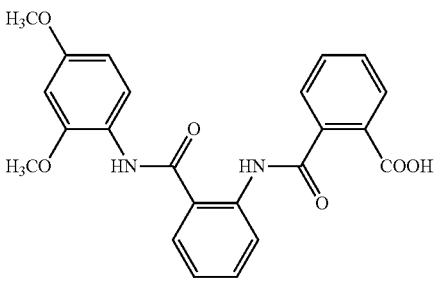
443
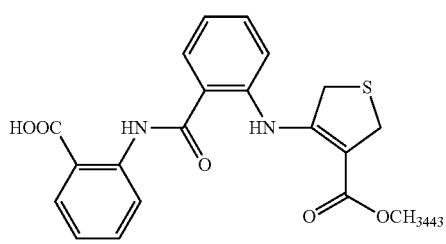
444
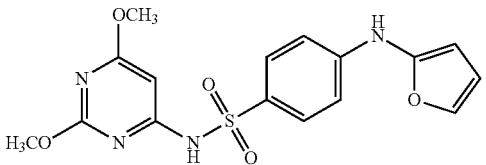
445
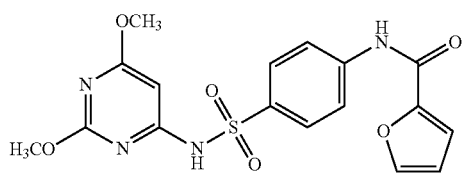
446
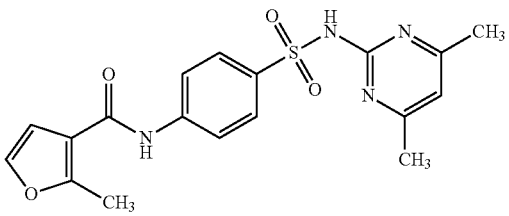

| 73 | 74 |
|---|---|
| | -continued |
| | 447 |
| | 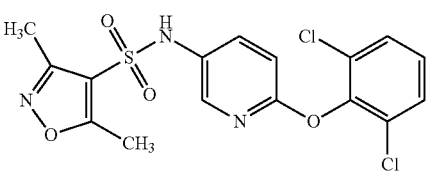 |
| | 448 |
| | 449 |
| 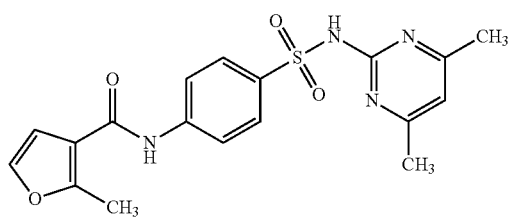 | |
| | 450 |
| | 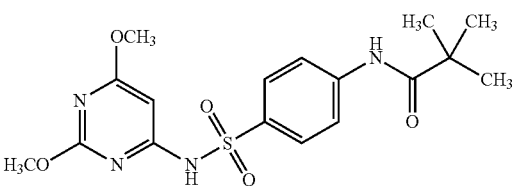 |
| | 451 |
| 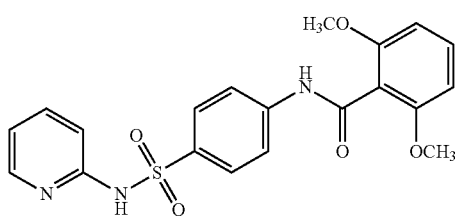 | |
| | 452 |
| 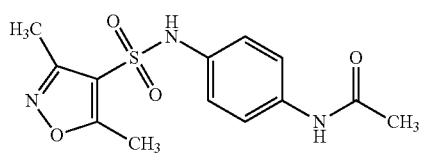 | 453 |
| | 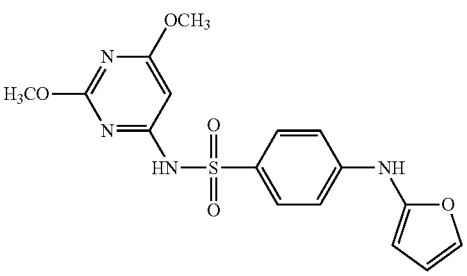 |
| | 454 |
| 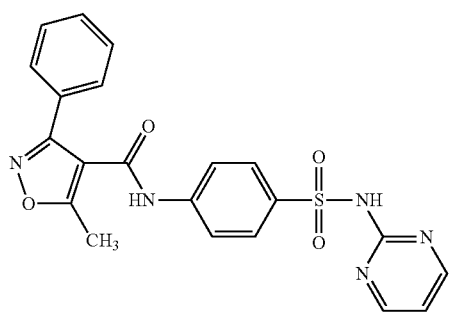 | 455 |
| | 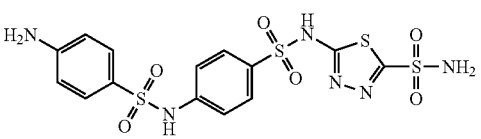 |
| | 456 |
| 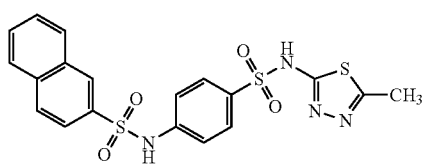 | 457 |
| | 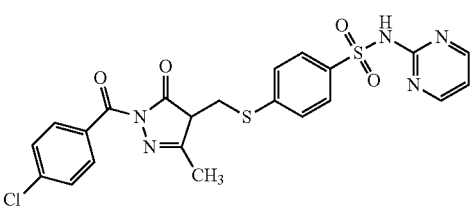 |
| | 458 |
| 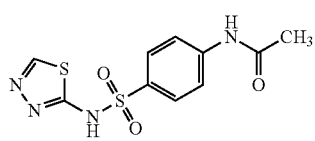 | 459 |
| 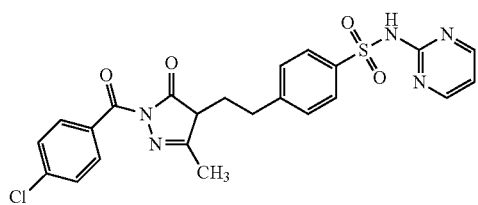 | 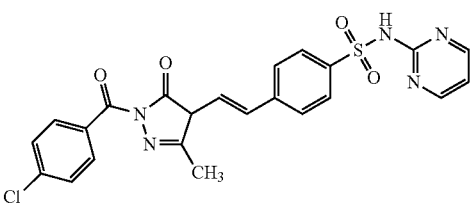 |
| | 460 |

-continued
461 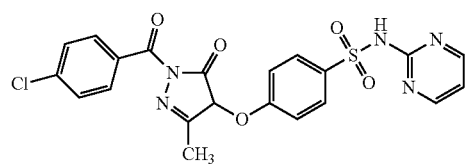
462 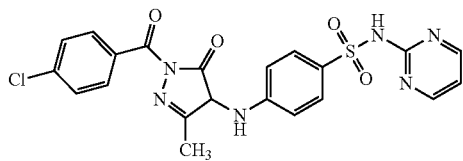
463 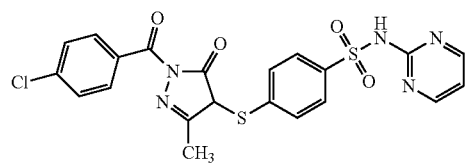
464
465 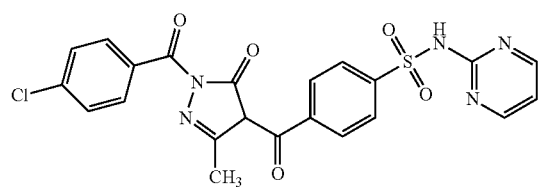
466
467 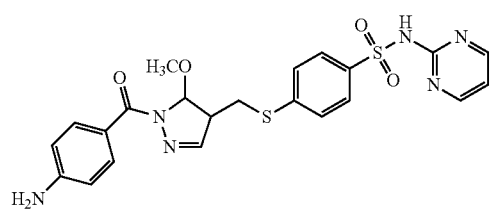
468
469 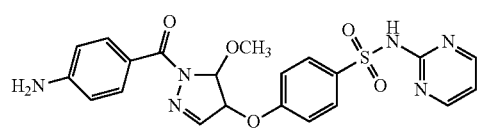
470
471 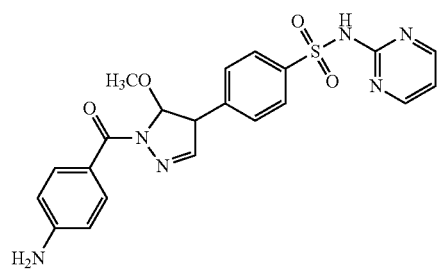
472
473 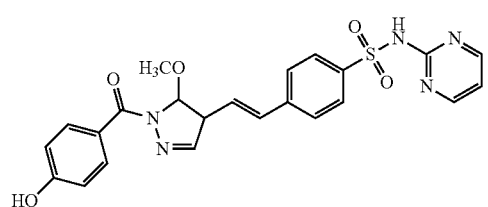
474 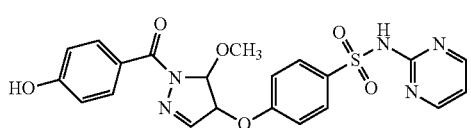

-continued
| 475 | 476 |
|---|---|
| 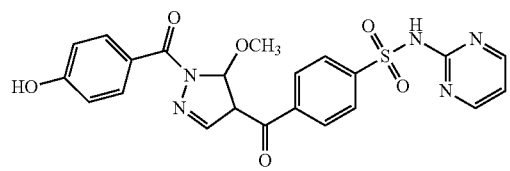 | 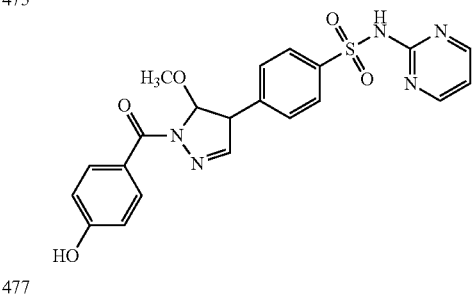 |
| 477 | 478 |
| 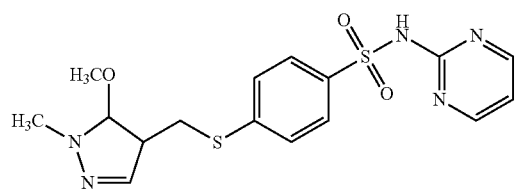 | |
| 479 | 480 |
| 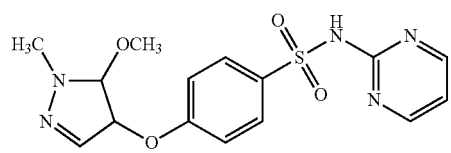 | |
| 481 | 482 |
| 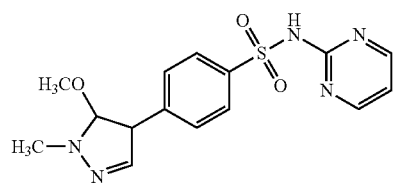 | |
| 483 | 484 |
| 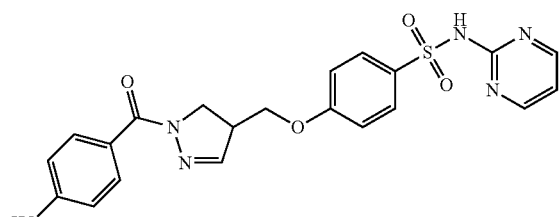 | |
| 485 | 486 |
| 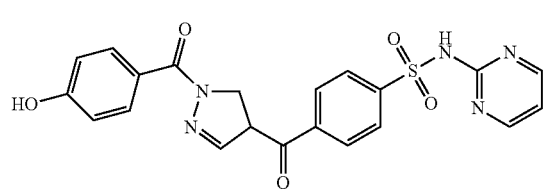 | |
| 487 | 488 |
| 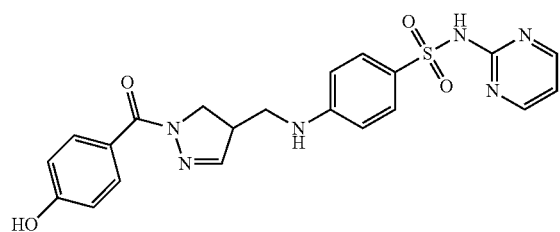 | 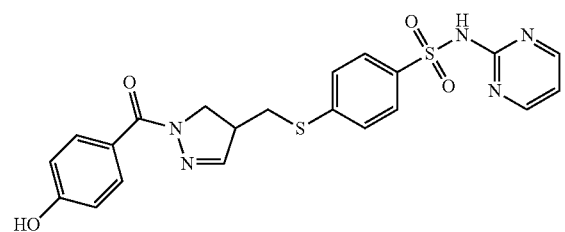 |

-continued
489
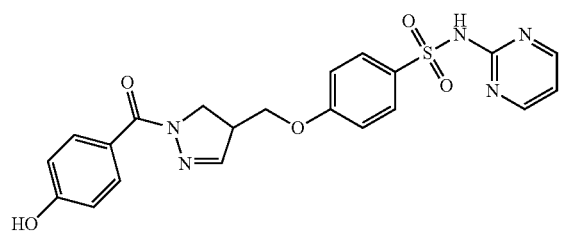
490
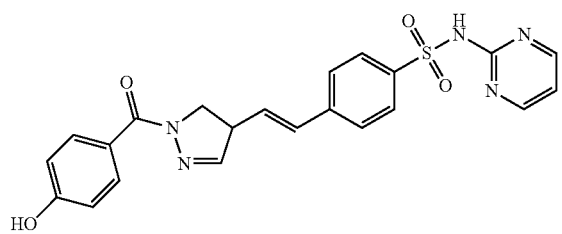
491
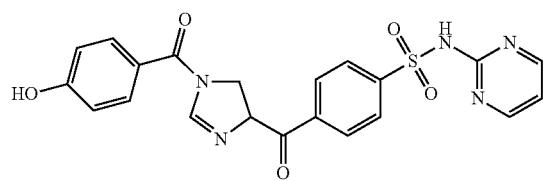
492
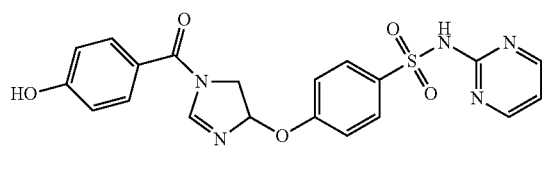
493
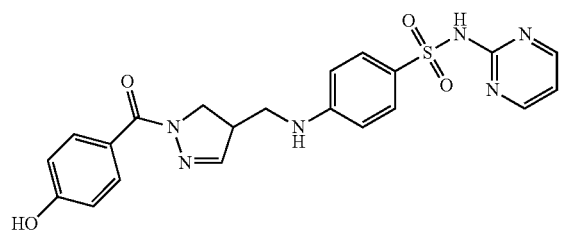
494
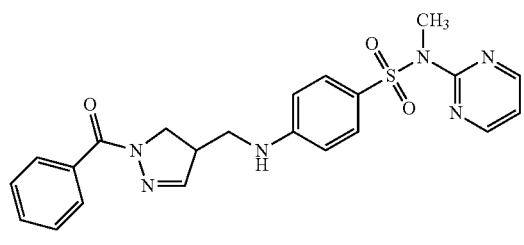
495
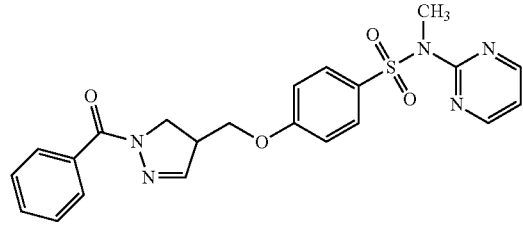
496
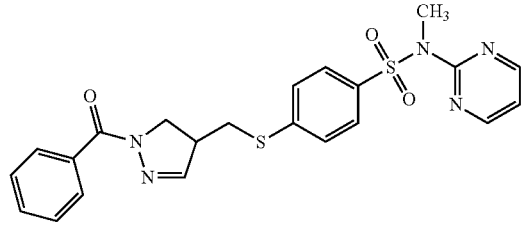
498
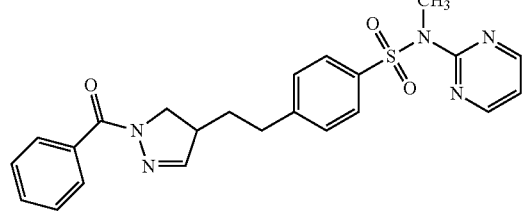
499
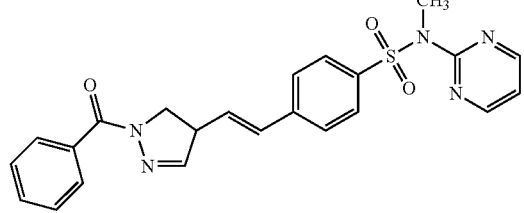
500
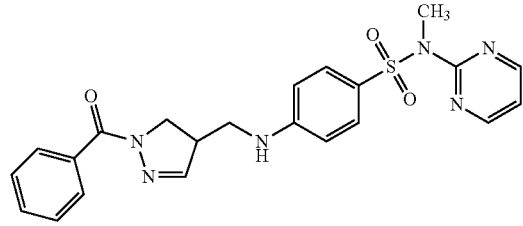
501
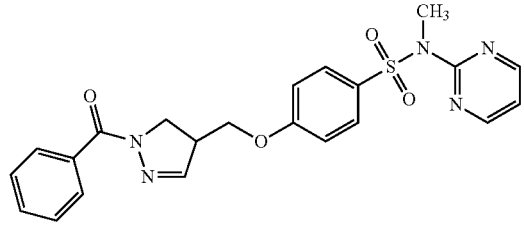
502
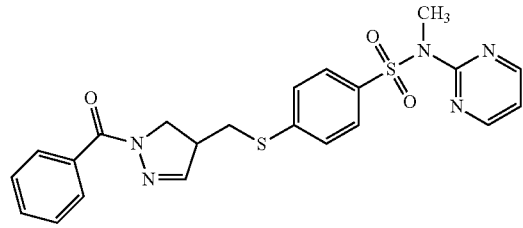
503
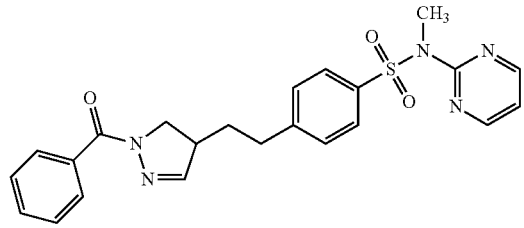

-continued
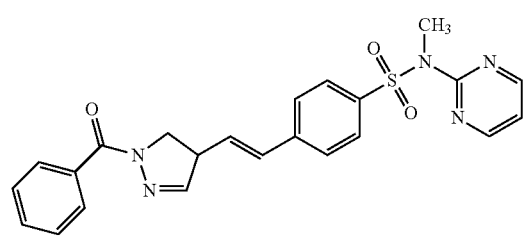
504
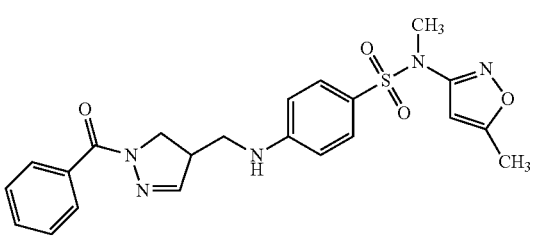
505
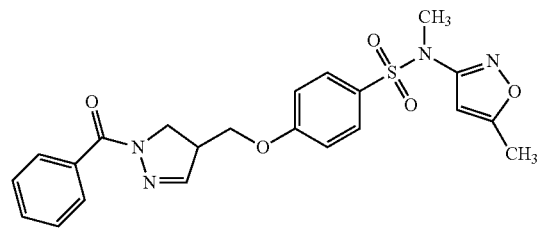
506
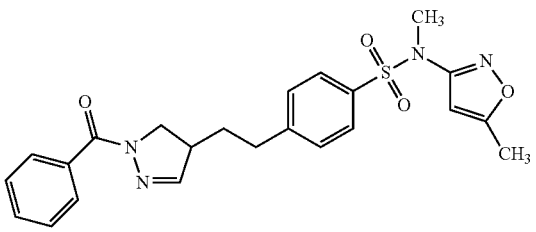
507
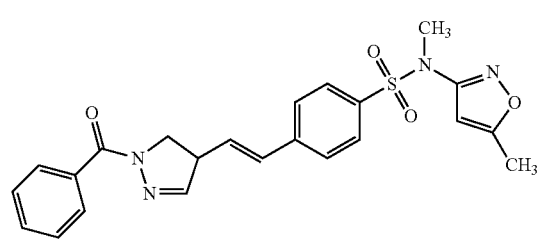
508
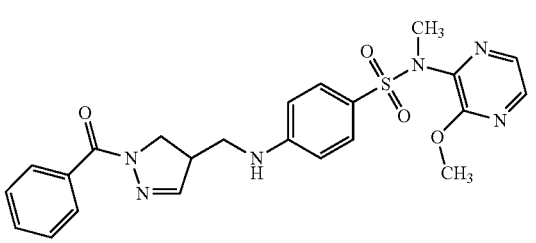
509
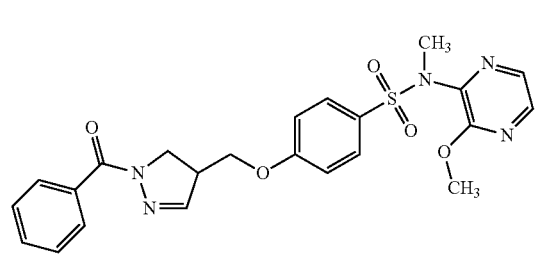
510
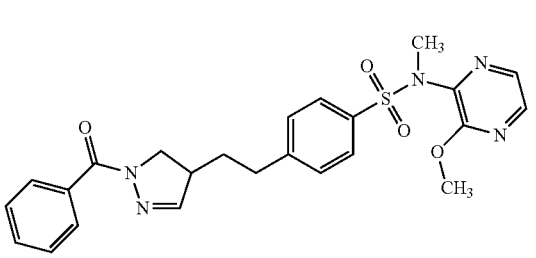
511
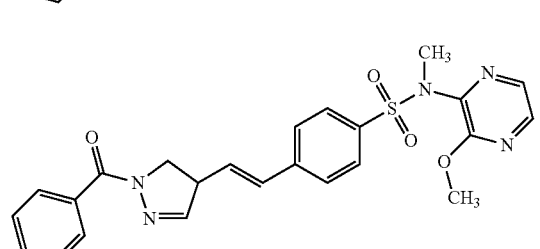
512
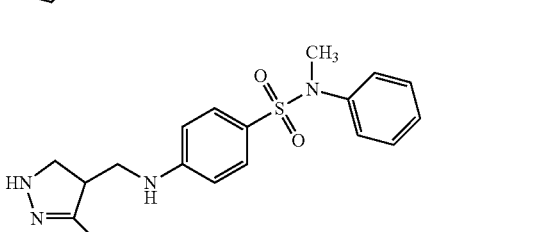
513
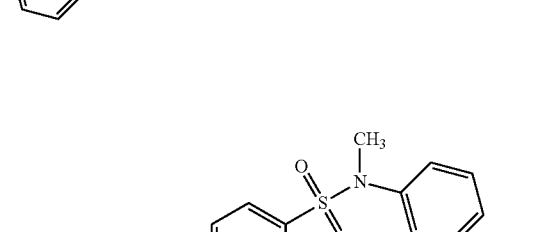
514
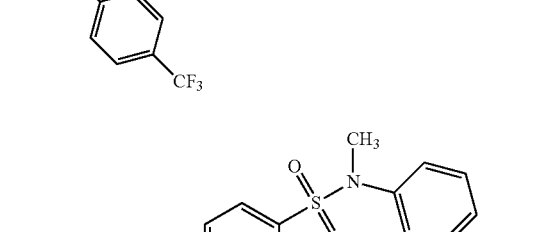
515
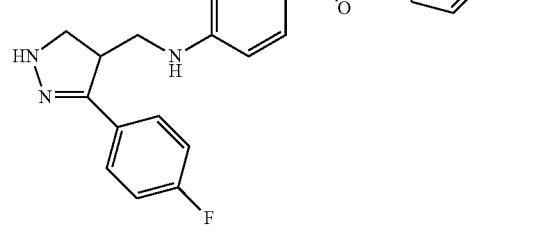

83 84
-continued
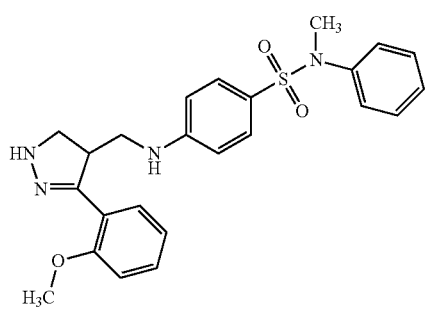
516
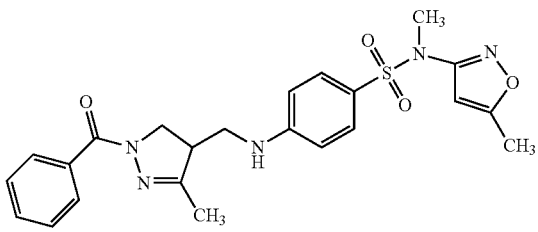
517
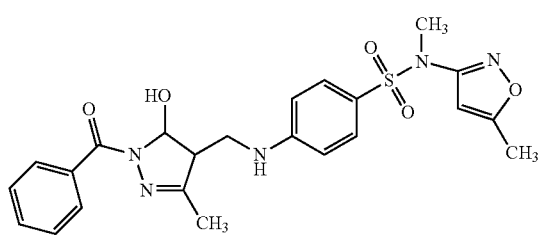
518
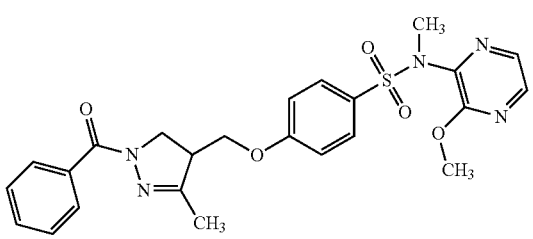
519
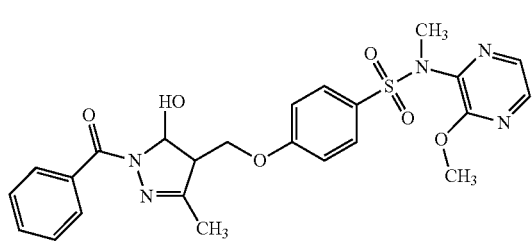
520
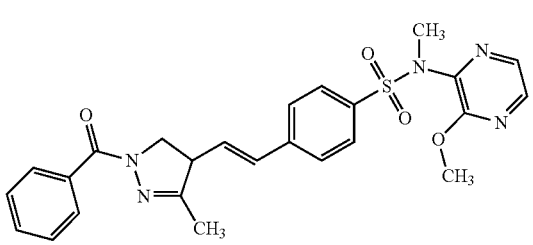
521
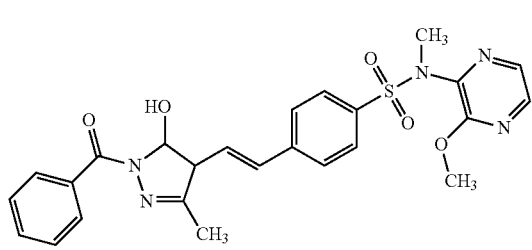
522
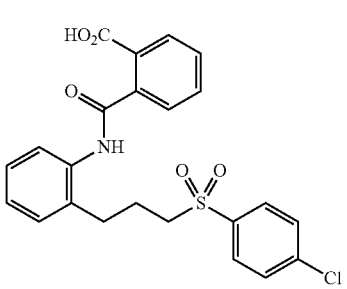
72
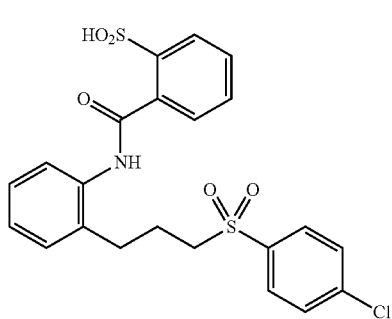
73
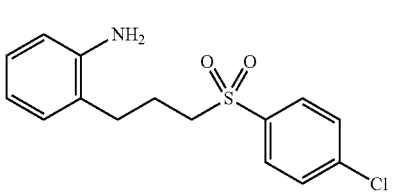
74

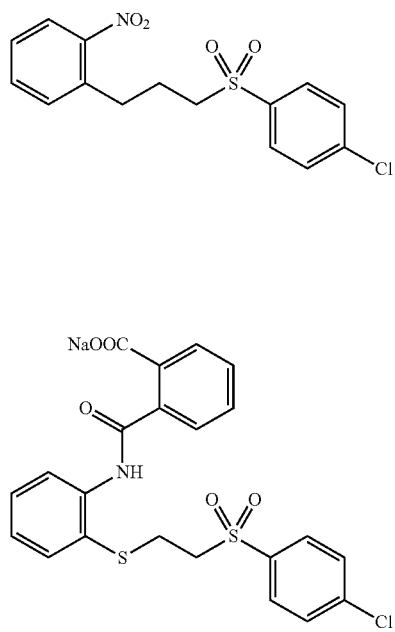
75
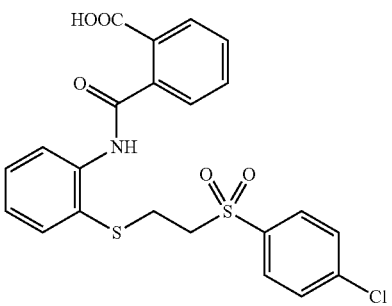
389
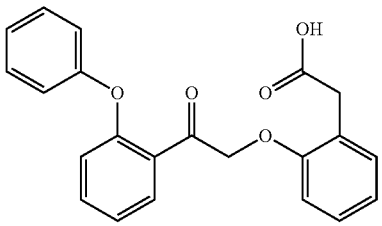
390
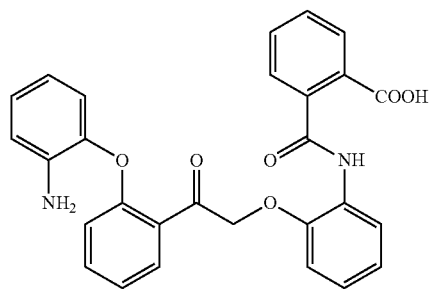
391
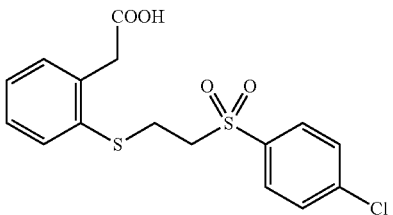
392
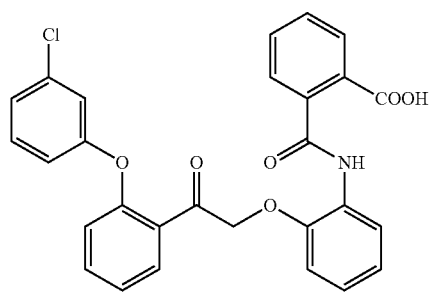
393
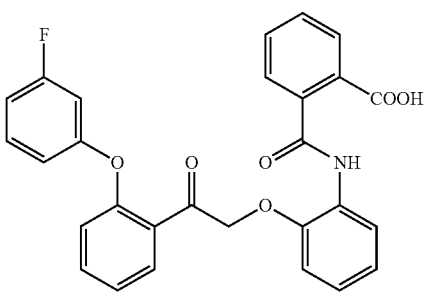
394
395
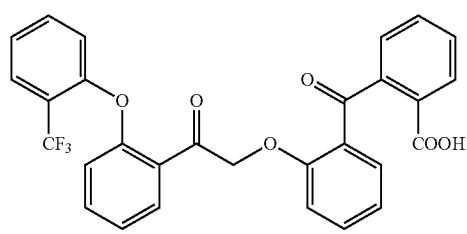
400
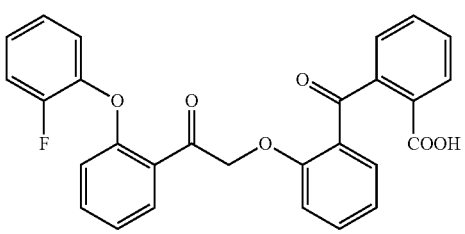
401

-continued

427 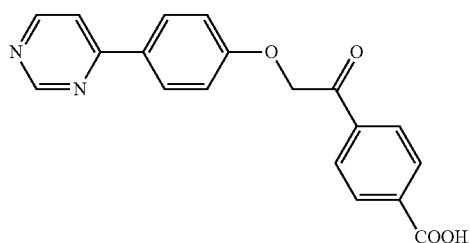
435 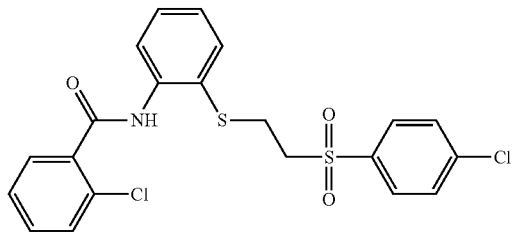
540 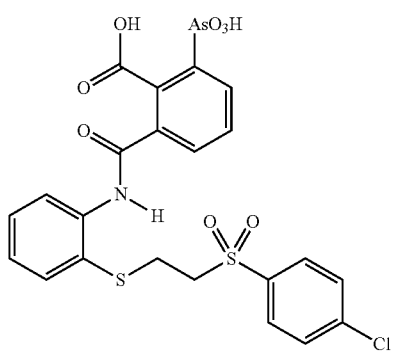
541 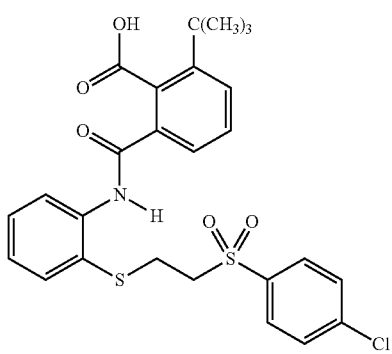
542 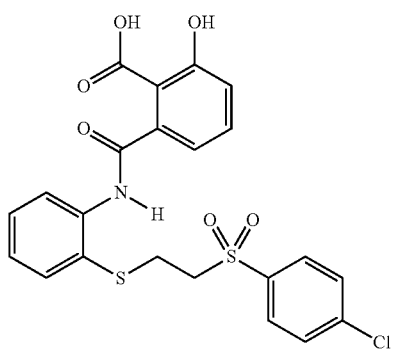
543 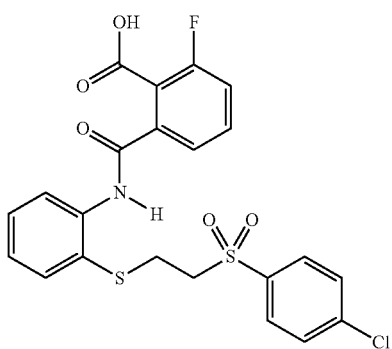
544 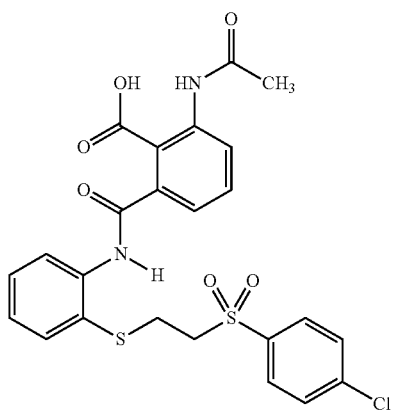
545 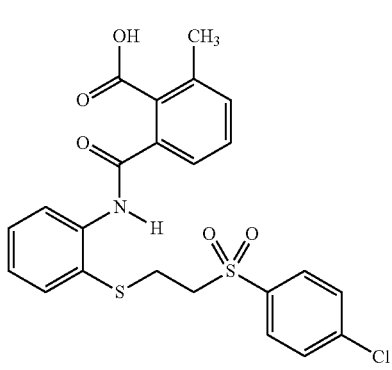

-continued
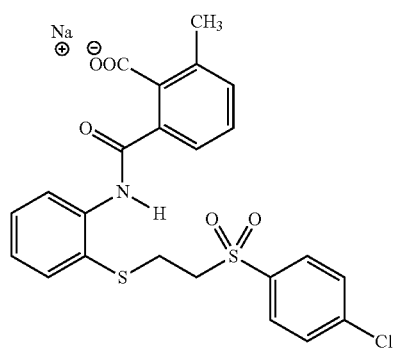
546
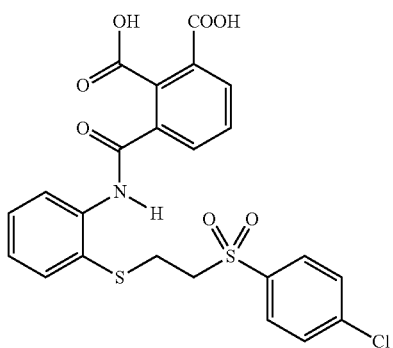
547
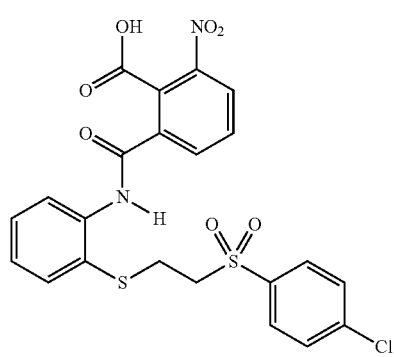
548
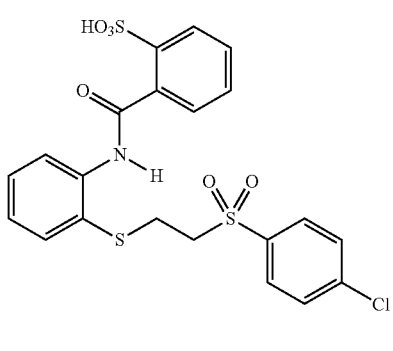
549
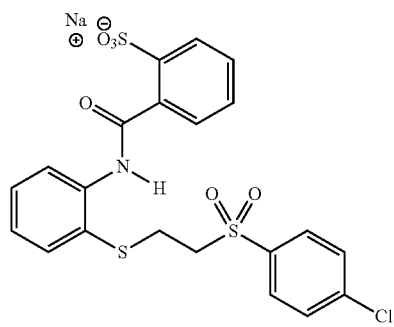
550
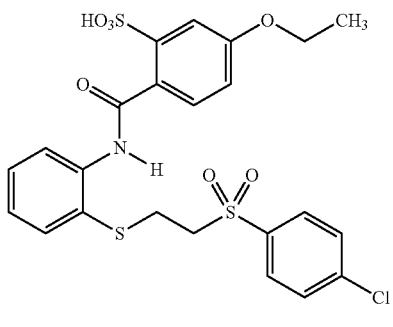
551
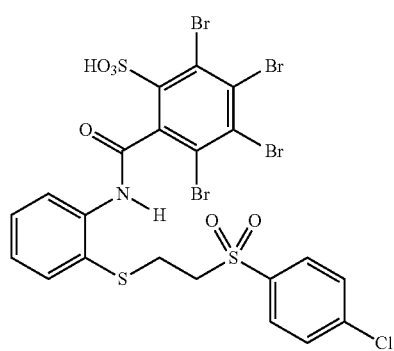
552
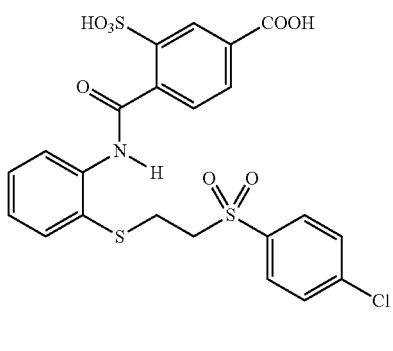
553

-continued
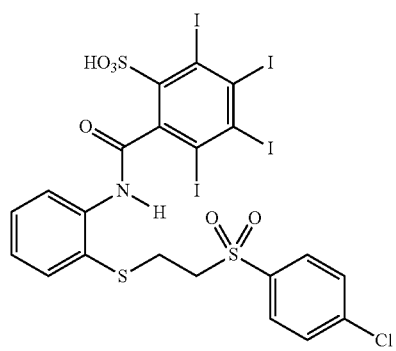
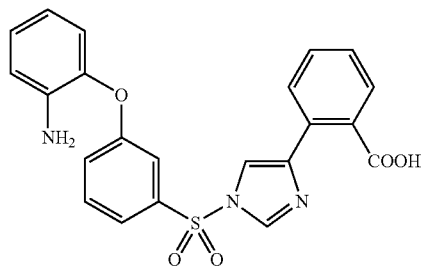
554
399
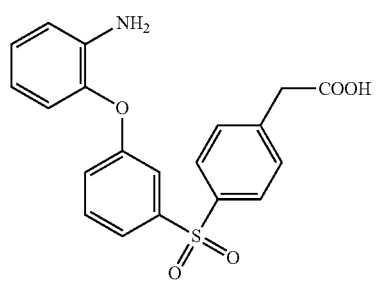
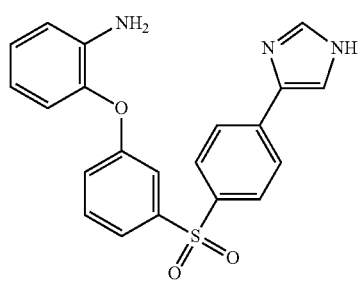
410
411
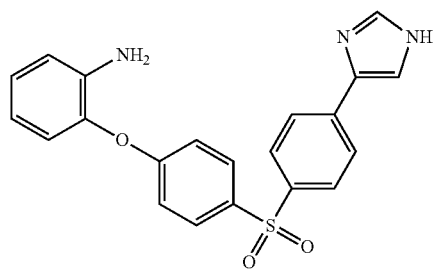
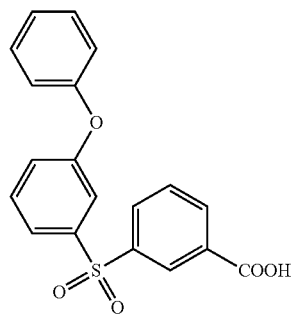
412
539
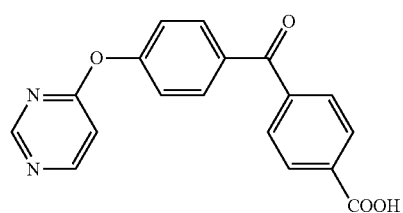
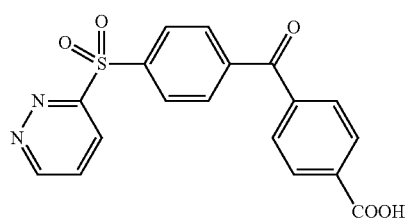
418
419
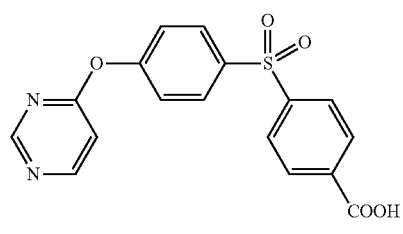
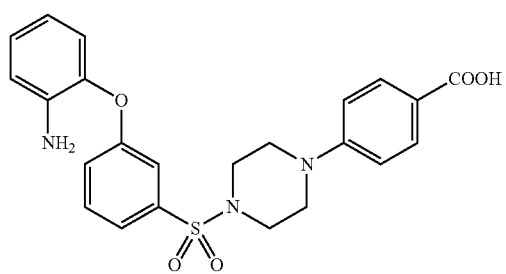
421
396

-continued
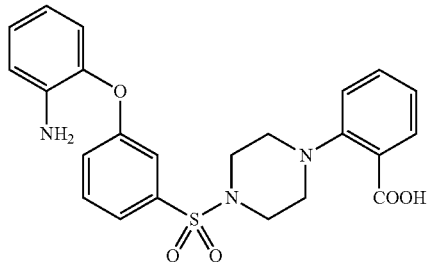
397
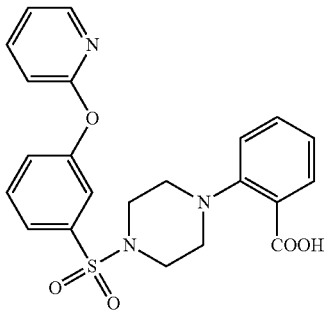
523
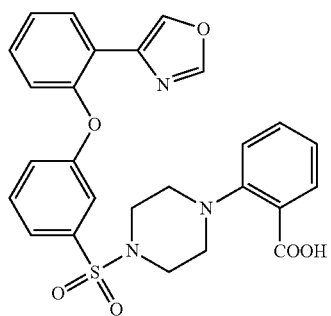
524
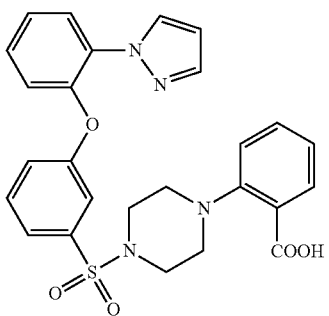
525
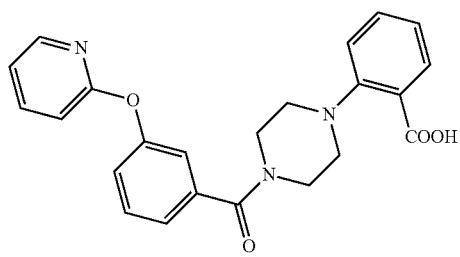
526
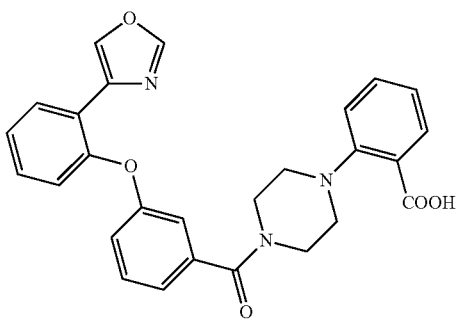
527
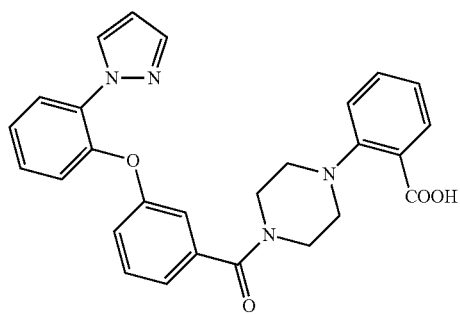
528
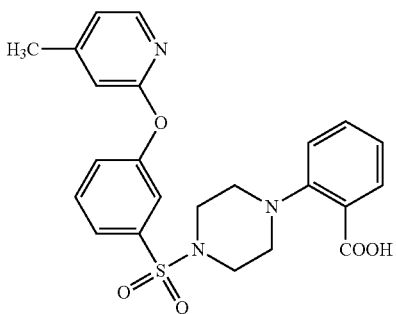
529

-continued
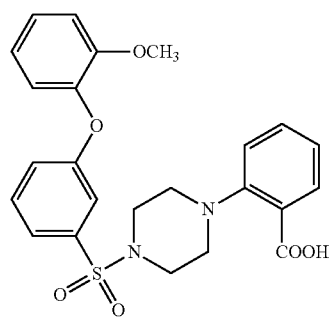
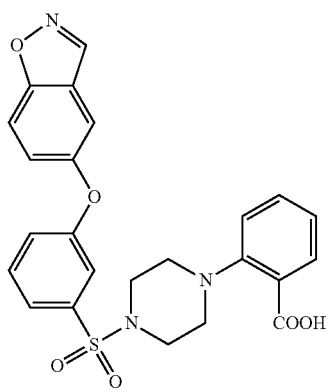
530
531
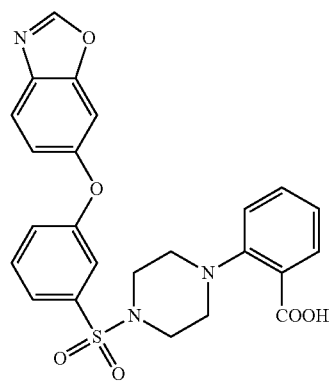
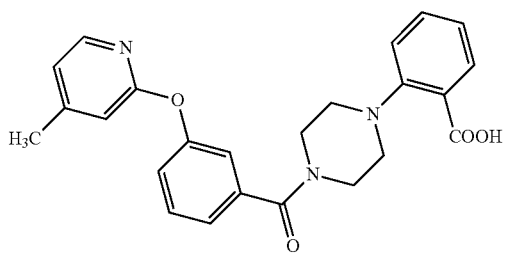
532
533
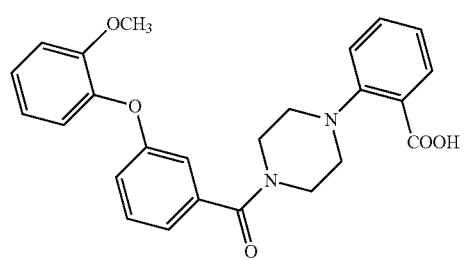
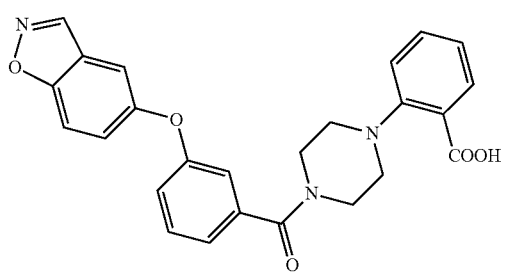
534
535
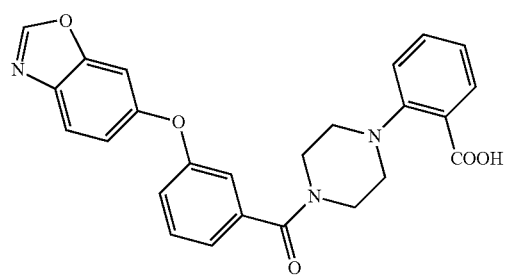
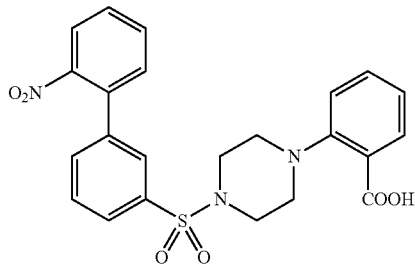
536
555
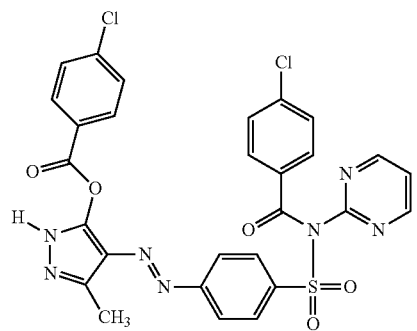
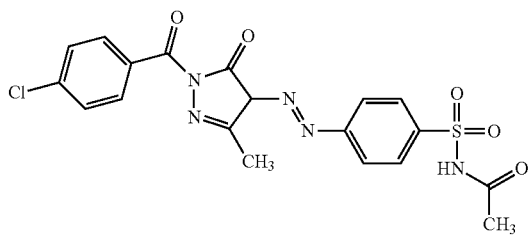
340
381

-continued

386 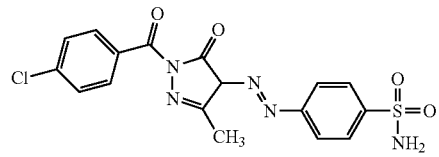

387 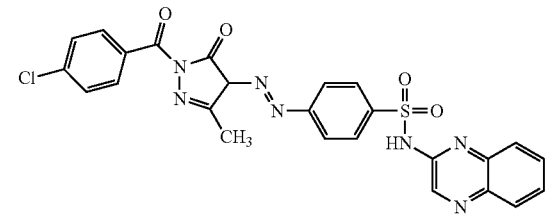

537 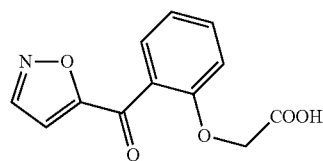

538

428 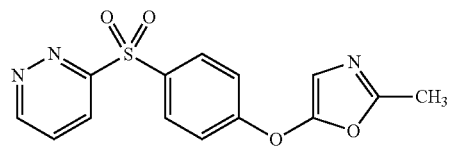

430

342 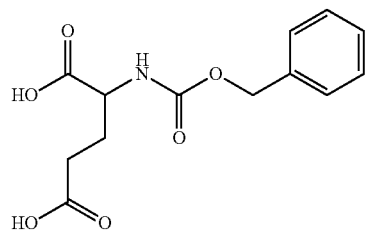

343

344 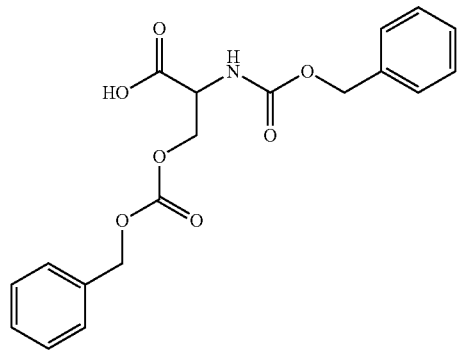

354 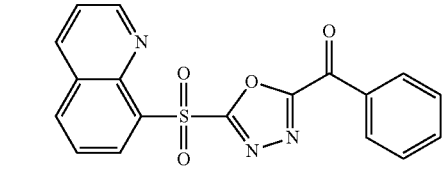

Embodiments of the invention encompass stereoisomers and optical isomers of the compounds described above including, e.g., mixtures of enantiomers, individual enantiomers and diastereomers, which can arise as a consequence of structural asymmetry of atoms in the compounds of the invention. Such embodiments further include the purified enantiomers, which may or may not contain trace amounts of a non-selected enantiomer or diastereomer.

Some embodiments of the invention include salts of the compounds described above. In general, the term salt can refer to an acid and/or base addition salt of a compound. For example, an acid addition salt can be formed by adding an appropriate acid to a free base form of any of the compounds embodied above. Similarly, a base addition salts can be formed by adding an appropriate base to a free base form of any of the compounds described above. Examples of suitable salts include, but are not limited to, sodium, potassium, carbonate, methylamine, hydrochloride, hydrobromide, acetate, fumate, maleate, oxalate, and succinate salts. Methods for preparing free base forms of compounds such as those described herein and acid addition or base addition salts of such compounds are well known in the art, and any such method may be used to prepare the acid or base addition salts of embodiments of the invention.

Other embodiments of the invention include solvates or hydrates of the compounds of the invention. In some cases, hydration of a compound may occur during manufacture of the compounds or compositions including the compounds as a consequence of the method for preparing the compound or as a result of a specific step used to create a hydrate or solvate of the compound. In other cases, hydration may occur over time due to the hygroscopic nature of the compounds. Such hydrated compounds whether intentionally prepared or naturally produced are encompassed by the invention.

Embodiments of the invention also include derivatives of the compounds of the invention which may be referred to as "prodrugs." The term "prodrug" as used herein denotes a derivative of a known drug that may have enhanced delivery characteristics, enhanced therapeutic value as compared to the active form of the drug, sustained release characteristics, reduced side-effects, or combinations thereof. For example, in some embodiments, a prodrug form of a compound of the invention may be administered in an inactive form or a form having reduced activity that is transformed into an active or more active form of the drug by an enzymatic or chemical process. For instance, in some embodiments, a prodrug form of a compound such as those described above may include one or more metabolically cleavable groups that are removed by solvolysis, hydrolysis or physiological metabolisms to release the pharmaceutically active form of the compound. In other embodiments, prodrugs may include acid derivatives of the compounds of the invention. Acid derivatives are well known in the art and include, but are not limited to, esters or double esters such as, for example, (acyloxy) alkyl esters or ((alkoxycarbonyl)oxy)alkyl esters prepared by reaction of an acid on the parent molecule with a suitable alcohol. Without wishing to be bound by theory, the compounds of the invention may have activity in both their acid and acid derivative forms. However, the acid derivative form may exhibit enhanced solubility, tissue compatibility or delayed release in the mammalian organism (see, e.g., Bundgard, H., Design of Prodrugs, pp. 7-9, 21-24, Elsevier, Amsterdam 1985). In still other embodiments, prodrugs that include an amide may be prepared by reacting a parent compound containing an acid with an amine, and in yet other embodiments, simple aliphatic or aromatic esters derived from acidic groups pendent on a compound of this invention may be prepared as prodrugs.

Embodiments of the invention also include pharmaceutical compositions or formulations including at least one compound embodied hereinabove, an acid or base addition salt, hydrate, solvate or prodrug of the at least one compound and one or more pharmaceutically acceptable carriers or excipients. Pharmaceutical formulations and pharmaceutical compositions are well known in the art, and can be found, for example, in Remington's Pharmaceutical Sciences, Mack Publishing Co., Easton, Pa., USA, which is hereby incorporated by reference in its entirety. Any formulations described therein or otherwise known in the art are embraced by embodiments of the invention.

Pharmaceutical excipients are well known in the art and include, but are not limited to, saccharides such as, for example, lactose or sucrose, mannitol or sorbitol, cellulose preparations, calcium phosphates such as tricalcium phosphate or calcium hydrogen phosphate, as well as binders, such as, starch paste such as, for example, maize starch, wheat starch, rice starch, potato starch, gelatin, tragacanth, methyl cellulose, hydroxypropylmethylcellulose, sodium carboxymethylcellulose, polyvinyl pyrrolidone or combinations thereof.

In particular embodiments, pharmaceutical formulations may include the active compound described and embodied above, a pharmaceutically acceptable carrier or excipient and any number of additional or auxiliary components known in the pharmaceutical arts such as, for example, binders, fillers, disintegrating agents, sweeteners, wetting agents, colorants, sustained release agents, and the like, and in certain embodiments, the pharmaceutical composition may include one or more secondary active agents. Disintegrating agents, such as starches as described above, carboxymethyl-starch, cross-linked polyvinyl pyrrolidone, agar, alginic acid or a salt thereof, such as sodium alginate and combinations thereof. Auxiliary agents may include, for example, flow-regulating agents and lubricants, such as silica, talc, stearic acid or salts thereof, such as magnesium stearate or calcium stearate, polyethylene glycol and combinations thereof. In certain embodiments, dragee cores may be prepared with suitable coatings that are resistant to gastric juices, such as concentrated saccharide solutions, which may contain, for example, gum arabic, talc, polyvinyl pyrrolidone, polyethylene glycol, titanium dioxide, lacquer solutions and suitable organic solvents or solvent mixtures and combinations thereof. In order to produce coatings resistant to gastric juices, solutions of suitable cellulose preparations, such as acetylcellulose phthalate or hydroxypropylmethyl-cellulose phthalate may also be used. In still other embodiments, dye stuffs or pigments may be added to the tablets or dragee coatings, for example, for identification or in order to characterize combinations of active compound doses.

Pharmaceutical compositions of the invention can be administered to any animal, and in particular, any mammal, that may experience a beneficial effect as a result of being administered a compound of the invention including, but not limited to, humans, canines, felines, livestock, horses, cattle, sheep, and the like. The dosage or amount of at least one compound according to the invention provided pharmaceutical compositions of embodiments may vary and may depend, for example, on the use of the pharmaceutical composition, the mode of administration or delivery of the pharmaceutical composition, the disease indication being treated, the age, health, weight, etc. of the recipient, concurrent treatment, if any, frequency of treatment, and the nature of the effect desired and so on. Various embodiments of the invention include pharmaceutical compositions that include one or more compounds of the invention in an amount sufficient to treat or prevent diseases such as, for example, cancer. An effective amount of the one or more compounds may vary and may be, for example, from about 0.001 mg to about 1000 mg or, in other embodiments, from about 0.01 mg to about 100 mg.

The pharmaceutical compositions of the invention can be administered by any means that achieve their intended purpose. For example, routes of administration encompassed by the invention include, but are not limited to, subcutaneous, intravenous, intramuscular, intraperitoneal, buccal, or ocular routes, rectally, parenterally, intrasystemically, intravaginally, topically (as by powders, ointments, drops or transdermal patch), oral or nasal spray are contemplated in combination with the above described compositions.

Embodiments of the invention also include methods for preparing pharmaceutical compositions as described above by, for example, conventional mixing, granulating, dragee-making, dissolving, lyophilizing processes and the like. For example, pharmaceutical compositions for oral use can be obtained by combining the one or more active compounds with one or more solid excipients and, optionally, grinding the mixture. Suitable auxiliaries may then be added and the mixture may be processed to form granules which may be used to form tablets or dragee cores. Other pharmaceutical solid preparations include push-fit capsules containing granules of one or more compound of the invention that can, in some embodiments, be mixed, for example, with fillers, binders, lubricants, stearate, stabilizers or combinations thereof. Push-fit capsules are well known and may be made of gelatin alone or gelatin in combination with one or more plasticizer such as glycerol or sorbitol to form a soft capsule. In embodiments in which soft capsules are utilized, compounds of the invention may be dissolved or suspended in one or more suitable liquids, such as, fatty oils or liquid paraffin and, in some cases, one or more stabilizers.

Liquid dosage formulations suitable for oral administration are also encompassed by embodiments of the invention. Such embodiments, may include one or more compounds of the invention in pharmaceutically acceptable emulsions, solutions, suspensions, syrups, and elixirs that may contain, for example, one or more inert diluents commonly used in the art such as, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (for example, cottonseed, groundnut, corn, germ, olive, castor, and sesame oils), glycerol, fatty acid derivatives of glycerol (for example, labrasol), tetrahydrofurfuryl alcohol, polyethylene glycols and fatty acid esters of sorbitan, and mixtures thereof. Suspensions may further contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations for parenteral administration may include one or more compounds of the invention in water-soluble form, for example, water-soluble salts, alkaline solutions, and cyclodextrin inclusion complexes in a physiologically acceptable diluent which may be administered by injection. Physiologically acceptable diluent of such embodiments, may include, for example, sterile liquids such as water, saline, aqueous dextrose, other pharmaceutically acceptable sugar solutions; alcohols such as ethanol, isopropanol or hexadecyl alcohol; glycols such as propylene glycol or polyethylene glycol; glycerol ketals such as 2,2-dimethyl-1,3-dioxolane-4-methanol; ethers such as poly(ethyleneglycol)-400; pharmaceutically acceptable oils such as fatty acid, fatty acid ester or glyceride, or an acetylated fatty acid glyceride. In some embodiments, formulations suitable for parenteral administration may additionally include one or more pharmaceutically acceptable surfactants, such as a soap or detergent; suspending agent such as pectin, carbomers, methylcellulose, hydroxypropylmethylcellulose, or carboxymethylcellulose; an emulsifying agent; pharmaceutically acceptable adjuvants or combinations thereof. Additional pharmaceutically acceptable oils which may be useful in such formulations include those of petroleum, animal, vegetable or synthetic origin including, but not limited to, peanut oil, soybean oil, sesame oil, cottonseed oil, olive oil, sunflower oil, petrolatum, and mineral oil; fatty acids such as oleic acid, stearic acid, and isostearic acid; and fatty acid esters such as ethyl oleate and isopropyl myristate. Additional suitable detergents include, for example, fatty acid alkali metal, ammonium, and triethanolamine salts; cationic detergents such as dimethyl dialkyl ammonium halides, alkyl pyridinium halides, and alkylamine acetates; and anionic detergents, such as alkyl, aryl, and olefin sulfonates, alkyl, olefin, ether and monoglyceride sulfates, and sulfosuccinates. In some embodiments, non-ionic detergents including, but not limited to, fatty amine oxides, fatty acid alkanolamides and polyoxyethylenepolypropylene copolymers or amphoteric detergents such as alkyl-β-aminopropionates and 2-alkylimidazoline quaternary salts, and mixtures thereof may be useful in parenteral formulations of the invention.

In particular embodiments, alkaline salts such as ammonium salts of compounds of the invention may be prepared by the addition of, for example, Tris, choline hydroxide, Bis-Tris propane, N-methylglucamine, or arginine to a free base form of the compound. Such alkaline salts may be particularly well suited for use as parenterally administered forms of the compounds of the invention. Buffers, preservatives, surfactants and so on may also be added to formulations suitable for parenteral administration. For example, suitable surfactants may include polyethylene sorbitan fatty acid esters, such as sorbitan monooleate, and the high molecular weight adducts of ethylene oxide with a hydrophobic base, formed by the condensation of propylene oxide with propylene glycol.

Pharmaceutical compositions for parenteral administration may contain from about 0.5 to about 25% by weight of one or more of the compounds of the invention and from about 0.05% to about 5% suspending agent in an isotonic medium. In various embodiments, the injectable solution should be sterile and should be fluid to the extent that it can be easily loaded into a syringe. In addition, injectable pharmaceutical compositions may be stable under the conditions of manufacture and storage and may be preserved against the contaminating action of microorganisms such as bacteria and fungi.

Topical administration includes administration to the skin or mucosa, including surfaces of the lung and eye. Compositions for topical administration, may be prepared as a dry powder which may be pressurized or non-pressurized. In non-pressurized powder compositions, the active ingredients in admixture are prepared as a finely divided powder. In such embodiments, at least 95% by weight of the particles of the admixture may have an effective particle size in the range of 0.01 to 10 micrometers. In some embodiments, the finely divided admixture powder may be additionally mixed with an inert carrier such as a sugar having a larger particle size, for example, of up to 100 micrometers in diameter. Alternatively, the composition may be pressurized using a compressed gas, such as nitrogen or a liquefied gas propellant. In embodiments, in which a liquefied propellant medium is used, the propellant may be chosen such that the compound and/or an admixture including the compound do not dissolve in the propellant to any substantial extent. In some embodiments, a pressurized form of the composition may also contain a surface-active agent. The surface-active agent may be a liquid or solid non-ionic surface-active agent or may be a solid anionic surface-active agent, which in certain embodiments, may be in the form of a sodium salt.

Compositions for rectal or vaginal administration may be prepared by mixing the compounds or compositions of the invention with suitable non-irritating excipients or carriers such as for example, cocoa butter, polyethylene glycol or a suppository wax. Such carriers may be solid at room temperature but liquid at body temperature and therefore melt in the rectum or vaginal cavity and release the drugs.

In still other embodiments, the compounds or compositions of the invention can be administered in the form of liposomes. Liposomes are generally derived from phospholipids or other lipid substances that form mono- or multilamellar hydrated liquid crystals when dispersed in an aqueous medium. Any non-toxic, physiologically acceptable and metabolizable lipid capable of forming liposomes can be used, and in particular embodiments, the lipids utilized may be natural and/or synthetic phospholipids and phosphatidyl cholines (lecithins). Methods to form liposomes are known in the art (see, for example, Prescott, Ed., Meth. Cell Biol. 14:33 (1976), which is hereby incorporated by reference in its entirety). Compositions including one or more compounds of the invention in liposome form can contain, for example, stabilizers, preservatives, excipients and the like.

In yet other embodiments, one or more compounds of the invention may be formulated for in vitro use in, for example, an assay for inhibition of AKT or an assay that requires inhibition of AKT. In such embodiments, the composition of the invention may include one or more compounds presented herein above in a carrier that is suitable for an assay. Such carriers may be in solid, liquid or gel form and may or may not be sterile. Examples of suitable carriers include, but are not limited to, dimethylsulfoxide, ethanol, dichloromethane, methanol and the like.

Embodiments of the invention are further directed to methods for using the compounds and compositions described herein above. For example, in some embodiments, the compounds or compositions of the invention may be used in the treatment or prevention of an AKT-mediated condition. Methods of such embodiments may generally include the step of administering to a subject in need of such treatment an effective amount of a compound or a composition selected from one or more of the embodiments described above to treat, prevent or ameliorate a AKT-mediated condition, and in particular embodiments, the condition or disease may be a proliferative disorder such as, for example, cancer. In other embodiments, methods of the invention may include the step of administering to a subject in need of such treatment an effective amount of a compound or composition selected from one or more of the embodiments described above to treat, prevent or ameliorate cancer or a cell proliferation related disease. Cancers that may be treated using compositions of the invention include but not limited to skin cancers, breast cancer, colorectal cancer, colon cancer, esophageal cancer, mesothelioma, ovarian cancer, and gastric cancer. In still other embodiments, the compound or composition of the invention may be used to treat cancer by blocking tumorigenesis, inhibiting metastasis or inducing apoptosis.

The type of proliferative disorder or cancer that can be treated using compounds of the invention is not limited in embodiments of the invention. For example, cancers that may be treated using compounds of any or formulae I-VIII described above include, but are not limited to, breast cancer, lung cancer, head and neck cancer, brain cancer, abdominal cancer, colon cancer, colorectal cancer, esophageal cancer, gastrointestinal cancer, glioma, liver cancer, tongue cancer, neuroblastoma, osteosarcoma, ovarian cancer, pancreatic cancer, renal cancer, prostate cancer, retinoblastoma, Wilm's tumor, multiple myeloma, skin cancer, lymphoma and blood cancer, and various forms of skin cancer and melanoma. In certain embodiments, the cancer treated using the methods of embodiments of the invention may be prostate, lung, breast, ovarian, pancreatic, skin cancer, and melanoma, and in particular embodiments, the cancer treated may be skin cancer or melanoma.

Other embodiments of the invention include methods in which one or more of the compounds or compositions described herein may be administered to a subject to inhibit or prevent a healthy subject from developing a AKT-mediated condition. As such, the compounds and compositions of the invention may be used as a prophylactic that prevents or inhibits the development of a AKT-mediated condition or disease. In such embodiments, the compound or composition may be administered to a subject who does not have an AKT-mediated condition or is not exhibiting the symptoms of an AKT-mediated condition but may be at risk of developing one to prevent or inhibit the onset of such a disorder. For example, the individual may be genetically predisposed to an AKT-mediated condition or has increased likelihood of developing such a disorder as a result of, for instance, an injury, surgery or other medical condition.

In general, methods of embodiments of the invention may include the step of administering or providing an "effective amount" or a "therapeutically effective amount" of a compound or composition of the invention to an individual. In such embodiments, an effective amount of the compounds of the invention may be any amount that produces the desired effect. As described above, this amount may vary depending on, for example, the circumstances under which the compound or composition is administered (e.g., to incite treatment or prophylactically), the type of individual, the size, health, etc. of the individual and so on. The dosage may further vary based on the severity of the condition. For example, a higher dose may be administered to treat an individual with a well-developed inflammatory condition, compared to the amount used to prevent a subject from developing the inflammatory condition. Those skilled in the art can discern the proper dosage based on such factors. For example, in some embodiments, the dosage may be within the range of about 0.01 mg/kg body weight to about 300 mg/kg body weight or between about 0.1 mg/kg body weight and about 100 mg/kg body weight, and in particular embodiments, the dosage may be from about 0.1 mg/kg body weight to about 10 mg/kg body weight.

The administration schedule may also vary. For example, in some embodiments, the compounds or compositions of the invention may be administered in a single dose once per day or once per week. In other embodiments, the compounds or compositions of the invention may be administered in two, three, four or more doses per day or per week. For example, in one embodiment, an effective amount for a single day may be divided into separate dosages that may contain the same or a different amount of the compound or composition and may be administered several times throughout a single day. Without wishing to be bound by theory, the dosage per administration and frequency of administration may depend, for example, on the specific compound or composition used, the condition being treated, the severity of the condition being treated, and the age, weight, and general physical condition of the individual to which the compound or composition is administered and other medications which the individual may be taking. In another exemplary embodiment, treatment may be initiated with smaller dosages that are less than the optimum dose of the compound, and the dosage may be increased incrementally until a more optimum dosage is achieved.

In each of the embodiments above, the compound administered can be provided as a pharmaceutical composition including compound as described above and a pharmaceutically acceptable excipient, or a pure form of the compound may be administered.

In additional embodiments, the compound or composition of the invention may be used alone or in combination with one or more additional agents. For example, in some embodiments, a compound or composition of invention may be formulated with one or more additional anti-inflammatory agents, anti-cancer agents or combinations thereof such that the pharmaceutical composition obtained including the compound or composition of the invention and the one or more additional agents can be delivered to an individual in a single dose. In other embodiments, the compound or composition of the invention may be formulated as a separate pharmaceutical composition that is delivered in a separate dose from pharmaceutical compositions including the one or more additional agents. In such embodiments, two or more pharmaceutical compositions may be administered to deliver effective amounts of a compound or composition of the invention and the one or more additional agents. For example, in some embodiments, one or more compound of formula I-VIII may be administered in combination with or co-administered with doxorubicin, paclitaxel, methotrexate, tamoxifen, cyclophosphamide, vincristine, etoposide, streptozotocin and 5-fluorouracil, and in particular embodiments, one or more of the compounds of the invention may be administered with paclitaxel.

Method of certain embodiments of the invention may include the step of selectively inhibiting AKT by, for example, contacting AKT with a compound or composition according to the invention. In such embodiments, the AKT may be contained within a living organism, living tissue or one or more living cells to provide in vivo inhibition, or the AKT may be isolated to provide in vitro inhibition. For example, compounds or compositions described herein may be useful in in vitro drug discovery assays in which the efficacy and/or potency of other AKT inhibitors. The amount of the compound or composition of the invention used to inhibit AKT not necessarily the same when used in vivo compared to in vitro. For example, factors such as pharmacokinetics and pharmacodynamics of a particular compound may require that a larger or smaller amount of the compound be used for in vivo applications. In another embodiment, a compound or composition according to the invention may be used to form a co-crystallized complex with AKT protein.

By "selectively" is meant that the compounds and compositions described herein inhibit the activity of AKT without interfering with the activity of the other proteins. For example, compounds or compositions of the invention can be administered to a cell that contains AKT, phosphorylated AKT or AKT that is otherwise activated or not activated as well as other proteins such as, for example, TORC2, PDK1, FKHR, AFX, GSK-3β, c-RAF, Flt3, JNK2α2, JNK3, Lck, Lyn, Tie2, TrkB, IGF-R, ERK1, ERK2, MEK1, PRAK, Yeo and/or ZAP-70. For instance, in some embodiments, the method of the invention can inhibit greater than about 80% of the activity of AKT while inhibiting less than about 5%, about 10%, about 20% or about 30% of the activity of other proteins such as those listed above.

One skilled in the art can evaluate the ability of a compound to inhibit or modulate the activity of a AKT and/or prevent, treat, or inhibit an conditions associated with AKT by one or more assays known in the art.

EXAMPLES

Example 1

Synthesis

The compounds of the invention can be synthesized by any method known in the art, and embodiments of the invention further include methods for preparing or the compounds described above. All commercial reagents were used without further purification. Analytical thin-layer chromatography (TLC) was carried out on pre-coated Silica Gel F254 plates. TLC plates were visualized with UV light (254 nm). $^1$H NMR spectra were recorded at 250, 300, or 500 MHz and $^{13}$C NMR at 62.5, 75, or 125 MHz. Chemical shifts (δ) are expressed in ppm and are internally referenced (7.26 ppm for $^1$H NMR and 77.00 ppm for $^{13}$C NMR in CDCl$_3$, 2.50 ppm for $^1$H NMR and 39.50 ppm for $^{13}$C NMR in DMSO-d$_6$). Mass spectra and high resolution mass spectra were obtained in the Mass Spectrometry Laboratory in the Department of Chemistry at the University of Arizona. Various properties of the synthesized compounds are provided in table I below. Melting points are uncorrected.

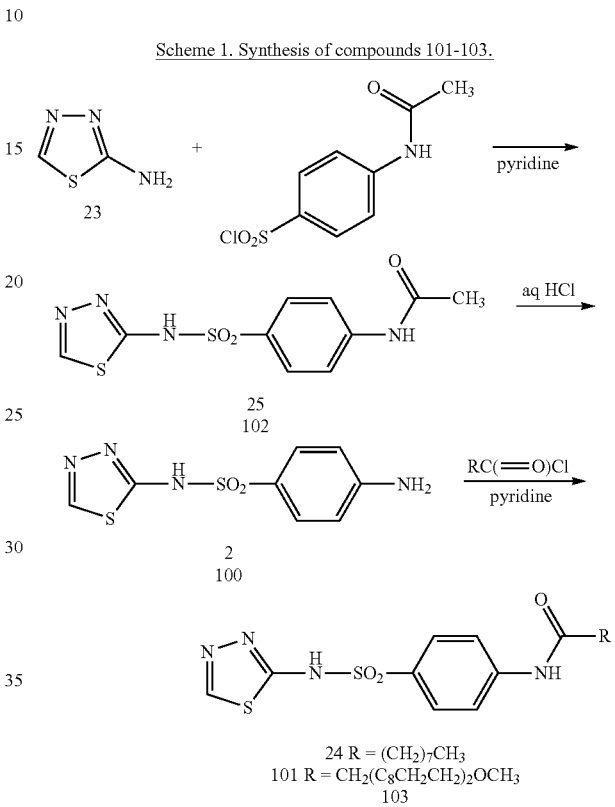

Scheme 1. Synthesis of compounds 101-103.

N-(4-(N-1,3,4-Thiadiazol-2-ylsulfamoyl)phenyl)acetamide (102). 2-Amino-1,3,4-thiadiazole (500 mg, 4.95 mmol) was suspended in pyridine (1.26 mL). p-Acetamidobenzenesulfonyl chloride (1.2 g, 5.15 mmol) was added and the mixture was heated to 95° C. for 1 h. The mixture was dissolved in 10% aqueous HCl and extracted with ethyl acetate. The organic extracts were washed with water and dried over anhydrous Na$_2$SO$_4$. Evaporation of the solvent yielded the crude product (1.4 g, 4.7 mmol, 95%). Recrystallization from CH$_2$Cl$_2$/MeOH gave pure product, mp 216-217° C. (lit$^1$ mp 214-215° C.); $^1$H NMR (250 MHz, CDCl$_3$) δ 2.07 (3, s), 7.73 (4, s), 8.74 (1, s), 10.35 (1, s), 14.35 (1, br s); $^{13}$C NMR (62.5 MHz, DMSO) δ 24.2, 118.7, 127.0, 135.6, 143.0, 144.9, 167.2, 169.

4-Amino-N-(1,3,4-thiadiazol-2-yl)benzenesulfonamide (100). Compound 102 (1.0 g, 3.6 mmol) was suspended in 3N HCl (10 mL) and heated to reflux for 30 min. The acidic mixture was neutralized with Na$_2$CO$_3$ solution. The precipitated product was collected by filtration, washed with water, and dried to give the product (450 mg, 1.8 mmol, 49%), mp 226° C. (lit$^1$ mp 221-222° C.); $^1$H NMR (250 MHz, CDCl$_3$) δ 5.95 (2, s), 6.57 (2, d, J=6.5 Hz), 7.41 (2, d, J=6.5 Hz), 8.68 (1, s), 14.03 (1, br s).

N-(4-(N-1,3,4-Thiadiazol-2-ylsulfamoyl)phenyl)decanamide (101). Compound 100 (50 mg, 0.20 mmol) was suspended in pyridine (0.3 mL). Decanoyl chloride (39.1 mg, 0.21 mmol) was added gradually over 15 min. The reaction mixture was heated to 95° C. and stirred at this temperature for 1 h, then poured into 10% aqueous HCl solution and extracted with EtOAc (3×0.5 mL). The combined organic extracts were washed with water (3×5 mL), brine (3×5 mL), and dried over anhydrous Na$_2$SO$_4$. Evaporation of the solvent yielded the product (80 mg, 0.20 mmol, 95%). It was recrystallized from hexanes/ethyl acetate to yield an analytical sample, mp 151-152° C.; $^1$H NMR (250 MHz, CD$_3$OD) δ 0.88 (3, t, J=7.5 Hz), 1.24-1.45 (12, m), 1.68 (2, t, J=7.5 Hz), 2.37 (2, t, J=7.5 Hz), 7.72 (2, d, J=8.5 Hz), 7.79 (2, d, J=8.5 Hz), 8.49 (1, S); $^{13}$C NMR (125 MHz, CD$_3$OD) δ 14.4, 23.7, 26.7, 30.3, 30.4, 30.5, 30.6, 33.0, 38.1, 102.4, 128.3, 137.5, 144.0, 145.0, 170.0, 174.9; MS (ESI$^+$) 411.1 (M+H)$^+$; HRMS (IonSpec. HiRES ESL$^+$) calcd. for C$_{18}$H$_{27}$N$_4$O$_3$S$_2$ (M+H)$^+$ 411.1525, obsd. 411.1524.

Scheme 2. Synthesis of compound 104.

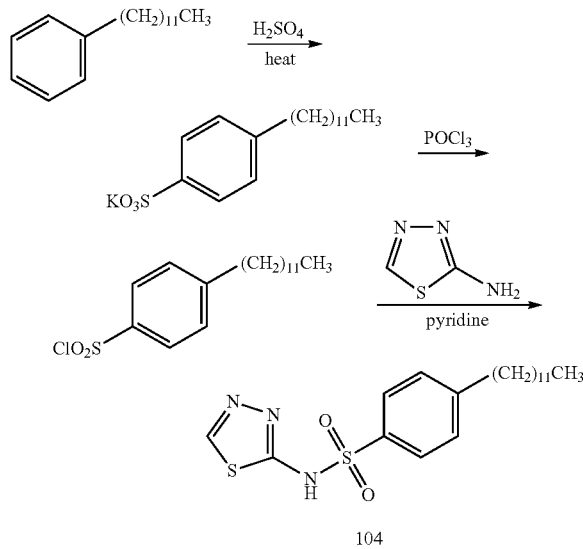

4-Dodecyl-N-(1,3,4-thiadiazol-2-yl)benzenesulfonamide (104). 2-Amino-1,3,4-thiadiazole (439 mg, 4.3 mmol) was suspended in pyridine (1.5 mL). p-Dodecylbenzenesulfonyl chloride (1.0 mg, 2.9 mmol) was added slowly at 0° C. The reaction mixture was then heated to 95° C. and was stirred at this temperature for 1 h. The reaction mixture was then added to aqueous 10% HCl (15 mL) and the resulting mixture extracted with ethyl acetate (3×30 mL). The organic extracts were washed with water (3×50 mL), brine (3×50 mL), dried over anhydrous Na$_2$SO$_4$, filtered, and volatiles evaporated to yield a solid mass. Chromatography on silica gel (70-230 mesh) eluted with 2% MeOH in CH$_2$Cl$_2$ gave the product (600 mg, 1.5 mmol, 51%). Recrystallization from hexanes: ethyl acetate (3:7) gave an analytical sample, mp 126-127° C.; $^1$H NMR (500 MHz, CDCl$_3$) δ 0.87 (3, t, J=6.5 Hz), 1.20-1.36 (18, m), 1.54-1.63 (2, m), 2.62 (2, t, J=7.5 Hz), 7.25 (2, d, J=8.0 Hz), 7.83 (2, d, J=8.0 Hz), 8.28 (1, s), 12.81 (1, br s); $^{13}$C NMR (125 MHz, CDCl$_3$) δ 14.0, 22.6, 29.2, 29.3, 29.4, 29.5, 29.6, 31.0, 31.8, 35.8, 126.4, 128.9, 138.0, 142.8, 148.5, 167.5; MS (LCQ, ESL$^+$) Calcd for C$_{20}$H$_{32}$N$_3$O$_2$S$_2$ 410.1936, found 410.10 (M+H)$^+$; HRMS (ESL$^+$, m/z) Calcd C$_{20}$H$_{32}$N$_3$O$_2$S$_2$ 410.1936, found 410.1932 (M+H)$^+$.

p-Dodecylbenzenesulfonyl Chloride. A mixture of 1-phenyldodecane (7.5 g, 30.5 mmol) and concentrated H$_2$SO$_4$ (8.4 mL) was stirred vigorously at 90° C. for 1 h, cooled to room temperature, and then gradually poured with stirring into 10% aqueous KOH solution (175 mL). The resulting white precipitate was collected by filtration, washed with cold water (40 mL) and dried to give potassium 4-dodecylbenzene sulfonate (10.6 g, 29.1 mmol, 84%). This salt (10.0 g, 27.5 mmol) and POCl$_3$ (4.2 g, 27.4 mmol) were stirred at room temperature and gradually heated to 170° C. The hot reaction mixture was poured into cold water and extracted with CHCl$_2$. The organic layer was washed with water, dried over anhydrous Na$_2$SO$_4$, and filtered. Evaporation of the volatiles yielded p-dodecylbenzenesulfonyl chloride as a pale yellow liquid (9.2 g, 97%) which eventually became crystalline, mp 33° C.; $^1$H NMR (300 MHz, CDCl$_3$) δ 0.88 (t, 3H, J=6.5), 1.20-1.38 (m, 18H), 1.60-1.68 (m, 2H), 2.72 (t, 2H, J=7.5 Hz), 7.40 (d, 2H, J=8.4 Hz), 7.79 (d, 2H, J=8.4 Hz); $^{13}$C NMR (75 MHz, CDCl$_3$) δ 14.1, 22.6, 29.1, 29.3, 29.3, 29.5, 29.6, 30.9, 31.9, 36.0, 127.0, 129.6, 141.7, 151.6.

4-Dodecyl-N-(5-methyl-1,3,4-thiadiazol-2-yl)benzenesulfonamide (108). 2-Amino-5-methyl-1,3,4-thiadiazole (150 mg, 1.3 mmol) was suspended in pyridine (0.5 mL). p-Dodecylbenzenesulfonyl chloride (300 mg, 0.87 mmol) was added slowly at 0° C. The reaction mixture was then heated to 95° C. and was stirred at this temperature for 1 h. The reaction mixture was then added to aqueous 10% HCl (5 mL) and the resulting mixture extracted with ethyl acetate (3×10 mL). The organic extracts were washed with water, brine, dried over anhydrous Na$_2$SO$_4$, filtered, and volatiles evaporated to yield a solid mass. Chromatography on silica gel (70-230 mesh) eluted with 2% MeOH in CH$_2$Cl$_2$ gave the product (310 mg, 0.73 mmol, 84%). Recrystallization from hexanes:ethyl acetate (3:7) gave an analytical sample, mp 149-150° C.; $^1$H NMR (500 MHz, CDCl$_3$) δ 0.88 (3, t, J=7.0 Hz), 1.20-1.36 (18, m), 1.54-1.63 (2, m), 2.51 (3, s), 2.63 (2, t, J=7.5 Hz), 7.25 (2, d, J=7.5 Hz), 7.83 (2, d, J=7.5 Hz), 12.36 (1, br s); $^{13}$C NMR (125 MHz, CDCl$_3$) δ 14.1, 16.5, 22.7, 29.2, 29.3, 29.4, 29.5, 29.6, 31.1, 31.9, 35.9, 126.4, 128.8, 138.3, 148.3, 154.1, 168.6; MS (ESI$^+$, m/z) Calcd for C$_{21}$H$_{34}$N$_3$O$_2$S$_2$ 424.2092 found 424.20 (M+H)$^+$; HRMS (ESI$^+$, m/z) Calcd for C$_{21}$H$_{34}$N$_3$O$_2$S$_2$ 424.2092, found 424.2085 (M+H)$^+$.

4-Dodecyl-N-(5-ethyl-1,3,4-thiadiazol-2-yl)benzenesulfonamide (112). 2-Amino-5-ethyl-1,3,4-thiadiazole (169 mg, 1.3 mmol) was suspended in pyridine (0.5 mL). p-Dodecylbenzenesulfonyl chloride (300 mg, 0.87 mmol) was added slowly at 0° C. The reaction mixture was then heated to 95° C. and was stirred at this temperature for 1 h. The reaction mixture was then added to aqueous 10% HCl (5 mL) and the resulting mixture extracted with ethyl acetate (3×10 mL). The organic extracts were washed with water, brine, dried over anhydrous Na$_2$SO$_4$, filtered, and volatiles evaporated to yield a solid mass. Chromatography on silica gel (70-230 mesh) eluted with 2% MeOH in CH$_2$Cl$_2$ gave the product (225 mg, 0.51 mmol, 59%). Recrystallization from hexanes:ethyl acetate (3:7) gave an analytical sample, mp 93-94° C.; $^1$H NMR (500 MHz, CDCl$_3$) δ 0.88 (3, t, J=6.5 Hz), 1.20-1.36 (18, m), 1.33 (3, t, J=7.5 Hz), 1.54-1.63 (2, m), 2.63 (2, t, J=7.5 Hz), 2.84 (2, q, J=7.5 Hz), 7.25 (2, d, J=8.5 Hz), 7.83 (2, d, J=8.5 Hz), 12.30 (1, br s); $^{13}$C NMR (125 MHz, CDCl$_3$) δ 12.6, 14.1, 22.7, 24.4, 29.2, 29.3, 29.4, 29.5, 29.6, 31.1, 31.9, 35.9, 126.5, 128.8, 138.4, 148.2, 160.1 168.2; MS (ESI$^+$, m/z) Calcd for C$_{22}$H$_{36}$N$_3$O$_2$S$_2$ 438.2249, found 438.30 (M+H)$^+$; HRMS (ESI$^+$, m/z) Calcd for C$_{22}$H$_{36}$N$_3$O$_2$S$_2$ 438.2249, found 438.2247 (M+H)$^+$.

N-(5-tert-Butyl-1,3,4-thiadiazol-2-yl)-4-dodecylbenzenesulfonamide (116). 2-Amino-5-tert-butyl-1,3,4-thiadiazole (204 mg, 1.3 mmol) was suspended in pyridine (0.5 mL). p-Dodecylbenzenesulfonyl chloride (300 mg, 0.87 mmol)

was added slowly at 0° C. The reaction mixture was then heated to 95° C. and was stirred at this temperature for 1 h. The reaction mixture was then added to aqueous 10% HCl (5 mL) and the resulting mixture extracted with ethyl acetate (3×10 mL). The organic extracts were washed with water, brine, dried over anhydrous $Na_2SO_4$, filtered, and volatiles evaporated to yield a solid mass. Chromatography on silica gel (70-230 mesh) eluted with 2% MeOH in $CH_2Cl_2$ gave the product (350 mg, 0.75 mmol, 87%). Recrystallization from hexanes:ethyl acetate (3:7) gave an analytical sample, mp 117-118° C.; $^1$H NMR (500 MHz, $CDCl_3$) δ 0.88 (3, t, J=6.5 Hz), 1.20-1.36 (18, m), 1.38 (9, s), 1.56-1.64 (2, m), 2.63 (2, t, J=7.5 Hz), 7.25 (2, d, J=8.0 Hz), 7.86 (2, d, J=8.0 Hz), 12.24 (1, br s); $^{13}$C NMR (125 MHz, $CDCl_3$) δ 14.1, 22.7, 29.2, 29.3, 29.4, 29.5, 29.6, 29.7, 31.1, 31.8, 35.8, 36.5, 126.5, 128.7, 138.5, 148.1, 167.8, 168.0; MS ($ESL^+$, m/z) Calcd for $C_{24}H_{40}N_3O_2S_2$ 466.3, found 466.2 $(M+H)^+$; HRMS ($ESI^+$, m/z) Calcd for $C_{24}H_{40}N_3O_2S_2$ 466.2562, found 466.2562 $(M+H)^+$.

2-(5-(4-Dodecylphenylsulfonamido)-1,3,4-thiadiazol-2-yl)acetic Acid (120). Distilled water (3.0 mL) and 10% aqueous NaOH (0.65 mL) were added to compound 37 (200 mg, 0.40 mmol) and the mixture was heated under reflux for 2 h. The pH of the solution was then adjusted to 4.0 by addition of 1.0 M HCl, the resulting precipitate was isolated by filtration, washed with cold water, and dried to give 161 mg (0.34 mmol, 86%) of the product as a solid, mp 194-195° C.; $^1$H NMR (300 MHz, DMSO-$d_6$) δ 0.85 (t, 3H, J=6.6 Hz), 1.23 (m, 18H), 1.53 (m, 2H), 2.57 (t, 2H, J=7.5 Hz), 7.24 (d, 2H, J=8.1 Hz), 7.61 (d, 2H, J=7.8 Hz); $^{13}$C NMR (75 MHz, DMSO-$d_6$) δ 14.0, 22.1, 28.8, 28.9, 29.1, 30.7, 31.3, 34.9, 37.4, 125.8, 128.4, 141.2, 146.0, 153.3, 168.9, 170.8; MS (LCQ, $ESI^+$) Calcd for $C_{22}H_{34}N_3O_4S_2$ 468.2, found 468.2 $(M+H)^+$; HRMS ($ESI^+$, m/z) Calcd for $C_{22}H_{34}N_3O_4S_2$ 468.1991, found 468.1977 $(M+H)^+$.

Ethyl 2-(5-(4-Dodecylphenylsulfonamido)-1,3,4-thiadiazol-2-yl)acetate (120E). To a solution of p-dodecylbenzenesulfonyl chloride (1.01 g, 2.94 mmol) in pyridine (10 mL) was added ethyl 2-(5-amino-1,3,4-thiadiazol-2-yl)acetate (500 mg, 2.67 mmol). The reaction mixture was stirred at room temperature for 4.5 h, then 2 M HCl (20 mL) was added to quench the reaction. The mixture was extracted with ethyl acetate (3×50 mL). The organic extracts were washed with water (20 mL), brine (20 mL), dried over $Na_2SO_4$, filtered, and concentrated. The residue was purified by chromatography over silica gel (70-230 mesh) eluted with $CH_2Cl_2$:methanol 19:1 to give the product as a solid, mp 108-109° C., in 43% yield (570 mg, 1.15 mmol); $^1$H NMR (300 MHz, $CDCl_3$) δ 0.87 (t, 3H, J=7.2 Hz), 1.24-1.34 (m, 21H), 1.55-1.66 (m, 2H), 2.63 (t, 2H, J=7.2 Hz), 3.88 (s, 2H), 4.25 (q, 2H, J=7.5 Hz), 7.25 (d, 2H, J=8.1 Hz), 7.81 (d, 2H, J=7.8 Hz); $^{13}$C NMR (75 MHz, $CDCl_3$) δ 14.0, 14.1, 22.7, 29.3, 29.5, 29.6, 29.7, 31.2, 31.9, 35.9, 38.1, 61.9, 126.7, 128.4, 138.8, 147.2, 152.1, 168.3, 170.3; MS (LCQ, $ESI^+$) Calcd for $C_{24}H_{38}N_3O_4S_2$ 496.2, found 496.2 $(M+H)^+$; HRMS ($ESI^+$, m/z) Calcd for $C_{24}H_{38}N_3O_4S_2$ 496.2304, found 496.2295 $(M+H)^+$.

Ethyl 2-(5-Amino-1,3,4-thiadiazol-2-yl)acetate. Thiosemicarbazide (1.0 g, 11.0 mmol) and ethyl 3-ethoxy-3-iminopropionate hydrochloride (2.0 g, 10.0 mmol) were mixed in glacial acid (2 mL) for 10 min at 55° C. and then boiled for 1.5 h. The reaction mixture was evaporated, diluted with cold water, carefully neutralized with $NaHCO_3$, and cooled to 5° C. The precipitate was collected and crystallized from water to yield 0.88 g (4.70 mmol, 47%) of the product, mp 149-150° C.; $^1$H NMR (300 MHz, DMSO-$d_6$) δ 1.19 (t, 3H, J=7.2 Hz), 3.96 (s, 2H), 4.10 (q, 2H, J=6.9 Hz), 7.11 (s, 2H); $^{13}$C NMR (75 MHz, DMSO-$d_6$) δ 14.0, 35.4, 60.9, 150.4, 168.9, 169.6.

Ethyl 5-(4-dodecylphenylsulfonamido)-1,3,4-thiadiazole-2-carboxylate (124E). To a solution of p-dodecylbenzenesulfonyl chloride (260 mg, 0.75 mmol) in pyridine (3 mL) was added ethyl 5-amino-1,3,4-thiadiazole-2-carboxylate (100 mg, 0.58 mmol). The reaction mixture was stirred at room temperature for 4.5 h, then 2 M HCl was added to quench the reaction. The mixture was extracted with ethyl acetate (3×40 mL). The organic extracts were washed with water (20 mL), brine (20 mL), dried over $Na_2SO_4$, filtered, and concentrated. The residue was purified by chromatography over silica gel (70-230 mesh) eluted with $CH_2Cl_2$:methanol 49:1 to give the product as a solid, mp 96-97° C., in 34% yield (95 mg, 0.20 mmol); $^1$H NMR (300 MHz, $CDCl_3$) δ 0.85 (t, 3H, J=6.6 Hz), 1.20-1.35 (m, 21H), 1.57 (m, 2H), 2.60 (t, 2H, J=7.0 Hz), 4.43 (q, 2H, J=7.2 Hz), 7.26 (d, 2H, J=8.0 Hz), 7.77 (d, 2H, J=7.7 Hz); $^{13}$C NMR (300 MHz, $CDCl_3$) δ 14.1, 22.7, 29.3, 29.4, 29.6, 29.6, 31.1, 31.9, 35.9, 63.4, 126.6, 128.9, 136.9, 145.8, 159.9, 163.7, 167.9; MS (LCQ, $ESI^+$) Calcd for $C_{23}H_{36}N_3O_4S_2$ 482.2, found 482.1 $(M+H)^+$; HRMS ($ESI^+$, m/z) Calcd for $C_{23}H_{36}N_3O_4S_2$ 482.2140, found 482.2134 $(M+H)^+$.

4-Dodecyl-N-(5-(hydroxymethyl)-1,3,4-thiadiazol-2-yl) benzenesulfonamide (128). To a solution of p-dodecylbenzenesulfonyl chloride (200 mg, 0.58 mmol) in pyridine (3 mL) was added 2-amino-5-hydroxymethyl-1,3,4-thiadiazole (70 mg, 0.53 mmol). The reaction mixture was stirred at room temperature for 4.5 h, then 2 M HCl (8 mL) was added to quench the reaction. The mixture was extracted with ethyl acetate (3×20 mL). The organic extracts were washed with water (10 mL), brine (10 mL), dried over $Na_2SO_4$, filtered, and concentrated. The residue was purified by chromatography on silica gel (70-230 mesh) eluted with $CH_2Cl_2$:methanol 19:1 to give the product as a solid, mp 138-139° C., in 65% yield (151 mg, 0.34 mmol); $^1$H NMR (300 MHz, DMSO-$d_6$) δ 0.84 (t, 3H, J=6.6 Hz), 1.22 (m, 18H), 1.54-1.57 (m, 2H), 2.64 (t, 2H, J=7.8 Hz), 4.57 (s, 2H), 6.05 (br, 1H), 7.35 (d, 2H, J=8.1 Hz), 7.67 (d, 2H, J=7.8 Hz); $^{13}$C NMR (75 MHz, DMSO-$d_6$) δ 13.9, 22.1, 28.6, 28.7, 28.8, 29.0, 30.6, 31.3, 34.9, 58.4, 125.8, 128.9, 139.2, 147.5, 161.1, 167.5; MS (LCQ, $ESI^+$) Calcd for $C_{21}H_{34}N_3O_3S_2$ 440.2, found 440.2 $(M+H)^+$; HRMS ($ESI^+$, m/z) Calcd for $C_{21}H_{34}N_3O_{352}$ 440.2042, found 440.2029 $(M+H)^+$.

2-Amino-5-hydroxymethyl-1,3,4-thiadiazole. Thiosemicarbazide (3.0 g, 32.9 mmol) and glyconitrile (55% in water, 3.10 g, 29.9 mmol) were added to trifluoroacetic acid (24 mL). The mixture was heated to 63° C. for 2 h and then kept at room temperature for 72 h, after which time the solvent was removed. The residue was dissolved in distilled water (10 mL) and neutralized with 1M NaOH, then stirred for 2 h at room temperature. The precipitate was collected by filtration and recrystallized from water to yield 2.5 g (19.1 mmol, 64%) of the product, mp 185-186° C.; $^1$H NMR (300 MHz, DMSO-$d_6$) δ 4.54 (d, 2H, J=6.0 Hz), 5.75 (t, 1H, J=6.0 Hz), 7.08 (s, 2H); $^{13}$C NMR (75 MHz, DMSO-$d_6$) δ 58.5, 160.9, 169.2.

N-(4-(N-(5-Methyl-1,3,4-thiadizol-2-yl)sulfamoyl)phenyl)acetamide (106). 2-Amino-5-methyl-1,3,4-thiadiazole (250 mg, 2.19 mmol) was suspended in pyridine (0.5 mL). N-Acetylsulfanilyl chloride (410 mg, 1.75 mmol) was added slowly at 0° C. The reaction mixture was then heated to 95° C. and was stirred at this temperature for 1 h. The reaction mixture was then added to aqueous 3N HCl and the mixture extracted with ethyl acetate. The organic extracts were washed with water (3×20 mL), brine (3×20 mL), dried over anhydrous $Na_2SO_4$, filtered, and volatiles evaporated. The residue was crystallized from MeOH to give the product (491 mg, 1.6 mmol, 97%) as a solid, mp 239-240° C.; $^1$H NMR (500 MHz, DMSO) δ 2.07 (3, s), 2.44 (3, s), 7.74 (4, s), 10.82 (1, s), 13.85 (1, s); $^{13}$C NMR (125 MHz, DMSO) δ 16.1, 24.1, 118.6, 126.9, 135.7, 142.8, 154.3, 167.7, 168.9; MS (ESI$^+$, m/z) Calculated for $C_{11}H_{13}N_4O_3S_2$ 313.0, found 313.0 (M+H)$^+$; HRMS (FAB$^+$, m/z) Calculated for $C_{11}H_{13}N_4O_3S_2$ 313.0429, found 313.0428 (M+H)$^+$.

4-Amino-N-(5-methyl-1,3,4-thiadiazol-2-yl)benzenesulfonamide (105). Compound 106 (250 mg, 0.8 mmol) was suspended in 3 N HCl (4 mL) and the suspension heated to reflux for 30 min. Following neutralization with saturated aqueous $Na_2CO_3$ solution, the precipitated product was collected by filtration, washed with water (3×20 mL), and dried under vacuum. The residue was crystallized from MeOH to give the product (155 mg, 0.58 mmol, 72%) as a solid, mp 207-208° C. (lit mp 208)[1]; $^1$H NMR (500 MHz, DMSO) δ 2.47 (3, s), 5.89 (2, s), 6.58 (2, d, J=8.5 Hz), 7.40 (2, d, J=8.5 Hz), 10.48 (1, s); $^{13}$C NMR (125 MHz, DMSO) δ 16.0, 112.5, 127.2, 127.6, 152.4, 153.6, 166.8.

N-(4-(N-(5-Methyl-1,3,4-thiadiazol-2-yl)sulfamoyl)phenyl)decanamide (107). Compound 105 (250 mg, 0.93 mmol) was suspended in pyridine (0.5 mL). Decanoyl chloride (141 mg, 0.74 mmol) was added slowly at 0° C. The reaction mixture was then heated to 95° C. and was stirred for 1 h. The reaction mixture was then added to aqueous 3 N HCl solution (5 mL) and the mixture extracted with ethyl acetate (3×10 mL). The organic extracts were washed with water (3×20 mL), brine (3×20 mL), dried over anhydrous $Na_2SO_4$, and filtered. Evaporation of the solvent left a residue which was crystallized from hexanes and ethyl acetate (1:2) to give the product (297 mg, 0.70 mmol, 95%) as a solid, mp 141-142° C.; $^1$H NMR (500 MHz, DMSO) δ 0.82 (3, t, J=7.0 Hz), 1.10-1.30 (12, m), 1.54-1.63 (2, m), 2.32 (2, t, J=7.0 Hz), 2.45 (3, s), 8.25 (2, d, J=8.0 Hz), 8.28 (2, d, J=8.0 Hz), 10.25 (1, s), 13.87 (1, s); $^{13}$C NMR (125 MHz, DMSO) δ 13.9, 16.0, 22.1, 24.9, 28.5, 28.6, 28.8, 28.9, 31.2, 36.4, 118.5, 126.8, 135.5, 142.7, 154.1, 167.6, 171.7; MS (LCQ, ESI$^+$) Calculated for $C_{19}H_{29}N_4O_3S_2$ 425.2, found 425.1 (M+H)$^+$; HRMS (FAB$^+$, m/z) Calculated for $C_{19}H_{29}N_4O_3S_2$ 425.1681, found 425.1678 (M+H)$^+$.

N-(4-(N-(5-Ethyl-1,3,4-thiadizol-2-yl)sulfamoyl)phenyl)acetamide (110). 2-Amino-5-ethyl-1,3,4-thiadiazole (250 mg, 1.93 mmol) was suspended in pyridine (0.5 mL). N-Acetylsulfanilyl chloride (361 mg, 1.54 mmol) was added slowly at 0° C. The reaction mixture was then heated to 95° C. and was stirred for 1 h. The reaction mixture was then added to aqueous 3N HCl and the mixture extracted with ethyl acetate. The organic extracts were washed with water (3×20 mL), brine (3×20 mL), dried over anhydrous $Na_2SO_4$, filtered, and volatiles evaporated. The residue was crystallized from MeOH to give the product (350 mg, 1.07 mmol, 70%) as a solid, mp 197-198° C.; $^1$H NMR (500 MHz, DMSO) δ 1.28 (3, t, J=7.0 Hz), 2.07 (3, s), 2.82 (2, q, J=7.0 Hz), 7.72 (4, s), 10.32 (1, s), 13.91 (1, s); $^{13}$C NMR (125 MHz, DMSO) δ 12.2, 23.7, 24.1, 48.6, 118.5, 126.9, 135.6, 142.7, 159.8, 167.3, 168.9; MS (LCQ, ESI$^+$) Calculated for $C_{12}H_{15}N_4O_3S_2$ 327.1, found 327.1 (M+H)$^+$; HRMS (FAB$^+$, m/z) Calculated for $C_{12}H_{15}N_4O_3S_2$ 327.0586, found 327.0585 (M+H)$^+$.

4-Amino-N-(5-ethyl-1,3,4-thiadiazol-2-yl)benzenesulfonamide (109). Compound 110 (200 mg, 0.61 mmol) was suspended in 3 N HCl (3 mL) and the suspension heated to reflux for 30 min. Following neutralization with saturated aqueous $Na_2CO_3$ solution, the precipitated product was collected by filtration, washed with water (3×15 mL), and dried under vacuum. The residue was crystallized from MeOH to give the product (120 mg, 0.42 mmol, 69%) as a solid, mp 190-191° C.; $^1$H NMR (500 MHz, DMSO) δ 1.20 (3, t, J=7.5 Hz), 2.79 (2, q, J=7.5 Hz), 5.91 (2, S), 6.57 (2, d, J=8.5 Hz), 7.41 (2, d, J=8.5 Hz), 13.65 (1, s); $^{13}$C NMR (125 MHz, DMSO) δ 12.3, 23.6, 112.5, 127.1, 127.6, 152.5, 159.1, 166.8; MS (LCQ, ESI$^+$) Calculated for $C_{10}H_{13}N_4O_2S_2$ 285.0, found 285.0 (M+H)$^+$; HRMS (FAB$^+$, m/z) Calculated for $C_{10}H_{13}N_4O_2S_2$ 285.0480, found 285.0478 (M+H)$^+$.

N-(4-(N-(5-Ethyl-1,3,4-thiadiazol-2-yl)sulfamoyl)phenyl)decanamide (111). Compound 109 (250 mg, 0.88 mmol) was suspended in pyridine (1.3 mL). Decanoyl chloride (134 mg, 0.70 mmol) was added slowly at 0° C. The reaction mixture was then heated to 95° C. and was stirred for 1 h. The reaction mixture was then added to aqueous 3 N HCl solution (4.5 mL) and the mixture extracted with ethyl acetate (3×10 mL). The organic extracts were washed with water (3×20 mL), brine (3×20 mL), dried over anhydrous $Na_2SO_4$, and filtered. Evaporation of the solvent left a residue which was crystallized from hexanes and ethyl acetate (1:2) to give the product (372 mg, 0.85 mmol, 97%) as a solid, mp 121-122° C.; $^1$H NMR (500 MHz, DMSO) δ 0.82 (3, t, J=7.0 Hz), 1.17-1.30 (14, m), 1.57 (2, t, J=7.0 Hz), 2.32 (3, t, J=7.0 Hz), 2.80 (2, q, J=7.0 Hz), 7.72 (2, d, J=8.5 Hz), 7.76 (2, d, J=8.5 Hz), 10.21 (1, s), 13.89 (1, s); $^{13}$C NMR (125 MHz, DMSO) δ 12.2, 13.9, 22.1, 23.6, 24.9, 28.6, 28.7, 28.8, 28.9, 31.2, 36.5, 118.5, 126.8, 135.5, 142.7, 159.7, 167.2, 171.8; MS (LCQ, ESI$^+$) Calculated for $C_{20}H_{31}N_4O_3S_2$ 439.2, found 439.1 (M+H)$^+$; HRMS (FAB$^+$, m/z) Calculated for $C_{20}H_{31}N_4O_3S_2$ 439.1838, found 439.1843 (M+H)$^+$.

N-(4-(N-(5-tert-Butyl-1,3,4-thiadiazol-2-yl)sulfamoyl)phenyl)acetamide (114). 2-Amino-5-tert-butyl-1,3,4-thiadiazole (1.0 g, 6.36 mmol) was suspended in pyridine (1.6 mL). N-Acetylsulfanilyl chloride (1.9 g, 5.1 mmol) was added slowly at 0° C. The reaction mixture was then heated to 95° C. and was stirred for 1 h. The reaction mixture was then added to aqueous 3N HCl and the mixture extracted with ethyl acetate. The organic extracts were washed with water (3×65 mL), brine (3×65 mL), dried over anhydrous $Na_2SO_4$, filtered, and volatiles evaporated. The residue was crystallized from MeOH to give the product (1.59 mg, 4.3 mmol, 84%) as a solid, mp 137-138° C.; $^1$H NMR (500 MHz, DMSO) δ 1.28 (9, t, J=7.0 Hz), 2.08 (3, s), 7.73 (2, d, J=8.5 Hz), 7.78 (2, d, J=8.5 Hz), 10.48 (1, s), 14.00 (1, brs); $^{13}$C NMR (125 MHz, DMSO) δ 24.1, 29.3, 36.1, 118.6, 126.8, 135.6, 142.8, 166.9, 167.2, 169.0; MS (LCQ, ESI$^+$) Calculated for $C_{14}H_{19}N_4O_3S_2$ 355.1, found 355.1 (M+H)$^+$; HRMS (FAB$^+$, m/z) Calculated for $C_{14}H_{19}N_4O_3S_2$ 355.0899, found 355.0900 (M+H)$^+$.

4-Amino-N-(5-tert-butyl-1,3,4-thiadiazol-2-yl)benzenesulfonamide (113). Compound 114 (1.0 g, 2.82 mmol) was suspended in 3 N HCl (15 mL) and the suspension heated to reflux for 30 min. Following neutralization with saturated aqueous $Na_2CO_3$ solution, the precipitated product was collected by filtration, washed with water (70 mL), and dried under vacuum. The residue was crystallized from MeOH to give the product (655 mg, 2.1 mmol, 74%) as a solid, mp 220-221° C.; $^1$H NMR (500 MHz, DMSO) δ 1.28 (9, s), 5.91 (2, br s), 6.60 (2, d, J=7.0 Hz), 7.45 (2, d, J=7.0 Hz), 13.95 (1, br s); $^{13}$C NMR (125 MHZ, DMSO) δ 29.3, 36.0, 112.6, 127.3, 127.7, 152.5, 166.1, 166.6; MS (LCQ, ESI$^+$) Calculated for $C_{12}H_{17}N_4O_2S_2$ 313.1, found 313.0 (M+H)$^+$; HRMS (FAB$^+$, m/z) Calculated for $C_{12}H_{17}N_4O_2S_2$ 313.0793, found 313.0793 (M+H)$^+$.

N-(4-(N-(5-tert-Butyl-1,3,4-thiadiazol-2-yl)sulfamoyl)phenyl)decanamide (115). Compound 113 (250 mg, 0.80 mmol) was suspended in pyridine (1.5 mL). Decanoyl chloride (122 mg, 0.64 mmol) was added slowly at 0° C. The reaction mixture was then heated to 95° C. and was stirred for 1 h. The reaction mixture was then added to aqueous 3 N HCl solution (4 mL) and the mixture extracted with ethyl acetate (3×10 mL). The organic extracts were washed with water (3×20 mL), brine (3×20 mL), dried over anhydrous $Na_2SO_4$, and filtered. Evaporation of the solvent left a residue which was crystallized from hexanes and ethyl acetate (1:2) to give the product (294 mg, 0.63 mmol, 98%) as a solid, mp 156-157° C.; $^1$H NMR (500 MHz, DMSO) δ 0.80 (3, t, J=7.0 Hz), 1.15-1.33 (21, m), 1.56 (2, t, J=7.0 Hz), 2.32 (3, t, J=7.0 Hz), 7.74 (2, d, J=8.0 Hz), 7.77 (2, d, J=8.0 Hz), 10.21 (1, s), 13.90 (1, s); $^{13}$C NMR (125 MHz, DMSO): δ 13.9, 22.1, 25.0, 28.6, 28.7, 28.8, 28.9, 29.3, 31.1, 36.0, 36.5, 118.6, 126.9, 135.7, 142.9, 167.0, 167.2, 171.9; MS (LCQ, ESI$^+$) Calculated for $C_{22}H_{35}N_4O_3S_2$ 467.2, found 467.2 (M+H)$^+$; HRMS (FAB$^+$, m/z) Calculated for $C_{22}H_{35}N_4O_3S_2$ 467.2151, found 467.2131 (M+H)$^+$.

Ethyl 2-(5-(4-Acetamidophenylsulfonamido)-1,3,4-thiadiazol-2-yl)acetate (118E). To a solution of p-acetamidobenzenesulfonyl chloride (275 mg, 1.18 mmol) in pyridine (5 mL) was added ethyl 2-(5-amino-1,3,4-thiadiazol-2-yl)acetate (200 mg, 1.07 mmol). The reaction mixture was stirred at room temperature for 4.5 h, then 2 M HCl (10 mL) was added to quench the reaction. The mixture was extracted with ethyl acetate (3×50 mL). The organic extracts were washed with water (20 mL), brine (20 mL), dried over $Na_2SO_4$, filtered, and concentrated. The residue was purified by chromatography over silica gel (70-230 mesh) eluted with $CH_2Cl_2$:methanol 19:1 to give the product as a solid, mp 156-157° C., in 76% yield (312 mg, 0.81 mmol); $^1$H NMR (300 MHz, DMSO-$d_6$) δ 1.20 (t, 3H, J=7.0 Hz), 2.07 (s, 3H), 4.06 (s, 2H), 4.15 (q, 2H, J=7.0 Hz), 7.72 (m, 4H), 10.29 (s, 1H); $^{13}$C NMR (75 MHz, DMSO-$d_6$) δ 14.0, 24.1, 35.7, 61.3, 118.6, 127.0, 135.5, 142.9, 151.6, 167.8, 168.1, 169.0; MS (LCQ, ESI$^+$) Calcd for $C_{14}H_{17}N_4O_5S_2$ 385.1, found 385.1 (M+H)$^+$; HRMS (ESI$^+$, m/z) Calcd for $C_{14}H_{17}N_4O_5S_2$ 385.0640, found 385.0638 (M+H)$^+$.

2-(5-(4-Aminophenylsulfonamido)-1,3,4-thiadiazol-2-yl)acetic Acid (117). Distilled water (3.0 mL) and 10% aqueous NaOH (1.5 mL) were added to compound 118E (300 mg, 0.78 mmol) and the mixture was heated under reflux for 2 h. The pH of the solution was then adjusted to 4.0 by addition of 1.0 M HCl, the resulting precipitate was isolated by filtration, washed with cold water, and dried to give 201 mg (0.64 mmol, 82%) of the product as a solid, mp 209-210° C.; $^1$H NMR (600 MHz, DMSO-$d_6$) δ 3.59 (s, 2H), 6.52 (d, 2H, J=8.1 Hz), 7.42 (d, 2H, J=8.9 Hz); $^{13}$C NMR (75 MHz, DMSO-$d_6$) δ 36.6, 113.3, 127.8, 128.4, 152.4, 153.3, 167.7, 170.4; MS (LCQ, ESI$^+$) Calcd for $C_{10}H_{11}N_4O_4S_2$ 315.0, found 315.0 (M+H)$^+$; HRMS (ESI$^+$, m/z) Calcd for $C_{10}H_{11}N_4O_4S_2$ 315.0222, found 315.0220 (M+H)$^+$.

2-(5-(4-Acetamidophenylsulfonamido)-1,3,4-thiadiazol-2-yl)acetic Acid (118). To a solution of compound 118E (128 mg, 0.33 mmol) in THF (15 mL) was added 0.1 M aqueous LiOH (3.75 mL) and the mixture was stirred at room temperature. After 24 h, the resultant solution was acidified to pH 4 and the mixture was extracted with ethyl acetate (3×50 mL). The combined organic extracts were washed with water (20 mL) and concentrated to give the crude product, which was further purified by chromatography on 70-230 mesh silica gel eluted with $CH_2Cl_2$:methanol:water 40:10:1 to afford 104 mg (0.29 mmol, 88%) of the product as a solid, mp 206-207° C.; $^1$H NMR (300 MHz, DMSO-$d_6$) δ 2.05 (s, 3H), 3.81 (s, 2H), 7.65 (m, 4H); $^{13}$C NMR (75 MHz, DMSO-$d_6$) δ 24.8, 37.3, 119.0, 127.5, 137.9, 142.6, 153.3, 169.4, 169.5, 170.9; MS (LCQ, ESI$^+$) Calcd for $C_{12}H_{13}N_4O_5S_2$ 357.0, found 357.0 (M+H)$^+$; HRMS (ESI$^+$, m/z) Calcd for $C_{12}H_{13}N_4O_5S_2$ 357.0327, found 357.0326 (M+H)$^+$.

Ethyl 2-(5-(4-Decanamidophenylsulfonamido)-1,3,4-thiadiazol-2-yl)acetate (199E). To a solution of the 4-decanamidobenzenesulfonyl chloride (608 mg, 1.76 mmol) in pyridine (8 mL) was added ethyl 2-(5-amino-1,3,4-thiadiazol-2-yl)acetate (300 mg, 1.60 mmol). The reaction mixture was stirred at room temperature for 4.5 h, than 2 M HCl was added to quench the reaction. The mixture was extracted with ethyl acetate (3×40 mL). The organic extracts were washed with water (30 mL), brine (30 mL), dried over $Na_2SO_4$, filtered, and concentrated. The residue was purified by chromatography over silica gel (70-230 mesh) eluted with $CH_2Cl_2$:methanol 19:1 to give the product as a solid, mp 89-90° C., in 63% yield (500 mg, 1.01 mmol); $^1$H NMR (300 MHz, CDCl$_3$) δ 0.87 (t, 3H, J=6.9 Hz), 1.25-1.34 (m, 15H), 1.65-1.76 (m, 2H), 2.39 (t, 2H, J=7.5 Hz), 3.87 (s, 2H), 4.24 (q, 2H, J=7.2 Hz), 7.58 (d, 2H, J=9.0 Hz), 7.74 (d, 2H, J=8.7 Hz); $^{13}$C NMR (75 MHz, DMSO-$d_6$) δ 14.0, 14.0, 22.0, 25.5, 29.0, 29.0, 29.2, 31.3, 36.4, 37.9, 60.1, 118.9, 127.0, 139.4, 142.3, 154.0, 168.9, 169.9, 172.3; MS (LCQ, ESI$^+$) Calcd for $C_{22}H_{33}N_4O_5S_2$ 497.2, found 497.1 (M+H)$^+$; HRMS (ESI$^+$, m/z) Calcd for $C_{22}H_{33}N_4O_5S_2$ 497.1875, found 497.1873 (M+H)$^+$.

4-Decanamidobenzenesulfonyl Chloride. Aniline (2.03 g, 25.0 mmol) was dissolved in $CH_2Cl_2$ (30 mL). To the solution were added pyridine (2.22 mL, 27.5 mmol) and decanoyl chloride (5.25 g, 27.5 mmol) in an ice bath. After stirring for 3 h at room temperature, the reaction mixture was poured into 1M HCl (30 mL) and the mixture extracted with $CH_2Cl_2$ (3×100 mL). The organic extracts were washed with water (50 mL), brine (50 mL), dried over $Na_2SO_4$, filtered, and concentrated to give 5.62 g (22.8 mmol, 91%) of N-phenyldecanamide as a white solid, mp 65-66° C. (lit$^5$ mp 65-66° C.); $^1$H NMR (300 MHz, CDCl$_3$) δ 0.87 (t, 3H, J=6.9 Hz), 1.26 (m, 12H), 1.72 (m, 2H), 2.35 (t, 2H, J=7.8 Hz), 7.10 (t, 2H, J=7.8 Hz), 7.31 (t, 1H, J=7.8 Hz) 7.50 (t, 2H, J=7.9 Hz); $^{13}$C NMR (75 MHz, CDCl$_3$) δ 13.9, 22.5, 25.7, 29.2, 29.2, 29.3, 29.3, 31.7, 37.5, 120.1, 124.0, 128.7, 138.1, 172.3.

2-(5-(4-Decanamidophenylsulfonamido)-1,3,4-thiadiazol-2-yl)acetic Acid (119). To a solution of compound 119E (160 mg, 0.32 mmol) in THF (15 mL) was added 0.1 M aqueous LiOH (3.2 mL) and the mixture was stirred at room temperature. After 24 h, the resultant solution was acidified to pH 4 and the mixture was extracted with ethyl acetate (4×40 mL). The combined organic extracts were washed with water (20 mL) and concentrated to give the crude product, which was further purified by chromatography on 70-230 mesh silica gel eluted with $CH_2Cl_2$:methanol:water 40:10:1 to afford 125 mg (0.27 mmol, 83%) of the product as a solid, mp 190-191° C.; $^1$H NMR (300 MHz, DMSO-$d_6$) δ 0.84 (t, 3H, J=7.2 Hz), 1.24 (m, 12H), 1.56 (m, 2H), 2.29 (t, 2H, J=7.5 Hz), 3.63 (s, 2H), 7.59-7.61 (m, 4H); $^{13}$C NMR (75 MHz, DMSO-$d_6$) δ 14.0, 22.1, 25.0, 28.7, 28.8, 28.9, 31.3, 36.4, 37.6, 118.2, 126.8, 138.4, 141.4, 153.2, 169.0, 169.1, 171.7; MS (LCQ, ESI$^+$) Calcd for $C_{20}H_{29}N_4O_5S_2$ 469.2, found 469.1 (M+H)$^+$; HRMS (ESI$^+$, m/z) Calcd for $C_{20}H_{29}N_4O_5S_2$ 469.1579, found 469.1570 (M+H)$^+$.

N-(4-(N-(5-(hydroxymethyl)-1,3,4-thiadiazol-2-yl)sulfamoyl)phenyl)acetamide (126). To a solution of p-acetamidobenzenesulfonyl chloride (510 mg, 2.18 mmol) in pyridine (6 mL) was added 2-amino-5-hydroxymethyl-1,3,4-thiadiazole (260 mg, 1.98 mmol). The reaction mixture was stirred at room temperature for 4.5 h, then 2 M HCl (20 mL) was added to quench the reaction. The mixture was extracted with ethyl acetate (4×50 mL). The organic extracts were washed with water (40 mL), brine (40 mL), dried over $Na_2SO_4$, filtered, and concentrated. The residue was purified by chromatography on silica gel (70-230 mesh) eluted with $CH_2Cl_2$:methanol 9:1 to give the product as a solid, mp 101-102° C., in 82% yield (533 mg, 1.62 mmol); $^1$H NMR (300 MHz, DMSO-d$_6$) δ 2.07 (s, 3H), 4.56 (d, 2H, J=5.1 Hz), 6.09 (t, 1H, J=4.8 Hz), 7.73 (m, 4H); $^{13}$C NMR (75 MHz, DMSO-d$_6$) δ 24.8, 59.1, 119.3, 127.7, 136.2, 143.5, 161.7, 168.1, 169.6; MS (LCQ, ESI$^+$) Calcd for $C_{11}H_{13}N_4O_4S_2$ 329.0, found 329.1 (M+H)$^+$; HRMS (ESI$^+$, m/z) Calcd for $C_{11}H_{13}N_4O_4S_2$ 329.0378, found 329.0376 (M+H)$^+$.

4-Amino-N-(5-(hydroxymethyl)-1,3,4-thiadiazol-2-yl)benzenesulfonamide (125). Distilled water (3.0 mL) and 10% NaOH (1.5 mL) were added to compound 126 (328 mg, 0.94 mmol) and the mixture was heated under reflux for 2 h. The pH of the solution was then adjusted to 4.0 by addition of 1.0 M HCl and the mixture was extracted with ethyl acetate (3×50 mL). The combined organic extracts were washed with water (20 mL) and concentrated to give a crude product which was purified by chromatography on silica gel eluted with $CH_2Cl_2$:methanol 4:1 to afford 182 mg (0.64 mmol, 68%) of the product as a solid, mp 89-90° C.; $^1$H NMR (300 MHz, DMSO-d$_6$) δ 4.54 (s, 2H), 5.91 (br, 1H), 6.55 (d, 2H, J=8.7 Hz), 7.39 (d, 2H, J=9.0 Hz); $^{13}$C NMR (75 MHz, DMSO-d$_6$) δ 59.1, 113.2, 128.0, 128.4, 153.2, 161.0, 167.5; MS (LCQ, ESI$^+$) Calcd for $C_9H_{11}N_4O_3S_2$ 287.0, found 287.0 (M+H)$^+$; HRMS (ESI$^+$, m/z) Calcd for $C_9H_{11}N_4O_3S_2$ 287.0273, found 287.0269 (M+H)$^+$.

N-(4-(N-(5-Sulfamoyl-1,3,4-thiadiazol-2-yl)sulfamoyl)phenyl)acetamide (138). 5-Amino-1,3,4-thiadiazolo-2-sulfonamide (540 mg, 3.0 mmol) was dissolved in aqueous NaOH (2.5 M, 1.6 mL) and the solution was cooled to 10° C. 4-Acetamidobenzenesulfonyl chloride (140 mg, 0.6 mmol) and aqueous NaOH (5M, 0.3 mL) were added to this solution and the mixture was stirred at 10° C. until all the sulfonyl chloride had reacted. This procedure was repeated four times (a total of 3.0 mmol of the sulfonyl chloride and 1.5 mL of 5M NaOH). The solution was stirred for 5 h at room temperature, then brought to pH 2 with aqueous 5% HCl. The precipitated product was collected by filtration, washed with cold water, and air-dried. Recrystallization from 95% aqueous ethanol afforded the product (710 mg, 1.88 mmol, 63%), mp 280-281° C. (lit[16] mp 285-290° C.); $^1$H NMR (300 MHz, DMSO-d$_6$) δ 2.06 (s, 3H), 7.74 (s, 4H), 8.45 (s, 2H), 10.32 (s, 1H); $^{13}$C NMR (75 MHz, DMSO-d$_6$) δ 24.2, 118.7, 127.2, 134.7, 143.3, 157.9, 167.2, 169.1; LRMS (LCQ, ESI) calcd for $C_{10}H_{10}N_5O_5S_3$ 376.0, found 376.0 (M−H)$^−$; HRMS (ESI$^−$, m/z) calcd for $C_{10}H_{10}N_5O_5S_3$ 375.9850, found 375.9850 (M−H).

5-Amino-1,3,4-thiadiazolo-2-sulfonamide. A solution of acetazolamide (15 g, 67.5 mmol, from Aldrich) in a mixture of ethanol (100 mL) and concentrated hydrochloride acid (30 mL) was heated at reflux for 4.5 h, during which time a solid slowly deposited. Upon cooling the solution, the solvents were removed in vacuo and the solid residue was redissolved in $H_2O$ (75 mL). The solution was basified to pH 7 with 5 M sodium hydroxide, the precipitated product was collected by filtration, and then recrystallized from water to give the product (10.6 g, 58.9 mmol, 87%), mp 228-229° C. (lit[15] mp 230-232° C.); $^1$H NMR (300 MHz, DMSO-d$_6$) δ 8.06 (s, 2H), 7.81 (s, 2H); $^{13}$C NMR (75 MHz, DMSO-d$_6$) 171.9, 158.1.

5-(4-Aminophenylsulfonamido)-1,3,4-thiadiazole-2-sulfonamide (131). Compound 138 (1.0 g, 2.6 mmol) was heated at reflux with aqueous HCl (6 M, 10 mL) for 50 min. The homogeneous solution was evaporated to dryness and the residue was taken up in distilled water (10 mL). The pH was adjusted to 9 with 25% aqueous ammonia, the resulting solution was filtered to remove insoluble matter, and the solution acidified to pH 4 with glacial acetic acid. Cooling the solution overnight gave a solid, which was collected by filtration, washed with cold water, and air-dried. Recrystallization from 20% ethanol/$H_2O$ gave the pure product (500 mg, 1.5 mmol, 57%), mp 241-242° C. (lit[17] mp 247-248° C.); $^1$H NMR (300 MHz, DMSO-d$_6$) δ 6.58 (d, 2H, J=7.8 Hz), 7.43 (d, 2H, J=8.1 Hz), 8.43 (s, 2H); $^{13}$C NMR (75 MHz, DMSO-d$_6$) δ 112.8, 125.9, 128.0, 153.1, 157.6, 166.0; LRMS (LCQ, ESI$^+$) calcd for $C_8H_{10}N_5O_4S_3$ 336.0, found 335.8 (M+H)$^+$; HRMS (ESI$^+$, m/z) calcd for $C_8H_{10}N_5O_4S_3$ 335.9889, found 335.9883 (M+H)$^+$.

Ethyl 5-(4-Acetamidophenylsulfonamido)-1,3,4-thiadiazole-2-carboxylate (122E). To a solution of p-acetamidobenzenesulfonyl chloride (1.98 g, 8.47 mmol) in pyridine (20 mL) was added ethyl 5-amino-1,3,4-thiadiazole-2-carboxylate (1.2 g, 7.06 mmol). The reaction mixture was stirred at room temperature for 4.5 h, than 2 M HCl (50 mL) was added to quench the reaction. The mixture was extracted with ethyl acetate (3×60 mL). The organic extracts were washed with water (50 mL), brine (50 mL), dried over $Na_2SO_4$, filtered, and concentrated. The residue was purified by chromatography on silica gel (70-230 mesh) eluted with $CH_2Cl_2$:methanol 19:1 to give the product as a solid, mp 201-202° C., in 73% yield (1.91 g, 5.15 mmol); $^1$H NMR (300 MHz, DMSO-d$_6$) δ 1.29 (t, 3H, J=6.9 Hz), 2.08 (s, 3H), 4.37 (q, 2H, J=7.8 Hz), 7.74 (m, 4H), 10.32 (s, 1H); $^{13}$C NMR (75 MHz, DMSO-d$_6$) δ 13.9, 14.0, 24.1, 62.9, 118.6, 127.1, 134.9, 143.2, 147.2, 157.5, 167.6, 169.0; MS (LCQ, ESI$^+$) Calcd for $C_{13}H_{15}N_4O_5S_2$ 371.0, found 371.0 (M+H)$^+$; HRMS (ESI$^+$, m/z) Calcd for $C_{13}H_{15}N_4O_5S_2$ 371.0484, found 371.0472 (M+H)$^+$.

Ethyl 5-(4-Decanamidophenylsulfonamido)-1,3,4-thiadiazole-2-carboxylate (123E). To a solution of 4-decanamidobenzenesulfonyl chloride (220 mg, 0.64 mmol) in pyridine (4 mL) was added ethyl 5-amino-1,3,4-thiadiazole-2-carboxylate (100 mg, 0.58 mmol). The reaction mixture was stirred at room temperature for 4.5 h, then 2 M HCl (10 mL) was added to quench the reaction. The mixture was extracted with ethyl acetate (3×30 mL). The organic extracts were washed with water (20 mL), brine (20 mL), dried over $Na_2SO_4$, filtered, and concentrated. The residue was purified by chromatography on silica gel (70-230 mesh) eluted with $CH_2Cl_2$:methanol 9:1 to give the product as a solid, mp 101-102° C., in 65% yield (183 mg, 0.38 mmol); $^1$H NMR (300 MHz, DMSO-d$_6$) δ 0.83 (t, 3H, J=6.6 Hz), 1.22-1.32 (m, 15H), 1.56 (m, 2H), 2.31 (t, 2H, J=6.0 Hz), 4.33 (q, 2H, J=7.6 Hz), 7.71 (m, 4H), 10.19 (s, 1H); $^{13}$C NMR (75 MHz, DMSO-d$_6$) δ 14.6, 14.6, 22.8, 25.6, 29.3, 29.4, 29.5, 29.6, 31.3, 31.9, 37.1, 62.8, 119.1, 127.6, 136.8, 143.2, 147.7, 159.2, 170.3, 172.5; MS (LCQ, ESI$^+$) Calcd for $C_{21}H_{31}N_4O_5S_2$ 483.2, found 483.1 (M+H)$^+$; HRMS (ESI$^+$, m/z) Calcd for $C_{21}H_{31}N_4O_5S_2$ 483.1736, found 483.1728 (M+H)$^+$.

N-(4-(N-(5-(hydroxymethyl)-1,3,4-thiadiazol-2-yl)sulfamoyl)phenyl)decanamide (127). To a solution of 4-decanamidobenzenesulfonyl chloride (435 mg, 1.26 mmol) in pyridine (5 mL) was added 2-amino-5-hydroxymethyl-1,3,4-thiadiazole (150 mg, 1.15 mmol). The reaction mixture was stirred at room temperature for 4.5 h, then 2 M HCl (15 mL) was added to quench the reaction. The mixture was extracted with ethyl acetate (3×30 mL). The organic extracts were washed with water (20 mL), brine (20 mL), dried over $Na_2SO_4$, filtered, and concentrated. The residue was purified by chromatography on silica gel (70-230 mesh) eluted with $CH_2Cl_2$:methanol 9:1 to give the product as a solid, mp 69-70° C., in 73% yield (370 mg, 0.84 mmol); $^1$H NMR (300 MHz, DMSO-d$_6$) δ 0.84 (t, 3H, J=7.2 Hz), 1.23 (m, 12H), 1.54-1.57 (m, 2H), 2.29 (t, 2H, J=7.5 Hz), 4.57 (d, 2H, J=4.8 Hz), 6.08 (t, 1H, J=5.0 Hz), 7.73 (m, 4H), 10.22 (s, 1H), 14.01 (s, 1H); $^{13}$C NMR (75 MHz, DMSO-d$_6$) δ 14.6, 22.8, 25.6, 30.0, 29.4, 29.5, 29.6, 31.9, 37.1, 59.1, 119.3, 127.6, 136.1, 143.5, 161.7, 168.1, 172.6; MS (LCQ, ESI$^+$) Calcd for $C_{19}H_{29}N_4O_4S_2$ 441.2, found 441.1 (M+H)$^+$; HRMS (ESI$^+$, m/z) Calcd for $C_{19}H_{29}N_4O_4S_2$ 441.1630, found 441.1624 (M+H)$^+$.

N-(4-(N-(5-Sulfamoyl-1,3,4-thiadiazol-2-yl)sulfamoyl) phenyl)decanamide (139). 5-(4-Aminophenylsulfonamido)-1,3,4-thiadiazole-2-sulfonamide (7, 50 mg, 0.15 mmol) was suspended in anhydrous acetonitrile (5 mL). Triethylamine (17.1 mg, 0.17 mmol) was added with stirring at 0° C. A solution of decanoyl chloride (32.4 mg, 0.17 mmol) dissolved in anhydrous acetonitrile (1 mL) was added dropwise, and the reaction mixture was stirred at 0° C. for 2 h and overnight at room temperature. Volatiles were removed in vacuo and the residue was washed with water (5 mL). The residue was subjected to chromatography on silica gel (70-230 mesh) eluted with $CH_2Cl_2$:methanol 9:1, giving the pure product as a solid (42 mg, 0.09 mmol, 60% yield), mp 242-243° C.; $^1$H NMR (300 MHz, DMSO-d$_6$) δ 0.84 (t, 3H, J=6.9 Hz), 1.24 (m, 12H), 1.56 (m, 2H), 2.32 (t, 2H, J=7.5 Hz), 7.66 (s, 4H), 7.91 (s, 2H), 10.13 (s, 1H); $^{13}$C NMR (75 MHz, DMSO-d$_6$) δ 14.1, 22.3, 25.2, 28.8, 29.0, 31.5, 36.6, 118.6, 127.0, 137.4, 142.2, 157.8, 170.8, 172.1; LRMS (LCQ, ESI) calcd for $C_{18}H_{26}N_5O_5S_3$ 488.1, found 488.1 (M−H)$^-$; HRMS (ESI$^-$, m/z) calcd for $C_{18}H_{26}N_5O_5S_3$ 488.1102, found 487.1101 (M−H).

5-(4-Dodecylphenylsulfonamido)-1,3,4-thiadiazole-2-sulfonamide (140). 5-Amino-1,3,4-thiadiazolo-2-sulfonamide (200 mg, 1.1 mmol) was suspended in anhydrous acetonitrile (5 mL). Triethylamine (123 mg, 1.2 mmol) was added with stirring at 0° C. followed by a solution of 4-dodecylbenzenesulfonyl chloride (383 mg, 1.1 mmol) in anhydrous acetonitrile (3 mL). The reaction mixture was stirred overnight at room temperature. Volatiles were then removed in vacuo and the residue was washed with water (5 mL) in order to eliminate the ammonium salt. The crude solid was subjected to chromatography on silica gel (70-230 mesh) eluted with $CH_2Cl_2$:methanol 19:1 to give the product in 39% yield. Recrystallization from absolute ethanol and a second round of chromatography gave an analytic sample, mp 249-250° C.; $^1$H NMR (300 MHz, DMSO-d$_6$) δ 0.85 (t, 3H, J=6.6 Hz), 1.23 (m, 18H), 1.55 (m, 2H), 2.58 (t, 2H, J=7.2 Hz), 7.23 (d, 2H, J=7.8 Hz), 7.34 (s, 2H), 7.59 (d, 2H, J=8.1 Hz); $^{13}$C NMR (75 MHz, DMSO-d$_6$) δ 13.9, 22.1, 28.7, 28.9, 29.0, 29.1, 30.8, 31.3, 34.9, 126.2, 127.8, 143.3, 145.1, 161.2, 170.9; LRMS (LCQ, ESI) calcd for $C_{20}H_{31}N_4O_4S_3$ 487.2, found 487.1 (M−H)$^-$; HRMS (ESI$^-$, m/z) calcd for $C_{20}H_{31}N_4O_4S_3$ 487.1513, found 487.1514 (M−H).

4-Butyl-N-(1,3,4-thiadiazol-2-yl)benzenesulfonamide (155). To a stirred solution of 2-amino-1,3,4-thiadiazole (2.0 g, 19.7 mmol) in pyridine (30 mL) under argon at −20° C. was added p-butylbenzenesulfonyl chloride (4.89 g, 21 mmol) over 10 min. The reaction mixture was stirred at room temperature for 16 hours. Water (300 mL) was added to quench the reaction. The mixture was extracted with $CH_2Cl_2$ and the organic extracts washed with 2N HCl (2×150 mL), brine, dried over anhydrous $Na_2SO_4$, filtered, and concentrated. The residue was purified by flash chromatography on silica gel eluted with methanol:DCM 1:33 to give the product (3.46 g, 11.6 mmol, 59% yield) as a solid, mp 120-121° C.; $^1$H NMR (300 MHz, CDCl$_3$) δ 0.91 (t, 3H, J=7 Hz), 1.29-1.37 (m, 2H), 1.56-1.61 (m, 2H), 2.65 (t, 2H, J=7 Hz), 7.27 (d, 2H, J=8 Hz), 7.84 (d, 2H, J=8 Hz), 8.25 (s, 1H); $^{13}$C NMR (75 MHz, CDCl$_3$) 13.9, 22.3, 33.2, 33.6, 126.5, 129.1, 138.1, 142.7, 148.6, 167.4; MS (Q-TOF) Calcd for $C_{12}H_{16}N_3O_2S_2$ 298.0684, found 298.0695 (M+H)$^+$; Calcd for $C_{12}H_{15}N_3NaO_2S_2$ 320.0503, found 320.0361 (M+Na)$^+$.

p-Butylbenzenesulfonyl Chloride. To a solution of butylbenzene (4.13 g, 30.8 mmol) in CHCl$_3$ (50 mL) was added chlorosulfonic acid (17 mL, 29.8 g, 256 mmol) and the mixture was stirred at rt for 20 h. The mixture was poured on ice (200 mL) and extracted with EtOAc (3×100 mL). The combined extracts were washed with water, a solution of NaHCO$_3$, and water, dried (Na$_2$SO$_4$), and concentrated in vacuo. The yellow oily residue (ca 88% yield) was used without further purification in the next reaction; $^1$H NMR (300 MHz, CDCl$_3$) δ 0.94 (t, 3H, J=7 Hz), 1.34-1.41 (m, 2H), 1.62-1.67 (m, 2H), 2.73 (t, 2H, J=8 Hz), 7.41 (d, 2H, J=8 Hz), 7.94 (d, 2H, J=8 Hz).

4-Octyl-N-(1,3,4-thiadiazol-2-yl)benzenesulfonamide (153). To a stirred solution of 2-amino-1,3,4-thiadiazole (2.0 g, 19.7 mmol) in pyridine (30 mL) under argon at −20° C. was added p-octylbenzenesulfonyl chloride (6.06 g, 21 mmol) over 10 min. The reaction mixture was stirred at room temperature for 16 hours. Water (300 mL) was added to quench the reaction. The mixture was extracted with $CH_2Cl_2$ and the organic extracts washed with 2N HCl (2×150 mL), brine, dried over anhydrous Na$_2$SO$_4$, filtered, and concentrated. The residue was purified by flash chromatography on silica gel eluted with methanol:DCM 1:33 to give the product (3.83 g, 10.8 mmol, 55% yield) as a solid, mp 123-124° C.; $^1$H NMR (300 MHz, CDCl$_3$) δ 0.87 (t, 3H, J=7 Hz), 1.36 (m, 10H), 1.59 (m, 2H), 2.63 (t, 2H, J=7 Hz), 7.27 (d, 2H, J=8 Hz), 7.82 (d, 2H, J=8 Hz), 8.23 (s, 1H); $^{13}$C NMR (75 MHz, CDCl$_3$) 14.1, 22.6, 29.2, 29.3, 29.4, 31.1, 31.8, 35.9, 126.5, 129.0, 138.1, 142.6, 148.7, 167.3; MS (Q-TOF) Calcd for $C_{16}H_{24}N_3O_2S_2$ 354.1310, found 354.1211 (M+H)$^+$; Calcd for $C_{16}H_{23}N_3NaO_2S_2$ 376.1129, found 376.1154 (M+Na)$^+$.

p-Octylbenzenesulfonyl Chloride. To a solution of 1-phenyloctane (5.86 g, 30.8 mmol) in CHCl$_3$ (50 mL) was added chlorosulfonic acid (17 mL, 29.8 g, 256 mmol) and the mixture was stirred at rt for 20 h. The mixture was poured on ice (200 mL) and extracted with EtOAc (3×100 mL). The combined extracts were washed with water, a solution of NaHCO$_3$, and water, dried (Na$_2$SO$_4$), and concentrated in vacuo. The yellow oily residue (ca 80% yield) was used without further purification in the next reaction; $^1$H NMR (300 MHz, CDCl$_3$) δ 0.87 (t, 3H, J=7 Hz), 1.27-1.32 (m, 10H), 1.64-1.66 (m, 2H), 2.72 (t, 2H, J=8 Hz), 7.42 (d, 2H, J=8 Hz), 7.93 (d, 2H, J=8 Hz).

4-Hexyl-N-(1,3,4-thiadiazol-2-yl)benzenesulfonamide (154). To a stirred solution of 2-amino-1,3,4-thiadiazole (2.0 g, 19.7 mmol) in pyridine (30 mL) under argon at −20° C. was added p-hexylbenzenesulfonyl chloride (5.48 g, 21 mmol) over 10 min. The reaction mixture was stirred at room temperature for 16 hours. Water (300 mL) was added to quench the reaction. The mixture was extracted with $CH_2Cl_2$ and the organic extracts washed with 2N HCl (2×150 mL), brine, dried over anhydrous Na$_2$SO$_4$, filtered, and concentrated. The residue was purified by flash chromatography on silica gel eluted with methanol:DCM 1:33 to give the product (3.72 g, 11.4 mmol, 58% yield) as a solid, mp 125-126° C.; $^1$H NMR (300 MHz, CDCl$_3$) δ 0.88 (t, 3H, J=7 Hz), 1.28 (m, 6H), 1.58 (m, 2H), 2.63 (t, 2H, J=7 Hz), 7.27 (d, 2H, J=8 Hz), 7.83 (d, 2H, J=8 Hz), 8.24 (s, 1H); $^{13}$C NMR (75 MHz, CDCl$_3$) 14.1, 22.6, 28.9, 31.1, 31.6, 35.9, 126.5, 129.0, 138.1, 142.6, 148.6, 167.4; MS (Q-TOF) Calcd for $C_{14}H_{20}N_3O_2S_2$ 326.0997, found 326.0931 (M+H)$^+$; Calcd for $C_{14}H_{19}N_3NaO_2S_2$ 348.0816, found 348.0816 (M+Na)$^+$.

p-Hexylbenzenesulfonyl Chloride. To a solution of 1-hexylbenzene (5.00 g, 30.8 mmol) in CHCl$_3$ (50 mL) was added chlorosulfonic acid (17 mL, 29.8 g, 256 mmol) and the mixture was stirred at rt for 20 h. The mixture was poured on ice (200 mL) and extracted with EtOAc (3×100 mL). The combined extracts were washed with water, a solution of NaHCO$_3$, and water, dried (Na$_2$SO$_4$), and concentrated in vacuo. The yellow oily residue (ca 81% yield) was used without further purification in the next reaction; $^1$H NMR (300 MHz, CDCl$_3$) δ 0.88 (t, 3H, J=7 Hz), 1.30-1.35 (m, 6H), 1.55-1.63 (m, 2H), 2.59 (t, 2H, J=8 Hz), 7.38 (d, 2H, J=8 Hz), 7.89 (d, 2H, J=8 Hz).

4-Tetradecyl-N-(1,3,4-thiadiazol-2-yl)benzenesulfonamide (156). To a solution of p-tetradecylbenzenesulfonyl chloride (440 mg, 1.18 mmol) in pyridine (8 mL) was added 1,3,4-thiadiazol-2-amine (179 mg, 1.77 mmol). The reaction mixture was stirred at room temperature for 6 hours, then 2 M HCl (40 mL) was added to quench the reaction. The mixture was extracted with ethyl acetate (3×50 mL), the organic layer was washed with water (40 mL) and brine (40 mL), dried over anhydrous Na$_2$SO$_4$ and concentrated. The residue was purified by chromatography over silica gel (70-230 mesh) eluted with methanol:DCM 1:19 to give the product as a solid (240 mg, 0.55 mmol, 47% yield), mp 116-117° C.; $^1$H NMR (300 MHz, CDCl$_3$) δ 0.88 (t, 3H, J=6.9 Hz), 1.25 (m, 22H), 1.60 (m, 2H), 2.64 (t, 2H, J=7.2 Hz), 7.29 (d, 2H, J=8.4 Hz), 7.84 (d, 2H, J=8.4 Hz), 8.23 (s, 1H); $^{13}$C NMR (75 MHz, CDCl$_3$) 14.1, 22.6, 29.2, 29.3, 29.4, 29.5, 29.6, 31.1, 31.9, 35.9, 126.5, 128.9, 138.1, 142.6, 148.6, 167.4; MS (LCQ, ESI$^+$) Calcd for C$_{22}$H$_{36}$N$_3$O$_2$S$_2$ 438.2, found 438.3 (M+H)$^+$; HRMS (ESI$^+$, m/z) Calcd for C$_{22}$H$_{36}$N$_3$O$_2$S$_2$ 438.2243, found 438.2243 (M+H)$^+$.

p-Tetradecylbenzenesulfonyl Chloride. To a solution of 1-phenyloctadecane (0.69 g, 2.5 mmol) in CHCl$_3$ (5 mL) was added chlorosulfonic acid (0.5 mL, 7.5 mmol) and the mixture was stirred at rt for 22 h. The mixture was poured on ice and extracted with CH$_2$Cl$_2$. The combined extracts were washed with water, a solution of NaHCO$_3$, and water, dried (Na$_2$SO$_4$), and concentrated in vacuo. The residue was chromatographed on silica gel (70-230 mesh) with hexane/ethyl acetate (49:1) to give the product as a white solid (0.63 g, 1.7 mmol, 68%), mp 32-33° C.; $^1$H NMR (300 MHz, CDCl$_3$) δ 0.88 (t, 3H, J=7.2 Hz), 1.25 (m, 22H), 1.65 (m, 2H), 2.72 (t, 2H, J=7.8 Hz), 7.42 (d, 2H, J=8.4 Hz), 7.93 (d, 2H, J=8.4 Hz); $^{13}$C NMR (75 MHz, CDCl$_3$) 14.1, 22.6, 29.1, 29.3, 29.5, 29.6, 29.7, 30.9, 31.9, 36.0, 126.9, 129.5, 141.7, 151.6.

4-Hexadecyl-N-(1,3,4-thiadiazol-2-yl)benzenesulfonamide (157). To a solution of p-hexadecylbenzenesulfonyl chloride (600 mg, 1.50 mmol) in pyridine (8 mL) was added 1,3,4-thiadiazol-2-amine (228 mg, 2.25 mmol). The reaction mixture was stirred at room temperature for 6 hours, then 2 M HCl (40 mL) was added to quench the reaction. The mixture was extracted with ethyl acetate (3×50 mL), the organic layer was washed with water (40 mL) and brine (40 mL), dried over anhydrous Na$_2$SO$_4$ and concentrated. The residue was purified by chromatography over silica gel (70-230 mesh) eluted with methanol:DCM 1:19 to give the product as a solid (320 mg, 0.69 mmol, 46% yield), mp 118-119° C.; $^1$H NMR (300 MHz, CDCl$_3$) δ 0.88 (t, 3H, J=6.9 Hz), 1.25 (m, 26H), 1.59 (m, 2H), 2.64 (t, 2H, J=8.1 Hz), 7.29 (d, 2H, J=7.8 Hz), 7.84 (d, 2H, J=7.8 Hz), 8.23 (s, 1H); $^{13}$C NMR (75 MHz, CDCl$_3$) 14.1, 22.7, 29.2, 29.3, 29.4, 29.6, 29.7, 31.1, 31.9, 35.9, 126.5, 128.9, 138.1, 142.5, 148.7, 167.5; MS (LCQ, ESI$^+$) Calcd for C$_{24}$H$_{40}$N$_3$O$_2$S$_2$ 466.3, found 466.3 (M+H)$^+$; HRMS (ESI$^+$, m/z) Calcd for C$_{24}$H$_{40}$N$_3$O$_2$S$_2$ 466.2556, found 466.2558 (M+H)$^+$.

p-Hexadecylbenzenesulfonyl Chloride. To a solution of 1-phenyloctadecane (0.76 g, 2.5 mmol) in CHCl$_3$ (5 mL) was added chlorosulfonic acid (0.5 mL, 7.5 mmol) and the mixture was stirred at rt for 22 h. The mixture was poured on ice and extracted with CH$_2$Cl$_2$. The combined extracts were washed with water, a solution of NaHCO$_3$, and water, dried (Na$_2$SO$_4$), and concentrated in vacuo. The residue was chromatographed on silica gel (70-230 mesh) with hexane/ethyl acetate (49:1) to give the product as a white solid (0.71 g, 1.8 mmol, 72%), mp 35-36° C.; $^1$H NMR (300 MHz, CDCl$_3$) δ 0.88 (t, 3H, J=7.2 Hz), 1.25 (m, 26H), 1.62 (m, 2H), 2.72 (t, 2H, J=7.8 Hz), 7.42 (d, 2H, J=8.4 Hz), 7.95 (d, 2H, J=8.4 Hz); $^{13}$C NMR (75 MHz, CDCl$_3$) 14.4, 22.9, 29.4, 29.64, 29.8, 29.9, 31.2, 32.2, 36.3, 127.3, 129.8, 142.0, 151.9.

4-Octadecyl-N-(1,3,4-thiadiazol-2-yl)benzenesulfonamide (158). To a solution of p-octadecylbenzenesulfonyl chloride (500 mg, 1.17 mmol) in pyridine (8 mL) was added 1,3,4-thiadiazol-2-amine (177 mg, 1.75 mmol). The reaction mixture was stirred at room temperature for 6 hours, then 2 M HCl (40 mL) was added to quench the reaction. The mixture was extracted with ethyl acetate (3×50 mL), the organic layer was washed with water (40 mL) and brine (40 mL), dried over anhydrous Na$_2$SO$_4$ and concentrated. The residue was purified by chromatography over silica gel (70-230 mesh) eluted with methanol:DCM 1:19 to give the product as a solid (296 mg, 0.60 mmol, 51% yield), mp 116-117° C.; $^1$H NMR (300 MHz, CDCl$_3$) δ 0.86 (t, 3H, J=6.9 Hz), 1.25 (m, 30H), 1.60 (m, 2H), 2.64 (t, 2H, J=7.8 Hz), 7.29 (d, 2H, J=7.8 Hz), 7.82 (d, 2H, J=7.8 Hz), 8.21 (s, 1H); $^{13}$C NMR (75 MHz, CDCl$_3$) 14.0, 22.7, 29.2, 29.3, 29.4, 29.5, 29.6, 29.7, 31.1, 31.9, 35.9, 126.5, 128.9, 138.1, 142.6, 148.6, 167.4; MS (LCQ, ESI$^+$) Calcd for C$_{26}$H$_{44}$N$_3$O$_2$S$_2$ 494.3, found 494.2 (M+H)$^+$; HRMS (ESI$^+$, m/z) Calcd for C$_{26}$H$_{44}$N$_3$O$_2$S$_2$ 494.2869, found 494.2869 (M+H)$^+$.

p-Octadecylbenzenesulfonyl Chloride. To a solution of 1-phenyloctadecane (0.84 g, 2.5 mmol) in CHCl$_3$ (5 mL) was added chlorosulfonic acid (0.5 mL, 7.5 mmol) and the mixture was stirred at rt for 22 h. The mixture was poured on ice and extracted with CH$_2$Cl$_2$. The combined extracts were washed with water, a solution of NaHCO$_3$, and water, dried (Na$_2$SO$_4$), and concentrated in vacuo. The residue was chromatographed on silica gel (70-230 mesh) with hexane/ethyl acetate (49:1) to give the product as a white solid (0.60 g, 1.4 mmol, 56%), mp 43-44° C.; $^1$H NMR (300 MHz, CDCl$_3$) δ 0.86 (t, 3H, J=6.9 Hz), 1.25 (m, 30H), 1.65 (m, 2H), 2.72 (t, 2H, J=7.8 Hz), 7.42 (d, 2H, J=8.4 Hz), 7.93 (d, 2H, J=8.4 Hz); $^{13}$C NMR (75 MHz, CDCl$_3$) 14.1, 22.7, 29.2, 29.4, 29.5, 29.7, 30.9, 31.9, 36.0, 127.1, 129.6, 141.8, 151.7.

Scheme 3. Synthesis of compound 137.

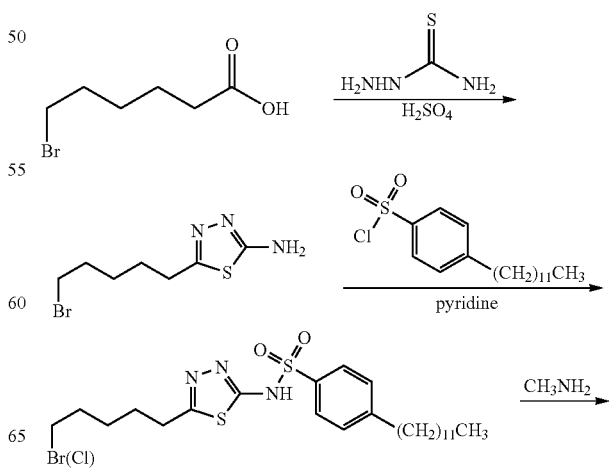

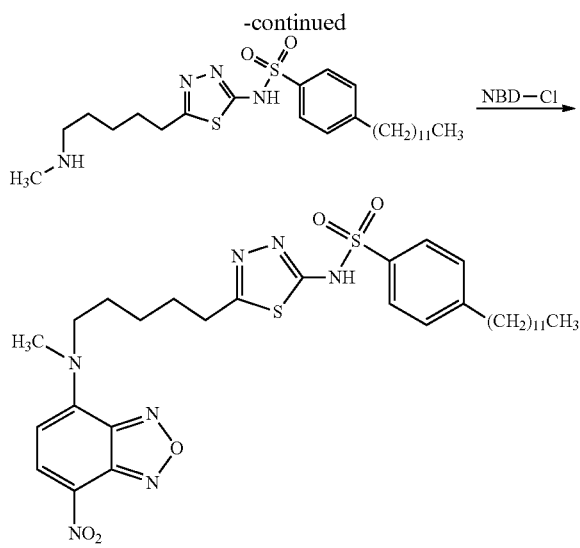

4-Dodecyl-N-(5-(5-(methyl(7-nitrobenzo[c][1,2,5]oxadiazol-4-yl)amino)pentyl)-1,3,4-thiadiazol-2-yl)benzenesulfonamide (137). 4-Chloro-7-nitro-2,1,3-benzoxadiazole (NBD-Cl) (18 mg, 0.085 mmol) was dissolved in methanol (1 mL). After the addition of 4-dodecyl-N-(5-(5-(methylamino)pentyl)-1,3,4-thiadiazol-2-yl)benzenesulfonamide (43 mg, 0.085 mmol) and NaHCO$_3$ (7 mg, 0.085 mmol) in methanol (2 mL), the solution was stirred for 2 h at 40° C. The reaction mixture was evaporated to dryness under reduced pressure and the residue was chromatographed on silica gel 60 (70-230 mesh) eluted with CH$_2$Cl$_2$:MeOH 49:1. Product 137 was obtained in 53% yield (30 mg, 0.045 mmol), mp 102-104° C. $^1$H NMR (300 MHz, CDCl$_3$) δ 0.87 (t, 3, J=7.2 Hz), 1.25 (m, 18), 1.51-1.57 (m, 4), 1.79-1.85 (m, 4), 2.63 (t, 2, J=6.6 Hz), 2.84 (t, 2, J=7.5 Hz), 3.45 (s, 3), 4.14 (s, 2), 6.11 (d, 1, J=9.3 Hz), 7.27 (d, 2, J=8.1 Hz), 7.79 (d, 2, J=8.4 Hz), 8.44 (d, 1, J=9.0 Hz); $^{13}$C NMR (75 MHz, CDCl$_3$) δ 14.1, 22.6, 25.7, 27.7, 29.2, 29.3, 29.4, 29.5, 29.6, 30.4, 31.1, 31.9, 35.9, 55.6, 101.2, 126.5, 128.9, 135.4, 138.3, 145.3, 148.5, 154.7, 158.3, 163.8, 167.9; HRMS (ESI$^+$, m/z) calculated for C$_{32}$H$_{46}$N$_7$O$_5$S$_2$ 672.3002, observed 672.2996 (M+H)$^+$.

5-(5-Bromopentyl)-1,3,4-thiadiazol-2-amine. 6-Bromohexanoic acid (5.35 g, 27.4 mmol), concentrated sulphuric acid (15 mL), and thiosemicarbazide (3.0 g, 32.9 mmol) were slowly heated to 80-90° C. for 12 h. After cooling, the content was poured onto crushed ice. The mixture was neutralized with 10% aqueous ammonia and extracted with ethyl acetate (3×100 mL). The organic extracts were washed with 10% Na$_2$CO$_3$ (2×50 mL), water (100 mL), and brine (100 mL), dried over Na$_2$SO$_4$, filtered, and concentrated. The residue was purified by chromatography over silica gel 60 (70-230 mesh) eluted with CH$_2$Cl$_2$:MeOH 19:1 to give the product as a solid, mp 128-130° C., in 59% yield (4.03 g, 16.2 mmol). $^1$H NMR (300 MHz, CDCl$_3$) δ 1.51-1.60 (m, 2), 1.71-1.79 (m, 2), 1.81-1.92 (m, 2), 2.92 (t, 2, J=7.5 Hz), 3.40 (t, 2, J=6.9 Hz), 5.33 (s, 2); $^{13}$C NMR (75 MHz, CDCl$_3$) δ 26.9, 28.1, 29.3, 31.8, 35.0, 158.1, 168.2; HRMS (ESI$^+$, m/z) calculated for C$_7$H$_{13}$BrN$_3$S 250.0014, observed 250.0005 (M+H)$^+$.

N-(5-(5-Bromopentyl)-1,3,4-thiadiazol-2-yl)-4-dodecylbenzenesulfonamide. To a solution of 4-dodecylbenzenesulfonyl chloride (1.53 g, 4.42 mmol) in pyridine (15 mL) was added 5-(5-bromopentyl)-1,3,4-thiadiazol-2-amine. (1.00 g, 4.02 mmol). The reaction mixture was stirred at room temperature for 5 h, then 2 mol/L HCl (25 mL) was added to quench the reaction. The mixture was extracted with ethyl acetate (3×50 mL). The organic extracts were washed with water (50 mL) and brine (50 mL), dried over Na$_2$SO$_4$, filtered, and concentrated. The residue was purified by chromatography over silica gel 60 (70-230 mesh) eluted with CH$_2$Cl$_2$:MeOH 49:1 to give 1.39 g of product as a solid contaminated with N-(5-(5-chloropentyl)-1,3,4-thiadiazol-2-yl)-4-dodecyl benzenesulfonamide in about 60% yield. $^1$H NMR (300 MHz, CDCl$_3$) δ 0.87 (t, 3, J=6.9 Hz), 1.25-1.30 (m, 18), 1.55-1.58 (m, 4), 1.73-1.88 (m, 4), 2.64 (t, 2, J=7.8 Hz), 2.83 (t, 2, J=7.8 Hz), 3.42 (t, 1, J=6.6), 3.55 (t, 1, J=6.3 Hz), 7.27 (d, 2, J=8.1 Hz), 7.84 (d, 2, J=8.1 Hz); $^{13}$C NMR (75 MHz, CDCl$_3$) δ 14.1, 22.6, 26.0, 27.3, 27.4, 27.5, 29.3, 29.4, 29.5, 29.6, 29.7, 30.5, 31.1, 31.8, 31.9, 32.0, 33.2, 35.8, 44.5, 126.5, 128.9, 138.3, 148.3, 158.5, 168.2; HRMS (ESI$^+$, m/z) calculated for C$_{25}$H$_{41}$BrN$_3$O$_2$S$_2$ 558.1824, observed 558.1819 (M+H)$^+$; HRMS (ESI$^+$, m/z) calculated for C$_{25}$H$_{41}$ClN$_3$O$_2$S$_2$ 514.2329, observed 514.2330 (M+H)$^+$.

4-Dodecyl-N-(5-(5-(methylamino)pentyl)-1,3,4-thiadiazol-2-yl)benzenesulfonamide. A mixture of N-(5-(5-bromopentyl)-1,3,4-thiadiazol-2-yl)-4-dodecylbenzenesulfonamide (100 mg, 0.18 mmol), CH$_3$NH$_2$ (0.42 mL, 40% solution in water, 5.4 mmol), K$_2$CO$_3$ (25 mg, 0.18 mmol), and KI (30 mg, 0.18 mmol) was heated at reflux for 2 d. The reaction mixture was diluted with ether (50 mL), washed with brine (20 mL), dried over Na$_2$SO$_4$, filtered, and concentrated. The crude product was purified by chromatography over silica gel 60 (70-230 mesh) eluted with CH$_2$Cl$_2$:methanol 2:3 to give the product as a solid, mp 158-160° C., in 61% yield (56 mg, 0.11 mmol). $^1$H NMR (300 MHz, CDCl$_3$) δ 0.87 (t, 3, J=7.2 Hz), 1.25-1.36 (m, 18), 1.53-1.67 (m, 8), 2.57-2.61 (m, 5), 2.68 (t, 2, J=7.2 Hz), 2.96 (t, 2, J=6.9 Hz), 7.20 (d, 2, J=8.4 Hz), 7.75 (d, 2, J=8.1 Hz); $^{13}$C NMR (75 MHz, CDCl$_3$) δ 14.1, 22.7, 25.5, 28.3, 29.3, 29.4, 29.5, 29.7, 30.5, 31.2, 31.9, 33.1, 35.8, 60.0, 126.1, 128.5, 140.7, 146.7, 163.7, 170.7; HRMS (ESI$^+$, m/z) calculated for C$_{26}$H$_{45}$N$_4$O$_2$S$_2$ 509.2984, observed 509.2972 (M+H)$^+$.

Scheme 4: Synthesis of compounds 316, 331-333, and 360

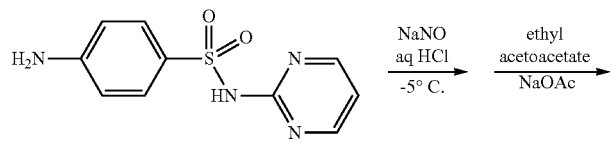

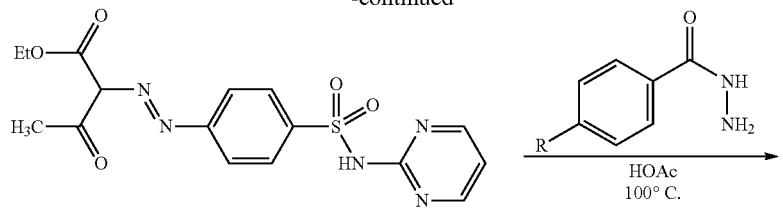
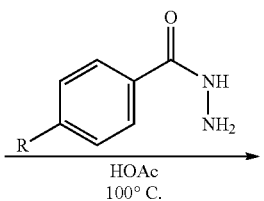
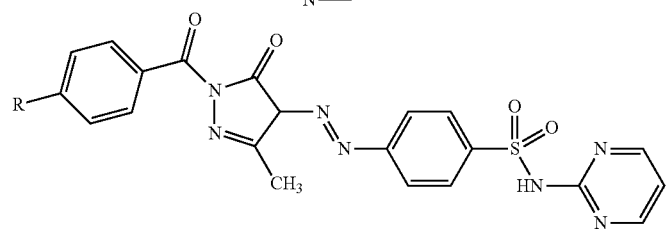

316 R = Cl
331 R = H
332 R = t-Bu
333 R = NH2
360 R = OH (E)-4-(1-(4-chlorobenzoyl)-3-methyl-5-oxo-4,5-dihydro-1H-pyrazol-4-yl)diazenyl)-N-(pyrimidin-2-yl)benzenesulfonamide (316). Sulfadiazine is diazotizated with sodium nitrite under acidic conditions, followed by treatment of the diazonium salt with ethyl acetoacetate and sodium acetate to give p-ketoester in 95% yield. Condensation of p-ketoester with different benzoylhydrazides (4-chlorobenzohydrazide) in glacial acetic acid at 100° C. produced compound 316 and other similar compounds in yields ranging from about 19%-71%. Compound 335 was prepared by treatment of compound 1 with sodium hydride and methyl iodide in THF.

TABLE 1

| Compound Number | Mp (° C.) | Yield (%) |
|---|---|---|
| 100 | 226 | 49 |
| 101 | 151-152 | 95 |
| 102 | 216-217 | 95 |
| 104 | 126-127 | 51 |
| 105 | 207-208 | 72 |
| 106 | 239-240 | 97 |
| 107 | 141-142 | 95 |
| 108 | 149-150 | 84 |
| 109 | 190-191 | 69 |
| 110 | 197-198 | 70 |
| 111 | 121-122 | 97 |
| 112 | 93-94 | 59 |
| 113 | 220-221 | 74 |
| 114 | 137-138 | 84 |
| 115 | 156-157 | 98 |
| 116 | 117-118 | 87 |
| 117 | 209-210 | 82 |
| 118 | 206-207 | 88 |
| 118E | 156-157 | 76 |
| 119 | 190-191 | 83 |
| 119E | 89-90 | 63 |
| 120 | 194-195 | 86 |
| 120E | 108-109 | 43 |
| 122E | 201-202 | 73 |
| 123E | 101-102 | 65 |
| 124E | 96-97 | 34 |
| 125 | 89-90 | 68 |
| 126 | 101-102 | 82 |
| 127 | 69-70 | 73 |
| 128 | 138-139 | 65 |
| 131 | | |

TABLE 1-continued

| Compound Number | Mp (° C.) | Yield (%) |
|---|---|---|
| 138 | | |
| 139 | | |
| 140 | | |
| 153 | | |
| 154 | | |
| 155 | | |
| 156 | | |
| 157 | | |
| 158 | | |

Example 2

In silico Screening

Computational docking was employed to study the interactions between the AKT1 PH domain and its inhibitors. One of the high resolution (0.98 Å) complex AKT PH domain crystal structures (1UNQ) was retrieved from Protein Data Bank (PDB) for docking simulations. Based on structural analysis and literature (28-30), residues Lys[14], Glu[17], Arg[23] and Arg[86] around the inositol-(1,3,4,5)-tetrakisphosphate (Ins(1,3,4,5)P$_4$) ligand were found to be essential for the protein-ligand interactions because they are involved in hydrogen bonds and responsible for the protein conformational change induced by the ligand binding. The binding pocket was, therefore, defined to include all residues within 6.5 Å around these four residues. Before docking, the ligand and crystal waters were removed from the complex structure, and then hydrogen atoms were added to the protein. The PDB 2PQR (30) was utilized to prepare the protein structures such as placing missing hydrogens, calculating the pKa values of protein residues, and so on. Default parameters were applied unless stated otherwise.

Commercially available docking packages, FlexX (FlexX [1.20.1], BioSolveIT GmbH: Sankt Augustin, Germany, 2007), GOLD (GOLD [3.2], CCDC: Cambridge, UK, 2007) and Glide (Glide [4.5], Schrodinger: Portland, Oreg., 2007), were used to dock the original ligand Ins(1,3,4,5)P$_4$ into the binding pocket to evaluate the applicability of each docking package to this target. FlexX produced 100 different docking poses for each ligand within the active site. No early determination was allowed in GOLD to terminate docking on a given ligand. The flexibility of ligand was taken into account by GOLD via flipping the ring corners and hydrogen atoms of the protonated carboxylic acids. Internal hydrogen bonds were included to restrict the flexibility. Glide was set to permit the conformational modification of amide bonds in order to consider the docking flexibility while the protein was treated as a rigid body. The best poses (poses with best scores) from these docking algorithms were re-evaluated using X-score to calculate their potential binding affinities. Because all showed reasonable predictions (small RMSD) of the binding mode compared with the crystal structure, all three programs were employed for all docking studies using default parameters unless otherwise noted. Among them GOLD could reproduce the crystal structure with the best predictions, and thus its docking results were used if there were any inconsistencies from the three packages.

GOLD, FlexX and Glide algorithms were employed to dock the compounds into the binding pocket of the AKT PH domain, see e.g. Table 3. The GOLD algorithm showed consistently better predictability for compound 100 and related compounds than either the FlexX or the Glide algorithms and thus was used to calculate the predicted binding affinities ($K_D$ values) by X-score. Docking programs and their related scoring functions cannot successfully rank putative ligands by binding affinity. Instead, these same functions were used to classify active and inactive ligands for the analog series in this system. The docking values were directly compared to the measured binding affinities obtained using surface plasmon resonance spectroscopy, see e.g., Table 2 and FIG. 6A. SPR was carried out by injecting the compounds over the surface of expressed and isolated AKT at the indicated concentrations and measuring binding of the compounds to the protein target.

A 3D pharmacophore search was carried out as described above based on the hydrogen-bonding pattern between the inositol(1,3,4,5)-tetrakisphosphate ligand and the PH domain of AKT (1H10) using UNITY (Tripos, L.P.). A virtual library of approximately 300,000 compounds generated from databases (the NCI Chemical and Natural Products Library, the Maybridge Available Chemicals Directory, and the LeadQuest Chemical Library) was searched. Twenty compounds from each database were selected, the compounds were pooled and duplicates removed. This process lead to the identification of the initial four compounds shown in Table 2, each of these compounds was examined in the active site using hand modeling and structure-based design. The four compounds identified using a pharmacophore screen (7% hit rate) each contain a series of ring structures connected by short flexible linker regions. The $IC_{50}$ of these compounds ranged from 1 μmmol/L to 50 mmol/L in a cellular AKT inhibition assay. Although compound 316 contains the undesirable alkyl, aryl-azo moiety, and compound 389 has a fairly high calculated LogP (4.4). Each of these compounds is a weak acid and will be an anion in typical intracellular compartments, which may allow binding to the strongly basic binding site of the PH domain.

TABLE 2

Structures, predicted in silico properties, ADME properties and biological activities of four novel hits

| Compound Number | FlexX score | Gold fitness | Glide score | LogP | Caco-2 Pe* ($10^{-6}$ cm/s) | $K_D$† (μmol/L) | AKT inhibition‡ ($IC_{50}$, μmol/L) | Cell survival§ ($IC_{50}$, μmol/L) |
|---|---|---|---|---|---|---|---|---|
| 316 | −34.84 | 60.94 | −2.75 | 3.7 | 163.9 | 0.39 ± 0.04 | 24.0 | 25.0 |
| 345 | −43.63 | 63.78 | −3.80 | 0.7 | 0.1 | 1.79 ± 0.26 | 50.0 | >100 |
| 389 | −35.44 | 54.25 | −3.80 | 2.6 | 124.2 | 4.58 ± 1.72 | 5.0 | >100 |
| 415 | −27.02 | 64.36 | −3.62 | 1.4 | 0.8 | 6.27 ± 1.16 | 1.0 | 3.1 |

*Caco-2 permeability (Pe) is calculated for pH = 7.4 and rpm = 500.
†The $K_D$ was obtained using SPR spectroscopy.
‡Inhibition of AKT was measured by Western blots using specific antibodies against phospho-Ser[473]–AKT in HT-29 lung cancer cells.
§Cell survival was measured using an MTT assay in HT-29 lung cancer cells.

To obtain additional SAR data and develop reliable binding models in the AKT system, a database of approximately 2.3 million unique compounds was assembled from vendor databases. After an initial collection of several hundred compounds was identified, a subset of 46 compounds was selected manually based on the following criteria: conservative analogs of the known hits, explore a range of new SAR data, challenge the need for an anion in the hits, and avoid non-medicinal, toxic, reactive and unstable functional groups.

An in silico screen of the subset of 46 compounds was conducted to identify small molecules that would be expected to bind to the PH domain of AKT, and twenty-two of these compounds were identified and tested for their ability to inhibit phospho-Ser[473]-AKT in Panc-1 (FIG. 1, black bars) and MiaPaCa-2 (FIG. 1, grey bars) pancreatic cancer cells. Human MiaPaca-2, BxPC-3 and Panc-1 pancreatic cancer cells were obtained from the American Type Culture Collection. Cells were maintained and drug treated as described in Mahadevan D, Powis G, Mash E A, et al. Discovery of a novel class of AKT pleckstrin homology domain inhibitors. Mol Cancer Ther 7:2621 (2008) which is hereby incorporated by reference in its entirety. Two compounds, 100 and 455 (9% hit rate), were found to be active against AKT in MiaPaCa-2 cells with $IC_{50}$ values of 20 μmmol/L and 25 μmmol/L, respectively. Furthermore they did not exhibit cytotoxicity in either cell line tested as indicated from Table 2.

Figures 3A, 3B, 3C, 3D:
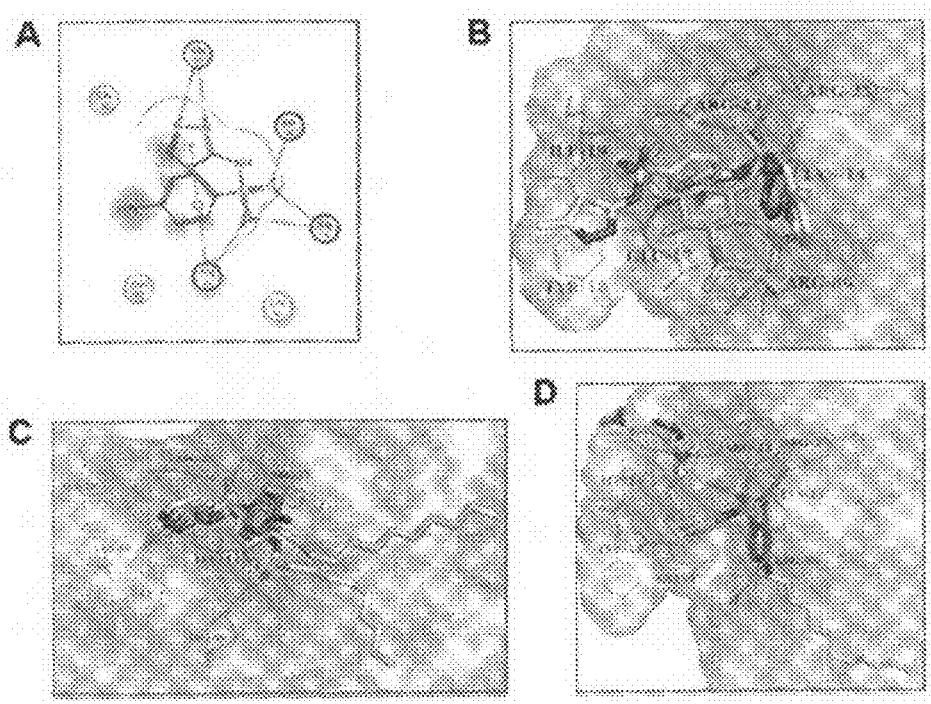
FIGS. 3A-3D show the modeling of interactions between compound 100 and compound 103b to AKT (FIG. 3A); between compound 100 and 103b to AKT (FIG. 3B); between compound 100, 101, 104 and 137 to AKT (FIG. 3C); and between 104 and 137 to AKT (FIG. 3D).

To further improve the potency of these two compounds, several computational approaches were employed to study their binding to the PH domain of AKT as well as their ADMET properties. According to the docking studies using the GOLD algorithm, the sulfonyl moiety of compound 100 acts as a hydrogen bond acceptor interacting with residues Arg[23], Arg[25] and Lys[14] while hydrogen bonding interactions were observed between the nitrogen atoms in the thiadiazolyl group and residue Glu[17] as shown in FIG. 3A. The hydrogen bonding interactions between compound 100 and the protein are similar to those in the original 1UNQ complex as shown in FIG. 3B. In particular, the sulfonyl group interacts with the protein by mimicking the 3-position phosphate of the Ins(1, 3,4,5)$P_4$ ligand. In contrast to compound 100, compound 455 possesses two sulfonyl fragments, which may mimic the 1- and 3-position phosphate groups on the inositol ring and interact with $Arg^{23}$, $Arg^{25}$ and $Lys^{14}$. The positively charged guanidinium cation of $Arg^{23}$ interacts with one of the benzyl rings of compound 100 via charge-charge interaction. Stacking interactions were observed between the thiadiazole ring of compound 455 and the phenyl ring of $Tyr^{18}$.

eling predictions may be enhanced by modificating by, for example, attaching a flexible hydrophobic group. The ADMET properties, such as Caco-2 permeability and LogP values, were calculated using ADMET predictors and ADME Boxes (ADME Boxes [4.0], Pharma Algorithms: Toronto, Ontario, Canada, 2007).

TABLE 3

Compound structures, modeling properties and biological activities

| Compound Number | FlexX score | G-score | X-score* (pK$_d$) | pAKT inhibition† (IC$_{50}$, µmol/L) | Cell viability‡ (IC$_{50}$, µmol/L) |
|---|---|---|---|---|---|
| 436 | −29.2 | −136 | 5.86 | N/I | N/I |
| 100 | −27.4 | −61.5 | 4.59 | 20 | N/I |
| 437 | −23.5 | −71.4 | 5.16 | N/I | N/I |
| 438 | −26.5 | −65.3 | 5.79 | N/I | N/I |
| 439 | −36.0 | −73.6 | 6.42 | 50 | N/I |
| 440 | −35.8 | −32.0 | 4.99 | N/I | N/I |
| 441 | −33.7 | −47.2 | 5.77 | 25 | N/I |
| 442 | −37.8 | −83.4 | 6.18 | N/I | N/I |
| 443 | −31.5 | −31.7 | 5.79 | N/I | N/I |
| 444 | −24.8 | −40.8 | 5.1 | 50 | N/I |
| 445 | −33.1 | −116.0 | 5.7 | 50 | N/I |
| 446 | −26.0 | −89.7 | 5.29 | N/I | N/I |
| 447 | −26.5 | −116.0 | 5.58 | N/I | N/I |
| 448 | −29.1 | −166.0 | 5.76 | N/I | 80 |
| 449 | −30.0 | −113.0 | 5.64 | N/I | 190 |
| 450 | −25.3 | −75.0 | 4.92 | 50 | N/I |
| 451 | −25.4 | −96.0 | 5.38 | N/I | N/I |
| 452 | −29.9 | −133.0 | 5.81 | N/I | N/I |
| 453 | −30.0 | −119.0 | 5.58 | N/I | N/I |
| 454 | −28.6 | −122.0 | 5.53 | N/I | N/I |
| 455 | −33.4 | −91.5 | 5.76 | 25 | N/I |
| 456 | −39.7 | −94.4 | 5.44 | 50 | N/I |

*Calculated pK$_d$ was obtained from the X-score.
†Inhibition of AKT was measured by Western blotting using specific antibodies against phospho-Ser$^{473}$–AKT in MiaPaCa-2 cells; N/I, for no inhibition at the highest concentration tested.
‡Inhibition of cell proliferation was estimated by viability assay as described in the Materials and Methods; N/I, for no inhibition at the highest concentration tested.

Example 3

Optimization

Figures 2A, 2B:
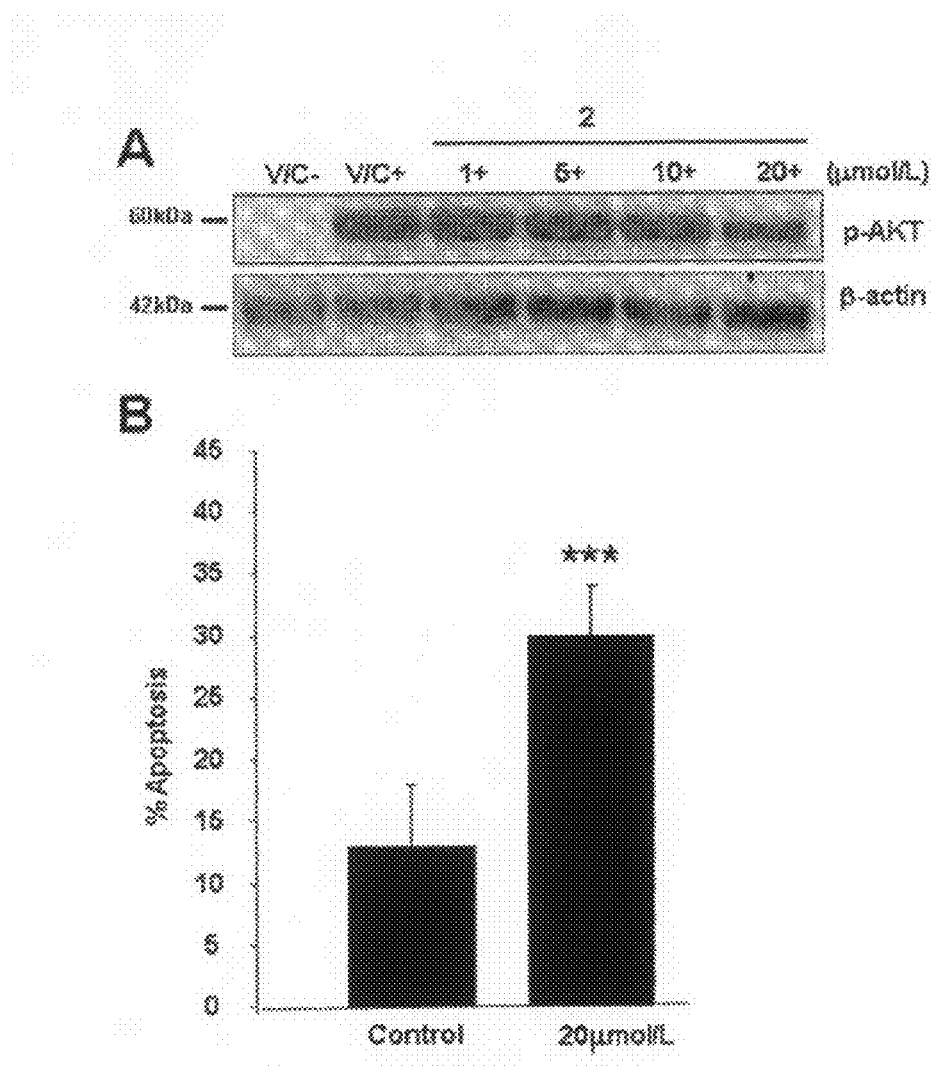
FIGS. 2A-2B show the biological activity of compound 100 in Panc-1 cells.

Experimental cellular AKT inhibition analysis demonstrated that compounds 100, 441 and 455 had approximately the same affinity, yet compound 100 had significantly better ligand efficiency (FIG. 1, FIG. 2, and Table 2). The smaller size of compound 100 may afford greater freedom for structural modification and optimization and therefore was selected for hit-to-lead optimization. Analysis of docking poses showed that the phenyl ring of compound 100 points away from the binding site, and so modifications of the para-amino group were not predicted to affect the binding (FIG. 36). Our docking results indicated that compound 455 might be stronger binder than compound 100. Therefore, the Caco-2 cell permeability of the molecule based on the Absorption, distribution, metabolism, and toxicological (ADMET) mod- Three compounds have a hydrophobic group attached to the phenyl of compound 100 were derived, compounds 101-104 and computationally docked into the PH domain of AKT, synthesized, and experimentally tested for AKT binding and inhibitory activity. The docking results and calculated ADMET properties for compounds 101-104 are summarized in Table 4. The docking studies suggested that compound 101 might be a better inhibitor than compound 100 with a higher LogP and Caco-2 permeability.

TABLE 4

Predicted in silico properties and ADMET properties

| Compound number* | FlexX score | Glide score | Gold fitness | X-score (pK$_D$) | K$_D$† (µmol/L) | Caco-2 permeability‡ (10$^{-6}$ cm/s) | LogP |
|---|---|---|---|---|---|---|---|
| 100 | −26.43 | −2.97 | 50.97 | 4.82 | 15.13 | 0.3 | 0.13 |
| 101 | −21.38 | −2.52 | 57.37 | 4.99 | 10.23 | 10.1 | 4.93 |
| 102 | −27.12 | −3.79 | 49.16 | 4.99 | 10.23 | 0.8 | 0.34 |
| 103 | −30.36 | −3.31 | 57.30 | 4.69 | 20.41 | 1.0 | 0.59 |
| 104 | −14.05 | −1.55 | 60.70 | 4.87 | 13.49 | 0.1 | 7.54 |

†The K$_D$ was obtained from the X-Score (pK$_D$) in mol/L.
‡Caco-2 permeability is calculated for pH = 7.4 and rpm = 500.

Examining Table 4, if compounds 100, 101, and 104 considered active, then Glide and FlexX categorize the five compounds incorrectly. While GOLD and X-score correctly place compound 102 as the least active, Glide and FlexX place compound 103 as either among the most active. Likewise, the 95% confidence interval of the mean FlexX, G-score or X-score for the inactive and active ligands, compounds 100, 439, 441, 444, 445, 450, 455, and 456 using pAKT IC$_{50}$, may have significant overlap. Therefore, docking scores may not successfully differentiate active from inactive ligands among the series represented. Despite this negative affinity categorization, the binding modes predicted by the docking experiments were helpful in the design of the most potent compounds.

Figures 4A, 4B, 4C:
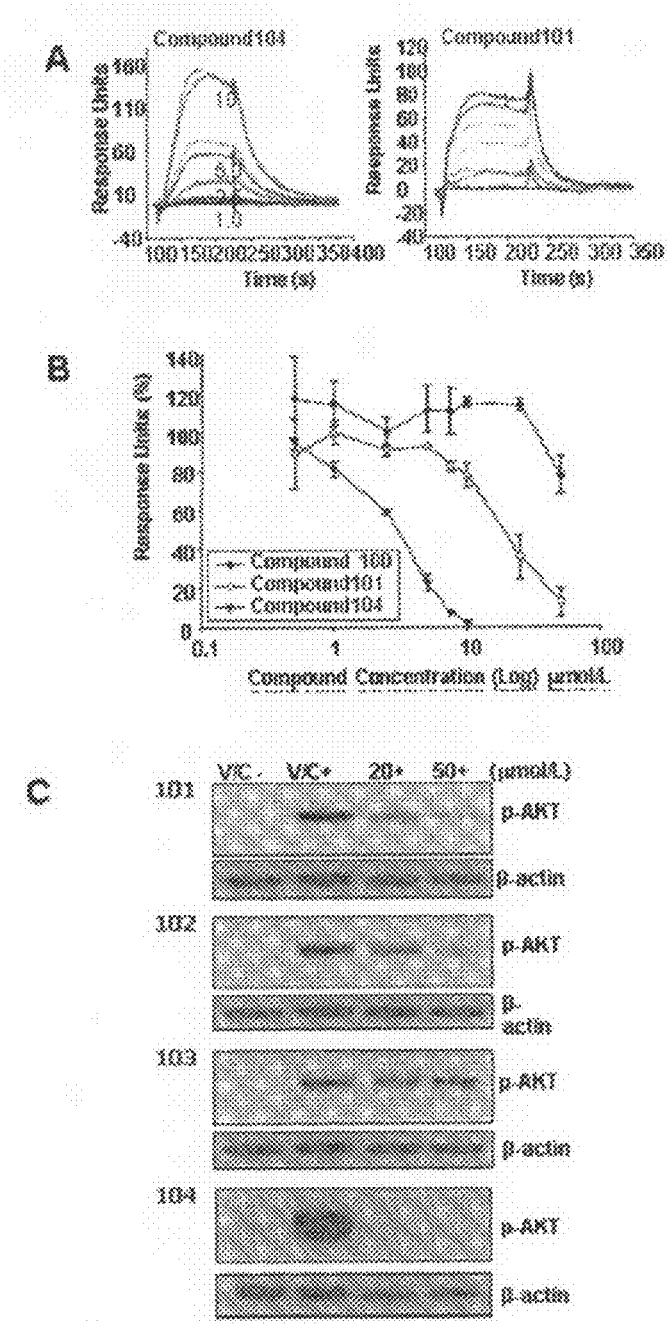
FIGS. 4A-4C show the biological properties of compounds 100, 101, 102, 103 and 104.

The predicted in silico were verified in cellular assays of AKT inhibition (Table 5). The K$_D$ measured using SPR spectroscopy binding assays for compound 100 and compound 101 was 0.45 μmmol/L and 19.6 μmmol/L, respectively. SPR interaction analyses were performed with a Biacore 2000, using Biacore 2000 Control Software v3.2 and BIAevaluation v4.1 analysis software (Biacore) as described in Mol Cancer Ther 7:2621 (2008). For the competitive binding assays and the K$_i$ determination, PtdIns(3,4,5)phosphate-biotin labeled liposomes (Echelon Biosciences) and SA chips were used with increasing concentrations of the compound tested. Data generated using these techniques indicate that compound 101 appears to inhibit AKT at lower concentration than compound 100. By comparison, PtdIns(3,4,5)P$_3$, a native substrate of AKT, appear to bind the PH domain of AKT with a K$_D$ of 3.08±0.49 μmmol/L. Compound 101 was further predicted to have better Caco-2 permeability than compound 100, which could explain its low IC$_{50}$ exhibited in the cellular AKT inhibition assay. Interestingly, calculation of a K$_i$ using liposome displacement and SPR spectroscopy indicate that compound 101 can displace PtdIns-3,4,5-phosphates liposomes at lower concentrations than compound 100 (FIG. 4B and Table 5).

In order to determine whether or not compound 101 is a prodrug of compound 100, a non-amide analog, compound 104, was synthesized and experimentally evaluated. As shown in FIG. 3C, docking studies indicate that the modification did not change the binding mode, and compound 104 showed a higher GOLD fitness of the binding to the PH domain. A lower IC$_{50}$ of 6.3±0.9 μmmol/L for AKT inhibition was observed for this compound in Panc-1 cells (Table 5). However, low Caco-2 cell permeability was predicted for compound 104 with a high LogP value compared to compound 101. Consistent with the prediction, the K$_i$ for compound 104 was significantly lower than those of compounds 100 and 104. For comparison, the displacement of diC8-PtdIns(3,4,5)P$_3$ exhibited a K$_i$ around 0.3 μmmol/L.

TABLE 5

Biochemical and biological activities*†

| Compound number | K$_D$‡ and K$_i$‡ (μmol/L) | pAKT inhibition§ (IC$_{50}$, μmol/L) | Apoptosis∥ at 20 μmol/L (%) | Cell survival** IC$_{50}$, μmol/L |
|---|---|---|---|---|
| 100 | K$_D$ = 0.45 ± 0.1<br>K$_i$ > 50.0 | 20/25 | 24.3 ± 3.2/<br>25.7 ± 2.6 | NI/NI |
| 101 | K$_D$ = 19.6 ± 4.9<br>K$_i$ = 21.8 ± 1.8 | 10/15 | 28.7 ± 0.3/<br>20.0 ± 1.5 | 127/90 |
| 102 | K$_D$ = NB<br>K$_i$ > 50 | >50/>50 | 6.8 ± 0.9/<br>10.3 ± 2.1 | NI/NI |
| 103 | K$_D$ = NB<br>K$_i$ > 50 | >50/>50 | 11.4 ± 0.5/<br>18.7 ± 3.1 | NI/NI |
| 104 | K$_D$ = 40.8 ± 2.5<br>K$_i$ = 2.4 ± 0.6 | 6.3 ± 0.9/10 | 40.0 ± 2.9/<br>31.3 ± 1.6 | 65/30 |

*All biological tests were made in Panc-1 (numbers on the left) and MiaPaca-2 (number on the right) pancreatic cell lines.
†NI, for not inhibitory and NB for not binding.
‡K$_D$ and K$_i$ (μM) were determined using purified AKT PH domain and SPR spectroscopy (Biacore 2000). The K$_i$ for PtdIns(3,4,5)trisphosphate was 0.26 μmol/L.
§Inhibition of AKT was measured by Western blots using specific antibodies against phospho-Ser$^{473}$-AKT.
∥Percentage of apoptosis was obtained by a morphological assay at 20 μmol/L.
**Cell survival was measured using an MTT assay.

Further compounds were prepared as described in Example 1 and characterized using the protocols described above. Such compounds are provided in Table 6 and Table 7 below. Compound 104 data are provided in each table for reference.

TABLE 6

Predicted in Silico Properties and ADME properties

| Compound Number[1] | FlexX score | Glide score | Gold fitness | X-score (pK$_D$) | K$_D$$^2$ (μM) | Caco-2 Permeability$^3$ (10$^{-6}$ cm/s) | LogP |
|---|---|---|---|---|---|---|---|
| 104 | −14.05 | −1.55 | 60.70 | 4.87 | 13.49 | 0.1 | 7.54 |
| 108 | −14.22 | −2.35 | 58.50 | 5.08 | 8.32 | 0.0 | 8.01 |
| 112 | −12.95 | −1.39 | 63.62 | 5.12 | 7.59 | 0.0 | 8.35 |
| 116 | −15.41 | −1.19 | 64.73 | 5.39 | 4.07 | 0.0 | 8.94 |
| 120 | −37.34 | −4.93 | 68.93 | | | 4.6 | 3.95 |
| 120E | −16.78 | −1.79 | 73.72 | | | 0.0 | 7.97 |
| 124E | −21.97 | −1.85 | 59.31 | | | 0.0 | 7.91 |
| 128 | −27.89 | −1.64 | 59.60 | | | 0.2 | 6.73 |

TABLE 6-continued

Predicted in Silico Properties and ADME properties

| Compound Number[1] | FlexX score | Glide score | Gold fitness | X-score (pK$_D$) | K$_D$[2] (μM) | Caco-2 Permeability[3] (10$^{-6}$ cm/s) | LogP |
|---|---|---|---|---|---|---|---|
| 140 | −28.51 | −1.96 | 51.27 | | | 0.0 | 6.50 |
| 106 | −27.13 | −3.35 | 50.38 | | | 1.4 | 0.75 |
| 110 | −25.56 | −3.30 | 52.40 | 5.22 | 6.03 | 2.1 | 1.09 |
| 114 | −26.11 | −3.34 | 53.56 | | | 6.2 | 1.91 |
| 118 | −38.16 | −5.64 | 61.94 | | | 0.1 | 0.01 |
| 118E | −24.76 | −2.79 | 61.28 | | | 1.6 | 1.08 |
| 122E | −31.83 | −2.53 | 49.47 | | | 1.0 | 0.72 |
| 126 | −27.34 | −2.45 | 50.97 | | | 0.1 | −0.28 |
| 138 | −38.27 | −3.08 | 51.03 | | | 0.0 | 0.33 |
| 105 | −26.684 | −2.25 | 51.85 | | | 0.5 | 0.56 |
| 109 | −22.14 | −2.67 | 53.30 | 5.11 | 7.76 | 0.8 | 0.90 |
| 113 | −22.71 | −2.76 | 54.57 | | | 2.3 | 1.73 |
| 117 | −34.77 | −6.28 | 70.27 | | | 0.0 | −0.15 |
| 125 | −27.89 | −2.66 | 52.34 | | | 0.1 | −0.46 |
| 131 | −37.12 | −3.40 | 53.50 | | | 0.0 | −0.05 |
| 107 | −18.95 | −2.37 | 60.19 | | | 3.2 | 5.49 |
| 111 | −19.420 | −1.58 | 59.61 | 5.28 | 5.25 | 1.5 | 5.83 |
| 115 | −21.01 | −1.87 | 59.62 | | | 0.2 | 6.69 |
| 119 | −31.10 | −4.93 | 68.93 | | | 4.6 | 3.95 |
| 119E | −20.18 | −2.16 | 72.43 | | | 3.0 | 5.41 |
| 123E | −24.46 | −2.66 | 55.90 | | | 3.9 | 5.28 |
| 127 | −21.22 | −2.73 | 60.30 | | | 9.0 | 4.28 |
| 129 | −26.61 | −3.50 | 50.95 | | | 0.2 | 0.23 |
| 155 | −38.45 | −2.88 | 61.08 | | | 0.7 | 6.91 |
| 154 | −33.99 | −2.10 | 53.78 | | | 77.3 | 3.91 |
| 153 | −33.00 | −2.06 | 55.99 | | | 13.8 | 5.30 |
| 156 | | | | | | | |
| 157 | | | | | | | |
| 158 | | | | | | | |

[†]The K$_D$ was obtained from the X-Score (pK$_D$) in mol/L.
[‡]Caco-2 permeability is calculated for pH = 7.4 and rpm = 500.

TABLE 7

Biochemical and biological activities[1,2]

| Compounds | K$_D$[3] and K$_i$[3] (μM) | % pAKT Inhibition[4], At 10 μM | Apoptosis[5] at 20 μM (%) | Cell Survival[6], IC$_{50}$ (μM) |
|---|---|---|---|---|
| 104 | K$_D$ = 40.8 ± 2.5 | 6.3 ± 0.9/10 | 40.0 ± 2.9/ | 65/30 |
|  | K$_i$ = 2.4 ± 0.6 | 64 | 31.3 ± 1.6 | |
| 108 | K$_D$ = 48.7/36.3 | 64 | | BxPC3 61 |
| 112 | K$_D$ = 73.0/7.9 | 88 | | 32 |
| 116 | K$_D$ = 587 | 36 | | 45 |
| 120 | K$_D$ = 110/114 | 67 | | >100 |
| 120E | K$_D$ = 20.7 | 62 | | 70 |
| 124E | K$_D$ = 736/616 | 72 | | 36 |
| 128 | K$_D$ = 429 | 68 | | 37 |
| 140 | K$_D$ = 4.6 | 29 | | 85 |
| 106 | NB | NI | | |
| 110 | NB | 45 | | |
| 114 | NB | 20 | | |
| 118 | NB | 19 | | |
| 118E | NB | 55 | | |
| 122E | NB | NI | | |
| 126 | NB | NI | | |
| 138 | NB | NI | | |
| 105 | NB | 11 | | |
| 109 | | 16 | | |
| 113 | NB | 13 | | |
| 117 | NB | 23 | | |
| 125 | NB | 10 | | |
| 131 | NB | 18 | | |
| 107 | K$_D$ = 46.7 | 11 | | |
| 111 | K$_D$ = 178.0 | 22 | | |
| 115 | K$_D$ = 284.0 | 16 | | |
| 119 | K$_D$ = 281.0 | 42 | | |
| 119E | K$_D$ = 105.0 | NI | | |
| 123E | K$_D$ = 109.0 | 10 | | |
| 127 | K$_D$ = 24.5 | 11 | | |

TABLE 7-continued

Biochemical and biological activities[1,2]

| Compounds | $K_D$[3] and $K_i$[3] (μM) | % pAKT Inhibition[4], At 10 μM | Apoptosis[5] at 20 μM (%) | Cell Survival[6], $IC_{50}$ (μM) |
|---|---|---|---|---|
| 129 | | | | |
| 155 | $K_D = 23.7$<br>$K_i > 50.0$ | NI | | |
| 154 | $K_D = 19.1$<br>$K_i > 50$ | NI | | |
| 153 | $K_D = 25.8$<br>$K_i = 8.4$ | 10 | | |
| 156 | $K_D = 58.9$<br>$K_i = 6.7$ | 70 | | |
| 157 | $K_D = 987.0$<br>$K_i = 6.9$ | 50 | | |
| 158 | NB<br>$K_i = 11.4$ | NI | | |

[1]All biological tests were made in BxPC-3 pancreatic cell lines.
[2]NI, for not inhibitory and NB for not binding.
[3]$K_D$ and $K_i$ (μM) were determined using purified AKT PH domain and SPR spectroscopy (Biacore 2000). The $K_i$ for PtdIns(3,4,5)trisphosphate was 0.26 μM.
[4]Inhibition of AKT was measured by Western blots using specific antibodies against phospho-Ser[473]–AKT in BxPC-3.
[5]Percentage of apoptosis was obtained by a morphological assay at 20 μM.
[6]Cell survival was measured using an MTT assay.

Example 4

Biological Activity

AKT inhibition leads to cellular apoptosis. Therefore, the ability of compounds 100 and 101 to 104 to induce cellular apoptosis was measured and correlated with the inhibition of AKT phosphorylation measured by Western blot analysis of phospho-Ser[473]-AKT, see FIGS. 4 and 2. Inhibition of the phosphorylation of AKT and its downstream targets was measured by Western blotting using rabbit polyclonal antibodies to phospho-Ser[473]-AKT, phospho-Thr[308]-AKT, total-AKT, phospho-Ser[9]-GSK3β, phospho-Ser[21]-GSK3β, phospho-Ser[241]-PDK1 and phospho-Thr[389]p70S6-kinase (New England Biolabs/Cell Signaling Technology Inc.) using β-Actin as a loading control as described in Mol Cancer Ther 7:2621 (2008). Bands corresponding to phospho-Ser[473]-AKT and total AKT were quantified using Eagle Eye software (BioRad) and Kodak X-Omat™ Blue XB (NEN™, Life Science Products). Cell growth inhibition was determined using a microcytotoxicity assay and apoptosis was measured as described in Mol Cancer Ther 7:2621 (2008). These protocols were performed with compounds 100 and 455 as shown in FIG. 2. Apoptosis was directly correlated with the inhibition of AKT observed at 20 μmmol/L by Western blot for both initial hits, compounds 100 and 455, see FIG. 2. Compounds 100 and 101 to 104 were also tested for their ability to inhibit cellular AKT activity as shown in FIG. 4C and to induce apoptosis as indicated in Table 5. These compounds induced apoptosis and inhibited AKT phosphorylation.

Figures 5A, 5B, 5C:
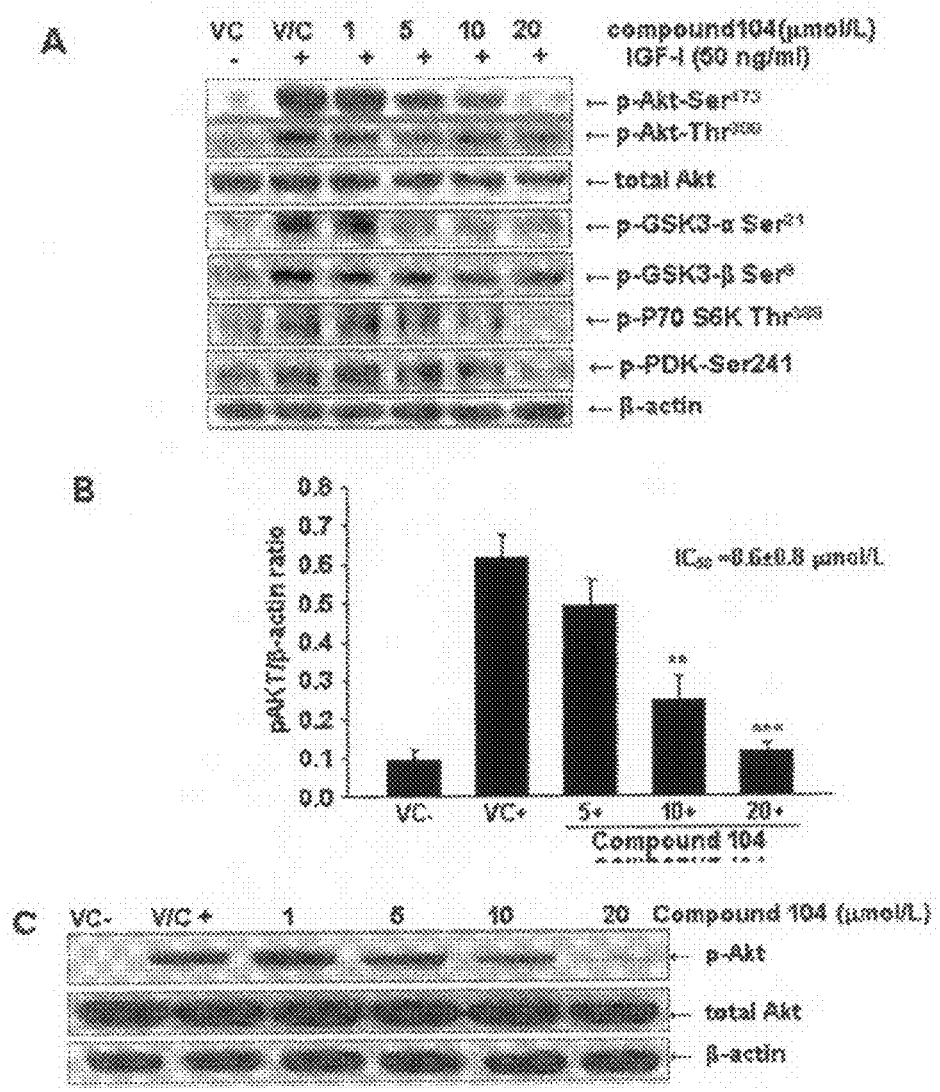
FIGS. 5A-5C show inhibition of AKT and downstream proteins by compound 104.

Additionally, in vitro binding assays using SPR spectroscopy were performed to directly determine the affinities of the lead compounds for the target PH domain. FIG. 5A shows representative sensorgrams obtained for the direct binding of compounds 101 and 104 and $K_D$ was calculated (Table 5). Compounds 102 and 103 did not appear to bind directly to the PH domain of AKT. These results correlate with a very weak inhibition of cellular AKT and weak induction of apoptosis. On the contrary, compound 104 exhibited all the characteristics of an AKT inhibitor with an $IC_{50}$ of 6.3±0.9 μmmol/L in Panc-1 cells, a strong induction of apoptosis at 20 μmmol/L and some cellular cytotoxicity. These data correlate with a low $K_D$ for the compound to the PH domain as measured by SPR spectroscopy. Interestingly again, the measurement of the $K_i$ appears to be the most reliable and predictive assay for compound cellular efficacy.

Moreover, for selectivity purposes, the binding of compound 104 to the PH domain of PDK1 was tested and a $K_D$ of 90.1 μmmol/L, a $K_i$ of 5.5 μmmol/L was obtained. These values correlated well with the Gold score obtained for the compound to the PH domain of PDK (53.5) as compared to 60.7 for the PH domain of AKT. These data suggest that compound 104 may represent an AKT selective compound with some activity on PDK1 at higher concentrations.

The biochemical properties of compound 104 on AKT function in BxPC-3 cells is summarizes in Table 5 ($IC_{50}$=8.6±0.8 μmol/L), and its effects on downstream targets are shown in FIGS. 4A and B and. In brief, compound 104 was able to reduce the phosphorylation of AKT on Ser[473] and less strongly on Thr[308] without affecting AKT expression. Furthermore, GSK3β and p70S6K phosphorylation were inhibited in a dose-dependent manner by compound 104. Phosphorylation of PDK1 Ser[241] was only slightly affected by compound 104 and was only affected at high concentrations of compound 104. These data appear to be in agreement with the SPR results and confirm the selectivity of compound 104 for AKT at low concentrations.

To further describe the action of compound 104, the fluorescent analog compound 137 was used (Scheme 3 and synthesis above). The addition of the fluorescent NBD moiety does not appear to alter the binding of compound 137 to the protein as indicated in FIG. 3D and compound 137 inhibited AKT phosphorylation in a fashion similar to 104 based on AKT inhibition in BxPC-3 cells as shown in FIG. 5C. Finally, confocal microscopy was used to determining the intracellular location of compound 137, which was found to be mainly located in the cytosol and/or lipid vesicles. BxPC-3 cells were grown on coverslips in DMEM plus 10% FBS media. Following 4 h of incubation with 10 mmol/L of compound 137 or with a DMSO control, cells were washed twice in PBS and fixed using 4% par formaldehyde. Coverslips were washed four times in PBS and mounted using mounting media containing DAPI obtained from Molecular Probes Invitrogen. Slides were then visualized using a Nikon PCM2000 confocal microscope (Nikon Instruments Inc.). Without wishing to be bound by theory, the accumulation of compound 137 in the cytosol suggests that AKT may trapped in the cytosol as a result of compound 104 administration as indicated in FIG. 5C.

Figures 6A, 6B, 6C:
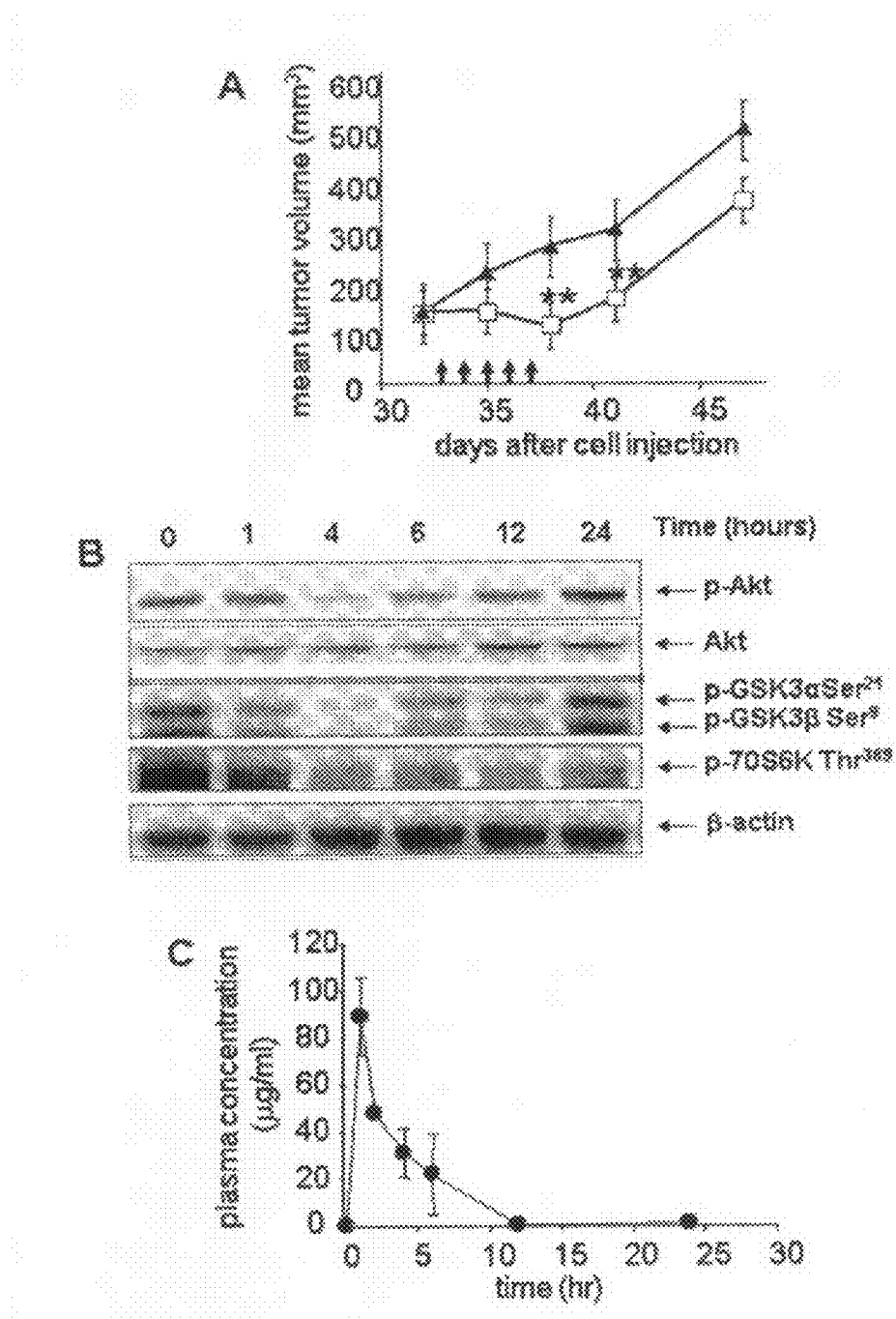
FIGS. 6A-6C show anti-tumor activity and inhibition of AKT by compound 104.

The anti-tumor activity of compound 104 measured against BxPC-3 pancreatic cancer xenografts in scid mice a dose of 125 mg/kg of compound 104 was administered i.p., twice a day for 5 d is shown in FIG. 6A. For these experiments, approximately $1 \times 10^7$ BxPC-3 pancreatic cancer cells in log cell growth suspended in 0.1 mL PBS were injected subcutaneously (s.c.) into the flanks of female severe combined immunodeficient (scid) mice. When the tumors reached volumes of approximately 150 mm$^3$, the mice were stratified into groups of eight animals having approximately equal mean tumor volumes. Compound 104 was suspended in 0.2 mL of an aqueous solution containing 2.5% ethanol and 20% Trappsol® (Cyclodextrin Technologies Development Inc.) by intraperitoneal (i.p.) injection at a dose of 125 mg/kg twice a day for 5 d. The animals were weighed weekly. Tumor diameters, measured twice weekly at right angles ($d_{short}$ and $d_{long}$) using electronic calipers, were converted to volume by the formula, volume=$(d_{short})^2 \times (d_{long})/2$ (32). Significant anti-tumor activity with cessation of tumor growth and even regression during the course of treatment can be observed by such treatment. Notably, tumor growth appears to have resumed at its original rate when the drug was removed (FIG. 6A).

This observation was tested using pharmacodynamic and pharmacokinetic studies. Pancreatic cancer cells ($1 \times 10^7$ BxPC-3) were injected s.c. into the flanks of female scid mice and allowed to grow to approximately 300 mm$^3$. Mice received a single i.p. dose of compound 104 of 125 mg/kg suspended in 0.2 mL of 0.25% ethanol/20% Trappsol® in water. Mice were killed after 1, 4, 6, 12 or 24 h, blood was collected into heparinized tubes, and plasma was stored frozen. The frozen tumors were removed and immediately frozen in liquid N$_2$. The tumors were then homogenized in 50 mmol/L HEPES buffer, pH 7.5, 50 mM NaCl, 1% Nonidet® P40 and 0.25% sodium deoxycholate. Western blotting was performed as described above. Plasma levels of compound 104 were measured by reverse phase high pressure liquid chromatography as described in Mol Cancer Ther 7:2621 (2008). Preliminary studies indicate that compound 104 is not toxic in single doses up to 250 mg/kg, which may be the maximum dose administered. As shown in FIG. 6B, a single 125 mg/kg i.p dose of compound 104 resulted in up to 70% inhibition at 6 hours, which is reduced to 50% inhibition after 12 hours and has returned to about untreated levels after 24 hours as measured by phospho-Ser$^{473}$-AKT concentration. These results correlate well with the plasma concentrations of compound 104 following the single dose as shown in FIG. 4C. Indeed, between 1 and 6 h, a peak corresponding to compound 104 was detected in the plasma.

Example 5

AKT Binding Alkylene R$^1$

Figure 7:
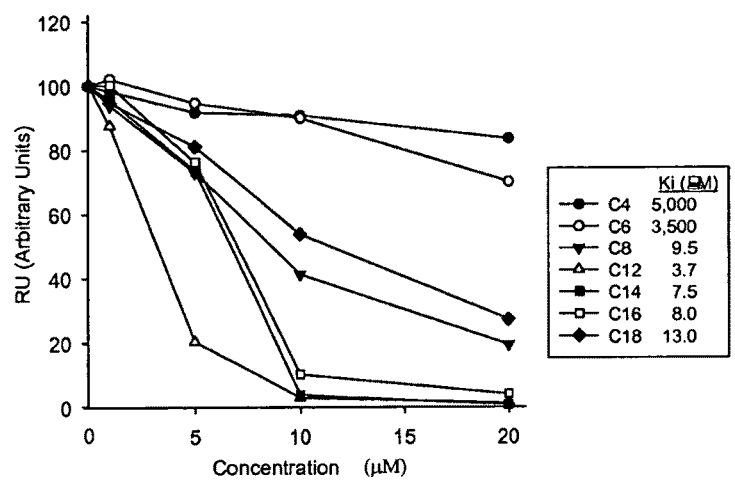
FIG. 7 shows the relative binding of compounds 104, 155, 154, 153, 156, 157 and 158 to the expressed PH domain of AKT.
Figure 8:
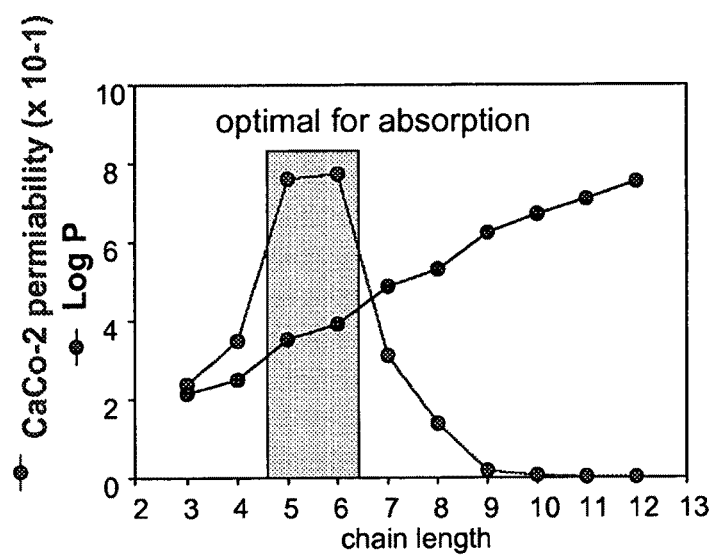
FIG. 8 shows the effects of $R^1$ alkyl chain length on calculated logP and CaCo-2 permeability of compound 104 like compounds.
Figure 9:
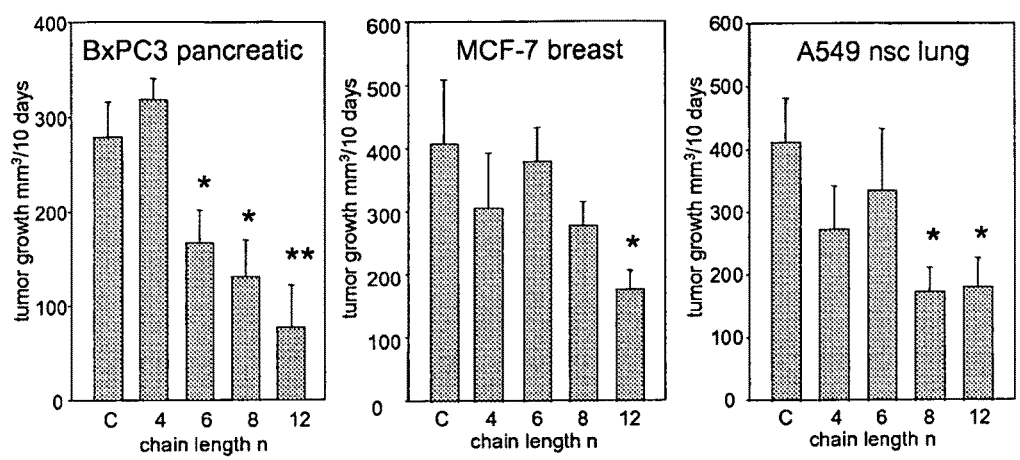
FIG. 9 shows the antitumor activity of compounds 104, 155, 154 and 153.

Analogs of compound 104 having different alkyl chain lengths were synthesized and tested to determine whether reducing the lipophilicity through a reduction in the carbon chain length and increasing the CaCO-2 permeability could improve antitumor activity. A series of compounds having an R$^1$ of a C4 (compound 155), C6 (compound 154), C8 (compound 153), C14 (compound 156), C16 (compound 157), and C18 (compound 158) alkyl chains [1] was synthesized, characterized and compared to compound 104 (C12). Initially, surface plasmon resonance spectroscopy (SPR) was used to measure the binding affinity (K$_i$) of compound 104, and 153 to 158 to the PH domain of AKT by competitive binding of each compound with the natural ligand, PI(3,4,5)-triphosphate. FIG. 7 shows binding curves for each compound. These data suggest that the binding affinity of compound 104 was at a maximum when the alkyl chain length was 12 (compound 104). The calculated CaCo-2 permeability of compounds 104 and 153 to 158 was is provided in FIG. 8 and appear to indicate optimal absorption occurs with compounds having a alkyl chain of 5 or 6 carbons. Therefore, the efficacy of compound 155 (C4), compound 154 (C6), and compound 153 (C8) were tested by administering 200 mg/kg of each of compounds 104, and 153 to 154 twice a day for 10 days to treat subcutaneous xenografts of BXPC3 pancreatic tumor cells, MCF-7 breast tumor cells, and A549 nscl lung cancer cells and determining the tumor growth rate. The results are provide in FIG. 9 and suggest that compound (C12) had the best antitumor activity in each of the tumors tested, followed by compound 153 (C8) and compound 154 (C6). Compound 155 (C4) appears to be inactive. Thus, carbon chain length may be a determinant of antitumor activity.

Example 6

Antitumor Activity of Compound 104

Figure 10:
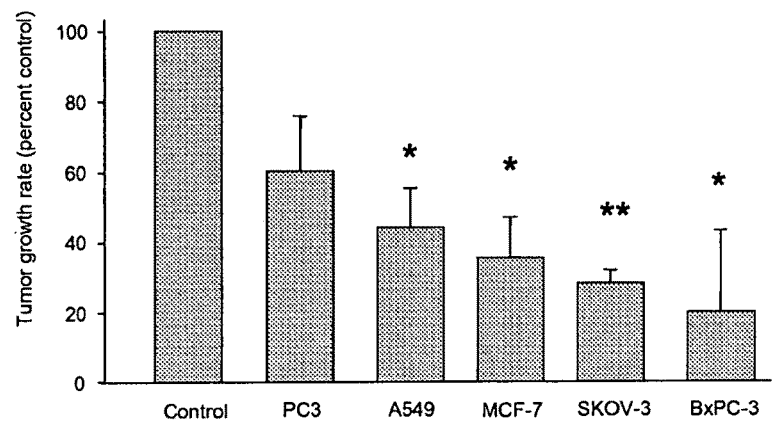
FIG. 10 shows tumor growth inhibition of compound 104 in different carcinogenic cell lines.

Female scid Mice were administered 0.1 ml of compound 104 or its analogs formulated at a concentration up to 50 mg/ml in a 8:2 mixture of Labrafil® (oleoyl macrogolglycerides): Labrasol® (caprylocaproyl macrogolglycerides) which was administered orally by gavage twice a day for 5 or 10 days as follows: PC3 prostate cancer 125 mg/kg twice a day (BID)×5 days; A549 nsc lung cancer 200 mg/kg BID×10 days; MCF-7 breast cancer 200 mg/kg BID×10 days; SKOV-3 ovarian cancer 250 mg/kg BID×10 days; BxPC-3 pancreatic cancer 250 mg/kg BID×5 days. Table 6 shows the antitumor activity of compound 104 at doses of 125 to 250 mg/kg in xenografts of different tumor types. Results are expressed as the growth rate of the compound 104 in treated tumors relative to the control tumors, and are illustrated graphically in FIG. 10. These data suggest that compound 104 provided up to about 80% inhibition of tumor growth in the most sensitive tumors. The pattern of inhibition in different tumors is similar to that of PI-3-kinase inhibitor suggesting that compound 104 may inhibit the PI-3-Kinase/PDK1/AKT signaling pathway.

TABLE 8

Antitumor activity of compound 104

| Tumor [1] | volume at start mm$^3$ | Dose mg/kg | Schedule | Growth rate mm$^3$/10 days | T/C % | p value [3] |
|---|---|---|---|---|---|---|
| BxPC-3 | 156 | control [2] | BID × 5 D | 228 ± 46 | | |
| | | 125 | BID × 5 D | 67 ± 35 | 29.4 | 0.030 |
| | | 250 | BID × 5 D | 46 ± 53 | 20.1 | 0.027 |
| | 97 | control [2] | BID × 10 D | 279 ± 37 | | |
| | | 100 | BID × 10 D | 181 ± 52 | 64.8 | NS [4] |
| | | 200 | BID × 10 D | 77 ± 44 | 27.6 | 0.004 |
| PC3 | 229 | control [2] | BID × 5 D | 780 ± 161 | | |
| | | 125 | BID × 5 D | 470 ± 121 | 60.3 | NS [4] |

TABLE 8-continued

Antitumor activity of compound 104

| Tumor [1] | volume at start mm[3] | Dose mg/kg | Schedule | Growth rate mm[3]/10 days | T/C % | p value [3] |
|---|---|---|---|---|---|---|
| SKOV-3 | 192 | control [2] | BID × 10 D | 432 ± 59 | | |
| | | 250 | BID × 10 D | 122 ± 16 | 28.3 | 0.001 [4] |
| A549 | 157 | control [2] | BID × 10 D | 413 ± 37 | | |
| | | 200 | BID × 10 D | 182 ± 47 | 44.1 | 0.016 [4] |
| MCF-7 | 142 | control [2] | BID × 10 D | 410 ± 101 | | |
| | | 100 | BID × 10 D | 383 ± 139 | 93.4 | NS [4] |
| | | 200 | BID × 10 D | 156 ± 30 | 38.0 | 0.042 |

[1] 8 mice per group;
[2] control received vehicle only ( );
[3] compared to vehicle control;
[4] not significantly different p > 0.05

Figure 11:
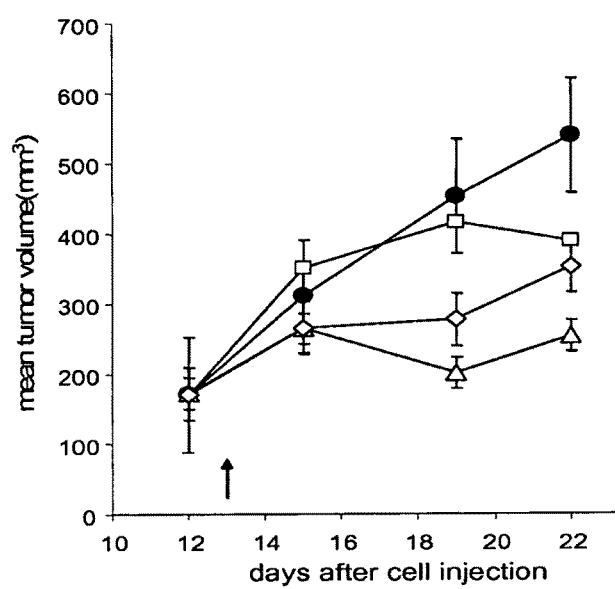
FIG. 11 shows anti-tumor activity of compound 104 alone or incombination with paclitaxel in MCF-7 human breast cancer xenografts.

To determine the efficacy of compound 104 as a sensitizer for tumor cells, compound 104 was administered alone or in combination with paclitaxel to scid mice with subcutaneous MCF-7 human breast cancer xenografts. Female scid mice with a s.c. implanted 60 day estradiol release pellets were injected s.c. with $10^7$ MCF-7 human breast cancer cells. When the tumors reached about 10 mm$^3$ the mice were stratified into groups of 8 mice and dosing was started on day 13 as indicated by the arrow (↑) in FIG. 11. Vehicle control mice (●) were administered 0.1 ml of 2:8 Labraso®1:Labrafil® orally twice per day for 10 days; compound 104 only mice (◇) were administered 200 mg/kg of compound 104 formulated as described above orally twice per day for 10 days; paclitaxel only mice (□) were administered 10 mg/kg of paclitaxel i.p. injection every other day for 5 doses; and combination mice (Δ) were administered 200 mg/kg of compound 104 orally twice a day for 10 days and 10 mg/kg of paclitaxel by i.p. injection every other day for 5 doses. As indicated in FIG. 11, compound 104 appears to have inhibited tumor growth, and the combination of compound 104 and paclitaxel showed improved antitumor activity over either compound 104 or paclitaxel alone.

Example 7

Compound 104 in HaCaT Cells

Human HaCaT, an immortalized cell line derived from adult human skin keratinocytes, and HaCat-II,4, HaCaT cells that were transfected with H-ras, were maintained in bulk culture in Dulbecco's modified Eagle medium (DMEM) supplemented with 10% heat-inactivated fetal bovine serum (FBS), 100 U/ml penicillin and 100 g/ml streptomycin in a 5% $CO_2$ atmosphere. Cells were passaged using 0.25% trypsin and 0.02% EDTA and confirmed to be mycoplasma free by testing them with an ELISA kit. Normal morphogenesis and differentiation features of skin keratinocytes are retained in the HaCaT cultures. Compound 104 was prepared in DMSO at a stock concentration of 10 mM and then added at different concentrations directly into the culture media of the cells. HaCaT cells and ras-transformed HaCaT cells were incubated with DMSO vehicle control or 10 μM compound 104 for 3 hours.

Figures 12A, 12B, 12C:
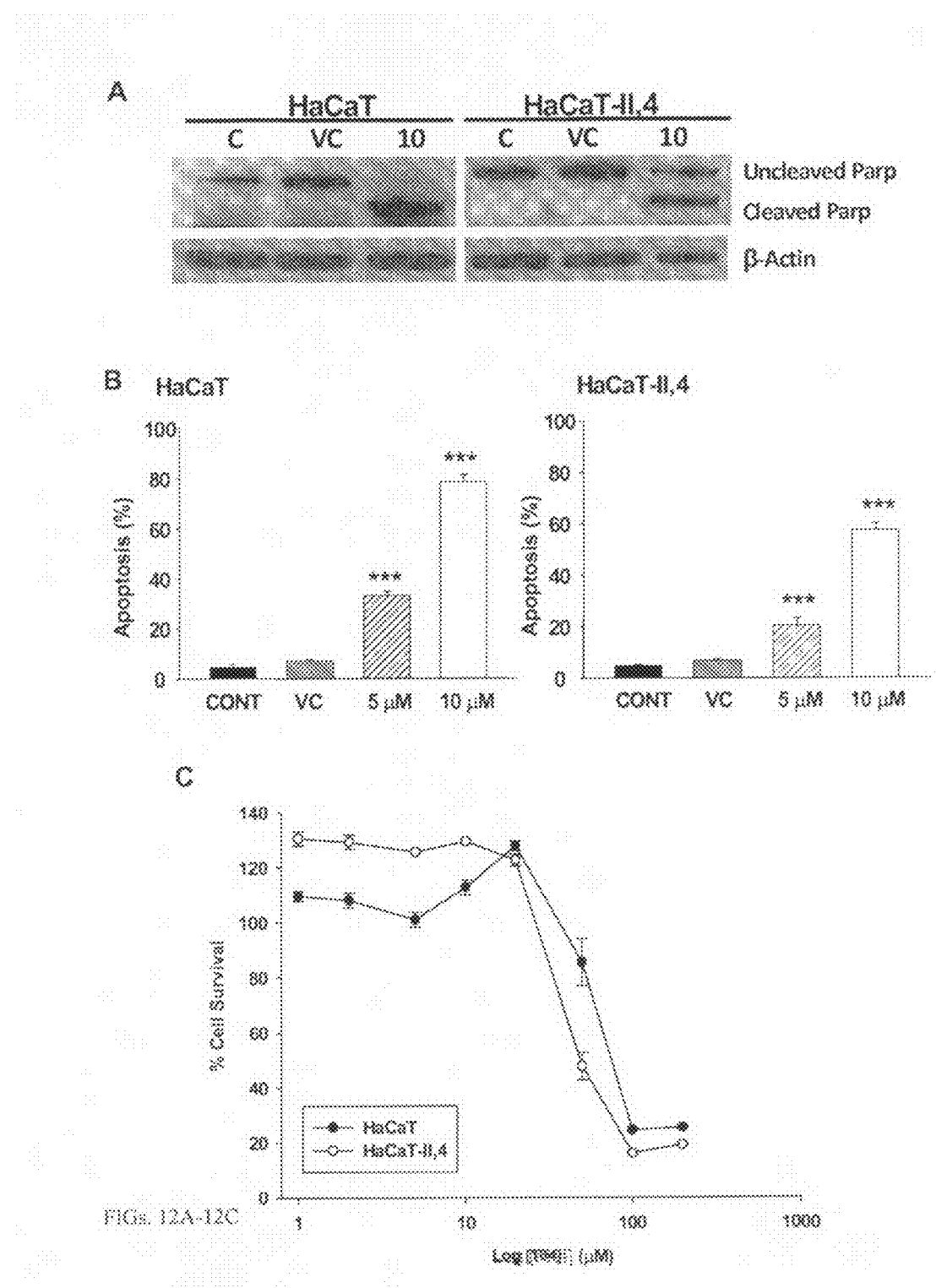
FIGS. 12A-12C show the induction of apoptosis in HaCaT cells.

FIG. 12 summarizes the effects of compound 104 in HaCaT and ras-transformed HaCaT and HaCat-II,4 cells. Apoptosis of treated HaCaT cells was measured by PARP cleavage observed through Western blotting. Cells were treated with increasing concentrations of compound 104 for three days and cell proliferation was evaluated using a MTT assay. FIG. 12A shows representative results from Western blot experiments. Both PARP and cleaved PARP are observed as independent species on the blot, and β-actin was used as an internal control. Statistically significant increases in apoptosis were noted in both cell lines in presence of 5 or 10 μM of compound 104 (p<0.001). As indicated in FIG. 12B, compound 104 induces PARP cleavage at 10 μM and induced 80% of apoptosis in HaCaT cells and 60% in HaCat-II,4 cells, while it did not affect cell survival at this concentration as shown in FIG. 12C. Survival was not affected until much higher concentrations were used as these data indicate that compound 104 exhibits an $IC_{50}$ of about 40 μM for HaCaT and 60 μM for HaCat-II,4, 4 and 6 times that of concentrations required for PARP cleavage.

Figure 13A:
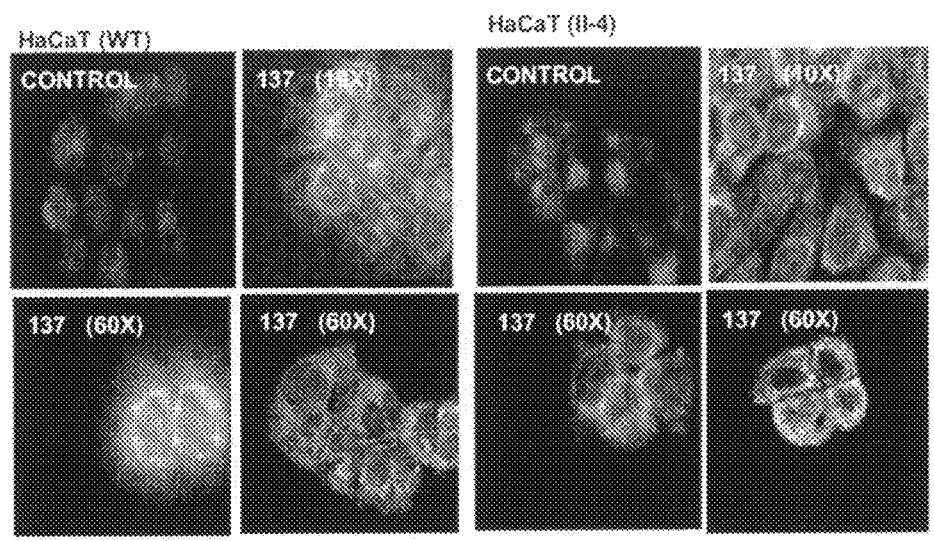
FIGS. 13A-13B show the localization of compound 137 in HaCaT cells and a comparison of inhibition of AKT phosphorylation for compound 104 and compound 137.

To better characterize the mechanism of action for compound 104, a compound 104 analog having a fluorescent marker, 7-nitroben-2-oxa-1,3-diazole, was prepared, compound 137, and HaCaT cells were treated for 3 hours with compound 137, the cells were fixed, and then visualized them under a fluorescent microscope using FITC filters. DAPI nuclear stain was used as an internal control. As illustrated in FIG. 13A, HaCaT or HaCaT-II,4 cells contacted with compound 137 and visualization under a fluorescent microscope show that the compound 137, and thus, compound 104, may enter the cells and locate both the plasma membrane and the cytosol.

Figure 13B:
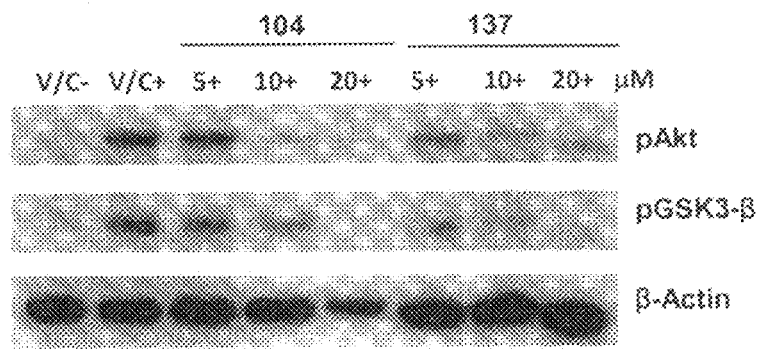

To ensure that compound 137 effects AKT phosphorylation similar to compound 104, either compound 104 or compound 137 was administered to HaCaT at various concentrations as indicated in FIG. 13B for 3 hours, the cells were then stimulated with 100 ng/ml EGF for 20 minutes and then lysed. Cells lysates were probed for phospho-Ser$^{473}$AKT and phosphor-Ser$^9$GSK3-β by Western blot analysis using rabbit polyclonal antibodies to phospho-Ser$^{473}$-AKT, phospho-Ser$^9$-GSK3-β or phospho-Thr$^{202}$/Tyr$^{204}$-ERK1/2 and anti-β-actin used as a loading control. These data suggest that although compound 137 possesses a fluorescent tag, it effects on Akt activity in cells HaCaT cells in the same way as compound 104.

Figure 14A:
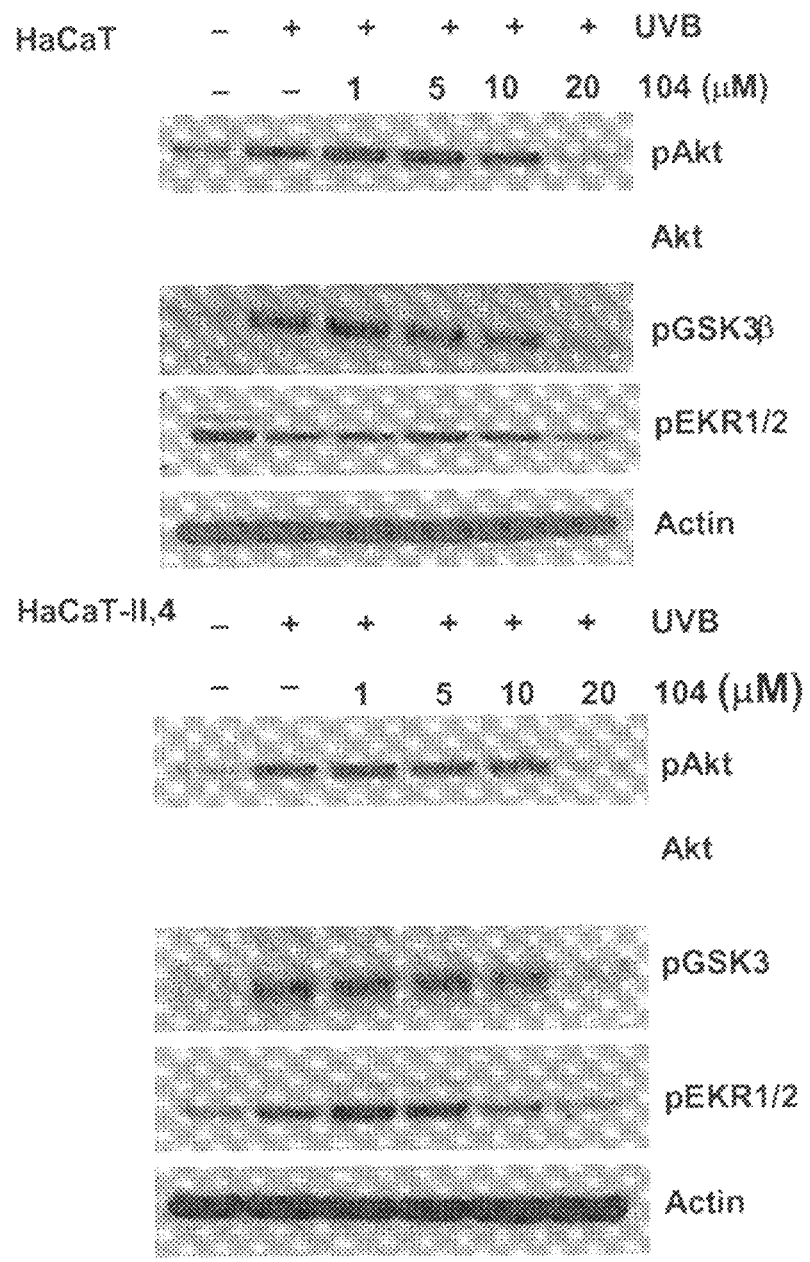
FIGS. 14A-14C show inhibition UVB-induced AKT phosphorylation in HaCaT cells by compound 104.

UV-B light is a major cause of non-melanoma skin cancer and induces PI3K/AKT activity in cultured human keratinocytes. Thus, the ability of compound 104 to mitigate or prevent UVB-induced AKT activation was tested. FIG. 14A shows the effect of increasing concentrations of compound 104 on HaCaT cells (top) and HaCaT-II,4 cells (bottom) that were irradiated with a single acute dose of UV-B light (250J/m2). Western blot analysis, as described above, was used to determine the extent of AKT phosphorylation in irradiated and control cells. As indicated, UV-B irradiation induced AKT phosphorylation in both cell lines. However, administration of 10 μM and 20 μM compound 104 appear to have reduced UVB-induced AKT phosphorylation as well as one downstream target, GSK3-β in both cell lines. Total AKT and pERK1/2 also appear to be down regulated in both cell lines. Notably, administration of 1 µM and 5 µM, or did not appear to affect UV-B induced AKT phosphorylation.

Figure 14B:
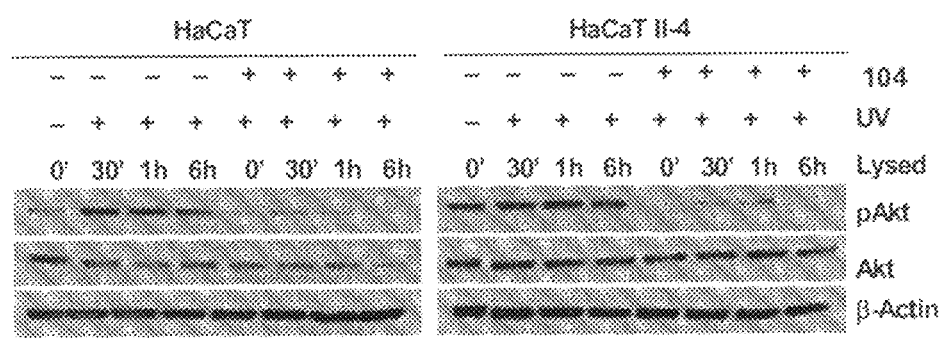
Figure 14C:
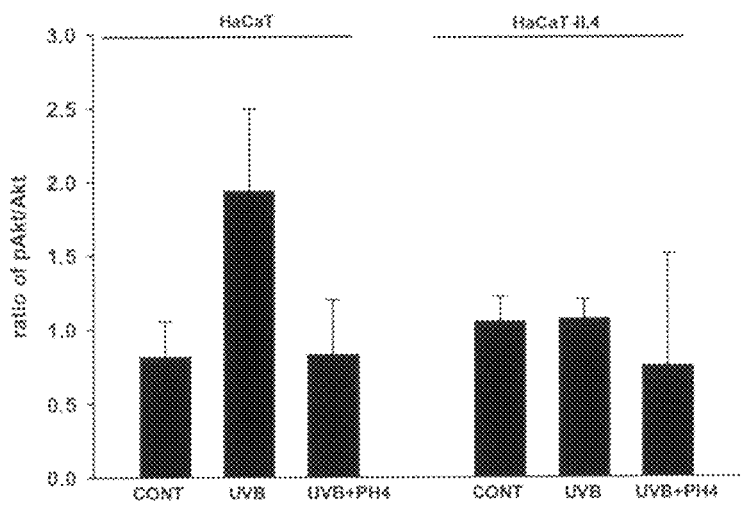
Figures 15A, 15B:
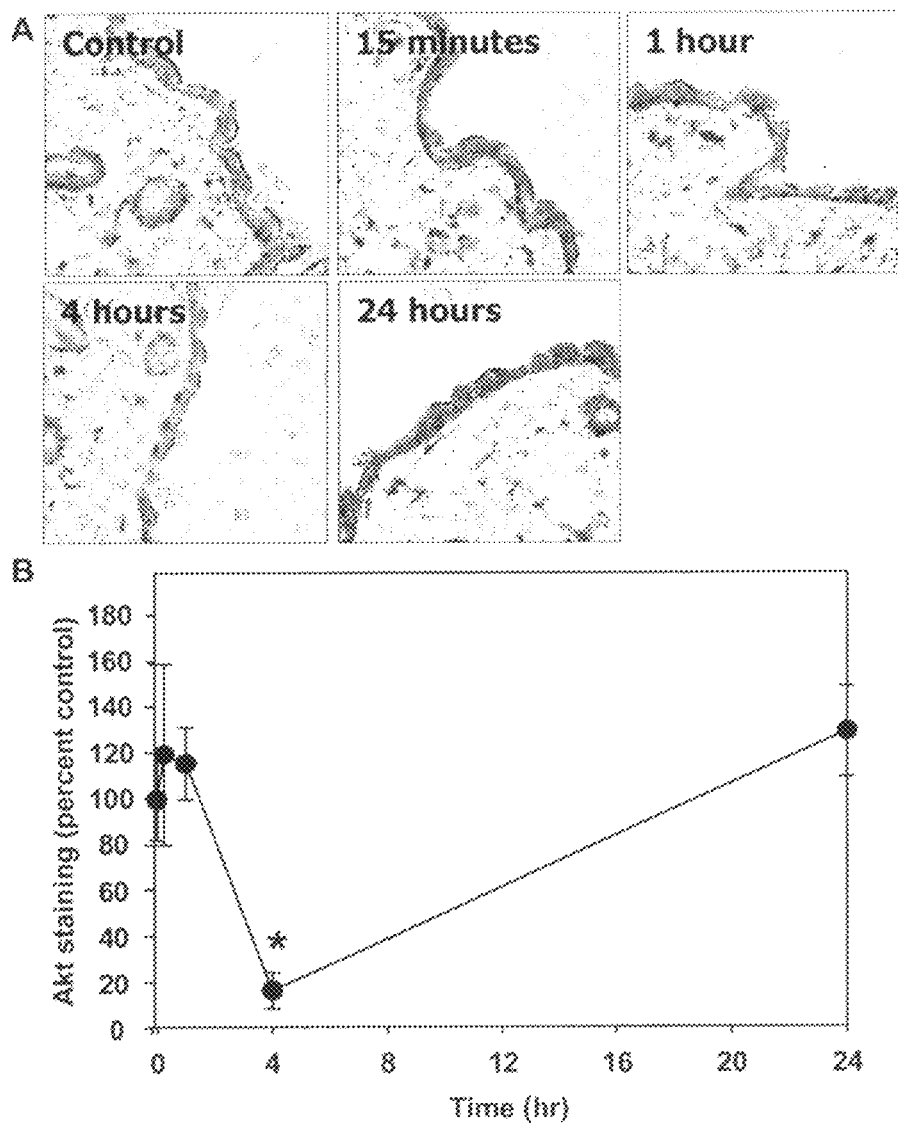
FIGS. 15A-15C show the effects of compound 104 on total AKT in scid mouse skin.
Figure 15C:
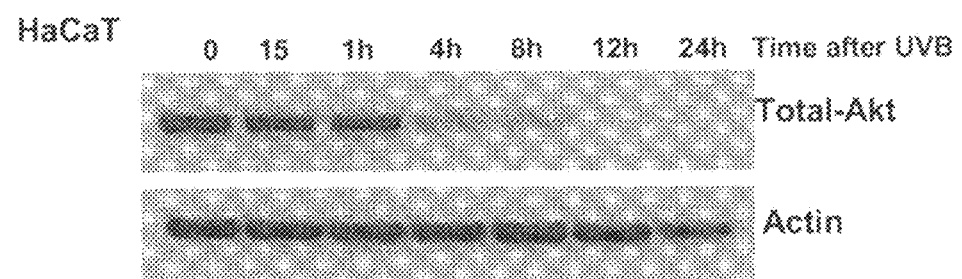
Figure 15C:
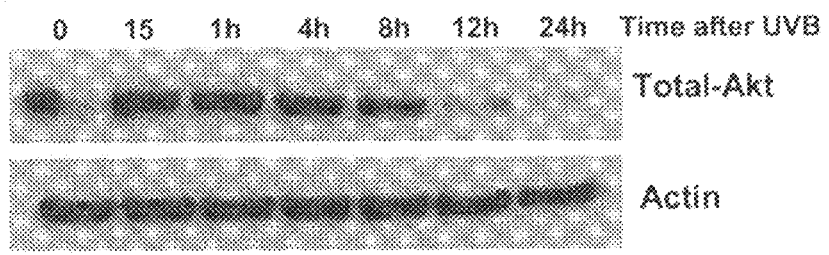

Data suggests that AKT activation may occur about one hour after UV-B exposure. Therefore, compound 104 activity overtime in UV-B stimulated cells was tested. Briefly, 10 µM compound 104 or DMSO vehicle control was administered to HaCaT cells and HaCaT-II,4, and a portion of the treated cells were with UV-B irradiation, and lysed, as described above, at the indicated time. Western blots prepared as described above with representative data provided in FIG. 14B suggest that UV-B irradiation induces rapid induction of AKT phosphorylation that appears to peak after about one hour, and pretreatment of irradiated cells with compound 104 may reduce phosphoylation of AKT in both cell lines. These data are represented graphically in FIG. 14C In vivo activity of compound 104 was tested by administering 20 mg/ml in 0.1 ml acetone topically to scid mice. Skin biopsies were taken and immunohistochemistry for AKT was performed on the sections. Total Akt staining was observed at the beginning of the experiment and decreased significantly overtime as indicated in FIG. 15A by the disappearance of the brown staining (AKT) between 1 and 4 hours. Notably, AKT staining reappears after 24 hours indicating that the effect of compound 104 may have dissipated. FIG. 15B shows a graphical representation quantifying AKT staining in the sections provided in FIG. 15A. Staining was measured by quantitative immunohistochemistry with correction for non-specific background staining (p<0.05). Phospho-Ser$^{473}$-AKT was not detectable in dermal layer. FIG. 15C summarizes the effects of compound over a 24 hour period as determined by Western blot analysis performed as described above. HaCaT cells (top) and HaCaT-II,4 (bottom) were incubated after administration of 10 µM compound 104 for the indicated period of time and then lysed. These data show a decrease in total AKT was after 4 hours in HaCaT cells and after 8 hours in HaCaT-II,4 cells and are in agreement with the immunohistochemistry data above.

Example 8

In silico Screening

AKT1 PH domain small molecule inhibitors were identified using the crystal structure of the AKT1 PH domain bound by PtdIns(1,3,4,5)P4 as descried in Thomas C C, Deak M, Alessi D R, van Aalten D M, High-resolution structure of the pleckstrin homology domain of protein kinase b/AKT bound to phosphatidylinositol (3,4,5)-trisphosphate, Curr Biol 12:1256 (2002), which is hereby incorporated by reference in its entirety, using a pharmacophore query search of the National Cancer Institute database. The high-resolution crystal structure of the isolated PH domain of human AKT1 in complex Ins(1,3,4,5)P$_4$ was utilized to define a pharmacophore pocket for screening using Unity in Sybyl (version 7.2; Tripos Inc., St Louis, Mo.). The pharmacophore pocket included all the residues of the AKT1 crystal structure within 5A of the Ins(1,3,4,5)P$_4$ binding site, i.e., Lys14, Arg15, Gly16, Gtu17, Tyr18, Ile19, Lys20, Thr21, Arg23, Pro24, Arg25, Lys39, Pro51, Leu52, Asn53, Asn54, Phe55, Gln79, ile84, Glu85, Arg86 and Phe88, and attributes to various atoms on the ligand and/or protein binding site were assigned. The defined pharmacophore pocket was then used to search virtual chemical databases and candidate compounds were identified. Various docking orientations were analyzed on the basis of FlexX scores, G-score, and X-score. Generally, the resulting scores are similar to interaction energy, and better/improved interactions are indicated by more negative values. The predicted K$_D$ is calculated by pK$_D$=10 exp(−Xscore). Using the FlexX docking algorithm in Sybyl for simulated docking of these compounds into the AKT1 PH domain active site resulted in 30 different docking orientations (poses) of the ligand within the active site. In order to investigate the possibility of specific binding of the identified small molecules at the AKT1 PH domain using in silico methods, known crystal structures of the IRS1 PH domain (IRS1, PDB:1QQG) and of the PDK1 PH domain (PDK1, PDB.iWID, 1W1G) were also used for docking studies similar to those described above.

A 2,000 molecule database (National Cancer Institute) was screened using Unity in Sybyl as described above. These compounds were docked and then ranked based on their docking scores. One of these molecules compound 316 exhibited good FlexX score and G-score values as summarized in Table 7 and was selected as a lead for future studies. The predicted binding affinity (K$_D$) of compound 316 to the AKT1 PH domain was 1.2 µM, which was three times better than the lipid-based compound, DPIEL with a predicted K$_D$ of 4.0 µM.

TABLE 9

| | Calculated docking scores | | | | | | | | |
|---|---|---|---|---|---|---|---|---|---|
| | AKT1 | | | PDK1 | | | RS1 | | |
| Compound | FlexX Score | G Score | cK$_D$ (µM) | FlexX Score | G Score | cK$_D$ (µM) | FlexX Score | G Score | cK$_D$ (µM) |
| DPIEL | NS | NS | 4.0 | NS | NS | NS | NS | NS | NS |
| 316 | −31.0 | −96.9 | 1.2 | −17.4 | −109.0 | 1.74 | −16.0 | −128.0 | 1.99 |
| 331 | −29.6 | −31.9 | 2.4 | −17.0 | −40.0 | 2.60 | −17.1 | −96.2 | 2.40 |
| 332 | −28.2 | −99.5 | 1.2 | −17.1 | −103.4 | 1.70 | −14.8 | −79.7 | 10.70 |
| 333 | −29.1 | −71.9 | 3.0 | −17.5 | −88.6 | 2.20 | −17.9 | −145.5 | 1.80 |
| 360 | −33.0 | −120.6 | 1.3 | −20.1 | −137.1 | 2.40 | −14.6 | −90.1 | 10.70 |
| 335 | −24.3 | −132.0 | 0.85 | −21.0 | −109.1 | 1.45 | −14.5 | −140.6 | 0.52 |

NS = not shown

Figures 16A, 16B, 16C, 16D:
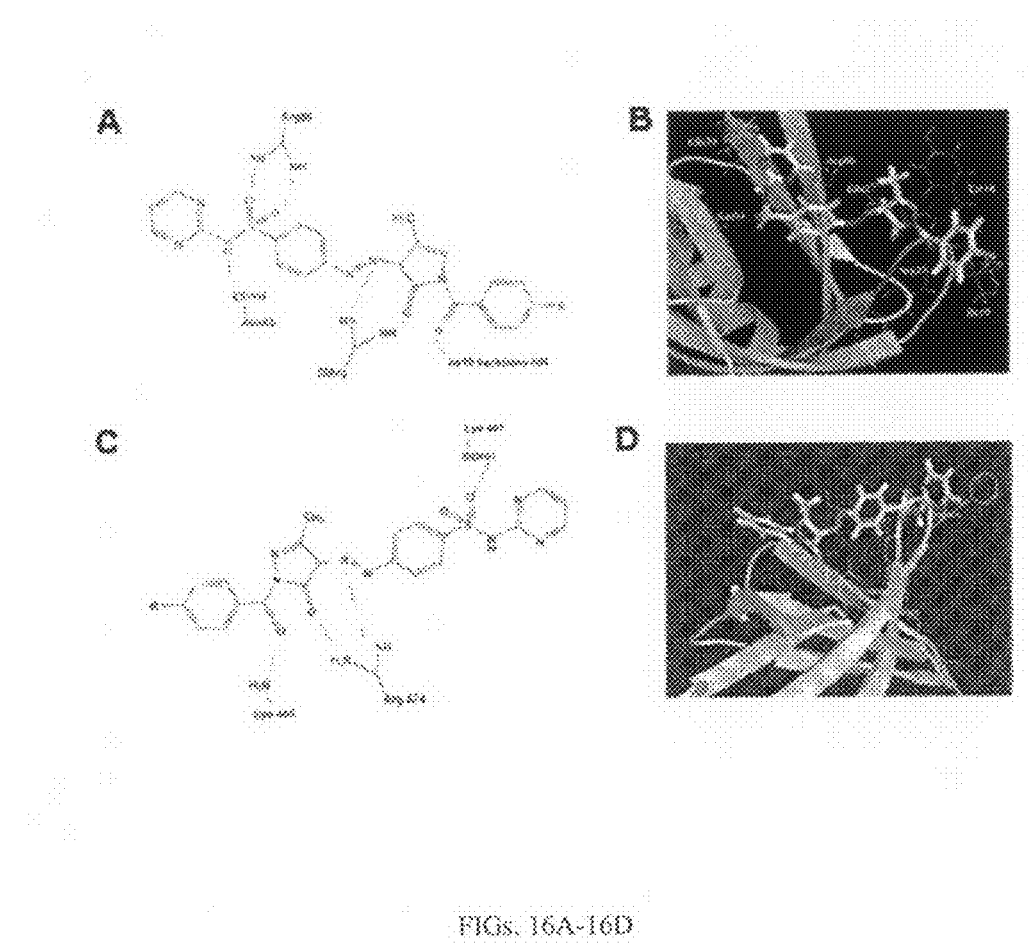
FIGS. 16A-16D show the interactions of compound 316 with the human AKT1 and PDK1 PH domain.

FIG. 16A shows the predicted binding of compound 316 to amino acid residues (Arg86, Asn53, Arg23 and Ile19) of the PH domain binding pocket of AKT1. Hydrogen bonding interactions are displayed as dotted lines. FIG. 16B represents hydrogen bonding interactions that occur between compound 316 and the amino acid side chains, as well as the backbone of the AKT1 PH domain binding pocket. The AKT1 PH domain is colored red and residues Arg23, Arg25 and Arg86 colored by atom type, and compound 316 is represented as capped stick and colored by atom type. The sulfonamide group appears to interact with Arg 86 through a hydrogen bond while a similar hydrogen bonding interaction is involved with the diazopyrazotyl group with Arg 23. These two arginine residues are involved in the strong interaction with the phosphate head groups of the substrate PtdIns(1,3,4,5)P$_4$. Other hydrogen bonds are also established between the backbones of Ile 19 and Asn 53 with the sulfonamide function of the compound. FIG. 16C and FIG. 16D represent binding of compound 316 in the binding pocket of the PH domain of PDK1 and the interactions with amino acids in the binding pocket. Notably, compound 316 is predicted to exhibit the reverse binding pose in the PH domain of PDK as compared to the PH domain of AKT1.

Based on the data for compound 316, five structurally similar compounds, 331, 332, 333, 360 and 335 with varying side chains were synthesized as described above. The structures and docking scores for these compounds are summarized in Table 7. Analyses of the docking poses of these compounds in the PH domain of AKT1 revealed different docking orientations between compounds 316, 332 and 360 as compared to compounds 331, 333 and 335. However, these differences in docking orientations may be due to limitations of the FlexX docking simulation since there are only small changes in the structures of these compounds. Therefore, compounds 331, 332, 333, 360 and 335 are expected exhibit similar binding to the AKT1 PH domain despite their FlexX score.

Binding affinities (K$_D$) were also calculated for compounds 331, 332, 333, 360 and 335 to the PH domain of PDK1 and were found to be very similar to those for AKT1 as shown in Table 6. FIG. 16C and FIG. 16D represent binding of compound 316 in the binding pocket of the PH domain of PDK1. There appears to be greater variability between 331, 332, 333, 360 and 335 based on calculated K$_S$S for the PH domain of IRS1 with compound 335 having the greatest affinity and compounds 332 and 360 having lower affinity.

Example 9

Measured Binding Affinity

Binding assays using SPR and an ELISA competitive binding assay were used to measure the binding affinity (K$_D$) of the compounds to all three PH domains. SPR was carried out as described above. For ELISA competitive binding assays, a 96-well Maxisorb plate was coated with 1pG/100 ul L-a-phosphatidylinositol(3,4,5)P$_3$. Purified GST-PH domains were incubated with increasing concentrations of the compounds under analysis for about 4 hours in 0.2 M carbonate buffer pH 9.4 and were added to the 96-well plate and incubated overnight at 4° C. Following incubation, the plate was washed 4 times with phosphate buffered 0.9% NaCl (PBS), blocked with 3% bovine serum albumin (BSA) in PBS and 0.01% Tween for 1 hour, washed again 4 times with PBS and mouse monoclonal anti-glutathione-5-transferase antibody in 3% BSA (1:2000) was added for 1 hr at room temperature with shaking. The plate was washed 4 times with PBS and an anti-mouse IgG horseradish peroxidase coupled antibody (dilution 1:2000 in 3% BSA) was added for 1 hr. After 4 washes with PBS, 2,2'-azinobis[3-ethylbenzothiazoline-6-sulfonic acid]-diammonium salt (ABST) was added and the reaction was allowed to develop for 30 min. A stop solution of 1% sodium dodecyl sulfate was then added and the plate was read at 405 nm in a plate reader.

Figures 17A, 17B:
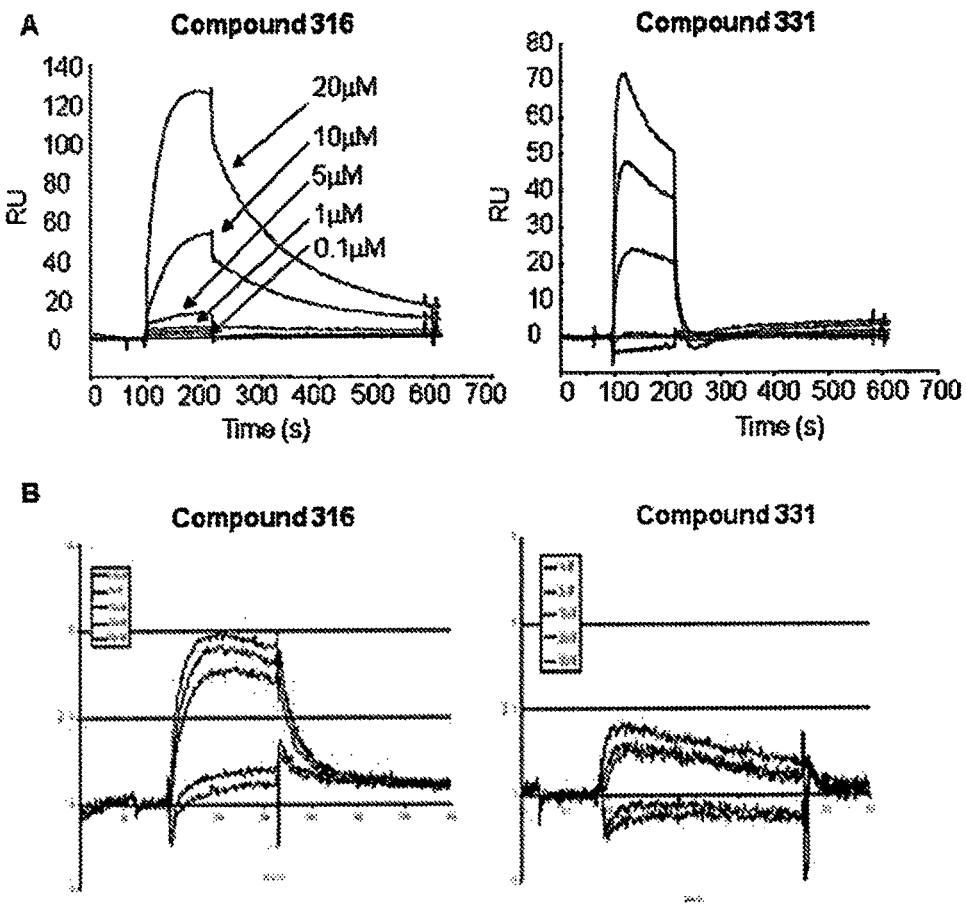
FIGS. 17A-17B show the binding of the compounds 316 and 331 to the PH domain of AKT1 and IRS1.
Figures 18A, 18B:
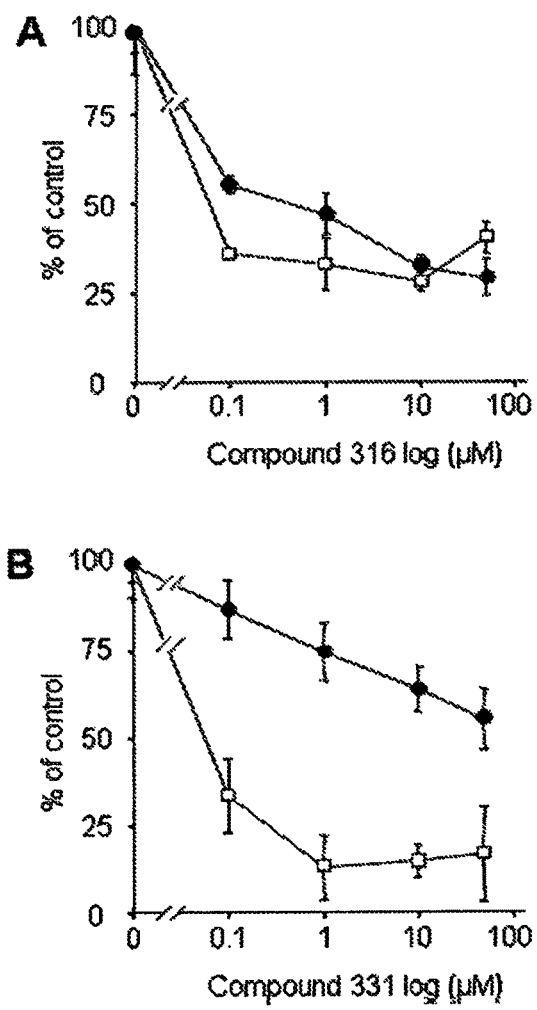
FIGS. 18A-18B show a graphical representation of ELISA competitive binding assays for compounds 316 and 331.

Table 8 summarizes the results obtained from the SPR measurements, and representative saturation curves as well dose response curves are shown in FIG. 17 for compounds 316 and 331 to the PH domain of AKT1 (FIG. 17A) and to the PH domain of IRS-1 (FIG. 17B). These results show an overlay plot of typical sensorgrams obtained with increasing concentrations of compound 316 or 331 as indicated by the arrows. These data correlated well with the predicted K$_D$ values for the compounds for each PH domain. Interestingly, modeling suggest that compounds 316 and 331 bind in a reverse binding pose in the PH domain binding pockets of the three different PH domains, which may explain differences in the SPR binding curves. ELISA competitive binding assay conducted using the PH domains of AKT1 and 1RS1 with compounds 316 (FIG. 18A) and 331 as shown in FIG. 18A and FIG. 18B, respectively, and resulted in an IC$_{50}$ for compounds 316 and 331 with AKT1 of 0.08 μM, and an IC50 with IRS1 for compound 316 of 1.0 μM and compound 331 of >100 μM. These data also compare well with the SPR data.

TABLE 10

Selectivity for PH Domains

| Compounds | AKT1 PH mK$_D$ (μM) | 1RS1 PH mK$_D$ (μM) | PDK1 PH mK$_D$ (μM) |
|---|---|---|---|
| PtdIns(3,4,5)P$_3$ | 3.08 ± 0.49 | ND | ND |
| DPIEL | 5.04 ± 0.48 | 31.56 ± 8.49 | NB |
| 316 | 0.37 ± 0.04 | 0.39 ± 0.01 | 31.28 ± 9.54 |
| 331 | 3.66 ± 0.03 | NB | 0.17 ± 0.10 |
| 332 | 1.37 ± 0.25 | NB | 3.5710.96 |
| 333 | 0.51 ± 0.06 | 0.14 ± 0.02 | NB |
| 360 | 1.35 ± 0.02 | 1.74 ± 0.41 | 0.42 ± 0.17 |
| 335 | 1.62 ± 0.02 | NB | 0.9810.48 |

NB = no measurable binding
ND = not determined.

Consistent with these docking studies, compounds 316, 333 and 360 exhibited low K$_D$ for the PH domain of IRS1 while compounds 331, 332 and 335 do not show any binding to IRS1 PH as measured by SPR. However, compounds 333 and 335 did not bind the PH domain of PDK1 with a predicted K$_D$ of 2.2 and 1.4, respectively. Taken together, these data suggest that the structural modifications in compounds 331, 332, 333, 360, and 335 as compared to compound 316 may have altered the binding positions of the compounds in the AKT 1 PH domain as well as their specificity against IRS1 or PDK1 PH domains.

Example 10

Biological Activity

Figures 19A, 19B:
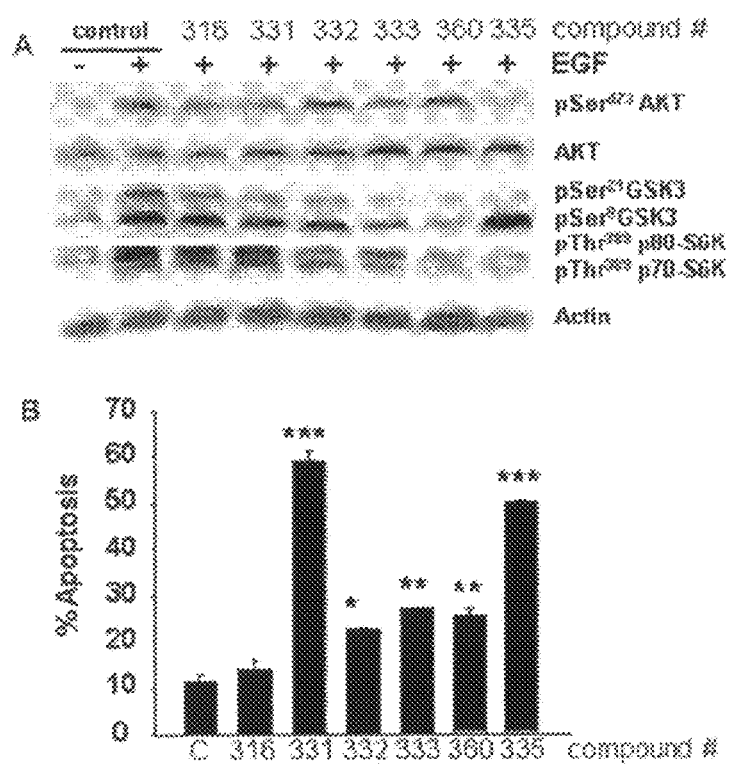
FIGS. 19A-19D show inhibition of AKT in cancer cells for compounds 316, 331, 332, 333, 360 and 335.

Table 9 shows inhibition of phospho-Ser$^{473}$ AKT by compounds 316, 331, 332, 333, 360 and 335 as measured in either mouse NIH3T3 or human HT-29 colon cancer cells. All of these compounds except compound 332, the most apparently lipophilic of the compounds, inhibited phospho-Ser$^{473}$AKT with as IC$_{50}$ from about 2 to about 10 fold higher than the IC$_{50}$ for AKT1 PH domain (see above). FIG. 19A shows typical Western blots obtained for the compounds in HT-29 colon cancer cells in which HT-29 colon cancer cells were treated with compounds I-6, at 20 nM for 2 hr and stimulated with 50 ng/nl EGF for 30 min. AKT activity was measured by Western blotting using anti-phosphoSer437 AKT antibody. Downstream targets of AKT were detected also by Western blotting using specific anti-phospho antibodies and anti-actin was used as a loading control. Compounds 331 and 335 appear to inhibit both AKT phosphorylation and GSK3 phosphorylation downstream.

FIG. 19B shows percentage of the HT-29 that undergo apoptosis as a result of administration of 20 nM of each of compounds 316, 331, 332, 333, 360 and 335. Apotposis was measured as described previously in reference Powell A A, LaRue J M, Batta A K, and Martinez J D, Bile acid hydrophobicity is correlated with induction of apoptosis and/or growth arrest in HCT116 cells, Biochem J 356:481-486 (2001), which is hereby incorporated by reference in its entirety. Briefly, HT-29 cells were grown to 70-75% confluency in 6-well tissue culture plates, and these cells were treated with the compounds for 24 hours. To measure apoptosis, 10 μl of cells were mixed with ethidium bromide and acridine orange solution (100 μg/ml each in DMEM) and visualized by immunofluorescence for morphological changes. A minimum of 200 cells was counted and the percentage of apoptotic cells was determined. Both compound 331 and 335 induce significant apoptosis at 20 μM as compared to controls. These data suggest that compounds 331 and 335 induced apoptosis in about 50% to about 60% of cells contacted with this amount of the compounds and suggest that these compounds inhibited AKT as well as downstream targets such as GSK3 phosphorylation (FIG. 19A).

Example 11

In Vivo Effects of the AKT1 pH Domain Inhibitors

Figures 20A, 20B, 20C:
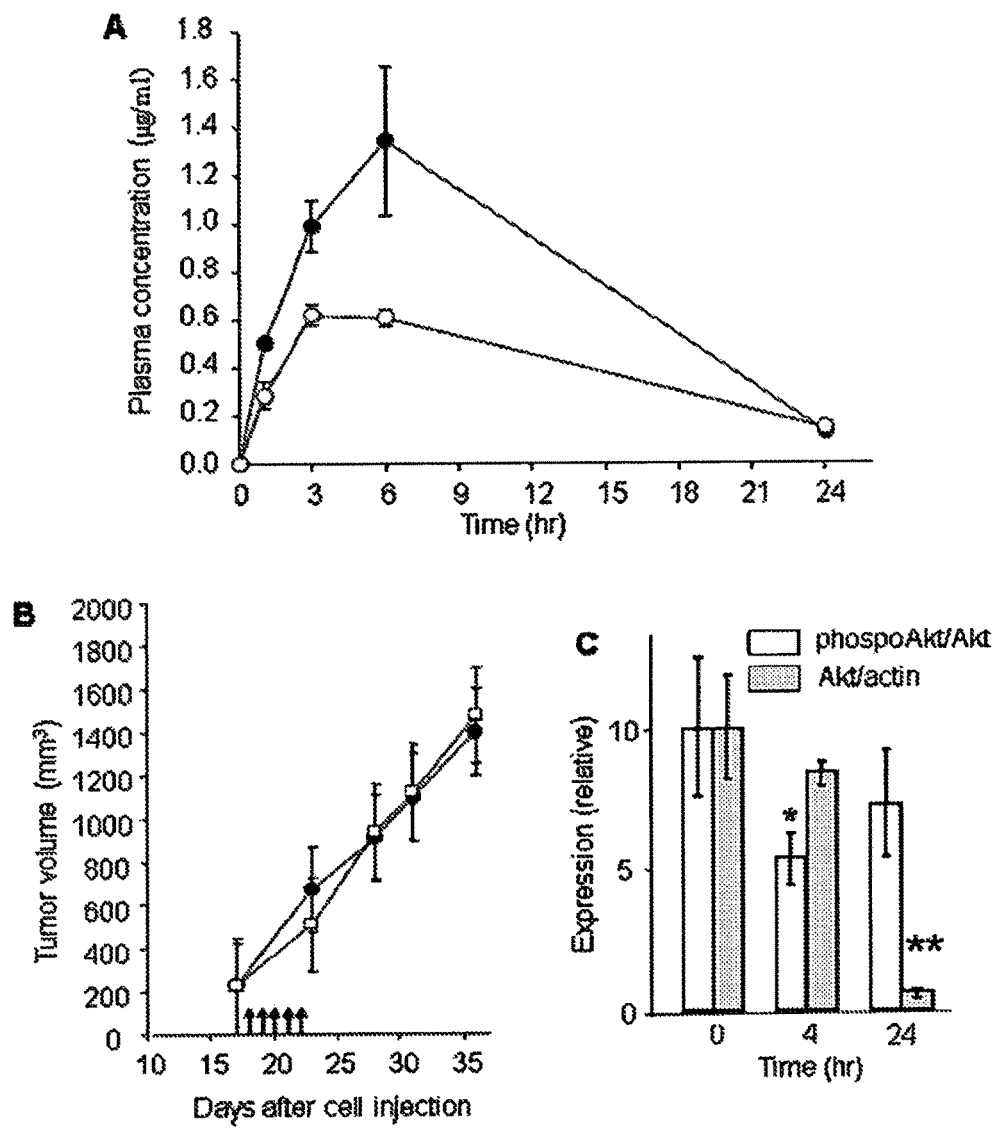
FIGS. 20A-20C show graphical representations of the in vivo activity of compound 316.

In vivo evaluation of compound 316 was carried out in female scid mice who were administered compound 316 at a dose 250 mg/kg either intraperitonealy (i.p.) or orally (p.o) by oral gavage and plasma concentrations measured. Because compound 316 is insoluble, a slurry in 25% DMSO 20% Trappsol® was prepared and administered. Preliminary studies indicate no toxicity of a single dose of up to 250 mg/kg, which was the maximum dose that could practically be administered i.p. FIG. 20A shows pharmacokinetic studies of a single dose of compound 316 of 250 mg/kg showed a peak concentration of 1.4 μM for i.p. administration (●) and 0.6 μM for oral administration (○) with a relative area under the plasma concentration time curve for oral compared to i.p. administration of about 53%. Plasma concentration values

TABLE 11

Biological Properties of compounds 316, 331, 332, 333, 360 and 335

| Compound | AKT inhibition (IC$_{50}$ μM) | | Cytotoxicity (IC$_{50}$ μM) | LogP | Metabolic half life (min) | Solubility (μM) | Permeability (nm/sec) | |
|---|---|---|---|---|---|---|---|---|
| | NIH3T3 | HT-29 | | | | | Caco2 | MDCK |
| 316 | 4 | 13 | 24 | 2.1 | 62 | 17.9 | 90 | 91 |
| 331 | 11 | 20 | 14 | 1.9 | 62 | 28.3 | 83 | 34 |
| 332 | >20 | >20 | 25 | 3.2 | 91 | 28.6 | 95 | 39 |
| 333 | ND | >20 | NI | 1.2 | >480 | 12.9 | 23 | 8 |
| 360 | 5 | >20 | NI | 1.5 | 138 | 13.1 | 185 | 200 |
| 335 | 3 | 5 | ND | 1.9 | ND | <0.1 | 14 | 5 |

Figures 19C, 19D:
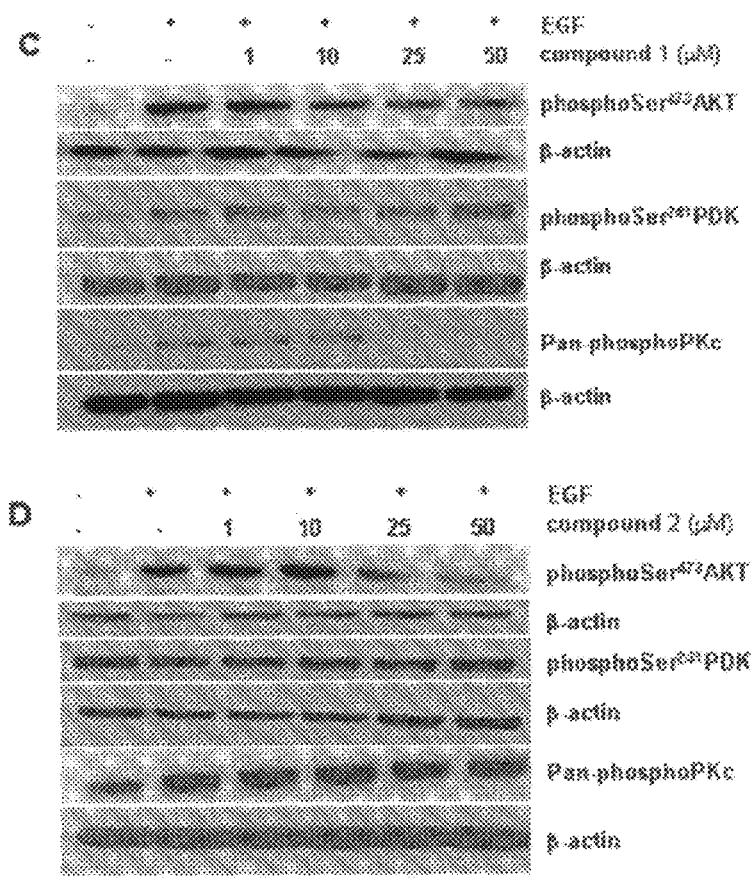

NI = not inhibitory (IC$_{50}$ >100 nM);
ND = not determined
Metabolic stability measured by incubating with HT-29 cells at maximum DMEM concentration at 37° C.
Apparent permeability (nm/sec obtained using the QikProp software (Schrodinger Inc., San Diego, CA).
<25 nm/sec = poor permeability
>500 nm/sec = excellent permeability FIG. 19 also shows response of HT-29 cells to various concentrations of compound 316 (FIG. 19C) and compound 331 (FIG. 19D). Compound 316 (FIG. 19C) and compound 331 (FIG. 19D) were tested at the concentrations shown for 2 hr, and in HT-29 cells stimulated with 50 ng/nl EGF for 30 min. AKT activity was measured by Western blotting using anti-phospho-Ser473 AKT antibody, PDK activity by anti-phospho-Ser241 PDK antibody as well as downstream target PKC using pan-phospho PKC antibodies. Anti-actin was used as a loading control. AKT phosphorylation appears to decrease in a concentration dependent manner as the concentrations of compounds 316 and 331 increase (FIG. 19C and FIG. 19D, respectively). Compound 316 may also inhibit phosphorylation of PDK and a downstream target of PDK, PKC (FIG. 19C). IRS1 phosphorylation could not be detected in these cells. Compound 331 appears to have inhibited AKT phosphorylation and appears to have had no effect on the phosphorylation of either PDK or PKC.

Table 8 also provides cytotoxicity was measured in HT-29 cells and appears to indicate that a cytotoxic concentration of compounds 316, 331, and 332 in about the same range as that required for inhibition of cell phospho-Ser$^{473}$AKT while compounds 333 and 360 appear to exhibit no cytotoxicity. Additionally, Table 9 shows the stabilities of compounds 316, 331, 332, 333, 360 and 335 under cell culture conditions. These data suggest that compounds 316, 331, 332 and 360 may breakdown relatively rapid with half lives of about 1 hour to about 2 hours. However, compound 4 was much more stable and did not appear to breakdown over the time period studied. Compound 6 was too insoluble to obtain data.

are the mean of 3 mice and bars are standard error (S.E.). Five daily doses of 250 mg/kg of compound 316 by i.p. gave moderate neutropenia but no other sign of toxicity, no change in body weight, blood lymphocyte, red blood cell and platelet count, or reduction of aspartate amino transferase (AST) or amino alanine transferase (ALT). However, despite the very large doses administered, high plasma concentrations could not be achieved, and the compound was eliminated relatively rapidly over about a 24 hr period suggesting rapid metabolism or elimination. Thus, concentrations of compound 316 required to inhibit AKT based on the cell culture studies described above, about 4 μM to about 13 μM, could not be achieved.

FIG. 20B shows the antitumor activity in female scid mice with HT-29 coion cancer xenografts treated orally daily for 5 days (arrows) with vehicle alone (●) or a 250 mg/kg daily dose of compound 316 (□). Tumor volume values are the mean of 10 mice and bars are S.E. These anti-tumor studies indicate that compound 316 may exhibit no activity against HT-29 colon cancer when administered orally for 5 days with a daily dose of 250 mg/kg. However, as indicated in FIG. 16C, inhibition of tumor phospho-Ser-AKT was observed when the HT-29 xenograft tumors were removed and blotted for phospho-Ser-AKT 4 hours after a single 250 mg/kg dose of compound 316 (open bar) as compared to vehicle alone (filled bars), but this inhibition appears to lost after at 24 hours. AKT and phospho-Ser-AKT values are the mean of 4 mice and bars are S.E., *p<0.05,** p<0.01. Additionally, 24 hours after administration there was an unexpected significant decrease in the apparent total AKT concentration compared to an actin loading control. Taken together, the results suggest that the limited solubility of compound 316 and metabolism or elimination of compound 316 may limit the plasma concentrations that can be achieved, and this may prevent effective inhibition of AKT activity. However, compound 316 may inhibit AKT phosphorylation and may be useful to sensitize tumor cells making them more susceptible to chemotherapy and/or radiation treatment.

What is claimed is:

1. A compound of the formula:

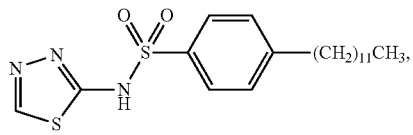

or pharmaceutically acceptable salt thereof.

2. A pharmaceutical composition comprising a compound of the formula:

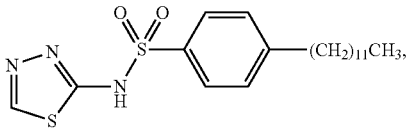

or pharmaceutically acceptable salt thereof; and
a pharmaceutically acceptable carrier or excipient.

3. The pharmaceutical composition of claim 1, wherein said compound is present in an effective amount.

* * * * *

UNITED STATES PATENT AND TRADEMARK OFFICE
CERTIFICATE OF CORRECTION

PATENT NO. : 8,420,678 B2
APPLICATION NO. : 12/937898
DATED : April 16, 2013
INVENTOR(S) : Daruka Mahadevan et al.

It is certified that error appears in the above-identified patent and that said Letters Patent is hereby corrected as shown below:

In the Claims

In claim 3, column 148, line 17, delete "claim 1" and insert --claim 2-- therefor.

Signed and Sealed this
Twenty-fifth Day of June, 2013

Teresa Stanek Rea
*Acting Director of the United States Patent and Trademark Office*